(12) United States Patent
Stonehouse et al.

(10) Patent No.: US 12,385,052 B2
(45) Date of Patent: Aug. 12, 2025

(54) YEAST STRAINS EXHIBITING PROLONGED PERSISTENCE DURING A PLURALITY OF FERMENTATION CYCLES

(71) Applicant: Lallemand Hungary Liquidity Management LLC, Budapest (HU)

(72) Inventors: Emily Agnes Stonehouse, Lebanon, NH (US); John McBride, Lebanon, NH (US); Justin Van Rooyen, Lebanon, NH (US); Zach Losordo, Lebanon, NH (US); Petra Deane, Lebanon, NH (US)

(73) Assignee: Danstar Ferment AG, Zug (CH)

( * ) Notice: Subject to any disclaimer, the term of this patent is extended or adjusted under 35 U.S.C. 154(b) by 0 days.

(21) Appl. No.: 17/843,741

(22) Filed: Jun. 17, 2022

(65) Prior Publication Data

US 2023/0026548 A1  Jan. 26, 2023

Related U.S. Application Data

(60) Provisional application No. 63/211,831, filed on Jun. 17, 2021.

(51) Int. Cl.
    *C12N 1/18*   (2006.01)
    *C12N 1/16*   (2006.01)
    *C12N 15/81*  (2006.01)

(52) U.S. Cl.
    CPC .............. *C12N 15/81* (2013.01); *C12N 1/165* (2021.05); *C12N 2510/02* (2013.01); *C12N 2511/00* (2013.01); *C12Y 101/01177* (2013.01)

(58) Field of Classification Search
    CPC ................ C12N 15/81; C12N 2510/02; C12N 2511/00; C12N 1/18; C12N 15/1034; C12Y 101/01177
    USPC .................................................... 435/254.2
    See application file for complete search history.

(56) References Cited

U.S. PATENT DOCUMENTS

| | | |
|---|---|---|
| 9,988,652 B2 | 6/2018 | McBride et al. |
| 10,385,345 B2 | 8/2019 | Brevnova et al. |
| 11,332,728 B2 | 5/2022 | Rice et al. |
| 2013/0323822 A1 | 12/2013 | Brevnova et al. |
| 2018/0265853 A1 | 9/2018 | Rice et al. |
| 2020/0224209 A1 | 7/2020 | Stonehouse et al. |
| 2022/0127564 A1 | 4/2022 | Argyros et al. |

OTHER PUBLICATIONS

Kiselev L., (Structure, 2002, vol. 10: 8-9.*
Kwiatkowski et al., (Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
Basso et al., "Ethanol Production in Brazil: The Industrial Process and Its Impact on Yeast Fermentation," *Biofuel Production—Recent Developments and Prospects,* Sep. 2011 (18 pages).
Brociner et al., "Thickening Flocculated Kaolinite Slurries in the Nozzle Discharge, Multi-Disc, Bowl Centrifuge," *Clay Minerals* 10:99, 1973 (14 pages).
Conrad et al., "Nutrient sensing and signaling in the yeast *Saccharomyces cerevisiae,*" *FEMS Microbiol Rev* 38:254-299, Feb. 2014.
Danecek et al., "The variant call format and VCFtools," *Bioinformatics* 27(15):2156-2158, Jun. 2011.
Fisher et al., "Adaptive genome duplication affects patterns of molecular evolution in *Saccharomyces cerevisiae,*" *PLoS Genet* 14(5):e 1007396, 2018 (15 pages).
Li, "A statistical framework for SNP calling, mutation discover, association mapping and population genetical parameter estimation from sequencing data," *Bioinformatics* 27(21):2987-2993, Sep. 2011.
Li et al., "The Sequence Alignment/Map format and SAMtools," *Bioinformatics* 25(16):2078-2079, Jun. 2009.
Oud et al., "Genome duplication and mutations in *ACE2* cause multicellular, fast-sedimenting phenotypes in evolved *Saccharomyces cerevisiae,*" *PNAS,* pp. E4223-E4231, Oct. 2013.
Purcell et al., "PLINK: A Tool Set for Whole-Genome Association and Population-Based Linkage Analyses," *The American Journal of Human Genetics* 81:559-575, Sep. 2007.
Scott et al., "The Influence of Polyploidy on the Evolution of Yeast Grown in a Sub-Optimal Carbon Source," *Mol. Biol. Evol.* 34(10): 2690-2703, Jul. 2017.
Selmecki et al., "Polyploidy can drive rapid adaptation in yeast," *Nature* 519(7543):349-352, Mar. 2015.
Zadrag-Tecza et al., "Cell Size Influences the Reproductive Potential and Total Lifespan of the *Saccharomyces cerevisiae* Yeast as Revealed by the Analysis of Polyploid Strains," *Oxidative Medicine and Cellular Longevity* 2018, Mar. 2018 (18 pages).
Zhang et al., "Effects of genome duplication on phenotypes and industrial applications of *Saccharomyces cerevisiae* strains," *App Microbiol Biotechnol* 101:5405-5414, 2017.
Basso et al., "Yeast selection for fuel ethanol production in Brazil," *FEMS Yeast Res* 8:1155-1163, 2008.
Basso et al., "Engineering topology and kinetics of sucrose metabolism in *Saccharomyces cerevisiae* for improved ethanol yield," *Metabolic Engineering* 13:694-703, 2011.
Bellon et al., "Introducing a New Breed of Wine Yeast: Interspecific Hybridisation between a Commercial *Saccharomyces cerevisiae* Wine Yeast and *Saccharomyces mikatae,*" *PLoS ONE* 8(4):e62053, 2013, 14 pages.
Panchal et al., "Yeast Stability in the Brewing and Industrial Fermentation Ethanol Industries," *Critical Reviews in Biotechnology* 4:3:253-262, 1986.
Stanhill et al., "The Yeast Ras/Cyclic AMP Pathway Induces Invasive Growth by Suppressing the Cellular Stress Response," *Molecular and Cellular Biology* 19(11):7529-7538, 1999.

(Continued)

*Primary Examiner* — Robert B Mondesi
*Assistant Examiner* — Mohammad Y Meah
(74) *Attorney, Agent, or Firm* — Seed IP Law Group LLP

(57) ABSTRACT

The present disclosure provides yeasts, which can be recombinant yeast host cells, exhibiting prolonged persistence when submitted to a plurality of fermentation cycles. The yeasts exhibit at least one of the following phenotypic trait: a fast settling phenotype, a rugose phenotype, an improved invertase activity, triploidy, increased signaling in a RAS/cAMP/PKA pathway or combinations thereof.

23 Claims, 19 Drawing Sheets
Specification includes a Sequence Listing.

(56) References Cited

OTHER PUBLICATIONS

Wang et al., "Increasing ethanol titer and yield in a gpd1 A gpd24 strain by simultaneous overexpression of *GLT1* and *STL1* in *Saccharomyces cerevisiae*," Biotechnol Lett 35:1859-1864, 2013.

Wu et al., "The transcription factor Ace2 and its paralog Swi5 regulate ethanol production during static fermentation through their targets Cts1 and Rps4a in *Saccharomyces cerevisiae*," *FEMS Yeast Research* 16:1-10, 2016.

Amorim et al., "Science and technology in the selection of yeasts for ethanol production," *Proceedings of the Symposium on Microorganisms in Agroenergy: from prospecting to bioprocesses*, 1 pg., Nov. 2013.

Entian et al., "25 Yeast Genetic Strain and Plasmid Collections," *Methods in Microbiology* 36:629-666, 2007.

Figueirêdo et al., "Molecular analysis of flocculation and foam formation by yeasts used in the industrial production of fuel alcohol in Brazil," *Dissertation to the Postgraduate Program in Biotechnology of the Federal University of Santa Catarina*, 1 pg., 2008.

Figueirêdo et al., "Study of the influence of the FLO8 gene on phenotypes of *Saccharomyces cerevisiae* strains isolated in the fuel ethanol production process in Brazil," Thesis (PhD in Biotechnology)—Institute of Biomedical Sciences, University of São Paulo, São Paulo, 2012, 1 pg., Oct. 2012.

Nascimento et al., "Effects of the carbon source on the physiology and invertase activity of the yeast *Saccharomyces cerevisiae* FT858," 3 *Biotech* 10:348, 9 pgs., 2020.

Zou et al., "Comparison of the Unfolded Protein Response in Cellobiose Utilization of Recombinant Angel-and W303-1A-Derived Yeast Expressing β-Glucosidase," *Frontiers in Bioengineering and Biotechnology* 10, 13 pgs., Mar. 2022.

\* cited by examiner

FIGURE 6

```
                           1,090        1,100 1,105 1,110      1,120        1,130
                              |           |    |    |           |            |
Consensus                  GTGATAAAAACAATAATGATNAAAAAAAAATAGTACTGGTGATAACAT
Translation Identity
1. M10682-ACE2-A(8)        GTGATAAAAACAATAATGATAAAAAAAAATAGTACTGGTGATAACAT
Translation                 S  D  K  N  N  D  K  K  N  S  T  G  D  N  I 2. M10682-ACE2-A(7)        GTGATAAAAACAATAATGAT-AAAAAAAAATAGTACTGGTGATAACAT
Translation                 S  D  K  N  N  D  -  K  K  I  V  L  V  I  T 1,140         1,150        1,160       1,170       1,1
                               |             |            |           |          |
Consensus                  ATTCCGTCTCTGTTCGAAAAGACTTCCCGGGTGGGCTAAGTATCTCTCCAA
Translation Identity
1. M10682-ACE2-A(8)        ATTCCGTCTCTGTTCGAAAAGACTTCCCGGGTGGGCTAAGTATCTCTCCAA
Translation                F  R  L  F  E  K  T  S  P  G  G  L  S  I  S  P 2. M10682-ACE2-A(7)        ATTCCGTCTCTGTTCGAAAAGACTTCCCGGGTGGGCTAAGTATCTCTCCAA
Translation                Y  S  V  C  S  K  R  L  P  R  V  G  *  V  S  L  Q
```

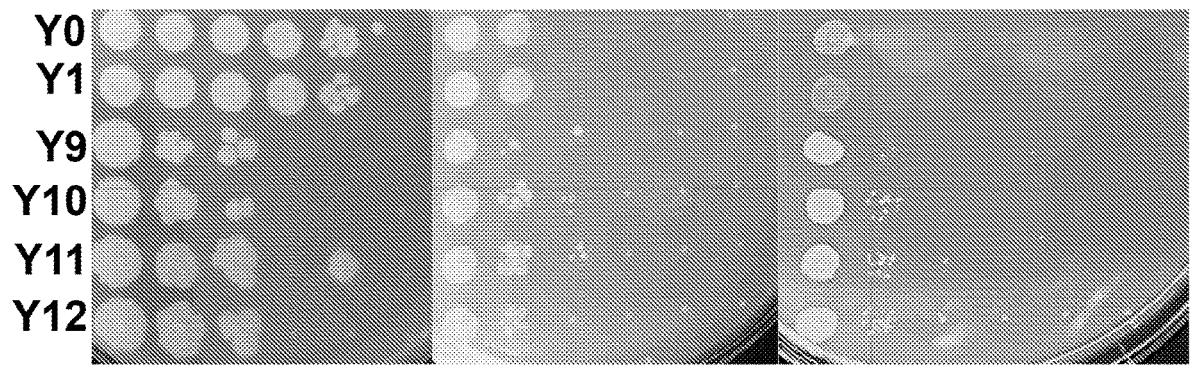
FIGURE 11A    FIGURE 11B    FIGURE 11C
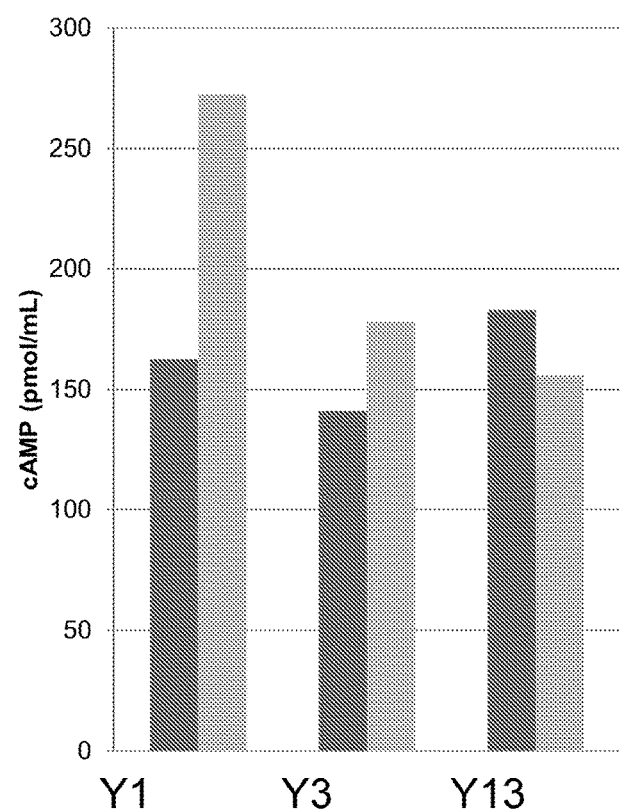
FIGURE 12

YEAST STRAINS EXHIBITING PROLONGED PERSISTENCE DURING A PLURALITY OF FERMENTATION CYCLES

CROSS-REFERENCE TO RELATED APPLICATION AND DOCUMENTS

This application claims priority from U.S. provisional application 63/211,831 filed on Jun. 17, 2021 and herewith incorporated in its entirety.

REFERENCE TO SEQUENCE LISTING SUBMITTED ELECTRONICALLY

The sequence listing associated with this application is provided in text format in lieu of a paper copy and is hereby incorporated by reference into the specification. The name of the text file containing the sequence listing is "580127_436_SEQ". The text file is 362,181 bytes, was created on Jun. 4, 2024, and is being submitted electronically.

TECHNOLOGICAL FIELD

The present disclosure concerns yeast host strains exhibiting prolonged persistence during a plurality of fermentation cycles in which the fermenting population is recycled.

BACKGROUND

Multiple fermentations cycles using a recycled biomass are susceptible to contaminations by wild yeasts. For example, in Brazilian fuel ethanol fermentations, the yeasts are pitched at the beginning of the sugarcane crushing season and are continually recycled for more than 200 days. The yeasts are recycled using continuous centrifugation and acid washing to improve productivity. Wild yeast contaminants are continually entering the fermentation since the fermentation substrates (e.g., sugarcanejuice and molasses) are not sterilized. In addition, the predominate *Saccharomyces cerevisiae* yeast strains used in the Brazilian fuel ethanol industry are highly heterozygous and are known to have genomic rearrangements which creates challenges to the traditional molecular identification methods used to monitor yeast populations (such as, for example, microsatellite and inter-delta sequence amplification, random amplified polymorphic DNA (RAPD) or karyotyping by pulse-field get electrophoresis (PFGE)).

Limiting contamination is important in continuous fermentations from both an economic and a processing perspective. Contaminating yeast have been associated with decreased ethanol yields, flocculation, and foaming. Greater than 95% of the contaminating yeasts are reported to be other *Saccharomyces* strains many of which have unfavorable fermentation characteristics and can lead to large productivity losses if allowed to proliferate. Less than 5% are non-*Saccharomyces* such as Dekkera bruxellensis, *Candida krusei* and *Schizosaccharomyces pombe*, but these strains can cause issues if left unchecked.

There is a need for limiting wild yeast contamination over numerous fermentation cycles using a recycled biomass or continuous fermentations so as to prolong the persistence of fermenting recombinant yeast host cells.

BRIEF SUMMARY

The present disclosure provides a yeast exhibiting prolonged persistence when submitted to a plurality of fermentation cycles. The yeast exhibits at least one of the following phenotypic trait: a fast settling phenotype, a rugose phenotype, an improved invertase activity, triploidy, increased signaling in a RAS/cAMP/PKA pathway or combinations thereof.

In a first aspect, the present disclosure provides a recombinant yeast host cell capable of modulating the activity or the expression of a first polypeptide and/or a second polypeptide for increasing, when compared to a parental cell, the conversion of a biomass into a fermentation product and/or for reducing the conversion of the biomass into a fermentation by-product. The recombinant yeast host cell comprises of at least one of phenotypic trait providing persistence of the recombinant yeast host cell in a plurality of fermentation cycles. The at least one phenotypic trait is: a fast settling phenotype, a rugose phenotype, an improved invertase activity, triploidy, increased signaling in a RAS/cAMP/PKA pathway or combinations thereof. In an embodiment, the recombinant yeast host cell, after a total of 40 fermentation cycles, is present in a proportion to at least 99% in a fermenting population. In an embodiment, the fermentation product is an alcohol, such as, for example, ethanol. In another embodiment, the fermentation by-product is glycerol.

In another embodiment, the recombinant yeast host cell is capable of increasing the expression of the first polypeptide. In yet another embodiment, the first polypeptide is a heterologous polypeptide capable of being expressed (and in some embodiments is expressed) in the recombinant yeast host cell and the recombinant yeast host cell comprises a first heterologous nucleic acid encoding the first polypeptide. In yet a further embodiments, the first polypeptide is a sugar transporter-like protein (STL1). In still another embodiment, STL1 has the amino acid sequence of SEQ ID NO: 8, is a variant of the amino acid sequence of SEQ ID NO: 8 having glycerol transport activity or is a fragment of the amino acid sequence of SEQ ID NO: 8 having glycerol transport activity and/or wherein the first heterologous nucleic acid molecule comprises the nucleic acid sequence of SEQ ID NO: 7 or is a degenerate sequence of SEQ ID NO: 7 encoding SEQ ID NO: 8. In still a further embodiment, the recombinant yeast host cell is capable of decreasing the expression of the second polypeptide, wherein the second polypeptide is a native polypeptide. In an embodiment, the native gene encoding the second polypeptide is inactivated. In some embodiments, the second polypeptide has NAD-dependent glycerol-3-phosphate dehydrogenase activity, such as, for example, NAD-dependent glycerol-3-phosphate dehydrogenase is glycerol-3-phosphate 1 (GPD1) and/or NAD-dependent glycerol-3-phosphate is glycerol-3-phosphate 2 (GPD2).

In some embodiments, the recombinant yeast host cell exhibits the fast settling phenotype. In some further embodiments, at least 5% of a population consisting essentially of the recombinant yeast host cells is able to sediment by gravity after 5 minutes. In some additional embodiment, a population consisting essentially of the recombinant yeast host cells is able to sediment by gravity after 5 minutes in a proportion equal to or higher than 15% than a control population consisting essentially of control yeast cells lacking the fast settling phenotypic trait. In an embodiment, the control yeast cells are from a *Saccharomyces cerevisiae* PE-2 strain.

In some embodiments, the recombinant yeast host cell exhibits the rugose phenotype. In some further embodiments, at least 90% of a population consisting essentially of the recombinant yeast host cells, after exponential growth in a medium inoculated at low recombinant yeast host cell density, has at least two daughter cells attached. In some additional embodiments, the recombinant yeast host cell is capable of reducing the transcription factor activity of a Activator of CUP1 Expression (ACE2) polypeptide. In some further embodiments, the recombinant yeast host cell is capable of expressing (and in some embodiments expresses) a mutated ACE2 polypeptide, wherein the mutated ACE2 polypeptide has decreased activity when compared to a wild type ACE2 polypeptide. In yet some additional embodiments, the mutated ACE2 polypeptide is a variant or a fragment of the amino acid sequence of SEQ ID NO: 10.

In some embodiments, the recombinant yeast host cell exhibits the improved invertase activity phenotypic trait. In some further embodiments, a population consisting essentially of the recombinant yeast host cells is able to consume hydrolyze more than 0.05 gram of sucrose per gram of dry cell weight per minute and/or exhibits more than 1.0 time more invertase activity than a control population consisting essentially of control yeast cells lacking the improved invertase activity phenotypic trait. The invertase activity can be measured after exponential growth of the population diluted to a concentration of 9 mg/mL on a wet cell weight in a buffer and wherein the buffer comprises 40 g/L of sucrose, is at of pH 5 and at a temperature of 35° C. In an embodiment, the control yeast cells are from a *Saccharomyces cerevisiae* PE-2 strain. In an embodiment, the recombinant yeast host cell is capable of increasing the enzymatic activity of at least one polypeptide having invertase activity. In still another embodiment, the at least one polypeptide having invertase activity comprises SUC1, SUC2, SUC3, SUC4, SUC5, SUC6, SUC7 SUC8 or SUC9.

In some embodiments, the recombinant yeast host cell is a triploid cell.

In some embodiments, the recombinant yeast host cell exhibits the increased signaling in the RAS/cAMP/PKA pathway phenotypic trait. In some additional embodiments, a population consisting essentially of the recombinant yeast host cells is able to exhibit a fold increase in the production of cAMP of equal to or less than 1.7 and/or a fold increase in the production of cAMP of less than 70% when compared a control population consisting essentially of control yeast cells lacking the increased signaling in the RAS/cAMP/PKA pathway. In some embodiments, the production of cAMP is measured in the population having been glucose depleted and 5 minutes after a glucose spike. In an embodiment, the control yeast cells are from a *Saccharomyces cerevisiae* PE-2 strain. In another embodiment, the recombinant yeast host cell is capable of expressing (and in some embodiments, expresses) a mutated polypeptide involved in the RAS/cAMP/PKA pathway. In some further embodiments, the mutated polypeptide involved in the RAS/cAMP/PKA pathway comprises a mutated RAS2 polypeptide having increased activity when compared to a wild-type RAS2 polypeptide. In yet additional embodiments, the mutated RAS2 polypeptide is a variant or a fragment of the amino acid sequence of SED ID NO: 19. In some further embodiments, the mutated polypeptide involved in the RAS/cAMP/PKA pathway comprises a mutated IRA2 polypeptide having a reduced inhibitory activity towards a wild-type RAS1 and/or a wild-type RAS2 polypeptide when compared to a wild-type IRA2 polypeptide. In still yet another embodiment, the mutated IRA2 polypeptide is a variant and/or a fragment of the amino acid sequence of SEQ ID NO: 22.

In some embodiments, the recombinant yeast host cell is from the genus *Saccharomyces* sp. or from the species *Saccharomyces cerevisiae*.

According to a second aspect, the present disclosure provides a process for prolonging the persistence of a yeast in a fermenting population in a plurality of fermentation cycles. The plurality of fermentation cycles comprises an initial fermentation cycle and at least one further fermentation cycle. The initial fermentation cycle comprises: (i) contacting an initial fermentation medium comprising a fermentable carbohydrate with an initial fermenting population to obtain a fermented medium comprising a fermentation product and a fermenting population and (ii) substantially isolating the fermenting population from the fermented medium. Each further fermentation cycle comprises: (iii) contacting the fermented population obtained from a previous fermentation cycle with a further fermentation medium comprising the fermentable carbohydrate to obtain a further fermented medium and (iv) substantially isolating the fermenting population from the further fermented medium. In the process, the initial fermenting population consists essentially of persistent yeast cells having at least one of the phenotypic trait as defined herein.

In some embodiments, the persistent yeast cell exhibits the fast settling phenotype. In some further embodiments, at least 5% of a population consisting essentially of the persistent yeast cells is able to sediment by gravity after 5 minutes. In some additional embodiment, a population consisting essentially of the persistent yeast cells is able to sediment by gravity after 5 minutes in a proportion equal to or higher than 15% than a control population consisting essentially of control yeast cells lacking the fast settling phenotypic trait. In an embodiment, the control yeast cells are from a *Saccharomyces cerevisiae* PE-2 strain.

In some embodiments, the persistent yeast cell exhibits the rugose phenotype. In some further embodiments, at least 90% of a population consisting essentially of the persistent yeast cells, after exponential growth in a medium inoculated at low persistent yeast cell density, has at least two daughter cells attached. In some additional embodiments, the persistent yeast cell is capable of reducing the transcription factor activity of a Activator of CUP1 Expression (ACE2) polypeptide. In some further embodiments, the persistent yeast cell is capable of expressing (and in some embodiments expresses) a mutated ACE2 polypeptide, wherein the mutated ACE2 polypeptide has decreased activity when compared to a wild type ACE2 polypeptide. In yet some additional embodiments, the mutated ACE2 polypeptide is a variant or a fragment of the amino acid sequence of SEQ ID NO: 10.

In some embodiments, the persistent yeast cell exhibits the improved invertase activity phenotypic trait. In some further embodiments, a population consisting essentially of persistent yeast cells is able to consume hydrolyze more than 0.05 gram of sucrose per gram of dry cell weight per minute and/or exhibits more than 1.0 time more invertase activity than a control population consisting essentially of control yeast cells lacking the improved invertase activity phenotypic trait. The invertase activity can be measured after exponential growth of the population diluted to a concentration of 9 mg/mL on a wet cell weight in a buffer and wherein the buffer comprises 40 g/L of sucrose, is at of pH 5 and at a temperature of 35° C. In an embodiment, the control yeast cells are from a *Saccharomyces cerevisiae* PE-2 strain. In an embodiment, the persistent yeast cell is capable of increasing the enzymatic activity of at least one polypeptide having invertase activity. In still another embodiment, the at least one polypeptide having invertase activity comprises SUC1, SUC2, SUC3, SUC4, SUC5, SUC6, SUC7, SUC8 or SUC9.

In some embodiments, the persistent yeast cell is a triploid cell.

In some embodiments, the persistent yeast cell exhibits the increased signaling in the RAS/cAMP/PKA pathway phenotypic trait. In some additional embodiments, a population consisting essentially of the persistent yeast cells is able to exhibit a fold increase in the production of cAMP of equal to or less than 1.7 and/or a fold increase in the production of cAMP of less than 70% when compared a control population consisting essentially of a control yeast cell lacking the increased signaling in the RAS/cAMP/PKA pathway. In some embodiments, the production of cAMP is measured in the population having been glucose depleted and 5 minutes after a glucose spike. In an embodiment, the control yeast cells are from a *Saccharomyces cerevisiae* PE-2 strain. In another embodiment, the persistent yeast cell is capable of expressing (and in some embodiments, expresses) a mutated polypeptide involved in the RAS/cAMP/PKA pathway. In some further embodiments, the mutated polypeptide involved in the RAS/cAMP/PKA pathway comprises a mutated RAS2 polypeptide having increased activity when compared to a wild-type RAS2 polypeptide. In yet additional embodiments, the mutated RAS2 polypeptide is a variant or a fragment of the amino acid sequence of SED ID NO: 19. In some further embodiments, the mutated polypeptide involved in the RAS/cAMP/PKA pathway comprises a mutated IRA2 polypeptide having a reduced inhibitory activity towards a wild-type RAS1 and/or a wild-type RAS2 polypeptide when compared to a wild-type IRA2 polypeptide. In still yet another embodiment, the mutated IRA2 polypeptide is a variant and/or a fragment of the amino acid sequence of SEQ ID NO: 22.

In some embodiments, the persistent yeast cell is from the genus *Saccharomyces* sp. or from the species *Saccharomyces cerevisiae*.

In some embodiments, the persistent yeast cells can be a recombinant yeast host cell as defined herein. In additional embodiments of the process, the persistent yeast cells, after a total of 40 fermentation cycles, are present in a proportion to at least 99% in the substantially isolated fermenting population. In an embodiment, the fermentation product is an alcohol, such as, for example, ethanol. In yet another embodiment, the fermentation by-product is glycerol. In still further embodiments, the initial and/or the further fermentation medium comprises sugarcane, a sugarcane derivative, molasses, a molasses derivative or a mixture thereof. In yet additional embodiments, the plurality of fermentation cycles comprises at least one continuous fermentation and/or at least one batch fermentation. In further embodiments, the substantially isolating step comprises centrifuging the fermented medium and/or the further fermented medium to substantially isolate the fermenting population. In yet some additional embodiments, each fermentation cycle further comprises acid washing the substantially isolated fermenting population prior to a further fermentation cycle. In some embodiments, the process comprises at least two or more fermentation cycles. In some embodiments, the process further comprises recuperating the fermentation product from the fermented medium and/or the further fermented medium.

According to a third aspect, the present disclosure provides a fermentation medium comprising the persistent yeast cell having the at least one phenotype trait defined herein. In some embodiments, the persistent yeast cell can be the recombinant yeast host cell described herein.

According to a fourth aspect, the present disclosure provides a fermenting population comprising a proportion of at least 99% of persistent yeast cells having the at least one phenotype trait defined herein. In some embodiments, the persistent yeast cells can be the recombinant yeast host cells described herein. In some embodiments, the persistent yeast cells have been submitted a substantially isolating step and/or an acid-washing step.

According to a fifth aspect, the present disclosure provides a process for making a yeast composition. The process comprises propagating a persistent yeast cell having the at least one phenotypic trait defined herein in a propagation medium to obtain a propagated medium, propagated persistent yeast cells. In some embodiments, the process can also comprise substantially isolating the propagated persistent yeast cells or the propagated recombinant yeast host cells from the propagated medium to obtain the yeast composition. In an embodiment, the persistent yeast cells can be the recombinant yeast host cells described herein.

According to a sixth aspect, the present disclosure provides a yeast composition comprising propagated persistent yeast cells having the at least one phenotypic trait defined herein. In an embodiment, the persistent yeast cells are propagated recombinant yeast host cells described herein.

According to a seventh aspect, the present disclosure provides a process for making a persistent yeast cell. The process comprises submitting an initial fermenting population consisting essentially of an initial cell to a plurality of fermentation cycles as defined herein and substantially isolating at least one yeast cell from the fermenting population to obtain the persistent yeast cell. In an embodiment, the process further comprises introducing at least genetic modification for modulating the activity or the expression of a polypeptide for increasing, when compared to a parental cell, the conversion of a biomass into a fermentation product and/or for reducing the conversion of the biomass into a fermentation by-product.

BRIEF DESCRIPTION OF THE DRAWINGS

Having thus generally described the nature of the invention, reference will now be made to the accompanying drawings, showing by way of illustration, a preferred embodiment thereof, and in which:

(FIG. 2A) provides the percentage of recombinant yeasts host cells (Y1 strain) (with respect to the total number of yeasts recuperated) in the beer (prior to centrifugation), the wine (the supernatant proceeding to distillation also referred to a "de-yeasted wine") and the cream (the pellet intended to be recycled in the process) as measured by qPCR. Microscopic (top panel) and macroscopic (bottom panel) of (FIG. 2B) the beer, (FIG. 2C) the wine, and (FIG. 2D) the cream.

(FIG. 4A) Example of rugose (multicellular) and smooth (monocellular or budding) occurring on a sample of yeast taken from a commercial ethanol mill. (FIG. 4B) Light (top panel) and electron scanning electron microscopy (middle (scale bar 10 μM) and lower panel (scale bar 3 μM)) images of a smooth yeast strain. (FIG. 4C) Light (top panel) and electron scanning microscopy (middle (scale bar 10 μM) and lower panel (scale bar 3 μM)) of a rugose yeast strain.

FIG. 6 shows the alignment of the functional A8 and nonfunctional A7 alleles at ACE2 for Y1, indicating the translation frameshift and early stop codon introduced at amino acid residue 389 (identified with an arrow).

(FIG. 10A) Sucrose consumption (measured by HPLC at time 0 (black bars), 1 (white bars) and 2 hrs (grey bars) after the start of feed in function of the yeast strains tested. (FIG. 10B) Fermentation kinetics monitored by $CO_2$ off gas over the course of the fermentation in function of the yeast strains tested (Y0=dark gray line; Y3=light grey line, Y5=stapled line).

FIGS. 11A to 11C shows the phenotypic characterization of wild yeast isolates (Y9, Y10, Y11 and Y12) compared to their parental strains Y0 and Y1. The strains or isolates were spot plated on (FIG. 11A) YPD medium, (FIG. 11B) YPS medium supplemented with 2-deoxyglucose and (FIG. 11C) YPD supplemented with rapamycin.

FIG. 12 compares the response of yeast produced cAMP in basal conditions (dark grey bars) and in response to a 100 mM glucose spike (light gray bars) for yeast strains Y1, Y3 and Y13. Results are shown as the cAMP produced (pmol/mL) in function of the experimental conditions and the strain tested.

(FIG. 14A): Y14 (triploid), Y15 (triploid), Y16 (triploid), Y17 (triploid), Y18 (triploid), Y19 (triploid), Y20 (triploid), Y21 (triploid), Y22 (triploid), Y23 (triploid), Y24 (triploid), Y25 (triploid); (FIG. 14B): Y26 (triploid), Y27 (triploid), Y28 (triploid), Y29 (triploid), Y30 (triploid), Y31 (triploid), Y32 (triploid), Y33 (diploid), Y34 (triploid); (FIG. 14C): Y35 (triploid), Y36 (triploid), Y3 (triploid), Y37 (diploid), Y38 (triploid), Y39 (triploid), Y40 (triploid), and Y10 (diploid).

(FIG. 16A) The percentage in yield increase (dark gray bars, left axis) and percentage glycerol reduction (light gray squares, right axis) are shown relative to the control strain Y0. (FIG. 16B) The fermentation kinetics were monitored by measuring $CO_2$ production during the 10 hour fermentation. Results are shown as $CO_2$ production (ml/min) in function of time (hours) and strain used (Y0: solid black line; Y2: dashed line; Y4: dotted line; Y6: solid light gray line).

(FIG. 18A) shows the % change in ethanol yield (top panel, grey bars) and in glycerol production (lower panel, black bars) in function of Y0. (FIG. 18B) shows the K value of each strain in function of contaminating strain Y7.

(FIG. 20A) provides the calculated exponential washout rates of each tested strains. The origin of different commercial substrates is identified with different symbols. (FIG. 20B) provides the percentage in ethanol change (top panel) and in glycerol change (bottom panel) for each of the tested strains when compared to yeast strain Y0.

DETAILED DESCRIPTION

Figure 1:
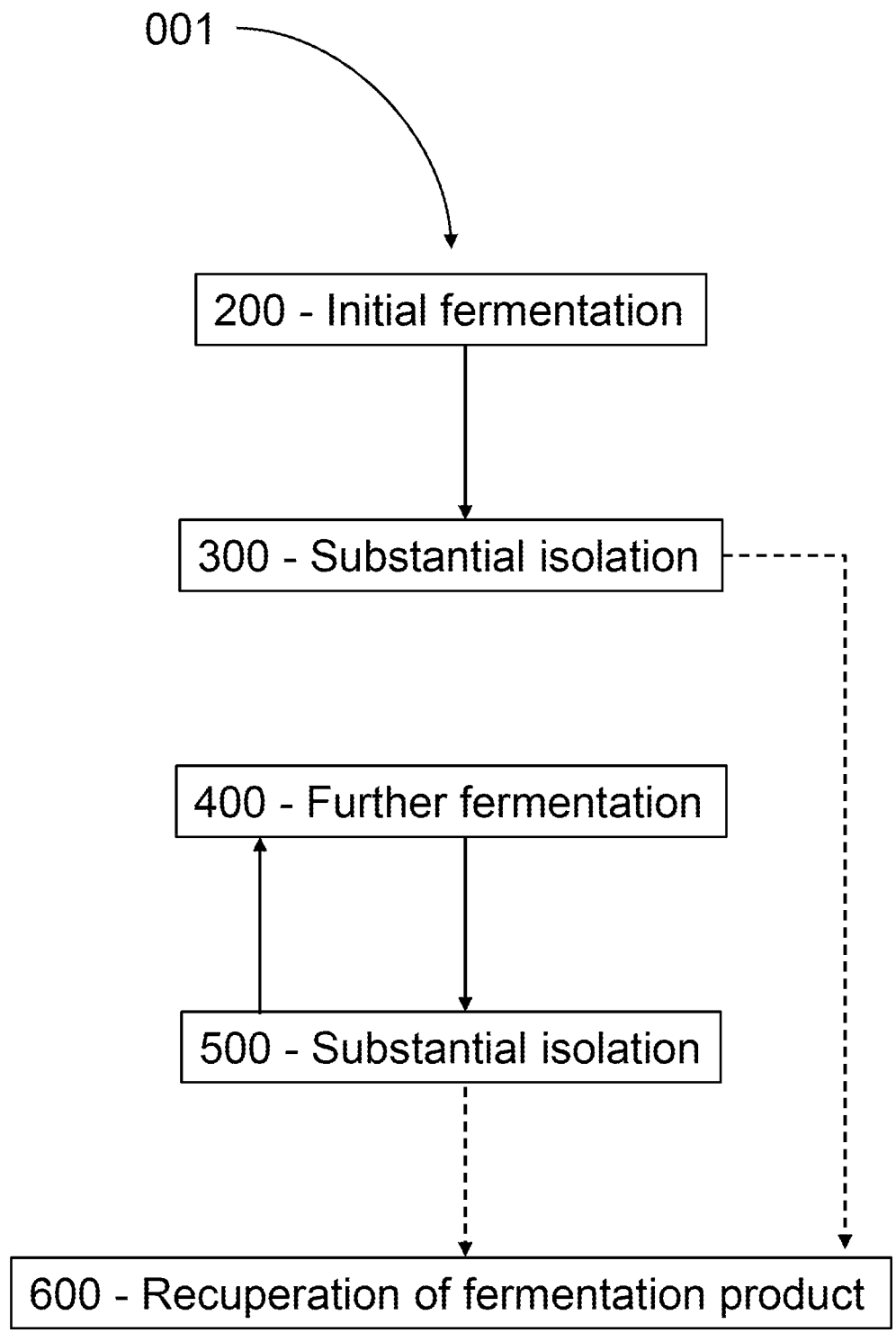
FIG. 1 is an embodiment of the process of the present disclosure.

It was sought to obtain yeasts having a prolonged presence (e.g., to persist) over a plurality of fermentation cycles. In order to do so, Applicant has identified phenotypic traits which allowed a recombinant yeast host cell to persist during a the plurality of fermentation cycles. Recombinant yeast host cells lacking such phenotypic traits were rapidly selected out from the fermenting population.

The persistent yeast cells of the present disclosure can be submitted to a plurality of fermentation cycles and persist in the fermenting population that is being used throughout the fermentation cycles. The plurality of fermentation cycles in which the persistent yeast cells are submitted comprises at least two distinct fermentation cycles: an initial fermentation cycle and one or more further fermentation cycles. In the initial fermentation cycle, a fermenting population consisting essentially of persistent yeast cells exhibiting the at least one phenotypic traits disclosed herein is contacted with a fermentation medium under conditions so as to obtain a fermentation product (and concurrently a fermented medium). As used in the present disclosure, "a fermenting population consisting essentially of the yeasts" refers to a population of cells which contains the yeasts having the at least one phenotypic traits and is substantially free of contaminating (wild) yeasts. In some embodiments, when the yeasts are recombinant yeast host cells, "a fermenting population consisting essentially of the recombinant yeast host" refers to a population of cells which contains the recombinant yeast host cells as described herein and is substantially free of contaminating (wild, non-genetically modified) yeasts. The fermenting population obtained at the end of this initial fermentation cycle is recycled for a further fermentation cycle (e.g., substantially isolated and used to inoculate a further fermentation medium). In this further fermentation cycle, no additional persistent yeast cells are added to the fermenting population. As such, the fermenting population used to inoculate the further fermentation medium consists essentially in the fermenting population substantially isolated in the initial fermentation cycle. It is recognized that the fermenting population used to inoculate the further fermentation medium can include contaminating wild yeasts which may have been introduced in the fermentation medium of the initial fermentation cycle. The inoculated further fermentation medium is then placed under conditions so as to obtain the fermented product and subsequently substantially isolate a (further) fermenting population (from a further fermented medium). The substantially isolated further fermenting population can be recycled and used to conduct one or more further fermentation cycle. It is understood that, in yet a further fermentation cycle, no additional persistent yeast cells are added to the further fermenting population. As such, the further fermenting population used to inoculate the yet further fermentation medium consists essentially in the fermenting population substantially isolated in the further fermentation cycle. It is recognized that the fermenting population used to inoculate the yet further fermentation medium can include contaminating wild yeasts which may have been introduced in the further fermentation medium of the further fermentation cycle. In an embodiment, a fermenting population obtained by using an initial fermenting population consisting essentially of the persistent yeast cells as described herein submitted to at least 40 fermentation cycles (total) comprises at least 90%, 99%, 99.9% or more persistent yeast cells having the at least one phenotype traits as described herein. In another embodiment, a fermenting population obtained by using an initial fermenting population consisting essentially of the recombinant persistent yeast host cells as described herein submitted to at least 40 fermentation cycles (total) comprises at least 90%, 99%, 99.9% or more of the recombinant persistent yeast host cells described herein.

An embodiment of a fermentation process 001 using a plurality of fermentation cycles is shown as FIG. 1. In the embodiments shown on FIG. 1, steps 200 and 300 refer to the initial fermentation cycle and steps 400 and 500 (which can be repeated) refer to the further fermentation cycle(s). In process 001, at step 200, an initial fermenting population is inoculated in a fermentation medium which is then submitted to an initial fermentation. The initial fermenting population that is added to the fermentation medium consists essentially of the persistent yeast cells (which include, in some embodiments, the recombinant yeast host cells exhibiting the one or more phenotypic trait as described herein). It is understood that the fermentation medium of step 200 can initially include contaminating wild yeasts or can be contaminated during fermentation with wild yeasts. Once the initial fermentation has been completed (e.g., a fermentation product and a fermenting population have accumulated in the fermentation medium to provide a fermented fermentation medium), the resulting fermenting population, at step 300, is substantially isolated from the fermented fermentation medium. As it will be explained below, the isolating step can include, without limitation, centrifuging the fermented fermentation medium and/or acid washing the substantially isolated fermenting population (not shown on FIG. 1). Once the initial fermentation cycle has been completed (at the conclusion of step 300), the substantially isolated fermenting population is placed, at step 400, into contact (e.g., used to inoculate) a further fermentation medium and allowed to perform a further fermentation. Once the further fermentation has been completed (e.g., a fermentation product and a further fermenting population have accumulated in the further fermentation medium to provide a further fermented fermentation medium), the resulting fermenting population, at step 500, is substantially isolated from the fermented fermentation medium. As it will be explained below, the isolating step can include, without limitation, centrifuging the further fermented fermentation medium and/or acid washing the substantially isolated fermenting population (not shown on FIG. 1). In some embodiments, no additional persistent yeast cell exhibiting the one or more phenotypic trait, including the recombinant yeast host cell described herein, is added to the fermentation medium after step 200, including during the one or more further fermentation cycles. However, in some embodiments, especially in the presence of contaminating microbes (such as bacteria and/or yeasts), it may be possible to add further persistent yeasts cells at the beginning of step 400 to perform the further fermentation. The substantially isolated fermenting population obtained at step 500 can be submitted to yet a further fermentation cycle at step 400. In some embodiments, the process can also include, after steps 300 or 500, recuperating, at step 600, the fermentation product from the fermented fermentation medium or the further fermented fermentation medium. This can be used, for example, by distilling the fermented fermentation medium or the further fermented fermentation medium (not shown on FIG. 1).

In some embodiments, the persistent yeast cells of the present disclosure are recombinant yeast host cells capable of modulating the expression of one or more polypeptide for increasing, when compared to a non-genetically modified parental cell, the conversion of a biomass into a fermentation product during a fermentation and/or for reducing the production of a fermentation by-product during the fermentation. In one embodiment, the recombinant yeast host cells of the present disclosure include at least one genetic modification to increase or decrease the activity (and in some embodiments the expression) of one or more polypeptide involved in the conversation of a biomass into a fermentation product and optionally the reduction of a fermentation by-product. In some optional embodiments, the recombinant yeast host cells of the present disclosure can also include one or more further genetic modification for providing the at least one phenotypic traits disclosed herein.

When the genetic modification is aimed at increasing the activity of a specific targeted polypeptide (which may native or heterologous) or the expression of a specific targeted gene (which may native or heterologous), the genetic modification can be made in one or multiple genetic locations. When the genetic modification is aimed at reducing or inhibiting the activity of a specific targeted polypeptide (which is native) or the expression of a specific targeted gene (which is native), the genetic modifications can be made in one or all copies of the targeted gene(s).

In the context of the present disclosure, the one or more genetic modifications are aimed at increasing, when compared to a parental cell, the conversion of a biomass into a fermentation product and/or at reducing the conversion of the biomass into a fermentation by-product in the recombinant yeast host cell. In an embodiment, when the one or more genetic modifications are aimed at increasing the conversion of a biomass (e.g., sugarcane or a biomass derived therefrom) into a fermentation product (e.g., an alcohol, for example, ethanol), an increase of at least 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5% or more of ethanol change in the recombinant yeast host cell when compared to a parental cell can be observed. In an embodiment, the parental cell is the *Saccharomyces cerevisiae* PE-2 strain. In another embodiment, when the one or more genetic modifications are aimed at reducing the conversion of the biomass (e.g., sugarcane or a biomass derived therefrom) into a fermentation by-product (e.g., glycerol), a decrease of at least 10, 11, 12, 13, 14, 15, 16, 17, 18, 19, 20, 21, 22, 23, 24, 25, 26, 27, 28, 29, 30% or more of glycerol change in in the recombinant yeast host cell when compared to a parental cell can be observed. In an embodiment, the parental cell is the *Saccharomyces cerevisiae* PE-2 strain.

In the context of the present disclosure, the recombinant yeast host cells are qualified as being "genetically engineered", e.g., they have been manipulated to either add at least one or more heterologous or exogenous nucleic acid residue and/or remove at least one endogenous (or native) nucleic acid residue. In some embodiments, the one or more nucleic acid residues that are added can be derived from a heterologous cell or the recombinant cell itself. In the latter scenario, the nucleic acid residue(s) is (are) added at a genomic location which is different than the native genomic location. The genetic manipulations did not occur in nature and are the results of in vitro manipulations of the native yeast.

In some embodiments, the genetic modification can be encoded on one or more heterologous molecules. In some embodiments, the heterologous nucleic acid molecule can encode one or more polypeptide (which may be additional copies of a native gene). In other embodiments, the heterologous nucleic acid molecules can encode a promoter or other regulatory sequence for upregulating or downregulating the expression of a native gene encoding a native polypeptide. In some embodiments, the heterologous nucleic acid molecules of the present disclosure can include a signal sequence to favor the secretion of the heterologous polypeptide or the native polypeptide.

The term "heterologous" when used in reference to a nucleic acid molecule (such as a promoter, a terminator or a coding sequence) or a protein/polypeptide refers to a nucleic acid molecule or a protein/polypeptide that is not natively found in the recombinant host cell. "Heterologous" also includes a native coding region/promoter/terminator, or portion thereof, that was removed from the source organism and subsequently reintroduced into the source organism in a form that is different from the corresponding native gene, e.g., not in its natural location in the organism's genome.

The heterologous nucleic acid molecule is purposively introduced into the recombinant yeast host cell. For example, a heterologous element could be derived from a different strain of host cell, or from an organism of a different taxonomic group (e.g., different kingdom, phylum, class, order, family genus, or species, or any subgroup within one of these classifications). As used herein, the term "native" when used in inference to a gene, polypeptide, enzymatic activity, or pathway refers to an unmodified gene, polypeptide, enzymatic activity, or pathway originally found in the recombinant host cell. In some embodiments, heterologous polypeptides derived from a different strain of host cell, or from an organism of a different taxonomic group (e.g., different kingdom, phylum, class, order, family genus, or species, or any subgroup within one of these classifications) can be used in the context of the present disclosure.

The heterologous nucleic acid molecules of the present disclosure can comprise a coding region for the heterologous polypeptide. A DNA or RNA "coding region" is a DNA or RNA molecule (preferably a DNA molecule) which is transcribed and/or translated into a heterologous polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, transcription terminators, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell (such as the recombinant yeast host cell of the present disclosure), a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The heterologous nucleic acid molecules described herein can comprise transcriptional and/or translational control regions. "Transcriptional and translational control regions" are DNA regulatory regions, such as promoters, enhancers, terminators, and the like, that provide for the expression of a coding region in a recombinant host cell. In eukaryotic cells, polyadenylation signals are considered control regions.

In some embodiments, the heterologous nucleic acid molecules of the present disclosure include a coding sequence for a heterologous polypeptide, optionally in combination with a promoter and/or a terminator. In some embodiments, the heterologous nucleic acid molecules of the present disclosure include a nucleic acid sequence encoding a promoter for overexpressing a native gene encoding a native polypeptide. In the heterologous nucleic acid molecules of the present disclosure, the promoter and the terminator (when present) are operatively linked to the nucleic acid coding sequence of the heterologous or native polypeptide, e.g., they control the expression and the termination of expression of the nucleic acid sequence of the heterologous or the native polypeptide. The heterologous nucleic acid molecules of the present disclosure can also include a nucleic acid sequence coding for a signal sequence, e.g., a short peptide sequence for exporting the heterologous polypeptide outside the host cell. When present, the nucleic acid sequence coding for the signal sequence is directly located upstream and in frame of the nucleic acid sequence coding for the heterologous polypeptide.

In the persistent yeast cells described herein, the nucleic acid molecule coding for the promoter and the nucleic acid molecule coding for the heterologous or the native polypeptide are operatively linked to one another. In the context of the present disclosure, the expressions "operatively linked" or "operatively associated" refers to fact that the promoter is physically associated to the nucleotide acid molecule coding for the heterologous or the native polypeptide in a manner that allows, under certain conditions, for expression of the heterologous polypeptide from the nucleic acid molecule. In an embodiment, the promoter can be located upstream (5') of the nucleic acid sequence coding for the heterologous polypeptide. In still another embodiment, the promoter can be located downstream (3') of the nucleic acid sequence coding for the heterologous polypeptide. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous or native polypeptide. The promoters can be located, in view of the nucleic acid molecule coding for the heterologous or native polypeptide, upstream, downstream as well as both upstream and downstream.

The term "promoter" refers to a DNA fragment capable of controlling the expression of a coding sequence or functional RNA. The term "expression," as used herein, refers to the transcription and stable accumulation of sense mRNA from the heterologous nucleic acid molecule or the native gene described herein. Expression may also refer to translation of mRNA into a polypeptide. Promoters may be derived in their entirety from the promoter of a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". Promoters which cause a gene to be expressed during the propagation phase of a yeast cell are herein referred to as "propagation promoters". Propagation promoters include both constitutive and inducible promoters, such as, for example, glucose-regulated, molasses-regulated, stress-response promoters (including osmotic stress response promoters) and aerobic-regulated promoters. Promoters which cause a gene to be expressed during the fermentation phase of a yeast cell are herein referred to as "fermentation promoters". Fermentation promoters include both constitutive and inducible promoters such as, for example, anaerobic promoters. In the context of the present disclosure, a "glycolytic promoter" is a promoter (or a combination of promoters) allowing the expression (or, in some embodiments, the overexpression) of a gene operatively associated thereto when the recombinant microbial cell is in placed in glycolytic conditions. The glycolytic promoter can be a constitutive promoter or a glucose-inducible promoter. Glycolytic promoters exclude glucose-repressible promoters. It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5 direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be native or heterologous to the nucleic acid molecule encoding the native or the heterologous polypeptide. The promoter can be heterologous to the native gene encoding the native polypeptide to be overexpressed. The promoter can be heterologous or derived from a strain being from the same genus or species as the recombinant host cell. In an embodiment, the promoter is derived from the same genus or species of the yeast host cell and the heterologous polypeptide is derived from a different genus than the host cell. The promoter can be a single promotor or a combination of different promoters.

In the context of the present disclosure, the promoter controlling the expression of the heterologous polypeptide or the native polypeptide can be a constitutive promoter (such as, for example, tef2p (e.g., the promoter of the tef2 gene), cwp2p (e.g., the promoter of the cwp2 gene), ssa1p (e.g., the promoter of the ssa1 gene), eno1p (e.g., the promoter of the eno1 gene), hxk1 (e.g., the promoter of the hxk1 gene) and pgk1p (e.g., the promoter of the pgk1 gene). In some embodiment, the promoter is tef2p (e.g., the promoter of the tef2 gene). In some embodiment, the promoter is adh1p (e.g., the promoter of the adh1 gene). However, in some embodiments, it is preferable to limit the expression of the polypeptide. As such, the promoter controlling the expression of the heterologous polypeptide or the native polypeptide can be an inducible or modulated promoters such as, for example, a glucose-regulated promoter (e.g., the promoter of the hxt7 gene (referred to as hxt7p)) or a sulfite-regulated promoter (e.g., the promoter of the gpd2 gene (referred to as gpd2p or the promoter of the fzf1 gene (referred to as the fzf1p)), the promoter of the ssu1 gene (referred to as ssu1p), the promoter of the ssu1-r gene (referred to as ssur1-rp). In an embodiment, the promoter is an anaerobic-regulated promoters, such as, for example tdh1p (e.g., the promoter of the tdh1 gene), pau5p (e.g., the promoter of the pau5 gene), hor7p (e.g., the promoter of the hor7 gene), adh1p (e.g., the promoter of the adh1 gene), tdh2p (e.g., the promoter of the tdh2 gene), tdh3p (e.g., the promoter of the tdh3 gene), gpd1p (e.g., the promoter of the gdp1 gene), cdc19p (e.g., the promoter of the cdc19 gene), eno2p (e.g., the promoter of the eno2 gene), pdc1p (e.g., the promoter of the pdc1 gene), hxt3p (e.g., the promoter of the hxt3 gene), dan1 (e.g., the promoter of the dan1 gene) and tpi1p (e.g., the promoter of the tpi1 gene). One or more promoters can be used to allow the expression of each heterologous polypeptides in the recombinant yeast host cell.

Still in the context of the present disclosure, the promoter controlling the expression of the heterologous polypeptide or the native polypeptide can be a glycolytic promoter. For example, the glycolytic promoter can be a promoter (or a combination of promoters) from an alcohol dehydrogenase gene, a glucose-6-phosphate isomerase gene, a phosphofructokinase gene, an aldolase gene, a triosephosphate isomerase gene, a glyceraldehyde-3-phosphate dehydrogenase gene, a 3-phosphoglycerate kinase gene, a phosphoglycerate mutase, an enolase and/or a pyruvate kinase gene.

One or more promoters can be used to allow the expression of each heterologous/native polypeptides in the persistent yeast cell. In the context of the present disclosure, the expression "functional fragment of a promoter" when used in combination to a promoter refers to a shorter nucleic acid sequence than the native promoter which retain the ability to control the expression of the nucleic acid sequence encoding the heterologous polypeptide. Usually, functional fragments are either 5' and/or 3' truncation of one or more nucleic acid residue from the native promoter nucleic acid sequence.

The heterologous nucleic acid molecule of the present disclosure can be integrated in the chromosome(s) of the recombinant yeast host cell. The term "integrated" as used herein refers to genetic elements that are placed, through molecular biology techniques, into the chromosome of a host cell. In some embodiments, the heterologous nucleic acid molecule(s) is/are integrated at one or more neutral integration site. For example, genetic elements can be placed into the chromosomes of the host cell as opposed to in a vector such as a plasmid carried by the host cell. Methods for integrating genetic elements into the chromosome of a host cell are well known in the art and include homologous recombination. The heterologous nucleic acid molecule can be present in one or more copies in the recombinant yeast host cell's chromosome. Alternatively, the heterologous nucleic acid molecule can be independently replicating from the yeast's chromosome. In such embodiment, the nucleic acid molecule can be stable and self-replicating. The heterologous nucleic acid molecules can be present in one or more copies in the recombinant yeast host cell. For example, each heterologous nucleic acid molecules can be present in 1, 2, 3, 4, 5, 6, 7, 8, 9, 10, 11, 12 copies or more per chromosome.

In some embodiments, the heterologous nucleic acid molecules which can be introduced into the recombinant host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons to optimize expression levels. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The heterologous nucleic acid molecules can be introduced in the yeast host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Phenotypic Traits

The persistent yeast cells of the present disclosure exhibits one or more phenotypic trait which allows them to be present over more fermentation cycles (e.g., persist during a plurality of fermentation cycles) than a corresponding control cell which lacks the phenotypic trait(s). The persistent yeast cells can be selected for the presence of one or more phenotypic trait or could be genetically engineered to provide one or more phenotypic trait. In some embodiments, the persistent yeast cells can be selected for the presence of at least one phenotypic trait and can be genetically engineered for the another phenotypic trait.

As it will be explained into more details below, the recombinant yeast host cells of the present disclosure necessarily includes at least one genetic modification (for modulating the activity or the expression of a first and/or a second polypeptide). It is possible to select/engineer a parental yeast host cell which possess the one or more phenotypic traits and modify such parental yeast host cell to include the genetic modification(s) for modulating the activity or the expression of a first and/or a second polypeptide. It is also possible to first introduce in a first yeast host cell the genetic modification(s) for modulating the activity or the expression of a first and/or a second polypeptide and afterwards select/engineer for the at least one phenotypic traits to obtain the recombinant yeast host cells of the present disclosure.

In an embodiment, the persistent yeast cells of the present disclosure exhibit at least one of the following phenotypic trait: a fast settling phenotype, a rugose phenotype, an improved invertase activity, triploidy, or increased signaling in a RAS/cAMP/PKA pathway. In another embodiment, the persistent yeast cells of the present disclosure exhibits at least two of the following phenotypic trait: a fast settling phenotype, a rugose phenotype, an improved invertase activity, triploidy, or increased signaling in a RAS/cAMP/PKA pathway. In a further embodiment, the persistent yeast cells of the present disclosure exhibits at least three of the following phenotypic trait: a fast settling phenotype, a rugose phenotype, an improved invertase activity, triploidy, or increased signaling in a RAS/cAMP/PKA pathway. In yet another embodiment, the persistent yeast cells of the present disclosure exhibits at least four of the following phenotypic trait: a fast settling phenotype, a rugose phenotype, an improved invertase activity, triploidy, or increased signaling in a RAS/cAMP/PKA pathway. In one embodiment, the persistent yeast cells of the present disclosure exhibits the following phenotypic traits: a fast settling phenotype, a rugose phenotype, an improved invertase activity, triploidy, and increased signaling in a RAS/cAMP/PKA pathway.

The persistent yeast cells of the present disclosure can advantageously be used in a plurality of fermentation cycles for converting a biomass into a fermentation product (e.g., an alcohol, such as, for example, ethanol) and in some optional embodiments, for reducing the conversion of the biomass into a fermentation by-product (e.g., distinct from ethanol, such as, for example, glycerol). In some embodiments, when the persistent yeast cells are provided as an initial fermenting population in a plurality of fermentation cycles, after 40, 45, 50, 55, 60, 65, 70, 75, 80, 90 or more fermentation cycles, the persistent yeast cells remain present in a proportion of at least 90, 91, 92, 93, 94, 95, 96, 97, 98, 99.0, 99.1, 99.2, 99.3, 99.4, 99.5, 99.6, 99.7, 99.8, 99.9% or more in the resulting fermenting population (when measured as its contribution to the DNA of the resulting fermenting population).

Fast Settling Phenotype

In some embodiments, the persistent yeast cells of the present disclosure can exhibit a fast settling phenotype. Yeasts exhibiting the fast settling phenotype are able to be centrifuged more efficiently and are therefore positively selected to be present in the substantially isolated fermenting population (and therefore persist further during subsequent fermentation cycles). As used in the context of the present disclosure, a "fast settling phenotype" refers to the ability of the persistent yeast cell to settle more rapidly (either by gravity or during centrifugation) than a control yeast lacking the fast settling phenotype. The fast settling phenotype can be due, at least in part, with an increased ability of the persistent yeast cell to flocculate when compared to a control yeast lacking the fast settling phenotype. The fast settling phenotype can be due, at least in part, by an increase ability of the persistent yeast cell to form cell clumps when compared to a control yeast lacking the fast settling phenotype. The fast setting phenotype can be due, at least in part, by the presence of the rugose phenotype in the persistent yeast cell.

In one embodiment, the persistent yeast cell of the present disclosure has the ability to settle more rapidly that the a control non-persistent yeast, e.g., the PE-2 strain. The commercially available strain PE-2 (described in Argueso et al., 2009 as well as Basso et al., 2011 and having the JAY291 genome in the *Saccharomyces* Genome Database (SGD)) lacks the fast settling phenotype. In the Example of the present disclosure, strain PE-2 is referred to as Y0.

In a specific embodiment, when a population consisting essentially of the persistent yeast cells of the present disclosure is provided in a relatively homogeneous distribution in a liquid medium, at least 5, 6, 7, 8, 9, 10, 11, 12, 13, 14, 15, 16, 17, 18, 19, 20% or more of the persistent yeast cells of the population will sediment by gravity after 5 minutes (when measured using optical density). In another specific embodiment, when a population consisting essentially of the persistent yeast cells of the present disclosure is provided in a relatively homogeneous distribution in a liquid medium, at least 5% of the persistent yeast cells of the population will sediment by gravity after 5 minutes (when measured using optical density). In still a further embodiment, a higher proportion (at least 15, 20, 25, 30, 35, 40, 45, 50, 60, 65, 70, 75, 80, 85, 90, 95 or 100%) of a population consisting essentially of persistent yeast cells of the present disclosure, when compared to a control population consisting essentially of control yeast cells, will sediment by gravity after 5 minutes (when measured using optical density). The control yeast cells lack the fast settling phenotype. In an embodiment, the control population consists essentially of the *Saccharomyces cerevisiae* PE-2 strain which is was shown in the Example to lack the fast settling phenotype. In order to determine the proportion of the populations that is able to sediment by gravity, the populations are provided in a relatively homogeneous distribution in a liquid medium and the proportion can be determined by optical density.

The persistent yeast cell can be selected, from a population, for the fast settling phenotype. This can be done, for example, by submitting a population of yeasts to a plurality of fermentation cycles which includes centrifuging the fermenting population in between cycles and selecting the persistent yeast cells having the ability to settle more rapidly during the process. Alternatively or in combination, the yeasts can be genetically engineered to provide a fast settling phenotype. This can be done, for example, by introducing one or more genetic modification to change the phenotype of a yeast from being smooth to rugose.

In an embodiment, the persistent yeast cell exhibits the fast settling phenotype optionally in combination with at least one of the following additional phenotypic traits: a rugose phenotype, an improved invertase activity, triploidy or increased signaling in a RAS/cAMP/PKA pathway. In another embodiment, the persistent yeast cell exhibits the fast settling phenotype optionally in combination with at least two of the following additional phenotypic traits: a rugose phenotype, an improved invertase activity, triploidy or increased signaling in a RAS/cAMP/PKA pathway. In another embodiment, the persistent yeast cell exhibits the fast settling phenotype optionally in combination with at least three of the following additional phenotypic traits: a rugose phenotype, an improved invertase activity, triploidy or increased signaling in a RAS/cAMP/PKA pathway. In a further embodiment, the persistent yeast cell exhibits the fast settling phenotype in combination with the following additional phenotypic traits: a rugose phenotype, an improved invertase activity, triploidy and increased signaling in a RAS/cAMP/PKA pathway.

Rugose Phenotype

In some embodiments, the persistent yeast cells of the present disclosure can exhibit the rugose phenotype. The rugose phenotype can be observed in cells after having been exponentially grown in a medium inoculated at low density. In an embodiment, low density refers to a density which would allow for 3 to 10 generations. In some embodiments, the low density refers to a density between about 0.01 and about 1 g/L of dry cell weight. The rugose phenotype is associated with the reduced ability of the persistent yeast cells to sever the septum between daughter cells. Yeasts exhibiting the rugose phenotype are able to form clumps in liquid medium which allows them to settle more rapidly (either by gravity or by centrifugation). Yeasts exhibiting the rugose phenotype are thus preferably selected to be present in the substantially isolated fermenting population (and therefore further persist in subsequence fermentation cycles). Colonies of persistent yeast cells exhibiting the rugose phenotype have irregular edges when cultured on a solid medium.

In a specific embodiment, when a population consisting essentially of the persistent yeast cells having the rugose phenotype is provided after exponential growth in a medium inoculated at low cell density, at least 90, 91, 92, 93, 94, 95, 96, 97, 98, 99% or more of the persistent yeast cells having at least two daughter cells attached. This assessment can be made, for example, by microscopic observation of the population after the exponential growth. In some embodiments, a population consisting essentially of persistent yeast cell exhibiting the rugose phenotype, after exponential growth in a medium inoculated at high cell density, may exhibit a lesser percentage of cells having at least two daughter cells attached. In some embodiments, the expression "high cell density" refers to a cell density of at least about 1, 2, 3, 4, 5, 6, 7, 8, 9, 10, 11, 12, 13, 14, 15, 16, 17, 18, 19, 20, 21, 22, 23, 24, 25, 26, 27, 28 29 pr 30 g/L of dry cell weight. In further embodiments, the expression "high cell density" refers to a cell density between about 1 to about 30 g/L of dry cell weight.

In an embodiment, the persistent yeast cells exhibiting the rugose phenotype have a reduced transcription factor activity of a Activator of CUP1 Expression (ACE2) polypeptide (when compared to a control yeast expressing a wild-type ACE2 polypeptide, such as, for example, the control PE-2 strain). This reduction in activity can be caused, in some embodiments, by the presence of a genetic modification (e.g., insertion, deletion, substitution or indel) in the regulatory region (e.g., promoter) or the coding region of the gene encoding the ACE2 polypeptide. In a further embodiment, the persistent yeast cells of the present disclosure includes at least one genetic modification (when compared to the wild-type nucleic acid sequence of the ACE2 gene provided as SEQ ID NO: 9 or a degenerate sequence encoding the amino acid sequence of SEQ ID NO: 10) in one, two or all alleles encoding the ACE2 gene. Modifications of the ACE2 gene to provide a rugose phenotype are known (Oud et al., 2013) and can introduced in the recombinant yeast host cell of the present disclosure to provide a persistent yeast cell. In a specific example, the persistent yeast cells of the present disclosure can include a deletion of at least one or more nucleic acid residues (which, in some embodiments, may be a deletion at or in the 3' region of the ACE2 gene) when compared to the to the wild-type nucleic acid sequence of the ACE2 gene provided as SEQ ID NO: 9 or a degenerate sequence encoding SEQ ID NO: 10. In some embodiments, this genetic modification is provided in FIG. 8, Tables 4 or 5. The genetic modification in the ACE2 gene may be present in one, two or all alleles of the ACE2 gene. As such, the persistent yeast cells of the present disclosure may be heterozygous or homozygous with respect to the genetic modification in the ACE2 gene.

In yet another embodiment, the persistent yeast cells of the present disclosure can include at least one amino acid modification (when compared to the wild-type amino acid sequence of the ACE2 polypeptide provided as SEQ ID NO: 10) in a mutated ACE2 polypeptide. In a specific embodiment, the persistent yeast cells exhibiting the rugose phenotype expresses a fragment of the wild-type ACE2 polypeptide, such as, for example, a C-terminal truncation of the wild-type ACE2 polypeptide (when compared to the wild-type amino acid sequence of the ACE2 polypeptide provided as SEQ ID NO: 10). In still further embodiments, the persistent yeast cells of the present disclosure can express a mutated ACE2 polypeptide having the amino acid sequence of SEQ ID NO: 12, 13, 14, 15 or 16. In some embodiments, the persistent yeast cells exhibiting the rugose phenotype are capable of expressing a variant of a mutated ACE2 polypeptide having the amino acid sequence of SEQ ID NO: 12, 13, 14, 15 or 16 having reduced transcription factor activity (when compared to the wild-type ACE2 polypeptide). In some further embodiments, the persistent yeast cells exhibiting the rugose phenotype are capable of expressing a fragment of a mutated ACE2 polypeptide having the amino acid sequence of SEQ ID NO: 12, 13, 14, 15 or 16 having reduced transcription factor activity (when compared to the wild-type ACE2 polypeptide).

In a specific embodiment, the persistent yeast cells of the present disclosure can express a mutated ACE2 polypeptide having the amino acid sequence of SEQ ID NO: 12. In such embodiment, the persistent yeast cells of the present disclosure can include one or both mutated ACE2 alleles comprising the nucleic acid sequence of SEQ ID NO: 11 (or a degenerate sequence encoding SEQ ID NO: 12). In some embodiments, the mutated allele for the ACE2 polypeptide can be located on a heterologous nucleic acid molecule introduced in the recombinant yeast host cell.

The persistent yeast cells can be selected, from a population of yeast cells, for the rugose phenotype. This can be done, for example, by submitting a population of yeast cells to a plurality of fermentation cycles which includes centrifuging the fermenting population in between cycles and selecting the yeast cells having the ability to settle more rapidly during the process (which are believed to have the rugose phenotype). This can also be done, for example, by culturing on a solid medium a population of yeast cells, and selecting the colonies exhibiting the rugose phenotype (either by visual observation or by microscopy for example). Alternatively or in combination, the yeast can be genetically engineered to provide a rugose phenotype. This can be done, for example, by introducing one or more genetic modification to change the phenotype of the yeast from being smooth to rugose and in some embodiments, for expressing a mutated ACE2 polypeptide.

In an embodiment, the persistent yeast cell exhibits the rugose phenotypic trait optionally in combination with at least one of the following additional phenotypic traits: a fast settling phenotype, an improved invertase activity, triploidy or increased signaling in a RAS/cAMP/PKA pathway. In an embodiment, the persistent yeast cell exhibits the rugose phenotypic trait optionally in combination with at least two of the following additional phenotypic traits: a fast settling phenotype, an improved invertase activity, triploidy or increased signaling in a RAS/cAMP/PKA pathway. In an embodiment, the persistent yeast cell exhibits the rugose phenotypic trait optionally in combination with at least three of the following additional phenotypic traits: a fast settling phenotype, an improved invertase activity, triploidy or increased signaling in a RAS/cAMP/PKA pathway. In an embodiment, the persistent yeast cell exhibits the rugose phenotypic trait in combination the following additional phenotypic traits: a fast settling phenotype, an improved invertase activity, triploidy and increased signaling in a RAS/cAMP/PKA pathway.

Improved Invertase Activity

In some embodiments, the persistent yeast cells of the present disclosure can exhibit improved invertase activity when compared to a control yeast cell lacking the phenotype. Yeasts exhibiting the improved invertase activity phenotype are able to hydrolyse more rapidly and/or at lower pH a carbohydrate source (e.g., a disaccharide (such as, for example, sucrose) or a trisaccharide (such as, for example, raffinose or kestose)) that is present in the biomass of the fermentation medium. In some embodiments, the persistent yeast cells of the present disclosure are used in fermentations in which the initial levels of fermentable glucose and fructose are relatively low (e.g., between 1 to 5 g/L) and as such their improved invertase activity can provide a selective advantage by accessing a complementary carbohydrate source (and consequently begin the fermentation process more rapidly).

In one embodiment, the persistent yeast cells of the present disclosure exhibit increased invertase activity when compared to the a control strain (e.g., such as the PE-2 strain) in comparable conditions. A population consisting essentially of the persistent yeast cells of the present disclosure is able to consume more than 1.0, 1.7, 2, 3, 4, 5, 6, 7, 8, 9, 10, 11 times sucrose when compared to a population consisting essentially of control yeasts (e.g., such as the PE-2 strain) in comparable conditions. In order to make such comparison, both populations, after exponential growth, can be diluted, on a wet cell basis, to a concentration of 9 mg/mL in a buffer and sucrose consumption can be measured (by HPLC for example) at a specified time interval. In some embodiments, invertase activity is measured prior to saturation of the assay. In some specific embodiments, invertase activity is measured within 1, 2, 3, 4, 5, 6, 7, 8, 9, 10, 11, 12, 13, 14 or 15 minutes of the beginning of the assay. In some additional embodiments, invertase activity is measured 12 to 15 minutes after the beginning of the assay. Still in such embodiment, the buffer initially comprises 40 g/L of sucrose, is at of pH 5 and at a temperature of 35° C.

In a specific embodiment, a population consisting essentially of the persistent yeast cells of the present disclosure, after exponential growth, diluted to a concentration of 9 mg/mL, on a wet cell basis, in a buffer is able to consume more than 0.05 gram of sucose per gram of dry cell weight per minute. In some additional embodiments, a population consisting essentially of the persistent yeast cells of the present disclosure, after exponential growth, diluted to a concentration of 9 mg/mL, on a wet cell basis, in a buffer is able to consume at least 0.06, 0.07, 0.08, 0.09, 0.10, 0.11, 0.12, 0.13, 0.14, 0.15, 0.16, 0.17, 0.18, 0.19, 0.20 or more gram of sucose per gram of dry cell weight per minute. As indicate above, the invertase assay can use a buffer initially comprising 40 g/L of sucrose, at of pH 5 and at a temperature of 35° C. In some embodiments, invertase activity is measured prior to saturation of the assay. In some specific embodiments, invertase activity is measured within 1, 2, 3, 4, 5, 6, 7, 8, 9, 10, 11, 12, 13, 14 or 15 minutes of the beginning of the assay. In some additional embodiments, invertase activity is measured 12 to 15 minutes after the beginning of the assay. Furthermore, in additional embodiments, the sugar consumption can be measured, for example, by HPLC.

The persistent yeast cells of the present disclosure can have increased enzymatic activity of at least one polypeptide having invertase activity. This increased enzymatic activity can be observed, in some embodiments, at low pH (for example, at a pH equal to or lower than 5.0, 4.9, 4.8, 4.7, 4.6, 4.5, 4.4, 4.3, 4.2, 4.1, 4.0 or lower). This increased invertase activity can be associated with a genetic modification in the regulatory region (e.g., promoter region) and/or the coding region of a gene encoding an invertase. This increased invertase activity can be associated with additional copies or duplications of a gene encoding an invertase. In yeasts, the following polypeptides are known to exhibit invertase activity: SUC1 (encoded by the SUC1 gene), SUC2 (encoded by the SUC2 gene), SUC3 (encoded by the SUC3 gene), SUC4 (encoded by the SUC4 gene), SUC5 (encoded by the SUC5 gene), SUC6 (encoded by the SUC6 gene), SUC7 (encoded by the SUC7 gene), SUC8 (encoded by the SUC8 gene) and SUC9 (encoded by the SUC9 gene). In some embodiments, the persistent yeast cells of the present disclosure have a genetic modification in one or more genes encoding an invertase. In further embodiments, the genetic modification(s) present in the persistent yeast cells can be associated with a modification in the amino acid sequence of the polypeptide having invertase activity (providing the modified polypeptide with increased invertase activity).

The persistent yeast cells can be selected, from a population of yeast cells, for the improved invertase activity phenotype. This can be done, for example, by submitting a population of yeast cells to a plurality of fermentation cycles which includes limiting the amount of fermentable sugars (like glucose and fructose) and selecting the yeast cells having the ability to digest unfermentable sugars more rapidly (like sucrose). Alternatively or in combination, the yeasts can be genetically engineered to provide an improved invertase activity phenotype. This can be done, for example, by introducing one or more genetic modification to increase the activity or the expression of one or more polypeptide having invertase activity.

In an embodiment, the persistent yeast cell exhibits the improved invertase activity phenotypic trait optionally in combination with at least one of the following additional phenotypic traits: a fast settling phenotype, a rugose, triploidy or increased signaling in a RAS/cAMP/PKA pathway. In an embodiment, the persistent yeast cell exhibits the improved invertase activity phenotypic trait optionally in combination with at least two of the following additional phenotypic traits: a fast settling phenotype, a rugose, triploidy or increased signaling in a RAS/cAMP/PKA pathway. In an embodiment, the persistent yeast cell exhibits the improved invertase activity phenotypic trait optionally in combination with at least three of the following additional phenotypic traits: a fast settling phenotype, a rugose, triploidy or increased signaling in a RAS/cAMP/PKA pathway. In an embodiment, the persistent yeast cell exhibits the improved invertase activity phenotypic trait in combination with the following additional phenotypic traits: a fast settling phenotype, a rugose, triploidy and increased signaling in a RAS/cAMP/PKA pathway.

Triploidy

In some embodiments, the persistent yeast cells of the present disclosure are triploids. Cell size (volume) is larger in higher ploidy strains and is associated with robustness to toxic compounds as well as increased adaptive fitness.

The persistent yeast cells can be selected, from a population of yeast cells, for a higher ploidy, like triploidy. This can be done, for example, by submitting a population of yeast cells to a plurality of fermentation cycles and selecting the yeast cells being triploids. Alternatively or in combination, the persistent yeast cells can be submitted to a process to provide triploidy. This can be done, for example, by using various mating techniques known in the art.

In an embodiment, the persistent yeast cell is a triploid optionally in combination with at least one of the following additional phenotypic traits: a fast settling phenotype, a rugose phenotype, improved invertase activity or increased signaling in a RAS/cAMP/PKA pathway. In an embodiment, the persistent yeast cell is a triploid optionally in combination with at least two of the following additional phenotypic traits: a fast settling phenotype, a rugose phenotype, improved invertase activity or increased signaling in a RAS/cAMP/PKA pathway. In an embodiment, the persistent yeast cell is a triploid optionally in combination with at least three of the following additional phenotypic traits: a fast settling phenotype, a rugose phenotype, improved invertase activity or increased signaling in a RAS/cAMP/PKA pathway. In an embodiment, the persistent yeast cell is a triploid optionally in combination with the following additional phenotypic traits: a fast settling phenotype, a rugose phenotype, improved invertase activity and increased signaling in a RAS/cAMP/PKA pathway.

Increased Signaling in a RAS/cAMP/PKA Pathway

In another embodiment, the persistent yeast cells exhibit increased signaling in a RAS/cAMP/PKA pathway when compared to control yeast cell lacking this phenotype (e.g., the PE-2 strain for example). Signaling via the RAS/cAMP/PKA pathway is important for nutrient signaling in yeasts and is associated to responses to glucose, nitrogen and phosphate levels. Increasing signaling in the RAS/cAMP/PKA pathway is associated with glucose derepression which eventually leads to better glucose and nitrogen uptake even in the presence of low levels of glucose (e.g., between 1 to 5 g/L) or other nutrients.

As used in the context of the present disclosure a persistent yeast cell having "increased signaling activity in the RAS/cAMP/PKA pathway" exhibits an increase in biological activity in one or more protein in the RAS/cAMP/PKA pathway. Persistent yeast cells exhibiting the increased signaling activity in the RAS/cAMP/PKA pathway phenotypic trait can show a decrease in the production of cAMP after a glucose spike, when compared to corresponding control yeasts lacking the increased signaling activity in the RAS/ cAMP/PKA pathway phenotype. Alternatively or in combination, persistent yeast cells exhibiting the increased signaling activity in the RAS/cAMP/PKA pathway phenotypic trait, can show an increase in the production of cAMP in a basal medium, when compared to corresponding control yeasts lacking the increased signaling activity in the RAS/cAMP/PKA pathway phenotype. In some embodiments, the the control yeasts lacking the increased signaling activity in the RAS/cAMP/PKA pathway phenotype are from the *Saccharomyces cerevisiae* PE-2 strain. As it is known in the art, the increase in cAMP caused by this biological pathway causes the dissociation of the PKA protein into the BCY1 protein and the TPK1-3 protein. This increase in RAS/cAMP/PKA signaling is preferably observed during fermentation (e.g., for example, in anaerobic conditions) and, in some embodiments, is not observed during propagation (e.g., for example, in glucose-limited aerobic conditions).

In one embodiment, the persistent yeast cells of the present disclosure exhibit increased signaling in the RAS/cAMP/PKA pathway when compared to a control strain lacking the increased signaling activity in the RAS/cAMP/PKA pathway phenotype (e.g., the PE-2 strain for example) in comparable conditions. In an embodiment, a population consisting essentially of the persistent yeast cells exhibits a fold increase in cAMP production less than 70, 65, 60, 55, 50, 45, 40, 35, 30, 25% or less when compared to the fold increase in cAMP production in a population consisting essentially of control yeast cells lacking the increased signaling activity in the RAS/cAMP/PKA pathway phenotype (e.g., the PE-2 strain) in comparable conditions. In order to make such comparison, both populations can be glucose depleted and submitted to a glucose spike. In addition, the cAMP production can be measured before and after a predetermined time (e.g., 5 min) of a glucose spike.

In a specific embodiment, a population consisting essentially of the persistent yeast cells having been glucose depleted and submitted to a glucose spike exhibits a fold increase in cAMP production equal to or less than 1.7, 1.6, 1.5, 1.4, 1.3 or less. In order to make such determination, the cAMP production can be measured before and after a predetermined time (e.g., 5 min) of a glucose spike.

In order to achieve such increase in RAS/cAMP/PKA signaling, the expression and/or activity of one or more polypeptide of the RAS/cAMP/PKA pathway can be increased (when compared to a corresponding control yeast lacking the phenotype, such as, for example, the PE-2 strain). The one or more polypeptides whose expression or biological activity can be increased include, but are not limited to a CDC25 polypeptide (a membrane bound guanine nucleotide exchange factor capable of activating a RAS1 polypeptide and/or a RAS2 polypeptide), a SDC25 polypeptide (a Ras guanine nucleotide exchange factor capable of activating the RAS1 polypeptide and/or the RAS2 polypeptide), a RAS1 polypeptide (GTPase whose activity increase the activity of the Cyr1 polypeptide) and/or a RAS2 polypeptide (a GTPase whose activity increases the activity of the Cyr1).

In an embodiment, the RAS2 polypeptide expression or its biological activity is increased to cause an increase in the signaling activity of the RAS/cAMP/PKA pathway in the persistent yeast cell. In such embodiment, the persistent yeast cell can include a mutation in the RAS2 polypeptide (herein referred to as a mutated RAS2 polypeptide) which increases its biological activity. For example, the mutated RAS2 polypeptide can be a variant or a fragment of the wild-type RAS2 polypeptide resulting in an increase in the biological activity of the RAS2 polypeptide. The RAS2 polypeptide is a GTPase and as such its biological activity includes binding to GTP and hydrolyzing GTP into GDP. As such, in the context of the present disclosure, a mutated RAS2 polypeptide having increased (biological) activity can exhibit a higher binding affinity for GTP, a higher GTP hydrolyzing activity or both, when compared to the wild-type RAS2 polypeptide. In an embodiment, the mutated RAS2 polypeptide can have one or more amino acid substitutions with respect to the amino acid sequence of the wild-type RAS2 polypeptide.

For example, the mutated RAS2 polypeptide can have an amino acid substitution at a residue corresponding to location 66 of SEQ ID NO: 19 (or a corresponding residue in another wild-type RAS2 polypeptide). In an embodiment, the amino acid substitution of the mutated RAS2 polypeptide is limited to the residue located at position 66 of SEQ ID NO: 19 (or a corresponding residue in another wild-type RAS2 polypeptide). In the wild-type RAS2 polypeptide of *S. cerevisiae* (SEQ ID NO: 19), the amino acid residue at location 66 is an alanine residue. In an embodiment, the mutated RAS2 polypeptide does not have an alanine residue located at position 66 of SEQ ID NO: 19 (or at a corresponding position in another wild-type RAS2 polypeptide), but instead has an histidine, an isoleucine, an arginine, a leucine, an asparagine, a lysine, an aspartic acid, a methionine, a cysteine, a phenylalanine, a glutamic acid, a threonine, a glutamine, a tryptophan, a glycine, a valine, a proline, a serine or a tyrosine residue. In an embodiment, the mutated RAS2 polypeptide has, at position 66 of SEQ ID NO: 19 (or at a corresponding position in another wild-type RAS2 polypeptide) does not have an aliphatic amino acid residue, such as, for example, a glycine, a valine, a leucine or an isoleucine residue. In still another embodiment, the mutated RAS2 polypeptide has, at position 66 of SEQ ID NO: 19 (or at a corresponding position in another wild-type RAS2 polypeptide) a hydroxyl or sulfur/selenium-containing amino acid, such as, for example, a serine, a cysteine, a threonine or a methionine residue. In yet another embodiment, the mutated RAS2 polypeptide has, at position 66 of SEQ ID NO: 19 (or at a corresponding position in another wild-type RAS2 polypeptide) a threonine residue. In still a further embodiment, the mutated RAS2 polypeptide has the amino acid sequence of SEQ ID NO: 17 and can be encoded by a nucleic acid molecule having a nucleic acid molecule having the sequence of SEQ ID NO: 18 or a degenerate sequence of SEQ ID NO: 18 encoding SEQ ID NO: 17.

In another example, the mutated RAS2 polypeptide can have an amino acid substitution at a residue corresponding to location 19 of SEQ ID NO: 19 (or a corresponding residue in another wild-type RAS2 polypeptide). In the wild-type RAS2 polypeptide of *S. cerevisiae* (SEQ ID NO: 19), the amino acid residue at location 19 is a glycine residue. In an embodiment, the mutated RAS2 polypeptide does not have a glycine residue located at position 19 of SEQ ID NO: 19 (or at a corresponding position in another wild-type RAS2 polypeptide), but instead has an histidine, an isoleucine, an arginine, a leucine, an asparagine, a lysine, an aspartic acid, a methionine, a cysteine, a phenylalanine, a glutamic acid, a threonine, a glutamine, a tryptophan, an alanine, a valine, a proline, a serine or a tyrosine residue. In yet another embodiment, the mutated RAS2 polypeptide has, at position 19 of SEQ ID NO: 19 (or at a corresponding position in another wild-type RAS2 polypeptide) a valine residue.

In another example, the mutated RAS2 polypeptide can have an amino acid substitution at a residue corresponding to location 77 of SEQ ID NO: 19 (or a corresponding residue in another wild-type RAS2 polypeptide). In the wild-type RAS2 polypeptide of *S. cerevisiae* (SEQ ID NO: 19), the amino acid residue at location 77 is a glutamine residue. In an embodiment, the mutated RAS2 polypeptide does not have a glutamine residue located at position 77 of SEQ ID NO: 19 (or at a corresponding position in another wild-type RAS2 polypeptide), but instead has an histidine, an isoleucine, an arginine, a leucine, an asparagine, a lysine, an aspartic acid, a methionine, a cysteine, a phenylalanine, a glutamic acid, a threonine, an alanine, a tryptophan, a glycine, a valine, a proline, a serine or a tyrosine residue. In yet another embodiment, the mutated RAS2 polypeptide has, at position 77 of SEQ ID NO: 19 (or at a corresponding position in another wild-type RAS2 polypeptide) a lysine residue.

In another example, the mutated RAS2 polypeptide can have an amino acid substitution at a residue corresponding to location 112 of SEQ ID NO: 19 (or a corresponding residue in another wild-type RAS2 polypeptide). In the wild-type RAS2 polypeptide of *S. cerevisiae* (SEQ ID NO: 19), the amino acid residue at location 112 is an aspartic acid residue. In an embodiment, the mutated RAS2 polypeptide does not have an aspartic acid residue located at position 112 of SEQ ID NO: 19 (or at a corresponding position in another wild-type RAS2 polypeptide), but instead has an histidine, an isoleucine, an arginine, a leucine, an asparagine, a lysine, a glutamine, a methionine, a cysteine, a phenylalanine, a glutamic acid, a threonine, an alanine, a tryptophan, a glycine, a valine, a proline, a serine or a tyrosine residue. In yet another embodiment, the mutated RAS2 polypeptide has, at position 112 of SEQ ID NO: 19 (or at a corresponding position in another wild-type RAS2 polypeptide) a tyrosine residue.

In an embodiment, the RAS1 polypeptide expression or biological activity is increased to cause an increase in the signaling activity of the RAS/cAMP/PKA pathway in the persistent yeast cell. In such embodiment, the persistent yeast cell includes a mutation in the RAS1 polypeptide (herein referred to as a mutated RAS1 polypeptide) which increases its biological activity. For example, the mutated RAS1 polypeptide can be a variant or a fragment of the wild-type RAS1 polypeptide resulting in an increase in the biological activity of the RAS1 polypeptide. The RAS1 polypeptide is a GTPase and as such its biological activity include binding to GTP and hydrolyzing GTP into GDP. As such, in the context of the present disclosure, a mutated RAS1 polypeptide having increased (biological) activity can exhibit a higher binding affinity for GTP, a higher GTP hydrolyzing activity or both, when compared to the wild-type RAS1 polypeptide. In an embodiment, the mutated RAS1 polypeptide can have an amino acid substitution. For example, the mutated RAS1 polypeptide can have an amino acid substitution at a residue corresponding to location 66 of SEQ ID NO: 26 (or at a corresponding residue in another wild-type RAS1 polypeptide). In an embodiment, the amino acid substitution of the mutated RAS1 polypeptide is limited to the residue located at position 66 of SEQ ID NO: 26 (or a corresponding residue in another wild-type RAS1 polypeptide). In the wild-type RAS1 polypeptide of *S. cerevisiae* (SEQ ID NO: 26), the amino acid residue at location 66 is an alanine residue. In an embodiment, the mutated RAS1 polypeptide does not have an alanine residue located at position 66 of SEQ ID NO: 26 (or at a corresponding position in another wild-type RAS1 polypeptide), but instead has an histidine, an isoleucine, an arginine, a leucine, an asparagine, a lysine, an aspartic acid, a methionine, a cysteine, a phenylalanine, a glutamic acid, a threonine, a glutamine, a tryptophan, a glycine, a valine, a proline, a serine or a tyrosine residue. In an embodiment, the mutated RAS1 polypeptide has, at position 66 of SEQ ID NO: 26 (or at a corresponding position in another wild-type RAS1 polypeptide) does not have an aliphatic amino acid residue, such as, for example, a glycine, a valine, a leucine or an isoleucine residue. In still another embodiment, the mutated RAS1 polypeptide has, at position 66 of SEQ ID NO: 26 (or at a corresponding position in another wild-type RAS1 polypeptide) a hydroxyl or sulfur/selenium-containing amino acid, such as, for example, a serine, a cysteine, a threonine or a methionine residue. In yet another embodiment, the mutated RAS1 polypeptide has, at position 66 of SEQ ID NO: 26 (or at a corresponding position in another wild-type RAS1 polypeptide) a threonine residue. In still a further embodiment, the mutated RAS1 polypeptide has the amino acid sequence of SEQ ID NO: 27.

In another example, the expression and/or activity of one or more polypeptide of the RAS/cAMP/PKA pathway can be decreased (when compared to a corresponding control yeast lacking the phenotype, such as the PE-2 strain) to achieve an increase in the signaling activity RAS/cAMP/PKA pathway. The one or more polypeptide whose expression or biological activity can be decreased include, but is not limited to, a IRA1 polypeptide (a GTPase-activating polypeptide whose activity decreases the activity of the wild-type Ras1 polypeptide and/or the wild-type RAS2 polypeptide) and/or an IRA2 polypeptide (a GTPase-activating polypeptide whose activity decreases the activity of the wild-type RAS1 polypeptide and/or the wild-type RAS2 polypeptide).

As indicated above, in an embodiment, the expression and/or activity of the IRA2 polypeptide can be decreased to achieve an increase in the signaling activity in the RAS/cAMP/PKA pathway in the persistent yeast cell. In an embodiment, the persistent yeast cell can include a mutation in the IRA2 polypeptide (herein referred to as a mutated IRA2 polypeptide) which decreases its biological activity. As it is known in the art, the IRA2 polypeptide converts the wild-type RAS1 polypeptide or the wild-type RAS2 polypeptide from their GTP-bound to their GDP-bound inactive form. The biological activity of the IRA2 polypeptide includes binding to the wild-type RAS1 polypeptide and to the wild-type RAS2 polypeptide. As such, in the context of the present disclosure, a mutated IRA2 polypeptide having decreased (biological activity) can exhibit a lower binding affinity for the wild-type RAS1 polypeptide, the wild-type RAS2 polypeptide or both, when compared to the wild-type IRA2. For example, the mutated IRA2 polypeptide can be a variant or a fragment of the wild-type IRA2 polypeptide (which can have, in some embodiments, the amino acid sequence of SEQ ID NO: 22 or be encoded by a nucleic acid molecule having the nucleic acid sequence of SEQ ID NO: 28 or be a degenerate sequence encoding the amino acid sequence of SEQ ID NO: 22) exhibiting in an increase in the biological activity of the wild-type RAS1 polypeptide and/or the wild-type RAS2 polypeptide. In an embodiment, the consensus sequence of the mutated IRA2 polypeptide can have the amino acid sequence of SEQ ID NO: 23. In yet a further embodiment, the mutated IRA2 polypeptide can have a mutation at the amino acid residue located at position 2440 of the wild-type IRA2 polypeptide of SEQ ID NO 22 (or a corresponding position in another wild-type IRA2 polypeptide). This mutation at position 2440 can cause the substitution of a glutamic acid residue to a lysine residue. In a specific embodiment, the mutated IRA2 polypeptide can have the amino acid sequence of SEQ ID NO: 20 and/or be encoded by a nucleic acid molecule having the nucleic acid sequence of SEQ ID NO: 21 or a degenerate sequence of SEQ ID NO: 21 encoding SEQ ID NO: 20. In a specific embodiment, the mutated IRA2 polypeptide can be a truncated IRA2 polypeptide encoded by a nucleic acid molecule or a gene which includes a frame-shift mutation. The mutated fragment of the IRA2 polypeptide can have the amino acid sequence of SEQ ID NO: 24.

In an embodiment, the expression and/or activity of the IRA1 polypeptide can be decreased to achieve an increase in the signaling activity in the RAS/cAMP/PKA pathway in the persistent yeast cell. In an embodiment, the persistent yeast cell expresses a mutation in the IRA1 polypeptide (herein referred to as a mutated IRA1 polypeptide) which decreases its biological activity. For example, the mutated IRA1 polypeptide can be a variant or a fragment of the wild-type IRA1 polypeptide resulting in an increase in the biological activity of the wild-type RAS1 polypeptide and/or the wild-type RAS2 polypeptide. The IRA1 polypeptide converts the wild-type RAS1 polypeptide or the wild-type RAS2 polypeptide from their GTP-bound to their GDP-bound inactive form. The biological activity of the IRA1 polypeptide includes binding to the wild-type RAS1 polypeptide and/or to the wild-type RAS2 polypeptide. As such, in the context of the present disclosure, a mutated IRA1 polypeptide having decreased (biological activity) can exhibit a lower binding affinity for the wild-type RAS1 polypeptide, the wild-type RAS2 polypeptide or both. In a specific embodiment, the mutated IRA1 polypeptide can be a truncated IRA1 polypeptide encoded by a nucleic acid molecule or a gene which includes a frame-shift mutation.

In yet another example, the expression and/or activity of one or more polypeptide of the RAS/cAMP/PKA pathway can be increased and the expression and/or activity of one or more polypeptide of the RAS/cAMP/PKA pathway can be decreased both in comparison with a corresponding control yeast lacking the phenotype (like the PE-2 strain for example) to achieve an increase in the signaling activity RAS/cAMP/PKA pathway.

In order to achieve such increase in RAS/cAMP/PKA signaling, it is also possible to regulate the activity of one or more polypeptide of the RAS/cAMP/PKA signaling pathway at the post-transcriptional level. For example, it is possible to genetically modify the recombinant yeast host cell to allow for the glucose-induced polypeptide turnover of one or more polypeptides in the RAS/cAMP/PKA signaling pathway (e.g., the IRA1 polypeptide and/or the IRA2 polypeptide for example).

The persistent yeast cell can be selected, from a population of yeast cells, for the increased signaling in the RAS/cAMP/PKA pathway. This can be done, for example, by submitting a population of yeast cells to a plurality of fermentation cycles in limited nutrient availability and selecting the yeast cells exhibiting increased signaling in the RAS/cAMP/PKA pathway. Alternatively or in combination, the persistent yeast cell can be genetically engineered to provide increased signaling in the RAS/cAMP/PKA pathway. This can be done, for example, by introducing one or more genetic modification to introduce one or more genetic modification in the polypeptides involved in the RAS/cAMP/PKA pathway.

In an embodiment, the persistent yeast cell exhibits the increased signaling in a RAS/cAMP/PKA pathway phenotypic trait optionally in combination with at least one of the following additional phenotypic traits: a fast settling phenotype, a rugose phenotype, an improved invertase activity or triploidy. In an embodiment, the persistent yeast cell exhibits the increased signaling in a RAS/cAMP/PKA pathway phenotypic trait optionally in combination with at least two of the following additional phenotypic traits: a fast settling phenotype, a rugose phenotype, an improved invertase activity or triploidy. In an embodiment, the persistent yeast cell exhibits the increased signaling in a RAS/cAMP/PKA pathway phenotypic trait optionally in combination with at least three of the following additional phenotypic traits: a fast settling phenotype, a rugose phenotype, an improved invertase activity or triploidy. In an embodiment, the persistent yeast cell exhibits the increased signaling in a RAS/cAMP/PKA pathway phenotypic trait in combination with the following additional phenotypic traits: a fast settling phenotype, a rugose phenotype, an improved invertase activity and triploidy.

Recombinant Yeast Host Cells

The recombinant yeast host cells of the present disclosure are capable of modulating the activity or the expression of at least one polypeptide for increasing, with compared to a parental cell, the conversion of a biomass into a fermentation product and optionally for reducing the production of a fermentation by-product. As used in the context of the present application, a "non-genetically modified parental cell" refer to the parental cell that was modified to provide the recombinant yeast host cell. The parental host cell does not include the one or more genetic modification that are present in the recombinant yeast host cell renders or augments the capacity of the latter capable to increase the conversion of a biomass into a fermentation product and optionally reducing the production of a fermentation by-product. The parental host cell can be a non-genetically modified cell. Alternatively, the parental host cell can include one or more genetic modifications that are unrelated to the conversion of a biomass into a fermentation product or in the production of a fermentation by-product. In some embodiments, the parental host cell can be a persistent yeast cell and include the one or more phenotypic traits described herein.

The recombinant yeast host cells of the present disclosure are intended to be used in a plurality of fermentation cycles as described herein. In each fermentation cycles, the recombinant yeast host cells of the present disclosure is involved in fermentation, e.g. the conversion of a biomass into a fermentation product (which can be an alcohol, such as, for example, ethanol). In one embodiment, the polypeptide(s) whose activity or expression is modulated in the recombinant yeast host cells can be directly involved in converting the biomass into the fermentation product. In another embodiment, the polypeptide(s) whose activity or expression is modulated in the recombinant yeast host cells can be indirectly involved in converting the biomass into the fermentation product by reducing or limiting the production of a fermentation by-product (such as, for example, glycerol) and ultimately increasing the fermentation yield (e.g., the yield of the fermentation product).

During yeast metabolism, a major by-product of biomass fermentation is glycerol. Glycerol is produced in microorganisms, such as yeasts, in response to a redox or osmotic stress. The glycerol produced is then exported from the cell where it is considered waste. While the production of glycerol is important to protect microorganisms from various stressors, it also tends to decrease ethanol yields, especially when the microorganisms are growing or encountering osmotic stress.

In yeasts, glycerol is a required metabolic end-product of ethanol fermentation allowing the yeast to balance its redox state and regenerate $NAD^+$ used as a cofactor during glycolysis. During anaerobic growth on carbohydrates, production of ethanol and carbon dioxide is redox neutral, while the reactions that create cell biomass and associated carbon dioxide are more oxidized relative to carbohydrates. The production of glycerol, which is more reduced relative to carbohydrates, functions as an electron sink to off-set cell biomass formation, so that overall redox neutrality is conserved. This is essential from a theoretical consideration of conservation of mass, and in practice strains unable to produce glycerol are unable to grow under anaerobic conditions. As glycerol is a byproduct with low value, it can be anundesirable by-product of fermentation. There is a strong commercial incentive to reduce glycerol as a by-product during the production of fuels and chemicals, as reduction typically results in an increased yield of the desired compound.

In an embodiment, the recombinant yeast host cells of the present disclosure are capable of increasing the activity or the expression of a first polypeptide involved in the conversion of a biomass into a fermentation product and/or the reduction in the production of a fermentation by-product. As such, the recombinant yeast host cells of the present disclosure can include one or more genetic modification for increasing the activity or the expression of a first polypeptide. In an embodiment, the genetic modification can be located in a regulatory region (such as a promoter region) of a native gene encoding a native (first) polypeptide so as to increase the expression (and ultimately the activity) of the native (first polypeptide). Alternatively or in combination, the genetic modification can be the introduction of one or more (first) heterologous nucleic acid molecules encoding a heterologous (first) polypeptide in the recombinant yeast host cells so as to increase or provide the recombinant yeast host cell with increased activity of the first polypeptide. In embodiments in which the genetic modification is intended to cause the expression of a secreted first polypeptide, the first nucleic acid heterologous nucleic acid molecule can also include a portion encoding a signal sequence operatively associated with another portion encoding the secreted polypeptide. The heterologous nucleic acid molecules that may be present in the recombinant yeast host cells can be integrated at the same or different integration sites.

In an embodiment, the first polypeptide is a saccharolytic enzyme (or a polypeptide having saccharolytic activity) and as such the recombinant yeast host cell comprises one or more first genetic modification for overexpressing a native saccharolytic or expressing heterologous saccharolytic enzymes. As used in the context of the present disclosure, a "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes. amylolytic enzyme. In an embodiment, the saccharolytic enzyme is an amylolytic enzyme. As used herein, the expression "amylolytic enzyme" refers to a class of enzymes capable of hydrolyzing starch or hydrolyzed starch. Amylolytic enzymes include, but are not limited to alpha-amylases (EC 3.2.1.1, sometimes referred to fungal alpha-amylase, see below), maltogenic amylase (EC 3.2.1.133), glucoamylase (EC 3.2.1.3), glucan 1,4-alpha-maltotetraohydrolase (EC 3.2.1.60), pullulanase (EC 3.2.1.41), iso-amylase (EC 3.2.1.68) and amylomaltase (EC 2.4.1.25).

In an embodiment, the one or more amylolytic enzymes can be, a maltogenic alpha-amylase from *Geobacillus stearothermophilus*, a glucoamylase from *Saccharomycopsis fibuligera*, a glucan 1,4-alpha-maltotetraohydrolase from *Pseudomonas saccharophila*, a pullulanase from *Bacillus naganoensis*, a pullulanase from *Bacillus acidopullulyticus*, an iso-amylase from *Pseudomonas amyloderamosa*, and/or amylomaltase from *Thermus thermophilus*. Some amylolytic enzymes have been described in US20220127564 and are incorporated herein by reference.

For example, the heterologous alpha-amylase can be from a *Rhizomucor* sp., such as, for example, from *Rhizomucor pusillus*. In an embodiment, the heterologous alpha-amylase corresponds to Uniprot M9T189. For example, the heterologous alpha-amylase can be from a *Aspergillus* sp., such as, for example, from *Aspergillus luchuensis*. In an embodiment, the heterologous alpha-amylase corresponds to Uniprot A0A146F6W4 or to GenBank Accession Number GAT21778. In an embodiment, the heterologous alpha-amylase corresponds to Uniprot 013296 or to GenBank Accession Number BAA22993. For example, the heterologous alpha-amylase can be from *Aspergillus oryzae*. In an embodiment, the heterologous alpha-amylase corresponds to Uniprot Q2UIS5 or to GenBank Accession Number XP_001820542. For example, the heterologous alpha-amylase can be from *Aspergillus niger*. In an embodiment, the heterologous alpha-amylase corresponds to Uniprot A2QTS4 or to GenBank Accession Number XP_001393626. In an embodiment, the heterologous alpha-amylase corresponds to Uniprot A2R6F9 or to GenBank Accession Number XP_001397301. In an embodiment, the heterologous alpha-amylase corresponds to GenBank Accession Number XP_001395328. In an embodiment, the heterologous alpha-amylase corresponds to Uniprot A0A370BQ30 or to GenBank Accession Number RDH15462. For example, the heterologous alpha-amylase can be from *Aspergillus fischeri*. In an embodiment, the heterologous alpha-amylase corresponds to Uniprot A1CYB1 or to GenBank Accession Number XP_001265628. For example, the heterologous alpha-amylase can be from a *Homo* sp., such as, for example, from *Homo sapiens*. In an embodiment, the heterologous alpha-amylase corresponds to GenBank Accession Number 1B2Y_A.

For example, the yeast cell can bear one or more genetic modifications allowing for the production of a heterologous glucoamylase. Many microbes produce an amylase to degrade extracellular starches. In addition to cleaving the last α(1-4) glycosidic linkages at the non-reducing end of amylose and amylopectin, yielding glucose, γ-amylase will cleave α(1-6) glycosidic linkages. The heterologous glucoamylase can be derived from any organism. In an embodiment, the heterologous polypeptide is derived from a γ-amylase, such as, for example, the glucoamylase of *Saccharomycopsis filbuligera* (e.g., encoded by the glu 0111 gene). Examples of recombinant yeast cells bearing such genetic modifications and expressing saccharolytic enzymes are described in US20130323822 as well as in US20180265853 and are both herewith incorporated in its entirety.

In another embodiment, the first polypeptide can be involved in the transport of a fermentation by-product, like glycerol, in the recombinant yeast cell. In an embodiment, the first polypeptide is a glycerol transporter and can, in some further embodiments, be responsible for the import of glycerol in the recombinant yeast host cells. In a specific embodiment, the first polypeptide is a sugar transporter-like protein (STL1). As such, the recombinant yeast host cells comprise one or more first genetic modification for overexpressing a native STL1 or expressing a heterologous STL1. By increasing the activity or expression of the STL1 polypeptide, it is possible to control, to some extent, glycerol synthesis and ultimately increase the fermentation (ethanol) yield.

The STL1 polypeptide is natively expressed in yeasts and fungi, therefore the heterologous polypeptide functioning to import glycerol can be derived from yeasts and fungi. STL1 genes encoding the STL1 polypeptide include, but are not limited to, Gene ID: 852149 (encoded by SEQ ID NO: 7 and shown in SEQ ID NO: 8), *Candida albicans*, *Kluyveromyces lactis* Gene ID: 2896463 (SEQ ID NO: 67), *Eremothecium gossypii* Gene ID: 4620396 (SEQ ID NO: 36), *Eremothecium sinecaudum* Gene ID: 28724161 (SEQ ID NO: 37), *Torulaspora delbrueckii* Gene ID: 11505245 (SEQ ID NO: 57), *Lachancea thermotolerans* Gene ID: 8290820 (SEQ ID NO: 60), *Phialophora attinorum* Gene ID: 28742143 (SEQ ID NO: 47), *Penicillium digitatum* Gene ID: 26229435 (SEQ ID NO: 46), *Aspergillus oryzae* Gene ID: 5997623 (SEQ ID NO: 61), *Aspergillus fumigatus* Gene ID: 3504696 (SEQ ID NO: 32), *Talaromyces atroroseus* Gene ID: 31007540 (SEQ ID NO: 53), *Rasamsonia emersonii* Gene ID: 25315795 (SEQ ID NO: 68), *Aspergillus terreus* Gene ID: 4322759 (SEQ ID NO: 33), *Penicillium rubens* Gene ID: 8310605 (SEQ ID NO: 58), *Alternaria alternata* Gene ID: 29120952 (SEQ ID NO: 31), *Paraphaeosphaeria sporulosa* Gene ID: 28767590 (SEQ ID NO: 45), *Pyrenophora tritici-repentis* Gene ID: 6350281 (SEQ ID NO: 49), *Metarhizium robertsii* Gene ID: 19259252 (SEQ ID NO: 41), *Isaria fumosorosea* Gene ID: 30023973 (SEQ ID NO: 39), *Cordyceps militaris* Gene ID: 18171218 (SEQ ID NO: 34), *Pochonia chlamydosporia* Gene ID: 28856912 (SEQ ID NO: 48), *Metarhizium majus* Gene ID: 26274087 (SEQ ID NO: 40), *Neofusicoccum parvum* Gene ID:19029314 (SEQ ID NO: 63), *Diplodia corticola* Gene ID: 31017281 (SEQ ID NO: 35), *Verticillium dahliae* Gene ID: 20711921 (SEQ ID NO: 56), *Verticillium alfalfa* Gene ID: 9537052 (SEQ ID NO: 55), *Paracoccidioides lutzii* Gene ID: 9094964 (SEQ ID NO: 44), *Trichophyton rubrum* Gene ID: 10373998 (SEQ ID NO: 59), *Nannizzia gypsea* Gene ID: 10032882 (SEQ ID NO: 42), *Trichophyton verrucosum* Gene ID: 9577427 (SEQ ID NO: 62), *Trichophyton benhamiae* Gene ID: 9523991 (SEQ ID NO: 54), *Pyricularia oryzae* Gene ID: 2678012 (SEQ ID NO: 50), *Gaeumannomyces tritici* Gene ID: 20349750 (SEQ ID NO: 38), *Phaeoacremonium minimum* Gene ID: 19329524 (SEQ ID NO: 65), *Eutypa lata* Gene ID: 19232829 (SEQ ID NO: 64), *Scedosporium apiospermum* Gene ID: 27721841 (SEQ ID NO: 51), *Aureobasidium namibiae* Gene ID: 25414329 (SEQ ID NO: 66), *Sphaerulina musiva* Gene ID: 27905328 (SEQ ID NO: 52) as well as *Pachysolen tannophilus* GenBank Accession Numbers JQ481633 (SEQ ID NO: 69) and JQ481634 (SEQ ID NO: 43).

The first polypeptide can be encoded by STL1 gene as indicated herein or a STL1 gene ortholog or paralog. The heterologous polypeptide functioning to import glycerol can be a STL1 polypeptide as defined herein, a variant of the STL1 polypeptide and/or a fragment of the STL1 polypeptide. In addition, when more than one copy of the first heterologous nucleic acid molecule encoding STL1 is included in the recombinant yeast host cell, the plurality of first heterologous nucleic acid molecules encoding the STL1 polypeptide could be the same or different, integrated at the same or different integration sites.

In a specific embodiment, the recombinant yeast host cells of the present disclosure is capable of expressing a STL1 polypeptide having the amino acid sequence of SEQ ID NO: 8, a variant of the amino acid sequence of SEQ ID NO:8 having glycerol transport activity or a fragment of the amino acid sequence of SEQ ID NO: 8 having glycerol transporter activity. In another specific embodiment, the recombinant yeast host cells of the present disclosure comprises a heterologous nucleic acid molecule comprising the nucleic acid sequence of SEQ ID NO: 7, corresponds to a degenerate sequence of the nucleic acid sequence of SEQ ID NO: 7 (encoding SEQ ID NO:8) or encodes the variant or the fragment of the amino acid sequence of SEQ ID NO: 8. The heterologous nucleic acid molecule encoding the STL1 polypeptide, variant or fragment can be present in one copy in the recombinant yeast host cell. The heterologous nucleic acid molecule encoding the STL1 polypeptide, variant or fragment can be present in two copies in the recombinant yeast host cell. The heterologous nucleic acid molecule encoding the STL1 polypeptide, variant or fragment can be present in three copies in the recombinant yeast host cell. The heterologous nucleic acid molecule encoding the STL1 polypeptide, variant or fragment can be present in four copies in the recombinant yeast host cell. The heterologous nucleic acid molecule encoding the STL1 polypeptide, variant or fragment can be present in five copies in the recombinant yeast host cell. The heterologous nucleic acid molecule encoding the STL1 polypeptide, variant or fragment can be present in six copies in the recombinant yeast host cell. The heterologous nucleic acid molecule encoding the STL1 polypeptide, variant or fragment can be present in seven copies in the recombinant yeast host cell. The heterologous nucleic acid molecule encoding the STL1 polypeptide, variant or fragment can be present in eight copies in the recombinant yeast host cell. The heterologous nucleic acid molecule encoding the STL1 polypeptide, variant or fragment can be present in nine copies in the recombinant yeast host cell. The heterologous nucleic acid molecule encoding the STL1 polypeptide, variant or fragment can be present in ten copies in the recombinant yeast host cell. The heterologous nucleic acid molecule encoding the STL1 polypeptide, variant or fragment can be present in eleven copies in the recombinant yeast host cell. The heterologous nucleic acid molecule encoding the STL1 polypeptide, variant or fragment can be present in twelve copies in the recombinant yeast host cell.

In an embodiment, the first polypeptide is a heterologous glyceraldehyde-3-phosphate dehydrogenase. Glyceraldehyde-3-phosphate dehydrogenases allow the catalysis of the reaction of glyceraldehyde-3-phosphate to 3-phosphoglycerate in glycolysis, using $NADP^+$ as a cofactor. In some embodiments, regeneration of NADPH and/or NADH by way a glycolytic pathway using glyceraldehyde-3-phosphate also improves ethanol production and reduces glycerol production. The glyceraldehyde-3-phosphate dehydrogenase is a non-phosphorylating glyceraldehyde-3-phosphate dehydrogenase, e.g., it is incapable of mediating a phosphorylation reaction. In some embodiments, the glyceraldehyde-3-phosphate dehydrogenase is of enzyme commission (EC) class 1.2.1, however it excludes the enzymes capable of mediating a phosphorylating reaction. The glyceraldehyde-3-phosphate dehydrogenase of the present disclosure specifically exclude enzymes capable of directly using or generating of 3-phospho-D-glyceroyl phosphate, such as enzymes of EC 1.2.1.13. Enzymes of EC 1.2.1.13 catalyze the following reaction:

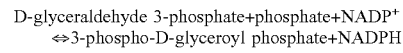

In one embodiment, the glyceraldehyde-3-phosphate dehydrogenase is $NADP^+$ dependent (EC1.2.1.9) and allows the conversion of $NADP^+$ to NADPH. Enzymes of EC1.2.1.9 can only use $NADP^+$ as a cofactor.

In one embodiment, the glyceraldehyde-3-phosphate dehydrogenase is bifunctional $NADP^+/NAD^+$ dependent (EC1.2.1.90) and allows the conversion of $NADP^+$ to NADPH and/or $NAD^+$ to $NAD^+$. Enzymes of EC1.2.1.90 can use $NADP^+$ or $NAD^+$ as a cofactor. In some embodiments, glyceraldehyde-3-phosphate dehydrogenase uses $NADP^+$ and/or $NAD^+$ as a cofactor. In one embodiment, the glyceraldehyde-3-phosphate dehydrogenase is encoded by a GAPN gene. In one embodiment, the glyceraldehyde-3-phosphate dehydrogenase is GAPN. In some embodiments, the recombinant yeast host cell includes two first genetic modifications and is capable of expressing STL1 and GAPN.

In some embodiments, the glyceraldehyde-3-phosphate dehydrogenase can be derived from a bacteria, for example, from the genus *Streptococcus* and, in some instances, from the species *Strepotococcus mutans*. The glyceraldehyde-3-phosphate dehydrogenase can be encoded by the GAPN gene from *Streptococcus mutans*, or a GAPN gene ortholog, or a GAPN gene paralog. In an embodiment, the GAPN gene comprises the nucleic acid sequence of SEQ ID NO: 30, is a variant of the nucleic acid sequence of SEQ ID NO: 30 (including but not limited to a degenerate variant of SEQ ID NO: 30 encoding the amino acid sequence of SEQ ID NO: 29) or is a fragment of the nucleic acid sequence of SEQ ID NO: 30. In an embodiment, the GAPN has the amino acid sequence of SEQ ID NO: 29, is a variant of the amino acid of SEQ ID NO: 29 or is a fragment of SEQ ID NO: 29.

In some embodiments, the glyceraldehyde-3-phosphate dehydrogenase can be derived from a bacteria, for example, from the genus *Lactobacillus* and, in some instances, from the species *Lactobacillus delbrueckii*. The glyceraldehyde-3-phosphate dehydrogenase can be encoded by the GAPN gene from *Lactobacillus delbrueckii*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Streptococcus thermophilus*. The glyceraldehyde-3-phosphate dehydrogenase can be encoded by the GAPN gene from *Streptococcus thermophilus*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Streptococcus macacae*. The glyceraldehyde-3-phosphate dehydrogenase can be encoded by the GAPN gene from *Streptococcus macacae*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Strepotococcus hyointestinalis*. The glyceraldehyde-3-phosphate dehydrogenase can be encoded by the GAPN gene from *Streptococcus hyointestinalis*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Strepotococcus urinalis*. The glyceraldehyde-3-phosphate dehydrogenase can be encoded by the GAPN gene from *Streptococcus urinalis*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Strepotococcus canis*. The glyceraldehyde-3-phosphate dehydrogenase can be encoded by the GAPN gene from *Streptococcus canis*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Strepotococcus thoraltensis*. The glyceraldehyde-3-phosphate dehydrogenase can be encoded by the GAPN gene from *Streptococcus thoraltensis*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Streptococcus dysgalactiae*. The glyceraldehyde-3-phosphate dehydrogenase can be encoded by the GAPN gene from *Streptococcus dysgalactiae*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Streptococcus pyogenes*. The glyceraldehyde-3-phosphate dehydrogenase can be encoded by the GAPN gene from *Streptococcus pyogenes*, or a GAPN gene ortholog, or a GAPN gene paralog.

In some embodiments, the glyceraldehyde-3-phosphate dehydrogenase can be derived from a bacteria, for example, from the genus *Streptococcus* and, in some instances, from the species *Streptococcus ictaluri*. The glyceraldehyde-3-phosphate dehydrogenase can be encoded by the GAPN gene from *Streptococcus ictaluri*, or a GAPN gene ortholog, or a GAPN gene paralog.

In some embodiments, the glyceraldehyde-3-phosphate dehydrogenase can be derived from a bacteria, for example, from the genus *Clostridium* and, in some instances, from the species *Clostridium perfringens*. The glyceraldehyde-3-phosphate dehydrogenase can be encoded by the GAPN gene from *Clostridium perfringens*, or a GAPN gene ortholog, or a GAPN gene paralog.

In some embodiments, the glyceraldehyde-3-phosphate dehydrogenase can be derived from a bacteria, for example, from the genus *Clostridium* and, in some instances, from the species *Clostridium chromiireducens*. The glyceraldehyde-3-phosphate dehydrogenase can be encoded by the GAPN gene from *Clostridium chromiireducens*, or a GAPN gene ortholog, or a GAPN gene paralog.

In some embodiments, the glyceraldehyde-3-phosphate dehydrogenase can be derived from a bacteria, for example, from the genus *Clostridium* and, in some instances, from the species *Clostridium botulinum*. The glyceraldehyde-3-phosphate dehydrogenase can be encoded by the GAPN gene from *Clostridium botulinum*, or a GAPN gene ortholog, or a GAPN gene paralog.

In some embodiments, the glyceraldehyde-3-phosphate dehydrogenase can be derived from a bacteria, for example, from the genus *Bacillus* and, in some instances, from the species *Bacillus cereus*. The glyceraldehyde-3-phosphate dehydrogenase can be encoded by the GAPN gene from *Bacillus cereus*, or a GAPN gene ortholog, or a GAPN gene paralog.

In some embodiments, the glyceraldehyde-3-phosphate dehydrogenase can be derived from a bacteria, for example, from the genus *Bacillus* and, in some instances, from the species *Bacillus anthracis*. The glyceraldehyde-3-phosphate dehydrogenase can be encoded by the GAPN gene from *Bacillus anthracis*, or a GAPN gene ortholog, or a GAPN gene paralog.

In some embodiments, the glyceraldehyde-3-phosphate dehydrogenase can be derived from a bacteria, for example, from the genus *Bacillus* and, in some instances, from the species *Bacillus thuringiensis*. The glyceraldehyde-3-phosphate dehydrogenase can be encoded by the GAPN gene from *Bacillus thuringiensis*, or a GAPN gene ortholog, or a GAPN gene paralog.

In some embodiments, the glyceraldehyde-3-phosphate dehydrogenase can be derived from a bacteria, for example, from the genus *Pyrococcus* and, in some instances, from the species *Pyrococcus furiosus*. The glyceraldehyde-3-phosphate dehydrogenase can be encoded by the GAPN gene from *Pyrococcus furiosus*, or a GAPN gene ortholog, or a GAPN gene paralog.

Embodiments of glyceraldehyde-3-phosphate dehydrogenase can also be derived, without limitation, from the following (the number in brackets correspond to the Gene ID number): *Triticum aestivum* (543435); *Streptococcus mutans* (1028095); *Streptococcus agalactiae* (1013627); *Streptococcus pyogenes* (901445); Clostridioides *difficile* (4913365); *Mycoplasma mycoides* subsp. *mycoides* SC str. (2744894); *Streptococcus pneumoniae* (933338); *Streptococcus sanguinis* (4807521); *Acinetobacter pittii* (11638070); *Clostridium botulinum* A str. (5185508); [*Bacillus thuringiensis*] *serovar konkukian* str. (2857794); *Bacillus anthracis* str. Ames (1088724); *Phaeodactylum tricornutum* (7199937); *Emiliania huxleyi* (17251102); *Zea mays* (542583); *Helianthus annuus* (110928814); *Streptomyces coelicolor* (1101118); *Burkholderia pseudomallei* (U.S. Pat. Nos. 3,097,058, 3,095,849); variants thereof as well as fragments thereof.

Additional embodiments of glyceraldehyde-3-phosphate dehydrogenase can also be derived, without limitation, from the following (the number in brackets correspond to the Pubmed Accession number): *Streptococcus macacae* (WP_003081126.1), *Streptococcus hyointestinalis* (WP_115269374.1), *Streptococcus urinalis* (WP_006739074.1), *Streptococcus canis* (WP_003044111.1), *Streptococcus pluranimalium* (WP_104967491.1), *Streptococcus equi* (WP_012678132.1), *Streptococcus thoraltensis* (WP_018380938.1), *Streptococcus dysgalactiae* (WP_138125971.1), *Streptococcus halotolerans* (WP_062707672.1), *Streptococcus pyogenes* (WP_136058687.1), *Streptococcus ictaluri* (WP_008090774.1), *Clostridium perfringens* (WP_142691612.1), *Clostridium chromiireducens* (WP_079442081.1), *Clostridium botulinum* (WP_012422907.1), *Bacillus cereus* (WP 000213623.1), *Bacillus anthracis* (WP 098340670.1), *Bacillus thuringiensis* (WP_087951472.1), *Pyrococcus furiosus* (WP_011013013.1) as well as variants thereof and fragments thereof.

Embodiments of glyceraldehyde-3-phosphate dehydrogenase as well as yeasts expressing same are disclosed in US patent application 20210380989, incorporated herewith in its entirety.

In an embodiment, the recombinant yeast host cells of the present disclosure are capable of decreasing the activity or the expression of a second polypeptide involved in the conversion of a biomass into a fermentation product and/or the reduction in the production of a fermentation by-product. In still another embodiment, the recombinant yeast host cells is capable of reducing the production of the fermentation by-product, such as, for example, glycerol. The recombinant yeast host cells of the present disclosure can include one or more genetic modification for decreasing the activity or the expression of a second polypeptide. In an embodiment, the genetic modification can be located in a regulatory region (such as a promoter region) of a native gene encoding a native (second) polypeptide and/or in the coding region of a native gene encoding a native (second) polypeptide. Alternatively or in combination, the genetic modification can be the introduction of one or more (second) heterologous nucleic acid molecules in the recombinant yeast host cells so as to inactivate, at least in part or totally, the expression of the second native polypeptide. In such embodiment, the second heterologous nucleic acid molecule(s) can be placed in the open-reading frame of the native gene to be inactivated. In still another embodiment, the second heterologous nucleic acid molecule(s) can be replace the open-reading frame of the native gene to be inactivated. The second genetic modification can be made in at least one (an in some embodiments in all) allele(s) of a copy of the native gene to be inactivated.

In still a further embodiment, the recombinant yeast host cells of the present disclosure are capable of reducing the activity or the expression of a (first) native NAD-dependent glycerol-3-phosphate dehydrogenase (GPD) polypeptide. Recombinant yeast host cells having decreased GPD activity have been described in US20200224209 which is herewith incorporated in its entirety.

Most mammalian cells express two different glycerol-3-phosphate dehydrogenases (GPDs) which are necessary for glycerol production and they are expressed in response to different cellular signals: the GPD1 and the GPD2 polypeptides. Both polypeptides share 75% amino acid identity and, while they catalyze the same reaction, the differences in their amino acid sequence make them more efficient enzymes under the environmental conditions that induce their expression. GPD2 is known to be unable to fully substitute for GPD1 in the production of osmotically induced glycerol production suggesting that this enzyme has lower activity than GPD1 under osmotic stress.

In an embodiment, the recombinant yeast host cells bear a genetic modification in at least one of the gpd1 gene (encoding the GPD1 polypeptide), the gpd2 gene (encoding the GPD2 polypeptide), the gpp1 gene (encoding the GPP1 polypeptide) or the gpp2 gene (encoding the GPP2 polypeptide). In another embodiment, the recombinant yeast host cells bear a genetic modification in at least two of the gpd1 gene (encoding the GPD1 polypeptide), the gpd2 gene (encoding the GPD2 polypeptide), the gpp1 gene (encoding the GPP1 polypeptide) or the gpp2 gene (encoding the GPP2 polypeptide). Examples of recombinant yeast cells bearing such genetic modification(s) leading to the reduction in the production of one or more native enzymes that function to produce glycerol are described in WO 2012/138942. In some embodiments, the recombinant yeast host cells have a genetic modification (such as a genetic deletion or insertion) only in one enzyme that functions to produce glycerol, in the gpd2 gene, which would cause the yeast cell to have a knocked-out gpd2 gene. In some embodiments, the recombinant yeast host cell can have a genetic modification in the gpd1 gene and the gpd2 gene resulting is a recombinant yeast host cell being knock-out for the gpd1 gene and the gpd2 gene. In some specific embodiments, the yeast cell can be a knock-out for the gpd1 gene and have duplicate copies of the gpd2 gene (in some embodiments, under the control of the gpd1 promoter). In yet another embodiment, the recombinant yeast host cells do not bear such genetic modification and includes its native genes coding for the GPP/GDP polypeptides.

The recombinant yeast host cells of the present disclosure can include a genetic modification to inhibit (at least partially or totally) the expression of a first NAD-dependent glycerol-3-phosphate dehydrogenase. This first NAD-dependent glycerol-3-phosphate dehydrogenase can be a NAD-dependent glycerol-3-phosphate 1 (GPD1) polypeptide or a GPD1 gene ortholog or paralog. The second genetic modification can include a deletion, deletion or substitution of one or more of a nucleic acid residue(s) in a gene (or a gene ortholog) encoding the GPD1 polypeptide (particularly in the gene's coding sequence) which would cause a reduction in the activity of the GPD1 polypeptide. In an embodiment, the second genetic modification can include the deletion of all of the coding sequence of a gene (or a gene ortholog) encoding the GPD1 polypeptide. Alternatively or in combination, the recombinant yeast host cell can express a heterologous GPD1 polypeptide variant or fragment having a reduced activity when compared to the native GPD1 polypeptide.

The GPD1 polypeptide is natively expressed in yeasts, fungi, mammalian and plant cells. GPD1 genes encoding the GPD1 polypeptide include, but are not limited to *Saccharomyces cerevisiae* Gene ID: 851539, *Schizosaccharomyces pombe* Gene ID: 2540547, *Schizosaccharomyces pombe* Gene ID: 2540455, *Neurospora crassa* Gene ID: 3873099, *Candida albicans* Gene ID: 3643924, *Scheffersomyces stipitis* Gene ID: 4840320, *Spathaspora passalidarum* Gene ID: 18874668, *Trichoderma reesei* Gene ID: 18482691, *Nectria haematococca* Gene ID: 9668637, *Candida dubliniensis* Gene ID: 8046432, *Chlamydomonas reinhardtii* Gene ID: 5716580, *Brassica napus* Gene ID: 106365675, *Chlorella variabilis* Gene ID: 17355036, *Brassica napus* Gene ID: 106352802, *Mus musculus* Gene ID: 14555, *Homo sapiens* Gene ID: 2819, *Rattus norvegicus* Gene ID: 60666, *Sus scrofa* Gene ID: 100153250, *Gallus gallus* Gene ID: 426881, *Bos taurus* Gene ID: 525042, *Xenopus tropicalis* Gene ID: 448519, *Pan troglodytes* Gene ID: 741054, *Canis lupus familiaris* Gene ID: 607942, *Callorhinchus milii* Gene ID: 103188923, *Columba livia* Gene ID: 102088900, *Macaca fascicularis* Gene ID: 101865501, *Myotis brandtii* Gene ID: 102257341, *Heterocephalus glaber* Gene ID: 101702723, *Nannospalax galili* Gene ID: 103746543, *Mustela putorius furo* Gene ID: 101681348, *Callithrix jacchus* Gene ID: 100414900, *Labrus bergylta* Gene ID: 109980872, *Monopterus albus* Gene ID: 109969143, *Castor canadensis* Gene ID: 109695417, *Paralichthys olivaceus* Gene ID: 109635348, *Bos indicus* Gene ID: 109559120, *Hippocampus comes* Gene ID: 109507993, *Rhinolophus sinicus* Gene ID: 109443801, *Hipposideros armiger* Gene ID: 109393253, *Crocodylus porosus* Gene ID: 109324424, *Gavialis gangeticus* Gene ID: 109293349, *Panthera pardus* Gene ID: 109249099, *Cyprinus carpio* Gene ID: 109094445, *Scleropages formosus* Gene ID: 108931403, *Nanorana parkeri* Gene ID: 108789981, *Rhinopithecus bieti* Gene ID: 108543924, *Lepidothrix coronata* Gene ID: 108509436, *Pygocentrus nattereri* Gene ID: 108444060, *Manis javanica* Gene ID: 108406536, *Cebus capucinus imitator* Gene ID: 108316082, *Ictalurus punctatus* Gene ID: 108255083, *Kryptolebias marmoratus* Gene ID: 108231479, *Miniopterus natalensis* Gene ID: 107528262, *Rousettus aegyptiacus* Gene ID: 107514265, *Coturnix japonica* Gene ID: 107325705, *Protobothrops mucrosquamatus* Gene ID: 107302714, *Parus major* Gene ID: 107215690, *Marmota marmota marmota* Gene ID: 107148619, *Gekko japonicus* Gene ID: 107122513, *Cyprinodon variegatus* Gene ID: 107101128, *Acinonyx jubatus* Gene ID: 106969233, *Poecilia latipinna* Gene ID: 106959529, *Poecilia mexicana* Gene ID: 106929022, *Calidris pugnax* Gene ID: 106891167, *Sturnus vulgaris* Gene ID: 106863139, *Equus asinus* Gene ID: 106845052, *Thamnophis sirtalis* Gene ID: 106545289, *Apteryx australis mantelli* Gene ID: 106499434, *Anser cygnoides domesticus* Gene ID: 106047703, *Dipodomys ordii* Gene ID: 105987539, *Clupea harengus* Gene ID: 105897935, *Microcebus murinus* Gene ID: 105869862, *Propithecus coquereli* Gene ID: 105818148, *Aotus nancymaae* Gene ID: 105709449, *Cercocebus atys* Gene ID: 105580359, *Mandrillus leucophaeus* Gene ID: 105527974, *Colobus angolensis palliatus* Gene ID: 105507602, *Macaca nemestrina* Gene ID: 105492851, *Aquila chrysaetos canadensis* Gene ID: 105414064, *Pteropus vampyrus* Gene ID: 105297559, *Camelus dromedarius* Gene ID: 105097186, *Camelus bactrianus* Gene ID: 105076223, *Esox lucius* Gene ID: 105016698, *Bison bison bison* Gene ID: 105001494, *Notothenia coriiceps* Gene ID: 104967388, *Larimichthys crocea* Gene ID: 104928374, *Fukomys damarensis* Gene ID: 04861981, *Haliaeetus leucocephalus* Gene ID: 104831135, *Corvus cornix cornix* Gene ID: 104683744, *Rhinopithecus roxellana* Gene ID: 104679694, *Balearica regulorum gibbericeps* Gene ID: 104630128, *Tinamus guttatus* Gene ID: 104575187, *Mesitornis unicolor* Gene ID: 104539793, *Antrostomus carolinensis* Gene ID: 104532747, *Buceros rhinoceros silvestris* Gene ID: 104501599, *Chaetura pelagica* Gene ID: 104385595, *Leptosomus discolor* Gene ID: 104353902, *Opisthocomus hoazin* Gene ID: 104326607, *Charadrius vociferus* Gene ID: 104284804, *Struthio camelus australis* Gene ID: 104144034, *Egretta garzetta* Gene ID: 104132778, *Cuculus canorus* Gene ID: 104055090, *Nipponia nippon* Gene ID: 104011969, *Pygoscelis adeliae* Gene ID: 103914601, *Aptenodytes forsteri* Gene ID: 103894920, *Serinus canaria* Gene ID: 103823858, *Manacus vitellinus* Gene ID: 103760593, *Ursus maritimus* Gene ID: 103675473, *Corvus brachyrhynchos* Gene ID: 103613218, *Galeopterus variegatus* Gene ID: 103598969, *Equus przewalskii* Gene ID: 103546083, *Calypte anna* Gene ID: 103536440, *Poecilia reticulata* Gene ID: 103464660, *Cynoglossus semilaevis* Gene ID: 103386748, *Stegastes partitus* Gene ID: 103355454, *Eptesicus fuscus* Gene ID: 103285288, *Chlorocebus sabaeus* Gene ID: 103238296, *Orycteropus afer afer* Gene ID: 103194426, *Poecilia formosa* Gene ID: 103134553, *Erinaceus europaeus* Gene ID: 103118279, *Lipotes vexillifer* Gene ID: 103087725, *Python bivittatus* Gene ID: 103049416, *Astyanax mexicanus* Gene ID: 103021315, *Balaenoptera acutorostrata scammoni* Gene ID: 103006680, *Physeter catodon* Gene ID: 102996836, *Panthera tigris altaica* Gene ID: 102961238, *Chelonia mydas* Gene ID: 102939076, *Peromyscus maniculatus bairdii* Gene ID: 102922332, *Pteropus alecto* Gene ID: 102880604, *Elephantulus edwardii* Gene ID: 102844587, *Chrysochloris asiatica* Gene ID: 102825902, *Myotis davidii* Gene ID: 102754955, *Leptonychotes weddellii* Gene ID: 102730427, *Lepisosteus oculatus* Gene ID: 102692130, *Alligator mississippiensis* Gene ID: 102576126, *Vicugna pacos* Gene ID: 102542115, *Camelus ferus* Gene ID: 102507052, *Tupaia chinensis* Gene ID: 102482961, *Pelodiscus sinensis* Gene ID: 102446147, *Myotis lucifugus* Gene ID: 102420239, *Bubalus bubalis* Gene ID: 102395827, *Alligator sinensis* Gene ID: 102383307, *Latimeria chalumnae* Gene ID: 102345318, *Pantholops hodgsonii* Gene ID: 102326635, *Haplochromis burtoni* Gene ID: 102295539, *Bos mutus* Gene ID: 102267392, *Xiphophorus maculatus* Gene ID:

102228568, *Pundamilia nyererei* Gene ID: 102192578, *Capra hircus* Gene ID: 102171407, *Pseudopodoces humilis* Gene ID: 102106269, *Zonotrichia albicollis* Gene ID: 102070144, *Falco cherrug* Gene ID: 102047785, *Geospiza fortis* Gene ID: 102037409, *Chinchilla lanigera* Gene ID: 102014610, *Microtus ochrogaster* Gene ID: 101990242, *Ictidomys tridecemlineatus* Gene ID: 101955193, *Chrysemys picta* Gene ID: 101939497, *Falco peregrinus* Gene ID: 101911770, *Mesocricetus auratus* Gene ID: 101824509, *Ficedula albicollis* Gene ID: 101814000, *Anas platyrhynchos* Gene ID: 101789855, *Echinops telfairi* Gene ID: 101641551, *Condylura cristata* Gene ID: 101622847, *Jaculus jaculus* Gene ID: 101609219, *Octodon degus* Gene ID: 101563150, *Sorex araneus* Gene ID: 101556310, *Ochotona princeps* Gene ID: 101532015, *Maylandia zebra* Gene ID: 101478751, *Dasypus novemcinctus* Gene ID: 101446993, *Odobenus rosmarus divergens* Gene ID: 101385499, *Tursiops truncatus* Gene ID: 101318662, *Orcinus orca* Gene ID: 101284095, *Oryzias latipes* Gene ID: 101154943, *Gorilla gorilla* Gene ID: 101131184, *Ovis aries* Gene ID: 101119894, *Felis catus* Gene ID: 101086577, *Takifugu rubripes* Gene ID: 101079539, *Saimiri boliviensis* Gene ID: 101030263, *Papio anubis* Gene ID: 101004942, *Pan paniscus* Gene ID: 100981359, *Otolemur garnettii* Gene ID: 100946205, *Sarcophilus harrisii* Gene ID: 100928054, *Cricetulus griseus* Gene ID: 100772179, *Cavia porcellus* Gene ID: 100720368, *Oreochromis niloticus* Gene ID: 100712149, *Loxodonta africana* Gene ID: 100660074, *Nomascus leucogenys* Gene ID: 100594138, *Anolis carolinensis* Gene ID: 100552972, *Meleagris gallopavo* Gene ID: 100542199, *Ailuropoda melanoleuca* Gene ID: 100473892, *Oryctolagus cuniculus* Gene ID: 100339469, *Taeniopygia guttata* Gene ID: 100225600, *Pongo abelii* Gene ID: 100172201, *Ornithorhynchus anatinus* Gene ID: 100085954, *Equus caballus* Gene ID: 100052204, *Mus musculus* Gene ID: 100198, *Xenopus laevis* Gene ID: 399227, *Danio rerio* Gene ID: 325181, *Danio rerio* Gene ID: 406615, *Melopsittacus undulatus* Gene ID: 101872435, *Ceratotherium simum simum* Gene ID: 101408813, *Trichechus manatus latirostris* Gene ID: 101359849 and *Takifugu rubripes* Gene ID: 101071719). In the present disclosure, the recombinant yeast cell can reduce or inhibit the expression of a GDP1 gene (or a GPD1 gene ortholog) encoding a GDP1 polypeptide, variant or fragment.

The recombinant yeast host cells of the present disclosure can include a genetic modification to inhibit (at least partially or totally) the expression of a second NAD-dependent glycerol-3-phosphate dehydrogenase. This second NAD-dependent glycerol-3-phosphate dehydrogenase can be a NAD-dependent glycerol-3-phosphate 2 (GPD2) polypeptide or a GPD2 gene ortholog or paralog. The genetic modification can include a deletion, deletion or substitution of one or more of a nucleic acid residue(s) in a gene (or a gene ortholog) encoding the GPD2 polypeptide (particularly in the gene's coding sequence) which would cause a reduction in the activity of the GPD2 polypeptide. In an embodiment, the second genetic modification can include the deletion of all of the coding sequence of a gene (or a gene ortholog) encoding the GPD2 polypeptide. Alternatively or in combination, the recombinant yeast host cell can express a heterologous GPD2 polypeptide variant or fragment having a reduced activity when compared to the native GPD2 polypeptide.

In some embodiments, the recombinant yeast host cells of the present disclosure, while having reduced activity or expression in a first NAD-dependent glycerol-3-phosphate (e.g., GPD1), can express a second NAD-dependent glycerol-3-phosphate dehydrogenase exhibiting less enzymatic activity than the first NAD-dependent glycerol-3-phosphate (e.g., GPD2). For example, the recombinant yeast host cells of the present disclosure, while having a reduced GPD1 activity or express, is capable of expressing a heterologous NAD-dependent glycerol-3-phosphate dehydrogenase 2 (GPD2) polypeptide (which exhibits less enzymatic activity than GPD1). As such, the second genetic modification can include modifying the recombinant host cells to express a heterologous NAD-dependent glycerol-3-phosphate dehydrogenase 2 (GPD2) polypeptide. This can be done, for example, by expressing a heterologous nucleic acid encoding the heterologous GPD2 polypeptide using an osmotic promoter (such as, for example, the promoter of the GPD1 gene). The second heterologous nucleic acid molecule can, in some additional embodiments, replace the open-reading frame of at least one copy of the native GPD1 gene. The second heterologous nucleic acid molecule can, in some embodiments, replace the open-reading frame of all copes of the native GPD1 gene. In some embodiments, at least a single native copy of the gene (or the gene ortholog) encoding the GPD2 polypeptide be under the control of the native GPD2 promoter.

The GPD2 polypeptide is expressed in bacteria, yeasts, fungi, mammalian and plant cells. GPD2 genes encoding the GPD2 polypeptide include, but are not limited to *Mus musculus* Gene ID: 14571, *Homo sapiens* Gene ID: 2820, *Saccharomyces cerevisiae* Gene ID: 854095, *Rattus norvegicus* Gene ID: 25062, *Schizosaccharomyces pombe* Gene ID: 2541502, *Mus musculus* Gene ID: 14380, *Danio rerio* Gene ID: 751628, *Caenorhabditis elegans* Gene ID: 3565504, *Mesocricetus auratus* Gene ID: 101825992, *Xenopus tropicalis* Gene ID: 779615, *Macaca mulatta* Gene ID: 697192, *Bos taurus* Gene ID: 504948, *Canis lupus familiaris* Gene ID: 478755, *Cavia porcellus* Gene ID: 100721200, *Gallus gallus* Gene ID: 424321, *Pan troglodytes* Gene ID: 459670, *Oryctolagus cuniculus* Gene ID: 100101571, *Candida albicans* Gene ID: 3644563, *Xenopus laevis* Gene ID: 444438, *Macaca fascicularis* Gene ID: 102127260, *Ailuropoda melanoleuca* Gene ID: 100482626, *Cricetulus griseus* Gene ID: 100766128, *Heterocephalus glaber* Gene ID: 101715967, *Scheffersomyces stipitis* Gene ID: 4838862, *Ictalurus punctatus* Gene ID: 108273160, *Mustela putorius furo* Gene ID: 101681209, *Nannospalax galili* Gene ID: 103741048, *Callithrix jacchus* Gene ID: 100409379, *Lates calcarifer* Gene ID: 108873068, *Nothobranchius furzeri* Gene ID: 07384696, *Acanthisitta chloris* Gene ID: 103808746, *Acinonyx jubatus* Gene ID: 106978985, *Alligator mississippiensis* Gene ID: 102562563, *Alligator sinensis* Gene ID: 102380394, *Anas platyrhynchos, Anolis carolinensis* Gene ID: 100551888, *Anser cygnoides domesticus* Gene ID: 106043902, *Aotus nancymaae* Gene ID: 105719012, *Apaloderma vittatum* Gene ID: 104281080, *Aptenodytes forsteri* Gene ID: 103893867, *Apteryx australis mantelli* Gene ID: 106486554, *Aquila chrysaetos canadensis* Gene ID: 105412526, *Astyanax mexicanus* Gene ID: 103029081, *Austrofundulus limnaeus* Gene ID: 106535816, *Balaenoptera acutorostrata scammoni* Gene ID: 103019768, *Balearica regulorum gibbericeps, Bison bison bison* Gene ID: 104988636, *Bos indicus* Gene ID: 109567519, *Bos mutus* Gene ID: 102277350, *Bubalus bubalis* Gene ID: 102404879, *Buceros rhinoceros silvestris* Gene ID: 104497001, *Calidris pugnax* Gene ID: 106902763, *Callorhinchus milii* Gene ID: 103176409, *Calypte anna* Gene ID: 103535222, *Camelus bactrianus* Gene ID: 105081921, *Camelus dromedarius* Gene ID: 105093713, *Camelus ferus* Gene ID: 102519983, *Capra hircus* Gene ID:

102176370, *Cariama cristata* Gene ID: 104154548, *Castor canadensis* Gene ID: 109700730, *Cebus capucinus imitator* Gene ID: 108316996, *Cercocebus atys* Gene ID: 105576003, *Chaetura pelagica* Gene ID: 104391744, *Charadrius vociferus* Gene ID: 104286830, *Chelonia mydas* Gene ID: 102930483, *Chinchilla lanigera* Gene ID: 102017931, *Chlamydotis macqueenii* Gene ID: 104476789, *Chlorocebus sabaeus* Gene ID: 103217126, *Chrysemys picta* Gene ID: 101939831, *Chrysochloris asiatica* Gene ID: 102831540, *Clupea harengus* Gene ID: 105902648, *Colius striatus* Gene ID: 104549356, *Colobus angolensis palliatus* Gene ID: 105516852, *Columba livia* Gene ID: 102090265, *Condylura cristata* Gene ID: 101619970, *Corvus brachyrhynchos*, *Coturnix japonica* Gene ID: 107316969, *Crocodylus porosus* Gene ID: 109322895, *Cuculus canorus* Gene ID: 104056187, *Cynoglossus semilaevis* Gene ID: 103389593, *Dasypus novemcinctus* Gene ID: 101428842, *Dipodomys ordii* Gene ID: 105996090, *Echinops telfairi* Gene ID: 101656272, *Egretta garzetta* Gene ID: 104135263, *Elephantulus edwardii* Gene ID: 102858276, *Eptesicus fuscus* Gene ID: 103283396, *Equus asinus* Gene ID: 106841969, *Equus caballus* Gene ID: 100050747, *Equus przewalskii* Gene ID: 103558835, *Erinaceus europaeus* Gene ID: 103114599, *Eurypyga helias* Gene ID: 104502666, *Falco cherrug* Gene ID: 102054715, *Falco peregrinus* Gene ID: 101912742, *Felis catus* Gene ID: 101089953, *Ficedula albicollis* Gene ID: 101816901, *Fukomys damarensis* Gene ID: 104850054, *Fundulus heteroclitus* Gene ID: 105936523, *Galeopterus variegatus* Gene ID: 103586331, *Gavia stellata* Gene ID: 104250365, *Gavialis gangeticus* Gene ID: 109301301, *Gekko japonicus* Gene ID: 107110762, *Geospiza fortis* Gene ID: 102042095, *Gorilla gorilla* Gene ID: 101150526, *Haliaeetus albicilla* Gene ID: 104323154, *Haliaeetus leucocephalus* Gene ID: 104829038, *Haplochromis burtoni* Gene ID: 102309478, *Hippocampus comes* Gene ID: 109528375, *Hipposideros armiger* Gene ID: 109379867, *Ictidomys tridecemlineatus* Gene ID: 101965668, *Jaculus jaculus* Gene ID: 101616184, *Kryptolebias marmoratus* Gene ID: 108251075, *Labrus bergylta* Gene ID: 109984158, *Larimichthys crocea* Gene ID: 104929094, *Latimeria chalumnae* Gene ID: 102361446, *Lepidothrix coronata* Gene ID: 108501660, *Lepisosteus oculatus* Gene ID: 102691231, *Leptonychotes weddellii* Gene ID: 102739068, *Leptosomus discolor* Gene ID: 104340644, *Lipotes vexillifer* Gene ID: 103074004, *Loxodonta africana* Gene ID: 100654953, *Macaca nemestrina* Gene ID: 105493221, *Manacus vitellinus* Gene ID: 103757091, *Mandrillus leucophaeus* Gene ID: 105548063, *Manis javanica* Gene ID: 108392571, *Marmota marmota marmota* Gene ID: 107136866, *Maylandia zebra* Gene ID: 101487556, *Mesitornis unicolor* Gene ID: 104545943, *Microcebus murinus* Gene ID: 105859136, *Microtus ochrogaster* Gene ID: 101999389, *Miniopterus natalensis* Gene ID: 107525674, *Monodelphis domestica* Gene ID: 100014779, *Monopterus albus* Gene ID: 109957085, *Myotis brandtii* Gene ID: 102239648, *Myotis davidii* Gene ID: 102770109, *Myotis lucifugus* Gene ID: 102438522, *Nanorana parkeri* Gene ID: 108784354, *Nestor notabilis* Gene ID: 104399051, *Nipponia nippon* Gene ID: 104012349, *Nomascus leucogenys* Gene ID: 100590527, *Notothenia coriiceps* Gene ID: 104964156, *Ochotona princeps* Gene ID: 101530736, *Octodon degus* Gene ID: 101591628, *Odobenus rosmarus divergens* Gene ID: 101385453, *Oncorhynchus kisutch* Gene ID: 109870627, *Opisthocomus hoazin* Gene ID: 104338567, *Orcinus orca* Gene ID: 101287409, *Oreochromis niloticus* Gene ID: 100694147, *Ornithorhynchus anatinus* Gene ID: 100081433, *Orycteropus afer afer* Gene ID: 103197834, *Oryzias latipes* Gene ID: 101167020, *Otolemurgarnettii* Gene ID: 100966064, *Ovis aries* Gene ID: 443090, *Pan paniscus* Gene ID: 100970779, *Panthera pardus* Gene ID: 109271431, *Panthera tigris altaica* Gene ID: 102957949, *Pantholops hodgsonii* Gene ID: 102323478, *Papio anubis* Gene ID: 101002517, *Paralichthys olivaceus* Gene ID: 109631046, *Pelodiscus sinensis* Gene ID: 102454304, *Peromyscus maniculatus bairdii* Gene ID: 102924185, *Phaethon lepturus* Gene ID: 104624271, *Phalacrocorax carbo* Gene ID: 104049388, *Physeter catodon* Gene ID: 102978831, *Picoides pubescens* Gene ID: 104296936, *Poecilia latipinna* Gene ID: 106958025, *Poecilia mexicana* Gene ID: 106920534, *Poecilia reticulata* Gene ID: 103473778, *Pongo abelii* Gene ID: 100452414, *Propithecus coquereli* Gene ID: 105807399, *Protobothrops mucrosquamatus* Gene ID: 107289584, *Pseudopodoces humilis* Gene ID: 102109711, *Pterocles gutturalis* Gene ID: 104461236, *Pteropus alecto* Gene ID: 102879110, *Pteropus vampyrus* Gene ID: 105291402, *Pundamilia nyererei* Gene ID: 102200268, *Pygocentrus nattereri* Gene ID: 108411786, *Pygoscelis adeliae* Gene ID: 103925329, *Python bivittatus* Gene ID: 103059167, *Rhincodon typus* Gene ID: 109920450, *Rhinolophus sinicus* Gene ID: 109445137, *Rhinopithecus bieti* Gene ID: 108538766, *Rhinopithecus roxellana* Gene ID: 104654108, *Rousettus aegyptiacus* Gene ID: 107513424, *Saimiri boliviensis* Gene ID: 101027702, *Salmo salar* Gene ID: 106581822, *Sarcophilus harrisii* Gene ID: 100927498, *Scleropages formosus* Gene ID: 108927961, *Serinus canaria* Gene ID: 103814246, *Sinocyclocheilus grahami* Gene ID: 107555436, *Sorex araneus* Gene ID: 101543025, *Stegastes partitus* Gene ID: 103360018, *Struthio camelus australis* Gene ID: 104138752, *Sturnus vulgaris* Gene ID: 106861926, *Sugiyamaella lignohabitans* Gene ID: 30033324, *Sus scrofa* Gene ID: 397348, *Taeniopygia guttata* Gene ID: 100222867, *Takifugu rubripes* Gene ID: 101062218, *Tarsius syrichta* Gene ID: 103254049, *Tauraco erythrolophus* Gene ID: 104378162, *Thamnophis sirtalis* Gene ID: 106538827, *Tinamus guttatus* Gene ID: 104572349, *Tupaia chinensis* Gene ID: 102471148, *Tursiops truncatus* Gene ID: 101330605, *Ursus maritimus* Gene ID: 103659477, *Vicugna pacos* Gene ID: 102533941, *Xiphophorus maculatus* Gene ID: 102225536, *Zonotrichia albicollis* Gene ID: 102073261, *Ciona intestinalis* Gene ID: 100183886, *Meleagris gallopavo* Gene ID: 100546408, *Trichechus manatus latirostris* Gene ID: 101355771, *Ceratotherium simum simum* Gene ID: 101400784, *Melopsittacus undulatus* Gene ID: 101871704, *Esox lucius* Gene ID: 10502249 and *Pygocentrus nattereri* Gene ID: 108411786.

In an embodiment, the GPD2 polypeptide is encoded by *Saccharomyces cerevisiae* Gene ID: 854095. In some embodiments, the GPD2 polypeptide has the amino acid sequence of SEQ ID NO: 6, is a variant of the amino acid sequence of SEQ ID NO: 6 having NAD-dependent glycerol-3-phosphate activity or is a fragment of the amino acid sequence of SEQ ID NO: 6 having NAD-dependent glycerol-3-phosphate activity. In some embodiments, the second heterologous nucleic acid molecule comprises the nucleic acid sequence of SEQ ID NO: 5, is a degenerate sequence of SEQ ID NO: 5 (encoding SEQ ID NO: 6) or encodes a variant or a fragment of the amino acid sequence of SEQ ID NO: 6.

In some embodiments, this overall reduction in GPD activity can be observed in high osmotic conditions. As used herein, the expression "high osmotic conditions" refers to the presence of a high osmotic pressure, usually caused by an increase in the solute concentration in the environment surrounding the recombinant yeast host cell. In yeasts, "high osmotic conditions" are associated with an upregulation of the HOG pathway, a concentration of sugars higher than about 50 g/L and/or equivalent to at least 1 g/L of a salt (such as NaCl). This decrease in NAD-dependent glycerol-3-phosphate activity can be observed with respect to the same recombinant yeast cell in normal or low osmotic conditions or with respect to a recombinant yeast host cell lacking the one or more second genetic modification. As also used in the present disclosure, the expression "normal or low osmotic conditions" refers to conditions that are not associated with high osmotic pressure.

The second heterologous nucleic acid molecules of the present disclosure can include or be operatively associated with an osmotic promoter. In the context of the present disclosure, an "osmotic promoter" can be a promoter (or a combination of promoters) allowing the expression (or, in some embodiments, the overexpression) of a gene when the recombinant yeast host cell is placed in high osmotic conditions but refraining the expression (or, in some embodiments, the overexpression) of a gene when the recombinant yeast host cell is placed in normal or low osmotic conditions. In this embodiment, the osmotic promoter can be an inducible promoter. Osmotic promoters are usually associated with genes in the HOG1 pathway and promoters controlling the expression of genes which are upregulated in the HOG1 pathway can be used in the recombinant yeast host cell of the present disclosure. Enzymes in the HOG1 pathway whose expression is upregulated in high osmotic conditions include, but are not limited to, a NAD-dependent glycerol-3-phosphate dehydrogenase 1 gene, a dihydroxyacetone kinase gene and a trehalose-phosphatase gene. As such, in the context of the present disclosure, the osmotic promoter can be a promoter (or a combination of promoters) from a NAD-dependent glycerol-3-phosphate dehydrogenase 1 gene, a dihydroxyacetone kinase gene and/or a trehalose-phosphatase gene. In Saccharomyces cerevisiae, enzymes in the HOG1 pathway whose expression is upregulated in the presence of high osmotic conditions include, but are not limited to, a GPD1 gene, a DAK1 gene and a TPS2 gene. As such, in the context of the present disclosure, the osmotic promoter can be a promoter (or a combination of promoters) from a GPD1 gene (referred to as the GPD1 promoter or gpd1p), a DAK1 gene (referred to as the DAK1 promoter or dak1p) and/or a TPS2 gene (referred to as the TPS2 promoter or tps2p).

An "osmotic promoter" can also be a constitutive promoter which allows the expression of coding sequences operatively associated thereto during osmotic conditions. In some embodiments, it is preferred that the constitutive promoter be a "low" constitutive promoter. Exemplary "low" constitutive promoters could be associated with the expression of housekeeping genes, and, for example, can include the promoter of the CYC1 gene. In some embodiment, the osmotic promoter is not a high constitutive promoter.

In yet another embodiment, the recombinant yeast host cells of the present disclosure are capable of reducing the activity or the expression of a second polypeptide capable of exporting glycerol from the recombinant yeast host cell. Exemplary polypeptides capable of functioning to export glycerol include aquaporins as well as glycerol facilitators. The fdp1 support (FPS1) polypeptide (encoded by Gene ID 850683 in Saccharomyces cerevisiae) is a glycerol facilitator capable of importing glycerol. As such, the polypeptide capable of functioning to export glycerol can be a FPS1 polypeptide or a polypeptide encoded by a FPS1 gene ortholog. The FPS1 polypeptide can be derived, for example, from Saccharomyces cerevisiae or a corresponding ortholog found in Pachysolen tannophilus, Komagataella pastoris, Yarrowia lipolytica and/or Cyberlindnera jadinii.

In the present disclosure, it is possible to express a variant of a first polypeptide or of a second polypeptide in the recombinant yeast host cells. A variant comprises at least one amino acid difference (substitution or addition) when compared to the amino acid sequence of the wild type polypeptide and still exhibits the biological activity of the wild type polypeptide (e.g., for a STL1 variant, glycerol transport activity; for a glucoamylase, a starch-degrading activity; for a GPD2 variant, a NAD-depending glycerol-3-phosphate dehydrogenase activity, etc.). In an embodiment, the variant polypeptide exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% of the activity of the wild-type polypeptide. The variants also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the wild-type polypeptide over its entire length. The term "percent identity", as known in the art, is a relationship between two or more polypeptide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant polypeptides described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine;

serine, threonine; lysine, arginine; and phenylalanine, tyrosine. Other conservative amino acid substitutions are known in the art and are included herein. Non-conservative substitutions, such as replacing a basic amino acid with a hydrophobic one, are also well-known in the art.

A variant polypeptide can also be a conservative variant or an allelic variant. As used herein, a conservative variant refers to alterations in the amino acid sequence that do not adversely affect the biological functions of the variant polypeptide. A substitution, insertion or deletion is said to adversely affect the polypeptide when the altered sequence prevents or disrupts a biological function associated with the variant polypeptide. For example, the overall charge, structure or hydrophobic-hydrophilic properties of the polypeptide can be altered without adversely affecting a biological activity. Accordingly, the amino acid sequence can be altered, for example to render the variant polypeptide more hydrophobic or hydrophilic, without adversely affecting its biological activity.

The present disclosure also provide fragments of the first and/or the second polypeptide described herein. A fragment comprises at least one less amino acid residue when compared to the amino acid sequence of the wild type polypeptide or variant and still possess the biological activity of the full-length wild type polypeptide. In an embodiment, the fragment exhibits at least 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% activity when compared to the full-length wild type polypeptide or variant. The fragments can also have at least 70%, 80%, 81%, 82%, 83%, 84%, 85%, 86%, 87%, 88%, 89%, 90%, 91%, 92%, 93%, 94%, 95%, 96%, 97%, 98% or 99% identity when compared to the wild type polypeptide or the variant. The fragment can be, for example, a truncation of one or more amino acid residues at the amino-terminus, the carboxy terminus or both termini of the wild type polypeptide or variant. Alternatively or in combination, the fragment can be generated from removing one or more internal amino acid residues.

Persistent Yeast Compositions and Processes for Propagating Persistent Yeast Cells The present disclosure provides compositions comprising the persistent yeast cells as well as processes for making such compositions. Broadly, the process for making the yeast composition comprises two steps: a first step of propagating the persistent yeast cells and a second step of formulating the persistent yeast cells into a composition. It is understood that the process for making the fermented product (described herein below in more details) can include some propagation of the persistent yeast cells but mainly concerns converting the biomass into the fermentation product. The propagation step of the process for making the persistent yeast cell composition minimizes the conversion of the biomass into the fermentation product and concerns mainly concerns maximizing cellular division of the persistent yeast cells.

The propagation can be performed by sampling the fermentation medium of an initial and/or a further fermentation (obtained, for example, at steps 200 or 400 described in FIG. 1) or the substantially isolated persistent yeast host cells (obtained, for example, at steps 300 and/or 500 of FIG. 1). The sample comprises persistent yeast cells. In some embodiments, the sample of the fermentation medium and/or the substantially isolated persistent yeast host cell can be placed into contact directly with a propagation medium allowing propagation in order to be propagated. In such embodiment, the propagation medium can be a fresh medium and/or also allow fermentation. The propagation medium can include, for example, molasses, cane juice, one or more nutrient and/or one or more antibiotic. In additional embodiments, the sample of the fermentation medium and/or the substantially isolated persistent yeast host cell can be placed directly in a fermentor or, in further embodiments, in a small vessel (such as, for example, a shake flask) to scale up the propagation prior to fermentation. In some embodiments, the sample of the fermentation medium and/or the substantially isolated persistent yeast host cell can be placed into contact with a solid medium (e.g., an agar plate for example) prior to propagation. Prior to being placed in a medium allowing for propagation, the sampled persistent yeast cells can be diluted or washed (with water for example) and/or concentrated (with centrifugation or filtration for example). The sampled persistent yeast cells can, prior to or during propagation, be supplemented with one or more nutrient or one or more antibiotic to maintain or prolong viability. The sampled persistent yeast cells can, prior to propagation, be stored. After having been propagated, the sampled persistent yeast cells can be diluted or washed (with water for example) and/or concentrated (with centrifugation or filtration for example).

The propagation can be conducted according to a traditional baker's yeast production process with the persistent yeast cells as described herein. The propagation step can be a continuous propagation, a batch propagation or a fed-batch propagation. The propagation medium intended to be inoculated with the persistent yeast cells can comprise a carbon source (such as, for example, molasses, sucrose, glucose, dextrose syrup, ethanol, corn, glycerol, corn steep liquor and/or a lignocellulosic biomass), a nitrogen source (such as, for example, ammonia or another inorganic source of nitrogen) and a phosphorous source (such as, for example, phosphoric acid or another inorganic source of phosphorous). The propagation medium can further comprise additional micronutrients such as vitamins and/or minerals to support the propagation of the persistent yeast cells. In some embodiments, the propagation medium can comprise molasses or be derived from molasses.

In the propagation process, the persistent yeast cells are placed in a propagation medium which can, in some embodiments, allow for a specific growth rate of 0.25, 0.24, 0.23, 0.22, 0.21, 0.20, 0.19, 0.18, 0.17, 0.16 or 0.15 $h^{-1}$ or less. In order to limit the growth rate of the persistent yeast cells, in some embodiments, the process can further comprise controlling the addition of nutriments, such as carbohydrates, during the propagation step. Limiting the growth rate of the persistent yeast cells during propagation can be achieved by maintaining the concentration of carbohydrates below 0.1, 0.01, 0.001 or 0.0001 weight % with respect to the volume of the fermentation medium. Controlling the concentration of carbohydrates of the propagation medium can be done by various means known in the art and can involve sampling the propagation medium at various intervals, determining the carbohydrate concertation, fermentation product (e.g., alcohol) concentration and/or gas (e.g., $CO_2$) concentration in those samples and adding or refraining from adding, if necessary, additional carbohydrates in the propagation medium to accelerate or decelerate the growth of the persistent yeast cells. In some embodiments, the process provides for adding nitrogen and/or phosphorous to match/support the growth rate of the persistent yeast cells.

The propagation process is preferably conducted under high aeration conditions. For example, in some embodiments, the process can include controlling the aeration of the propagation medium (which is contained in a vessel of a specific volume) to achieve a specific aeration rate, for example, of at least 0.2, 0.3, 0.4, 0.5, 0.6, 0.7, 0.8, 0.9, 1.0, 1.1, 1.2 or 1.3 air volume/vessel volume/minute.

The propagation process can be conducted at a specific pH and/or a specific temperature which may be optimal for the propagation of the persistent yeast cells. As such, in embodiments in which the persistent yeast cell is from the genus *Saccharomyces*, the process can comprise controlling the pH of the propagation medium to between about 3.0 to about 6.0, about 3.5 to about 5.5 or about 4.0 to about 5.5. In a specific embodiment, the pH is controlled at about 4.5. In another example, in embodiments in which the persistent yeast cell is from the genus *Saccharomyces*, the process can comprise controlling the temperature of the propagation medium between about about 20° C. to about 40° C., about 25° C. to about 30° C. or about 30° C. to about 35° C. In a specific embodiment, the temperature is controlled at between about about 30° C. to about 35° C. (32° C. for example).

At the end of the propagation step, a propagated medium comprising propagated persistent yeast cells (which can be propagated recombinant yeast host cells) is obtained. In some embodiments, a specific concentration of the propagated persistent yeast cells can be sought or achieved in the propagated medium. In some embodiments, the concentration of the propagated persistent yeast cells is at least about 0.1, 0.15, 0.2, 0.25, 0.3, 0.35, 0.4, 0.45, 0.5, 1.0, 1.5, 2.0, 2.5, 3.0, 3.5, 4.0, 4.5, 5.0 or more weight % with respect to the volume of the propagated medium. In a specific embodiment in which the persistent yeast cells are propagated using a fed-batch process, the concentration of the propagated persistent yeast cells is at least about 0.25 weight % with respect to the volume of the propagated medium.

In the formulating step, the mixture obtained after propagation (comprising the propagated persistent yeast cells) is modified to provide a yeast composition. In an embodiment of the formulating step, at least one component of the mixture obtained after propagation is removed from the propagated medium to provide the yeast composition. This component can be, without limitation, water, amino acids, peptides and proteins, nucleic acid residues and nucleic acid molecules, cellular debris, fermentation products, etc. In an embodiment, the formulating step comprises substantially isolating the propagated persistent yeast cells (e.g., the biomass) from the components of the propagated medium. As used in the context of the of the formulating step, the expression "substantially isolating" refers to the removal of the majority of the components of the propagated medium from the propagated persistent yeast cells. In some embodiments, "substantially isolating" refers to concentrating the propagated persistent yeast cells to at least 5, 10, 15, 20, 25, 30, 35, 45% or more when compared to the concentration of the persistent yeast cells prior to the substantial isolation. In order to provide the yeast composition, the propagated yeasts can be centrifuged (and the resulting cellular pellet comprising the propagated persistent yeast cells can optionally be washed), filtered and/or dried (optionally using a vacuum-drying technique). The formulation step can, in some embodiments, preserve the viability (at least in part) of the recombinant yeast host cells. As such, the yeast composition can be provided in an active or a semi-active form. The yeast composition can be provided in a liquid, semi-solid or dry form. In an embodiment, the composition can be provided in the form of a cream yeast.

Processes for Prolonging Persistence

The persistent yeast cells of the present disclosure are useful because their presence in a fermenting population over a plurality of fermentation cycles (in which the fermenting population is recycled) is prolonged. This prolonged presence is due, at least in part, by the presence of the one or more phenotypic traits present in the persistent yeast cells. As shown in the FIG. 1 and explained above, the plurality of fermentation cycles comprises at least one initial fermentation cycle and at least one or more further fermentation cycles. In the processes of the present disclosure, the persistent yeast cells are only exogenously added in the initial fermentation cycle and are then recycled in further fermentation cycles. Each fermentation cycle of the process includes contacting a fermentation medium (comprising a fermentable carbohydrate) with a fermenting population under conditions so as to allow the conversion of the fermentable carbohydrate in a fermentation product (e.g., fermentation). At the end of the fermentation, the fermenting population present in the fermented fermentation medium is substantially isolated from the fermented fermentation medium and use to initiate another fermentation cycle. It is understood that initial fermenting population consists essentially in the persistent yeast cells of the present disclosure and that, during the plurality of the fermentation cycles, the recycled fermenting population can include some contaminating wild (non-genetically modified) yeasts. The persistent yeast cells of the present disclosure persist for a longer time in the plurality of the fermentation cycles when compared to a control recombinant yeast host cell (having the ability to modulate the activity or the expression of the first and/or the second polypeptide) and lacking the phenotypic traits of the persistent yeast cell of the present disclosure. The plurality of fermentation cycles can include at least one continuous fermentation. The plurality of fermentation cycles can only include continuous fermentations. The plurality of fermentation cycles can include at least one batch fermentation. The plurality of fermentation cycles can only include batch fermentations. The processes of the present disclosure can include an initial fermentation cycle at least one, two, three, four, five, six, seven, eight, nine, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 or more further fermentation cycles. In a specific embodiments, the processes of the present disclosure include an initial fermentation cycle at least 39 further fermentation cycles. In a specific embodiments, the processes of the present disclosure include an initial fermentation cycle at least 49 further fermentation cycles. In a specific embodiments, the processes of the present disclosure include an initial fermentation cycle at least 59 further fermentation cycles. In a specific embodiments, the processes of the present disclosure include an initial fermentation cycle at least 69 further fermentation cycles. In a specific embodiments, the processes of the present disclosure include an initial fermentation cycle at least 79 further fermentation cycles. In a specific embodiments, the processes of the present disclosure include an initial fermentation cycle at least 89 further fermentation cycles. In a specific embodiments, the processes of the present disclosure include an initial fermentation cycle at least 99 further fermentation cycles. In a specific embodiments, the processes of the present disclosure include an initial fermentation cycle at least 109 further fermentation cycles. In a specific embodiments, the processes of the present disclosure include an initial fermentation cycle at least 119 further fermentation cycles. In a specific embodiments, the processes of the present disclosure include an initial fermentation cycle at least 129 further fermentation cycles. In a specific embodiments, the processes of the present disclosure include an initial fermentation cycle at least 139 further fermentation cycles. In a specific embodiments, the processes of the present disclosure include an initial fermentation cycle at least 149 further fermentation cycles. In a specific embodiments, the processes of the present disclosure include an initial fermentation cycle at least 159 further fermentation cycles. In a specific embodiments, the processes of the present disclosure include an initial fermentation cycle at least 169 further fermentation cycles. In a specific embodiments, the processes of the present disclosure include an initial fermentation cycle at least 179 further fermentation cycles. In a specific embodiments, the processes of the present disclosure include an initial fermentation cycle at least 189 further fermentation cycles. In a specific embodiments, the processes of the present disclosure include an initial fermentation cycle at least 199 further fermentation cycles.

In an embodiment, after a total 40 fermentation cycles (comprising both the initial fermentation cycle and 39 further fermentation cycles) according to the present process, the persistent yeast cells of the present disclosure are present in a proportion of at least 90% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 91% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 92% in the fermenting population (when measured with respect to its DNA contribution of the total fermenting population). In an embodiment, after a total 40 fermentation cycles (comprising both the initial fermentation cycle and 39 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 40 fermentation cycles (comprising both the initial fermentation cycle and 39 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 40 fermentation cycles (comprising both the initial fermentation cycle and 39 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 40 fermentation cycles (comprising both the initial fermentation cycle and 39 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 97% in the fermenting population (when measured with respect to its DNA contribution of the total fermenting population). In an embodiment, after a total 40 fermentation cycles (comprising both the initial fermentation cycle and 39 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.1% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.2% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.3% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.4% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.5% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.6% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.7% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.8% in the fermenting population (when measured with respect to its DNA contribution of the total fermenting population). In an embodiment, after a total 40 fermentation cycles (comprising both the initial fermentation cycle and 39 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 50 fermentation cycles (comprising both the initial fermentation cycle and 49 further fermentation cycles) according to the present process, the persistent yeast cells of the present disclosure are present in a proportion of at least 90% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 91% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 92% in the fermenting population (when measured with respect to its DNA contribution of the total fermenting population). In an embodiment, after a total 50 fermentation cycles (comprising both the initial fermentation cycle and 49 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 50 fermentation cycles (comprising both the initial fermentation cycle and 49 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 50 fermentation cycles (comprising both the initial fermentation cycle and 49 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 50 fermentation cycles (comprising both the initial fermentation cycle and 49 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 97% in the fermenting population (when measured with respect to its DNA contribution of the total fermenting population). In an embodiment, after a total 50 fermentation cycles (comprising both the initial fermentation cycle and 49 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.1% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.2% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.3% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.4% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.5% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.6% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.7% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.8% in the fermenting population (when measured with respect to its DNA contribution of the total fermenting population). In an embodiment, after a total 50 fermentation cycles (comprising both the initial fermentation cycle and 49 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 60 fermentation cycles (comprising both the initial fermentation cycle and 59 further fermentation cycles) according to the present process, the persistent yeast cells of the present disclosure are present in a proportion of at least 90% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 91% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 92% in the fermenting population (when measured with respect to its DNA contribution of the total fermenting population). In an embodiment, after a total 60 fermentation cycles (comprising both the initial fermentation cycle and 59 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 60 fermentation cycles (comprising both the initial fermentation cycle and 59 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 60 fermentation cycles (comprising both the initial fermentation cycle and 59 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 60 fermentation cycles (comprising both the initial fermentation cycle and 59 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 97% in the fermenting population (when measured with respect to its DNA contribution of the total fermenting population). In an embodiment, after a total 60 fermentation cycles (comprising both the initial fermentation cycle and 59 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.1% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.2% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.3% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.4% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.5% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.6% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.7% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.8% in the fermenting population (when measured with respect to its DNA contribution of the total fermenting population). In an embodiment, after a total 60 fermentation cycles (comprising both the initial fermentation cycle and 59 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 70 fermentation cycles (comprising both the initial fermentation cycle and 69 further fermentation cycles) according to the present process, the persistent yeast cells of the present disclosure are present in a proportion of at least 90% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 91% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 92% in the fermenting population (when measured with respect to its DNA contribution of the total fermenting population). In an embodiment, after a total 70 fermentation cycles (comprising both the initial fermentation cycle and 69 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 70 fermentation cycles (comprising both the initial fermentation cycle and 69 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 70 fermentation cycles (comprising both the initial fermentation cycle and 69 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 70 fermentation cycles (comprising both the initial fermentation cycle and 69 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 97% in the fermenting population (when measured with respect to its DNA contribution of the total fermenting population). In an embodiment, after a total 70 fermentation cycles (comprising both the initial fermentation cycle and 69 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.1% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.2% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.3% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.4% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.5% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.6% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.7% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.8% in the fermenting population (when measured with respect to its DNA contribution of the total fermenting population). In an embodiment, after a total 70 fermentation cycles (comprising both the initial fermentation cycle and 69 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 80 fermentation cycles (comprising both the initial fermentation cycle and 79 further fermentation cycles) according to the present process, the persistent yeast cells of the present disclosure are present in a proportion of at least 90% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 91% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 92% in the fermenting population (when measured with respect to its DNA contribution of the total fermenting population). In an embodiment, after a total 80 fermentation cycles (comprising both the initial fermentation cycle and 79 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 80 fermentation cycles (comprising both the initial fermentation cycle and 79 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 80 fermentation cycles (comprising both the initial fermentation cycle and 79 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 80 fermentation cycles (comprising both the initial fermentation cycle and 79 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 97% in the fermenting population (when measured with respect to its DNA contribution of the total fermenting population). In an embodiment, after a total 80 fermentation cycles (comprising both the initial fermentation cycle and 79 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.1% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.2% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.3% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.4% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.5% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.6% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.7% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.8% in the fermenting population (when measured with respect to its DNA contribution of the total fermenting population). In an embodiment, after a total 80 fermentation cycles (comprising both the initial fermentation cycle and 79 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 90 fermentation cycles (comprising both the initial fermentation cycle and 89 further fermentation cycles) according to the present process, the persistent yeast cells of the present disclosure are present in a proportion of at least 90% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 91% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 92% in the fermenting population (when measured with respect to its DNA contribution of the total fermenting population). In an embodiment, after a total 90 fermentation cycles (comprising both the initial fermentation cycle and 89 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 90 fermentation cycles (comprising both the initial fermentation cycle and 89 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 90 fermentation cycles (comprising both the initial fermentation cycle and 89 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 90 fermentation cycles (comprising both the initial fermentation cycle and 89 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 97% in the fermenting population (when measured with respect to its DNA contribution of the total fermenting population). In an embodiment, after a total 90 fermentation cycles (comprising both the initial fermentation cycle and 89 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.1% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.2% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.3% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.4% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.5% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.6% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.7% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.8% in the fermenting population (when measured with respect to its DNA contribution of the total fermenting population). In an embodiment, after a total 90 fermentation cycles (comprising both the initial fermentation cycle and 89 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 100 fermentation cycles (comprising both the initial fermentation cycle and 99 further fermentation cycles) according to the present process, the persistent yeast cells of the present disclosure are present in a proportion of at least 90% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 91% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 92% in the fermenting population (when measured with respect to its DNA contribution of the total fermenting population). In an embodiment, after a total 100 fermentation cycles (comprising both the initial fermentation cycle and 99 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 100 fermentation cycles (comprising both the initial fermentation cycle and 99 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 100 fermentation cycles (comprising both the initial fermentation cycle and 99 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 100 fermentation cycles (comprising both the initial fermentation cycle and 99 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 97% in the fermenting population (when measured with respect to its DNA contribution of the total fermenting population). In an embodiment, after a total 100 fermentation cycles (comprising both the initial fermentation cycle and 99 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.1% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.2% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.3% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.4% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.5% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.6% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.7% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.8% in the fermenting population (when measured with respect to its DNA contribution of the total fermenting population). In an embodiment, after a total 100 fermentation cycles (comprising both the initial fermentation cycle and 99 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 110 fermentation cycles (comprising both the initial fermentation cycle and 109 further fermentation cycles) according to the present process, the persistent yeast cells of the present disclosure are present in a proportion of at least 90% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 91% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 92% in the fermenting population (when measured with respect to its DNA contribution of the total fermenting population). In an embodiment, after a total 110 fermentation cycles (comprising both the initial fermentation cycle and 109 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 110 fermentation cycles (comprising both the initial fermentation cycle and 109 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 110 fermentation cycles (comprising both the initial fermentation cycle and 109 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 110 fermentation cycles (comprising both the initial fermentation cycle and 109 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 97% in the fermenting population (when measured with respect to its DNA contribution of the total fermenting population). In an embodiment, after a total 110 fermentation cycles (comprising both the initial fermentation cycle and 109 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.1% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.2% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.3% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.4% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.5% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.6% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.7% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.8% in the fermenting population (when measured with respect to its DNA contribution of the total fermenting population). In an embodiment, after a total 110 fermentation cycles (comprising both the initial fermentation cycle and 109 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 120 fermentation cycles (comprising both the initial fermentation cycle and 119 further fermentation cycles) according to the present process, the persistent yeast cells of the present disclosure are present in a proportion of at least 90% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 91% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 92% in the fermenting population (when measured with respect to its DNA contribution of the total fermenting population). In an embodiment, after a total 120 fermentation cycles (comprising both the initial fermentation cycle and 119 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 120 fermentation cycles (comprising both the initial fermentation cycle and 119 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 120 fermentation cycles (comprising both the initial fermentation cycle and 119 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 120 fermentation cycles (comprising both the initial fermentation cycle and 119 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 97% in the fermenting population (when measured with respect to its DNA contribution of the total fermenting population). In an embodiment, after a total 120 fermentation cycles (comprising both the initial fermentation cycle and 119 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.1% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.2% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.3% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.4% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.5% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.6% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.7% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.8% in the fermenting population (when measured with respect to its DNA contribution of the total fermenting population). In an embodiment, after a total 120 fermentation cycles (comprising both the initial fermentation cycle and 119 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 130 fermentation cycles (comprising both the initial fermentation cycle and 129 further fermentation cycles) according to the present process, the persistent yeast cells of the present disclosure are present in a proportion of at least 90% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 91% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 92% in the fermenting population (when measured with respect to its DNA contribution of the total fermenting population). In an embodiment, after a total 130 fermentation cycles (comprising both the initial fermentation cycle and 129 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 130 fermentation cycles (comprising both the initial fermentation cycle and 129 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 130 fermentation cycles (comprising both the initial fermentation cycle and 129 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 130 fermentation cycles (comprising both the initial fermentation cycle and 129 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 97% in the fermenting population (when measured with respect to its DNA contribution of the total fermenting population). In an embodiment, after a total 130 fermentation cycles (comprising both the initial fermentation cycle and 129 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.1% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.2% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.3% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.4% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.5% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.6% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.7% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.8% in the fermenting population (when measured with respect to its DNA contribution of the total fermenting population). In an embodiment, after a total 130 fermentation cycles (comprising both the initial fermentation cycle and 129 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 140 fermentation cycles (comprising both the initial fermentation cycle and 139 further fermentation cycles) according to the present process, the persistent yeast cells of the present disclosure are present in a proportion of at least 90% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 91% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 92% in the fermenting population (when measured with respect to its DNA contribution of the total fermenting population). In an embodiment, after a total 140 fermentation cycles (comprising both the initial fermentation cycle and 139 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 140 fermentation cycles (comprising both the initial fermentation cycle and 139 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 140 fermentation cycles (comprising both the initial fermentation cycle and 139 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 140 fermentation cycles (comprising both the initial fermentation cycle and 139 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 97% in the fermenting population (when measured with respect to its DNA contribution of the total fermenting population). In an embodiment, after a total 140 fermentation cycles (comprising both the initial fermentation cycle and 139 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.1% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.2% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.3% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.4% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.5% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.6% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.7% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.8% in the fermenting population (when measured with respect to its DNA contribution of the total fermenting population). In an embodiment, after a total 140 fermentation cycles (comprising both the initial fermentation cycle and 139 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 150 fermentation cycles (comprising both the initial fermentation cycle and 149 further fermentation cycles) according to the present process, the persistent yeast cells of the present disclosure are present in a proportion of at least 90% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 91% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 92% in the fermenting population (when measured with respect to its DNA contribution of the total fermenting population). In an embodiment, after a total 150 fermentation cycles (comprising both the initial fermentation cycle and 149 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 150 fermentation cycles (comprising both the initial fermentation cycle and 149 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 150 fermentation cycles (comprising both the initial fermentation cycle and 149 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 150 fermentation cycles (comprising both the initial fermentation cycle and 149 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 97% in the fermenting population (when measured with respect to its DNA contribution of the total fermenting population). In an embodiment, after a total 150 fermentation cycles (comprising both the initial fermentation cycle and 149 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.1% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.2% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.3% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.4% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.5% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.6% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.7% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.8% in the fermenting population (when measured with respect to its DNA contribution of the total fermenting population). In an embodiment, after a total 150 fermentation cycles (comprising both the initial fermentation cycle and 149 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 160 fermentation cycles (comprising both the initial fermentation cycle and 159 further fermentation cycles) according to the present process, the persistent yeast cells of the present disclosure are present in a proportion of at least 90% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 91% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 92% in the fermenting population (when measured with respect to its DNA contribution of the total fermenting population). In an embodiment, after a total 160 fermentation cycles (comprising both the initial fermentation cycle and 159 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 160 fermentation cycles (comprising both the initial fermentation cycle and 159 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 160 fermentation cycles (comprising both the initial fermentation cycle and 159 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 160 fermentation cycles (comprising both the initial fermentation cycle and 159 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 97% in the fermenting population (when measured with respect to its DNA contribution of the total fermenting population). In an embodiment, after a total 160 fermentation cycles (comprising both the initial fermentation cycle and 159 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.1% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.2% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.3% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.4% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.5% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.6% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.7% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.8% in the fermenting population (when measured with respect to its DNA contribution of the total fermenting population). In an embodiment, after a total 160 fermentation cycles (comprising both the initial fermentation cycle and 159 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 170 fermentation cycles (comprising both the initial fermentation cycle and 169 further fermentation cycles) according to the present process, the persistent yeast cells of the present disclosure are present in a proportion of at least 90% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 91% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 92% in the fermenting population (when measured with respect to its DNA contribution of the total fermenting population). In an embodiment, after a total 170 fermentation cycles (comprising both the initial fermentation cycle and 169 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 170 fermentation cycles (comprising both the initial fermentation cycle and 169 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 170 fermentation cycles (comprising both the initial fermentation cycle and 169 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 170 fermentation cycles (comprising both the initial fermentation cycle and 169 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 97% in the fermenting population (when measured with respect to its DNA contribution of the total fermenting population). In an embodiment, after a total 170 fermentation cycles (comprising both the initial fermentation cycle and 169 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.1% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.2% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.3% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.4% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.5% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.6% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.7% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.8% in the fermenting population (when measured with respect to its DNA contribution of the total fermenting population). In an embodiment, after a total 170 fermentation cycles (comprising both the initial fermentation cycle and 169 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 180 fermentation cycles (comprising both the initial fermentation cycle and 179 further fermentation cycles) according to the present process, the persistent yeast cells of the present disclosure are present in a proportion of at least 90% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 91% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 92% in the fermenting population (when measured with respect to its DNA contribution of the total fermenting population). In an embodiment, after a total 180 fermentation cycles (comprising both the initial fermentation cycle and 179 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 180 fermentation cycles (comprising both the initial fermentation cycle and 179 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 180 fermentation cycles (comprising both the initial fermentation cycle and 179 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 180 fermentation cycles (comprising both the initial fermentation cycle and 179 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 97% in the fermenting population (when measured with respect to its DNA contribution of the total fermenting population). In an embodiment, after a total 180 fermentation cycles (comprising both the initial fermentation cycle and 179 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.1% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.2% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.3% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.4% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.5% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.6% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.7% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.8% in the fermenting population (when measured with respect to its DNA contribution of the total fermenting population). In an embodiment, after a total 180 fermentation cycles (comprising both the initial fermentation cycle and 179 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 190 fermentation cycles (comprising both the initial fermentation cycle and 189 further fermentation cycles) according to the present process, the persistent yeast cells of the present disclosure are present in a proportion of at least 90% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 91% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 92% in the fermenting population (when measured with respect to its DNA contribution of the total fermenting population). In an embodiment, after a total 190 fermentation cycles (comprising both the initial fermentation cycle and 189 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 190 fermentation cycles (comprising both the initial fermentation cycle and 189 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 190 fermentation cycles (comprising both the initial fermentation cycle and 189 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 190 fermentation cycles (comprising both the initial fermentation cycle and 189 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 97% in the fermenting population (when measured with respect to its DNA contribution of the total fermenting population). In an embodiment, after a total 190 fermentation cycles (comprising both the initial fermentation cycle and 189 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.1% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.2% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.3% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.4% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.5% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.6% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.7% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.8% in the fermenting population (when measured with respect to its DNA contribution of the total fermenting population). In an embodiment, after a total 190 fermentation cycles (comprising both the initial fermentation cycle and 189 further fermentation cycles) according to the present process, the persistent yeast cells of the present disclosure are present in a proportion of at least 99.9% in the fermenting population (when measured with respect to its DNA contribution of the total fermenting population).

In an embodiment, after a total 200 fermentation cycles (comprising both the initial fermentation cycle and 199 further fermentation cycles) according to the present process, the persistent yeast cells of the present disclosure are present in a proportion of at least 90% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 91% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 92% in the fermenting population (when measured with respect to its DNA contribution of the total fermenting population). In an embodiment, after a total 200 fermentation cycles (comprising both the initial fermentation cycle and 199 further fermentation cycles of the total fermenting population) according to the present process, the persistent yeast cells of the present disclosure are present in a proportion of at least 93% in the fermenting population (when measured with respect to its DNA contribution of the total fermenting population). In an embodiment, after a total 200 fermentation cycles (comprising both the initial fermentation cycle and 199 further fermentation cycles of the total fermenting population) according to the present process, the persistent yeast cells of the present disclosure are present in a proportion of at least 94% in the fermenting population (when measured with respect to its DNA contribution of the total fermenting population). In an embodiment, after a total 200 fermentation cycles (comprising both the initial fermentation cycle and 199 further fermentation cycles of the total fermenting population) according to the present process, the persistent yeast cells of the present disclosure are present in a proportion of at least 95% in the fermenting population (when measured with respect to its DNA contribution of the total fermenting population). In an embodiment, after a total 200 fermentation cycles (comprising both the initial fermentation cycle and 199 further fermentation cycles of the total fermenting population) according to the present process, the persistent yeast cells of the present disclosure are present in a proportion of at least 96% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 97% in the fermenting population (when measured with respect to its DNA contribution of the total fermenting population). In an embodiment, after a total 200 fermentation cycles (comprising both the initial fermentation cycle and 199 further fermentation cycles of the total fermenting population) according to the present process, the persistent yeast cells of the present disclosure are present in a proportion of at least 98% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.1% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.2% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.3% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.4% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.5% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.6% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.7% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.8% in the fermenting population (when measured with respect to its DNA contribution of the total fermenting population). In an embodiment, after a total 200 fermentation cycles (comprising both the initial fermentation cycle and 199 further fermentation cycles) according to the present process, the persistent yeast cells of the present disclosure are present in a proportion of at least 99.9% in the fermenting population (when measured with respect to its DNA contribution of the total fermenting population).

The initial and further fermentation medium comprises or is derived from a biomass. The biomass that can be fermented with the recombinant host cell described herein includes any type of biomass known in the art and described herein. For example, the biomass can include, but is not limited to, starch, sugar and lignocellulosic materials. Starch materials can include, but are not limited to, mashes such as corn, wheat, rye, barley, rice, or milo. Sugar materials can include, but are not limited to, sugar beets, artichoke tubers, sweet sorghum, molasses or sugarcane. The terms "lignocellulosic material", "lignocellulosic substrate" and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, waste-water-treatment sludge, municipal solid waste, corn fiber from wet and dry mill corn ethanol plants and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan and galactoglucomannan), pectins (e.g., homogalacturonans, rhamnogalacturonan I and II, and xylogalacturonan) and proteoglycans (e.g., arabinogalactan-protein, extensin, and pro line-rich proteins). In a further embodiment, the initial and/or the further fermentation medium comprises sucrose as the main fermentable carbohydrate. In one embodiment, the initial and/or the further fermentation medium comprises or is derived from sugarcane, molasses, derivatives thereof as well as mixtures thereof.

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and *miscanthus*; or combinations thereof.

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, molasses, sugarcane, leaves, agricultural and forestry residues, grasses such as switchgrass, ruminant digestion products, municipal wastes, paper mill effluent, newspaper, cardboard or combinations thereof.

Paper sludge is also a viable feedstock for lactate or acetate production. Paper sludge is solid residue arising from pulping and paper-making, and is typically removed from process wastewater in a primary clarifier. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

In the process described herein, it is possible to add an exogenous source (e.g., to dose) of an enzyme to facilitate saccharification or improve fermentation yield. As such, the process can comprise including one or more dose(s) of one or more enzyme(s). The exogenous enzyme that can be used can include, without limitation, an alpha-amylase, a glucoamylase, a protease, a phytase, a pullulanase, a cellulase, a hemi-cellulase such as a xylanase, a trehalase, or any combination thereof. The exogenous enzyme can be provided, in some embodiments, in a purified form and/or provided as part of a cocktail.

The production of ethanol can be performed, for example, at temperatures of at least about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the production of ethanol from cellulose can be performed, for example, at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments, the persistent yeast can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In the processes described herein, at the end of the fermentation, the fermenting population is substantially isolated from the fermented fermentation medium. As used in the context of the present disclosure, the expression "substantially isolating" refers to the removal of the majority of the components of the fermented fermentation medium from the fermenting population. In some embodiments, "substantially isolating" refers to concentrating the fermenting population to at least 5, 10, 15, 20, 25, 30, 35, 45% or more when compared to the concentration of the fermenting population prior to the substantially isolation. In order to substantially isolate to fermenting population, the fermented fermentation medium can be centrifuged. Cell separation and recovery in the fuel ethanol process is carried out using stacked-disk, nozzle discharge type centrifuges (see Brociner et al.). In these machines, the feed-broth from the end of fermentation, often referred to in the process as "vinho bruto" or "beer" is introduced into the top of the machine, circulates to the bottom, and is then forced upward through a set of rotating disks. The rotation of these disks imparts a centrifugal force on the total feed, and particles. Yeast cells and other solids are forced downward and to the side of the machine. The cells then exit through nozzles at the outer edge of the machine creating a concentrated yeast cream. Clarified liquid, often called "vinho,", "vinho delevurado" or "wine" exits the machine out the top.

Optionally the substantially isolated fermenting population can be washed. In a specific embodiment, the substantially isolated fermenting population can be submitted to an acid washing step. In the acid washing step, an acid or an acidic solution is put into contact with the fermenting population. In some embodiments, the acid or the acidic solution has a pH of between 2.0 and 2.2. In some embodiments, the contact between the substantially isolated fermenting population and the acid/acidic solution is maintained so as to reduce the contaminating bacterial population that may be present. For example, the contact between the substantially isolated fermenting population and the acid or the acidic solution can last at least 30, 40, 50, 60, 70, 80, 90, 100, 110, 120 minutes or more. In certain embodiments, the acid is sulphuric acid and/or the acidic solution comprises sulphuric acid. After the acid washing step, the pH of the acid washed fermenting population can be adjusted prior to the further fermentation cycle.

In some embodiments, methods of producing ethanol can comprise contacting the fermentation substrate with a persistent yeast described herein and additionally contacting the substrate with externally produced enzymes which can be provided in a purified form. Exemplary externally produced enzymes include, but are not limited to starch degrading enzymes, dextran degrading enzymes, phytase, protease, cellulases and/orxylose isomerase. Specific externally produced (and optionally purified) enzymes include, but are not limited to, trehalases, glucoamylases, alpha-amylases, alpha-glucosidases, glucanases (endo/exo), pullulanases, phytases and/or proteases.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter or at least about 15 g per hour per liter.

In some embodiments, the persistent yeast cells can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter, at least about 15 g per hour per liter or more than a control strain (e.g., a wild-type strain, such as, for example, strain PE-2) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

Processes for Screening/Generating Persistent Yeast Cells

The present disclosure also provides for a process for determining if a test yeast is considered persistent or not. The process comprises conducting a plurality of fermentation cycles using, in the initial fermenting population a test yeast and determining, after a specific number of fermentation cycles, if the test yeast is present in the fermented medium and if so, the proportion of the test yeast in the fermentation medium. The test yeast has a detectable feature which is absent from other wild yeasts which may contaminate the fermentation medium. If the test yeast is present, after a total of 40, 50, 60, 70, 80, 90, 100, 110, 120, 130, 140, 150, 160, 170, 180, 190, 200 fermentation cycles or more, in a proportion at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more in the fermeting population, the test yeast is considered to be persistent. If the test yeast is present, after a total of 40, 50, 60, 70, 80, 90, 100, 110, 120, 130, 140, 150, 160, 170, 180, 190, 200 fermentation cycles or more, in a proportion lower than 90% in the fermenting population, the test yeast is not considered to be persistent. The process can include, prior to performing the plurality of fermentation cycles, providing a test yeast as a recombinant yeast host cell capable of modulating the activity or the expression of a first polypeptide and/or a second polypeptide for increasing, when compared to a parental cell, the conversion of a biomass into a fermentation product and/or for reducing the conversion of the biomass into a fermentation by-product as described herein. In some embodiments, the process can include introducing one or more genetic modification, for example those presented above, to modulate the activity or the expression of the first polypeptide and/or the second polypeptide in the test yeast which is considered to be persistent or intended to be screened for persistence phenotypes. The process can include, in some embodiments, determining if the test yeast is persistent by determining the presence or the absence of at least one or any combination of phenotypic traits. A test yeast comprising at least one or any combination of the phenotypic traits described herein is considered to be persistent.

The present disclosure also provides for a process for generating a persistent yeast. The process comprises conducting a plurality of fermentation cycles using, in the initial fermenting population comprising an initial yeast or a combination of initial yeasts and conducting a specific number of fermentation cycles. The initial yeast(s) may or may not be considered to be persistent. In some embodiments, it is not known if the initial yeast(s) is persistent or not. The fermenting population obtained after a total of 40, 50, 60, 70, 80, 90, 100, 110, 120, 130, 140, 150, 160, 170, 180, 190, 200 fermentation cycles or more is considered to include persistent yeast cells. The persistent yeast cells may or may not corresponding to the initial yeast(s) initially inoculated in the fermentation medium. The process can include, in some embodiments, determining if the fermenting population obtained after a total of at least 40 fermentation cycles is persistent by determining the presence or the absence of the at least one phenotypic traits in one or more cells of the fermenting population. A yeast cell obtained (and in some embodiments substantially isolated) from the fermenting population after at least 40 fermentation cycles exhibiting at least one or any combination of the phenotypic traits described herein is considered to be persistent. The persistent yeast cells obtained by this process can, in some embodiments, be genetically modified to have the ability of modulating the activity or the expression of a first polypeptide and/or a second polypeptide for increasing, when compared to a parental cell, the conversion of a biomass into a fermentation product and/or for reducing the conversion of the biomass into a fermentation by-product as described herein.

The present invention will be more readily understood by referring to the following examples which are given to illustrate the invention rather than to limit its scope.

EXAMPLE

Material and Methods

Gene sequencing. DNA was extracted from particular fermentation cycles throughout the implementation test and Illumina sequenced (2×126 bp read data; short reads of all DNA present).

Quantitative PCR (qPCR) assay. The amount of the recombinant yeast strain was measured by a quantitative polymerase chain reaction (qPCR) technique that quantifies the amount of the IME1 gene present in a sample compared to the amount of the ALG9 gene. Since the recombinant yeast strain does not have the IME1 gene (because it includes at least one genetic modification disrupting the IME1 gene), the amount of quantified IME1 DNA relative to the amount of ALG9 DNA increases as the amount of contaminating DNA (from wild yeasts) increases. The absolute quantification method was used to analyze the samples by comparison to a standard curve for each gene of interest. The qPCR reactions for the unknowns contains the following components, genomic DNA (loaded at 0.05 ng/µl), SsoAdvanced™ Universal SYBR® Green Supermix (Biorad #172-5271), and primer pairs specific to either the IME1 or the ALG9 gene at 0.5 uM final concentration. The IME1 gene was amplified with primer X33463 (cacgctgccttagaagatgg, SEQ ID NO: 1) and primer X33464 (gttctgcagctgagatgagg, SEQ ID NO: 2). The ALG9 gene was amplified with primer X34382 (gtttaatccgggctggttccat, SEQ ID NO: 3) and primer X34383 (TAGACCCAGTGGACAGATAGCG, SEQ ID NO: 4). The amplification was performed in a BioRad CFX96 Touch Real-Time PCR Detection System using 2-step PCR cycling conditions with a melting temperature of 60° C. for 30 seconds for a total of 40 cycles. Finally, the starting quantity (SQ) of the sample DNA was determined by comparing the cycle of quantitation (Cq) for the unknown to the Cq of the known DNA quantities in the standard curve for each primer set. The calculation (IME1 SQ/ALG9 SQ*100) determined the percentage of wild type DNA in the population and was used to estimate the presence of the recombinant yeast strain.

Scanning election microscopy. Scanning electron microscopy (SEM) was used to study the morphological shape of yeast cells. The cells were fixed in glutaraldehyde, post-fixed in $OsO_4$, dried and sputter-coated with gold/palladium (Au/Pd) for viewing. The specimen were fixed by immersing them in 2.5%-4% glutaraldehyde in 0.1 M sodium cacodylate or phosphate buffer solution (pH 6.8-7.4 as appropriate) and incubating for at least two hours. The specimen were washed by immersing them 3 times with the 0.1 M cacodylate or phosphate buffer solution for 10 minutes each to remove excess fixative. The specimen were then submitted to a post-fixation treatment by immersing them in a 1% $OsO_4$ in buffer at 4° C. and further washed in distilled or de-ionized water to remove all traces of fixative and buffer solutions. The specimens were dehydrated by immersing them for 10 minutes each in 25%, 50%, 70%, 85%, 95%, and three 100% ethanol solutions to remove all traces of water. The specimens were submitted to a critical point dry or three washes in HMDS for 10 minutes each followed by air drying. The specimens were mounted and a sputter coat a thin layer (~5 nm) of AuPd was applied.

Commercial fed batch fermentation process. A detailed description of the fermentation process with yeast recycle with its various forms can be found in Basso et al. (2001). Briefly, non-sterilized sugarcane juice and/or molasses with a typical concentration of between 18% and 22% total sugars was fermented at a high yeast inoculum (10 to 14% wet weight per volume) to achieve fast (8 to 12 hours) fermentations. The sugar concentration can vary over the course of the sugarcane harvest season, and is typically lowest at the start and end of the season. The yeast was repeatedly recycled over the crop season (~200 days). After each cycle of fermentation, yeast cells were separated from the whole fermentation broth by centrifugation, with some of the yeast being lost with the wine from the centrifuge and proceeding to distillation, and the retained yeast remaining as a concentrated yeast cream. The yeast cream was then subjected to a treatment with sulphuric acid where water and acid are added until the yeast cream reaches a pH of between 3.5 to 1.8 (although in some cases no acid treatment is used). This treatment lasted 1 to 2 hours and was used to decrease bacterial contamination and break up flocculation of the yeast cells. In some cases antimicrobials were added to the yeast cream prior to fermentation as well. After the treatment was complete, the yeast cell cream was repitched to a fermentation tank and fresh substrate (molasses, sugarcane juice, or a mixture) was then added to the cells and fermentation is started again. Fermentation temperatures varied based on the configuration of the industrial facility, but were generally targeted to between 32 and 35° C. In many cases, the temperature cannot be controlled in this range and can reach as high as 40° C. or higher. Fermentation vessels were typically only agitated by the $CO_2$ generated during fermentation escaping the broth and by the action of a pump around loop with a heat exchanger to remove excess heat.

Laboratory scale fed batch cell recycle fermentation process. Lab scale fermentations were set up to mimic the industrial scale process. They were carried out using 50 mL vessels filled with yeast cream either from propagation, or from a previous fermentation, at a level to reproduce standard yeast concentrations in fermentations recycling yeasts (~10% wet cell mass). This yeast cream was subjected to acid treatment under the conditions provided above in the section "Commercial fed batch fermentation process". A feeding system was used to provide a feed of substrate or "must" (sugar cane must sourced from operating facilities), again at rates and concentrations dictated by average conditions occurring in commercial facilities. This feed stream was provided via a syringe pump to each reactor. Fermentations were held under temperature controlled conditions (generally 32 to 35° C.) and gently agitated, and were allowed to proceed until the evolution of $CO_2$ falls below a minimum threshold. Once complete, samples were taken for analysis by HPLC to compare the production of ethanol, glycerol, organic acids, and other compounds. Yeast cultures were run as either pure cultures or as mixtures of yeast strains as indicated in the experimental description or figure legends. The amounts of different strains present after a particular number of cycles was determined using a qPCR technique specific to the strain of interest.

Batch laboraty scale fermentation. Anaerobic batch fermentations were run in 60 mL pressure bottles with 20 mL of media (commercially sourced must or defined laboratory media). Fermentations were held under temperature controlled conditions and gently agitated, and were allowed to proceed until the evolution of $CO_2$ falls below a minimum threshold. Once complete, samples were taken for analysis by HPLC to compare the production of ethanol, glycerol, organic acids, and other compounds. Aerobic cultures were similarly set-up but with a permeable cap. Cultures of yeast strains Y2, Y4 and Y8 were pitched in monoculture or in co-culture with ~15% of the wild type strain Y7. The fermentations were monitored by HPLC and yeast populations were monitored by qPCR.

Suspension assay. Cells were suspended evenly at time zero, taking a sample from the top of the suspension and measuring the sample's optical density at 600 nm. The sample was then incubated for a designated amount of time (3.5 or 5 min). After the incubation, another sample was obtained from the top of the suspension and the optical density is again measured at 600 nm. The percentage of sedimentation corresponds to the percentage change in optical density between the two samples. Samples in this assay included a control, which was a non-clustered yeast strain freshly grown up on media, as well as samples taken directly from the centrifugation process.

Wash out rate determination. Washout rates were determined by measuring the amount of non-engineered strain present in the fermentation system of the facility by carrying out qPCR of composite samples (as described above). Then, overall exponential washout rates (K value) were calculated using the formula $$K = \ln\left(\frac{C_{FINAL}}{C_{INITIAL}}\right)/(CYCLE_{FINAL} - CYCLE_{INITIAL})$$

where $C_{FINAL}$=the fraction of contaminant yeast DNA at the final cycle measured; $C_{INITIAL}$=the fraction of contaminant yeast DNA at the first cycle measured; $CYCLE_{FINAL}$=the number of the final cycle measured; $CYCLE_{INITIAL}$=the number of the first cycle measured.

Genome-wide association tests. The software Plink (Purcell et al. 2007) can conduct a genome-wide scan for alleles that significantly associate with a phenotype of interest. Following ploidy inference, the filtered variant callset of the appropriate ploidy were converted to Plink format using BCFtools (Li et al. 2009; Li, 2011) to create a chromosome-map file, and VCFtools (Danecek et al., 2011) to execute the conversion. Each strain was coded as being either smooth (0) or rugose (1) and conducted the association test for SNPs and indels independently, log-transforming the resulting p-values to plot the relative strength of the genotype-phenotype association across each position. In conventional genome-wide association studies (GWAS) involving hundreds to thousands of samples, p-values$<1\times10^{-5}$ are considered suggestive and p-values$<5\times10^{-8}$ are considered significant. In the present case, comparatively few samples (N=25), even perfect associations may not yield conventionally significant p-values depending on the level of noise in the genome-wide background, but the results can be used to narrow down the field of candidate causal mutations by quantifying the relative strength of the association across a genome-wide panel of variants.

Invertase assay. Cells were grown overnight in aerobic or anaerobic culture, or harvested at the end of one or more fermentation cycles in the fed-batch cell recycle system. Cultures were diluted to 9 mg/mL (wet weight basis, ~2 g/L dry weight basis) in a citrate-phosphate buffer pH 5 with 40 g/L sucrose and incubated at 35° C. for 12 to 15 minutes. The mixture is then incubated with 3,5-dinitrosalicylic acid (DNS). DNS reacts with reducing sugars and to form 3-amino-5-nitrosalicylic acid, which absorbs light at 540 nm. Glucose and fructose released by the yeast invertase activity is quantified by spectrophotometry at 540 nm. Dry weight measurements of cell samples are used to calculate the amount of dry cells added in each reaction and the sugar release per gram of dry cells loaded per time.

Response to cAMP. Cell were grown in YPD for 48 hours until they were glucose depleted followed by a spike of 100 mM glucose to the cells. Cells were snap frozen before glucose addition and after 5 minutes of incubation with the glucose. Cells were thawed, lysed and the amount of cAMP was then measured by a standard kit.

TABLE 1

Description of the strains that were made and/or characterizes. GPD2 had the amino acid sequence of SEQ ID NO: 5 was encoded by the nucleic acid sequence of SEQ ID NO: 6. STL1 had the amino acid sequence of SEQ ID NO: 7 was encoded by the nucleic acid sequence of SEQ ID NO: 8. SmGAPN had the amino acid sequence of SEQ ID NO: 29 and was encoded by the nucleic acid sequence of SEQ ID NO: 30. The presence of the a plurality of acronyms in a strain (STL1-STL1 for example) refers that two copies of a gene encoding for the polypeptide referred to by the acronym has been inserted at each integration site.

| Genetically modified strain phenotype | Parental strain phenotype | Genes overexpresses in the genetically modified strain |
|---|---|---|
| Y1: smooth | M710: smooth | gpd1Δ::gpd2 fcy1Δ::STL1-STL1 ime1Δ::STL1-STL1 |
| Y2: rugose | Isolate from Y1: smooth | gpd1Δ::gpd2 fcy1Δ::STL1-STL1 ime1Δ::STL1-STL1 |
| Y3: rugose, fast settling, high invertase activity, triploid, hyperactivated Ras/cAMP | NA - wild-type | NA - wild-type |
| Y4: rugose, fast settling, high invertase activity, triploid, hyperactivated Ras/cAMP | Y3 | fcy1Δ::STL1-STL1 ime1Δ::STL1-STL1 |
| Y5: rugose, fast settling, high invertase activity, triploid, hyperactivated Ras/cAMP | NA - wild-type | NA - wild-type |
| Y6: rugose, fast settling, high invertase activity, triploid, hyperactivated Ras/cAMP | Y5 | fcy1Δ::STL1-STL1 ime1Δ::STL1-STL1 |
| Y7: rugose, fast settling, triploid, hyperactivated Ras/cAMP | NA - wild-type | NA - wild-type |
| Y8: rugose, fast settling, triploid, hyperactivated Ras/cAMP | Y7 | gpd1Δ::gpd2 fcy1A::STL1-STL1 |

TABLE 1-continued

Description of the strains that were made and/or characterizes. GPD2 had the amino acid sequence of SEQ ID NO: 5 was encoded by the nucleic acid sequence of SEQ ID NO: 6. STL1 had the amino acid sequence of SEQ ID NO: 7 was encoded by the nucleic acid sequence of SEQ ID NO: 8. SmGAPN had the amino acid sequence of SEQ ID NO: 29 and was encoded by the nucleic acid sequence of SEQ ID NO: 30. The presence of the a plurality of acronyms in a strain (STL1-STL1 for example) refers that two copies of a gene encoding for the polypeptide referred to by the acronym has been inserted at each integration site.

| Genetically modified strain phenotype | Parental strain phenotype | Genes overexpresses in the genetically modified strain |
|---|---|---|
| Y61 | Y3: rugose, fast settling, high invertase activity, triploid, hyperactivated Ras/cAMP | gpd1Δ::gpd2-STL1-STL1 |
| Y62 | Y3: rugose, fast settling, high invertase activity, triploid, hyperactivated Ras/cAMP | fcy1Δ::SmGAPN-SmGAPN |
| Y63 | Y3: rugose, fast settling, high invertase activity, triploid, hyperactivated Ras/cAMP | zwf1Δ::SmGAPN-SmGAPN |
| Y64 | Y6: rugose, fast settling, high invertase activity, triploid, hyperactivated Ras/cAMP | fur1Δ::SmGAPN-SmGAPN fcy1Δ::STL1-STL1 ime1Δ::STL1-STL1 |
| Y65 | Y6 | fcy1Δ::STL1-STL1 ime1Δ::STL1-STL1 fur1Δ::SmGAPN-SmGAPN |
| Y66 | Y6 | zwf1Δ::SmGAPN-SmGAPN fcy1Δ::STL1-STL1 ime1Δ::STL1-STL1 |

Fast Settling and Rugose Phenotype

Figure 2A:
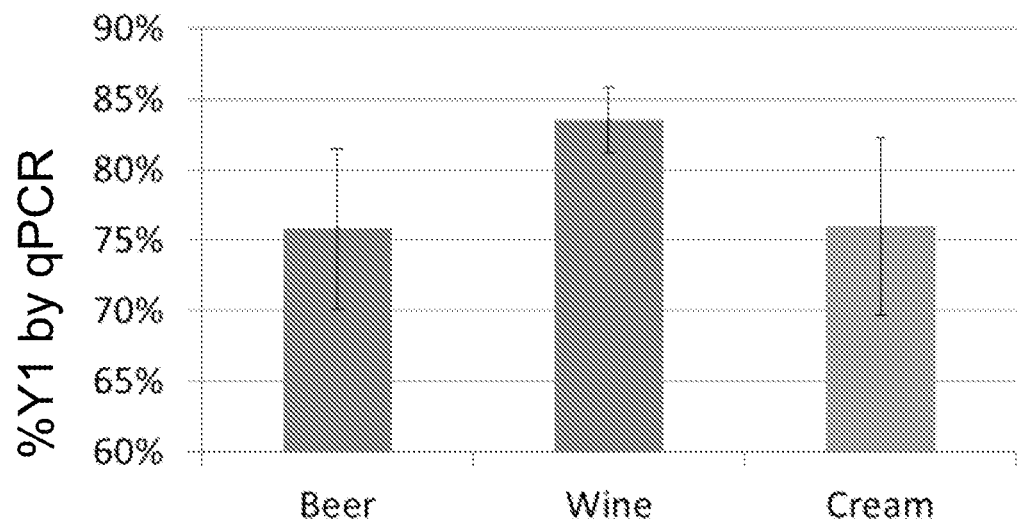
FIGS. 2A to 2D show the sampling of inputs and outputs of the centrifugation process. Microscopic and plating results from sampling of inputs and outputs from the centrifugation process.

Strain Y1 was submitted to a commercial fermentation. The input and output streams of yeast strain Y1 from a centrifuge obtained at a commercial ethanol mill were examined. FIG. 2A shows that the percentage of Y1 DNA is higher in the wine stream as compared to the beer stream, indicating that the yeasts exiting the fermentation process and heading to the distillation process is enriched for strain Y1 compared to wild yeast strains. In addition, the Y1 strain percentage of total yeast DNA in the yeast cream being recycled to the process is the same or somewhat lower than what is found in the beer. These results suggest that yeast strain Y1 is being selected against during the process (most likely during the centrifuge step).

The Y1 strain is a smooth colony on a plate and does not present the rugose morphology. Under the microscope, the Y1 strain forms single or doublet cells similar to what is depicted in FIGS. 4A and 4B.

Figure 2B:
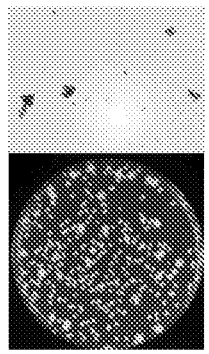
Figure 2C:
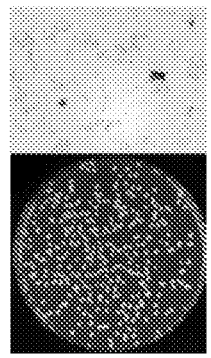
Figure 2D:

Microscopic analysis showed that the feed to the centrifuge, the beer, was composed of a mix of particle of different sizes (FIG. 2B), whereas the wine was composed of mostly small particles (FIG. 2C). The cream yeast, which is usually retained and sent back to the fermentation process, was composed of mostly larger particles (FIG. 2D). FIGS. 2B to 2D show the presence of "rugose" type colonies found in these streams. The feed to the centrifuge (beer) was composed of cells that form a mixture of rugose and smooth colonies (FIG. 2B). The wine was composed of cells that form exclusively smooth colonies (FIG. 2C). The yeast cream, which was retained, showed a mixture of cells forming smooth and rugose colonies, but was enriched for those cells that form rugose colonies relative to the beer (FIG. 2D). This data suggets that the centrifuge was preferentially selecting for cells that form rugose colonies to be retained in the process. Conversely, it showed that the centrifuge selected against those cells that form smooth colonies.

Figure 3:
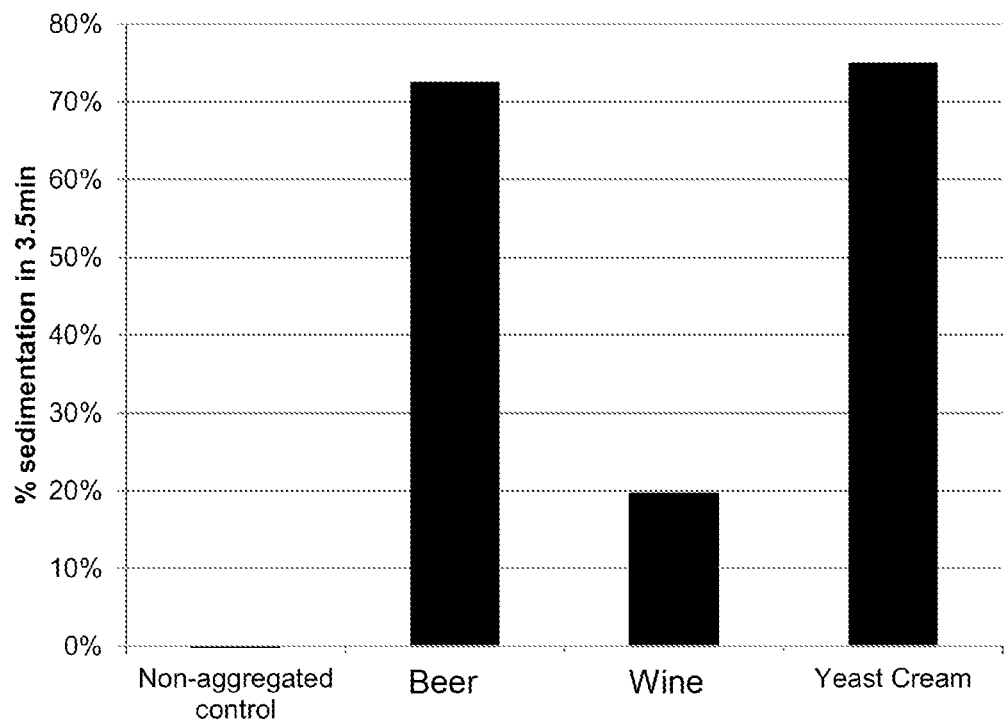
FIG. 3 provides the results of the settling assay data of a non-aggregated control, a sample of the beer, of the wine and of the cream. Results are shown as the % of sedimentation in 3.5 min in function of the sample tested.

The settling velocity of the various yeast samples was determined. FIG. 3 shows the measurements of the rate of settling by gravity in a suspension after incubation for 3.5 minutes. The control, non-aggregated strain, does not settle at all under the conditions used for the assay. The input to the centrifuge (the beer) settles rapidly, as does the yeast cream output that will be recycled to the process. The wine showed much less/much slower settling of the particles it contained. This supports the principle that the centrifuge was acting to retain those particles that settle more rapidly.

Figure 4A:
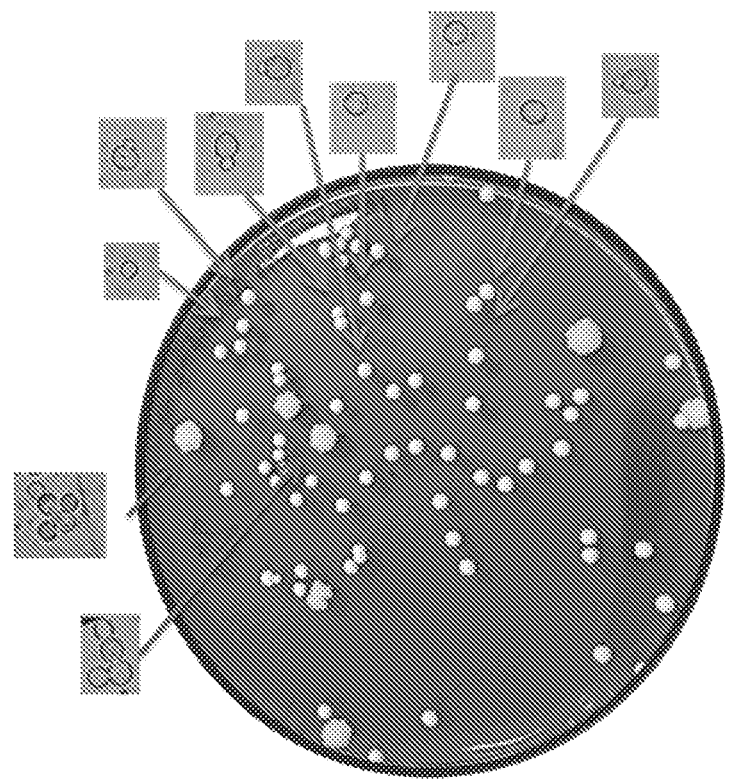
FIGS. 4A to 4C compares the characteristics of yeasts of the rugose and of the smooth phenotype.
Figure 4B:
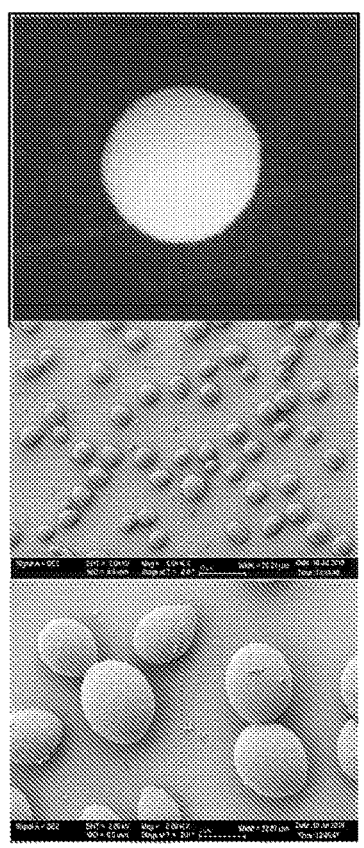
Figure 4C:
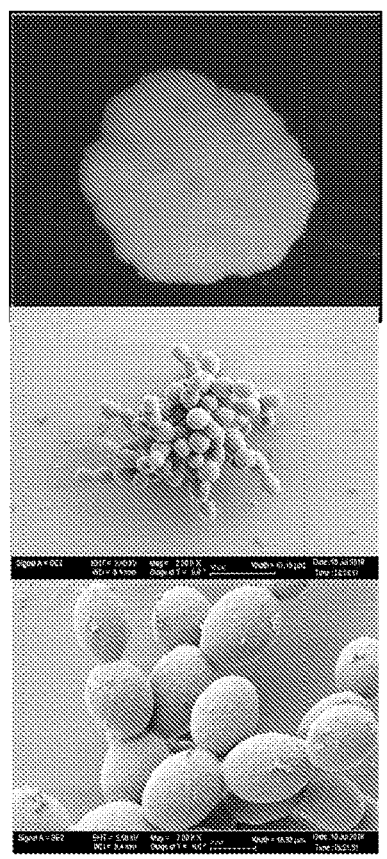

Colonies that appear rugose on a growth plate form clusters of daughter yeast cells still connected to their mother (FIGS. 4A and 4C), while those that are smooth show the typical single cell or the budding morphology typical of S. cerevisiae (FIGS. 4A and 4B). The rugose/smooth phenotype of various commercial wild yeast populations was determined and is provided in Table 2.

TABLE 2

Colony morphology of yeast isolated from various commercial cane fuel ethanol mills

| Sample | % Rugose |
|---|---|
| Mill 1 | 83% |
| Mill 2 | 91% |
| Mill 3 2017 | 90% |
| Mill 3 2018 | 100% |
| Mill 4 | 100% |
| Mill 4 End of season | 100% |
| Mill 5 | 100% |
| Mill 5 End of season | 100% |
| Mill 6 | 100% |
| Mill 6 End of season | 100% |
| Mill 7 | 80% |
| Mill 8 | 98% |
| All Mills | 95% |

Figure 5:
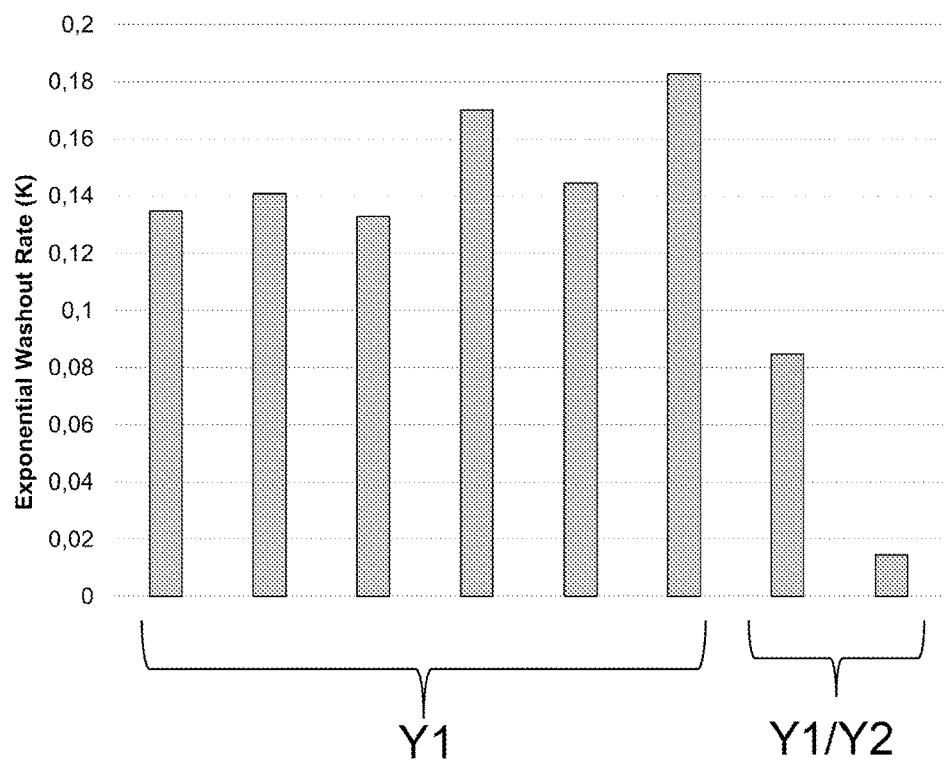
FIG. 5 provides the calculated exponential washout rates at eight commercial ethanol facilities. Strain(s) used to inoculate various facilities (each bar represents a different facility) is/are provided below each bar (Y1 alone, or a combination of Y1 and Y2).

Six commercial scale fermentations of the Y1 strain and two commercial scale fermentation of a 75:25 (weight) mixture of the Y1 and Y2 strains were conducted and the wash-out rates were determined. As shown in FIG. 5, when the rugose strain, Y2, was present, the exponential rate of washout slowed considerably. In one case (facility 7), it decreased by >40%, and in another (facility 8) it decreased by >90%.

Various isolates from the Y1 strain (like the Y2 strain) from the commercial process were found to be rugose after five months in a commercial fed batch fermentation process. Genome sequencing of various rugose isolates was performed to understand how yeasts can change from smooth to rugose during commercial implementations. Out of 53 936 SNPs and 7 273 indels present in the panel of 25 sequenced strains, only 1 SNP and 1 indel (both on a section of Y1 scaffold 6 corresponding to chromosome XII; data not shown) were associated with the rugose phenotype via genome-wide association test ($p=1\times10^{-6}$; data not shown). Both variants on scaffold 6 were nonsynonymous changes that predicted the rugose phenotype: a T→C variant in Choline Kinase (CKI1) converting phenylalanine (TTT) to serine (TCT) at scaffold position 858 413, and a deletion at scaffold position 854 924 causing a translation frameshift in the Activator of CUP1 Expression (ACE2). These two candidate variants may be in linkage disequilibrium due to their close proximity (3 489 bp) and both fall in a distinct region of lost heterozygosity among rugose strains (data not shown). Given the prior functional evidence for ACE2, it is reasonable to assume that the ACE2 deletion was the strongest candidate causal mutation for the rugose phenotype, and the association at the CKI1 SNP is a consequence of proximity.

All the characterized rugose strains were homozygous for a single base pair deletion at base pair 1,112 in the poly-A region of ACE2 (genotype A(7):A(7), SEQ ID NO: 11), causing a translation frameshift and introducing an early stop codon at amino acid residue 389, 21 residues downstream of the deletion (FIG. 6). In comparison, as shown in Table 3, all smooth mill inoculants and isolates were heterozygous for the deletion (retaining one functional copy of ACE2, genotype A(7):A(8)), including Y1 itself, and the wild type parental strain PE-2. In contrast to the smooth industrial mill isolates, neither of two smooth isolates from a laboratory experiment possessed the deletion (homozygous genotype A(8):A(8)).

TABLE 3

Source, phenotype, and ACE2 genotype for smooth and rugose strains sequenced for comparative genomics. A(8) is encoded by the gene having the nucleic acid sequence of SEQ ID NO: 9 and has the amino acid sequence of SEQ ID NO: 10. A(7) is encoded by the gene having the nucleic acid sequence of SEQ ID NO: 11 and has the amino acid sequence of SEQ ID: 12

| Source | Phenotype | Strain designation | ACE2 genotype |
|---|---|---|---|
| Wild type parental strain | Smooth | Y0 | A(7):A(8) |
| Industrial mill inoculants | Smooth | Y1 | A(7):A(8) |
| | Smooth | Y41 | A(7):A(8) |
| | Smooth | Y42 | A(7):A(8) |
| Lab experiment isolates | Smooth | Y43 | A(8):A(8) |
| | Smooth | Y44 | A(8):A(8) |
| | Rugose | Y45 | A(7):A(7) |
| | Rugose | Y46 | A(7):A(7) |
| Surviving mill isolates | Smooth | Y47 | A(7):A(8) |
| | Smooth | Y48 | A(7):A(8) |
| | Smooth | Y49 | A(7):A(8) |
| | Smooth | Y50 | A(7):A(8) |
| | Rugose | Y2 | A(7):A(7) |
| | Rugose | Y51 | A(7):A(7) |
| | Rugose | Y52 | A(7):A(7) |
| | Rugose | Y53 | A(7):A(7) |
| | Rugose | Y54 | A(7):A(7) |
| | Rugose | Y55 | A(7):A(7) |
| | Rugose | Y56 | A(7):A(7) |
| | Rugose | Y57 | A(7):A(7) |
| | Rugose | Y58 | A(7):A(7) |
| | Rugose | Y59 | A(7):A(7) |
| | Rugose | Y60 | A(7):A(7) |
| Contaminant mill isolates | Rugose | Y3 | A(7):A(7) |
| | Rugose | Y39 | A(7):A(7) |

As indicated above, the evaluation of wild contaminating yeasts in the fed batch fermentation process showed that >90% of colonies analyzed were rugose (Table 3) suggesting that the rugose morphology provides an advantage during the fermentation process.

Figure 7:
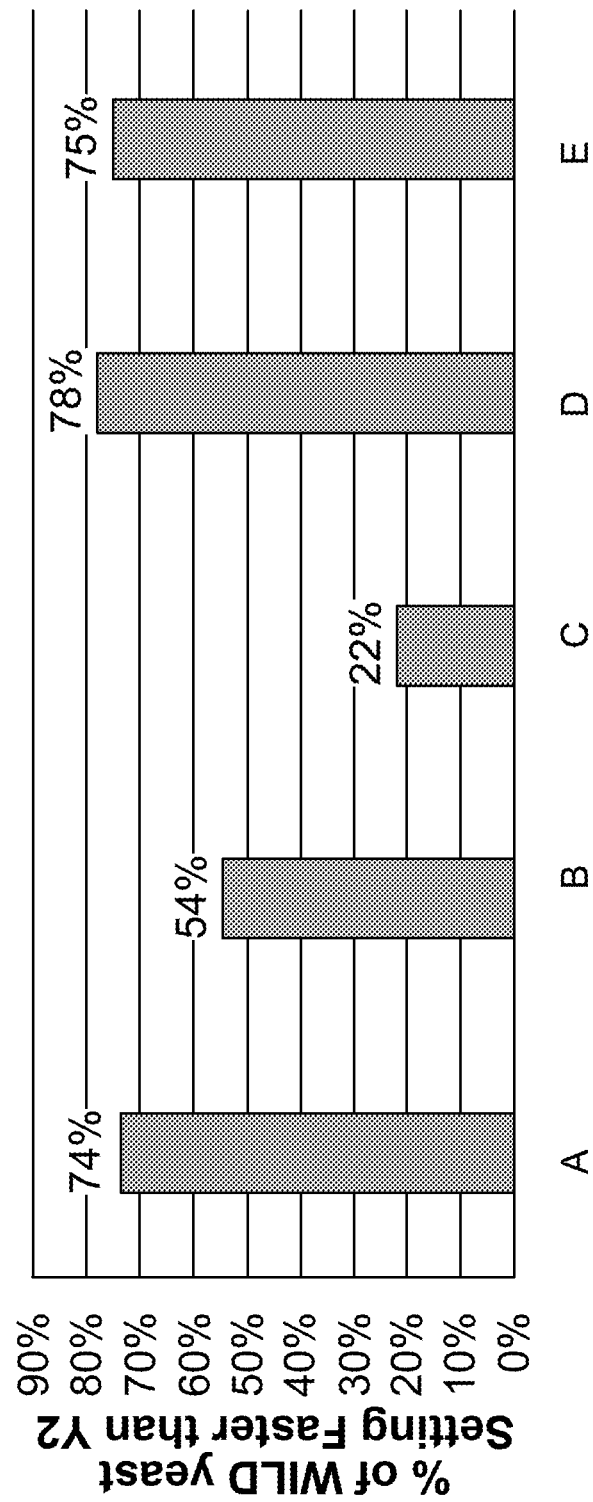
FIG. 7 provides the sedimentation of various isolates from commercial mills. Yeasts were isolated from five different mills and tested for their sedimentation in a liquid assay measuring the change in $OD_{600}$ in 5 minutes of settling. Results are shown as the percent of the wild yeast settling faster than strain Y2.

In addition, it was noted that the majority of yeasts in the mills were also extremely fast settling (e.g., fast sedimentation) when isolated and tested in a liquid settling assay (FIG. 7). The settling rate was maintained in the yeast even over 100 generations of passaging in rich glucose media showing that this is a stable feature of these mill yeasts (data not shown). Ninety (90) yeasts from various mills were tested in sedimentation and while all were fast settling, as expected due to their rugose phenotype, the majority at most mills settling even faster than the Y2 rugose natural isolate (data not shown).

Figure 8:
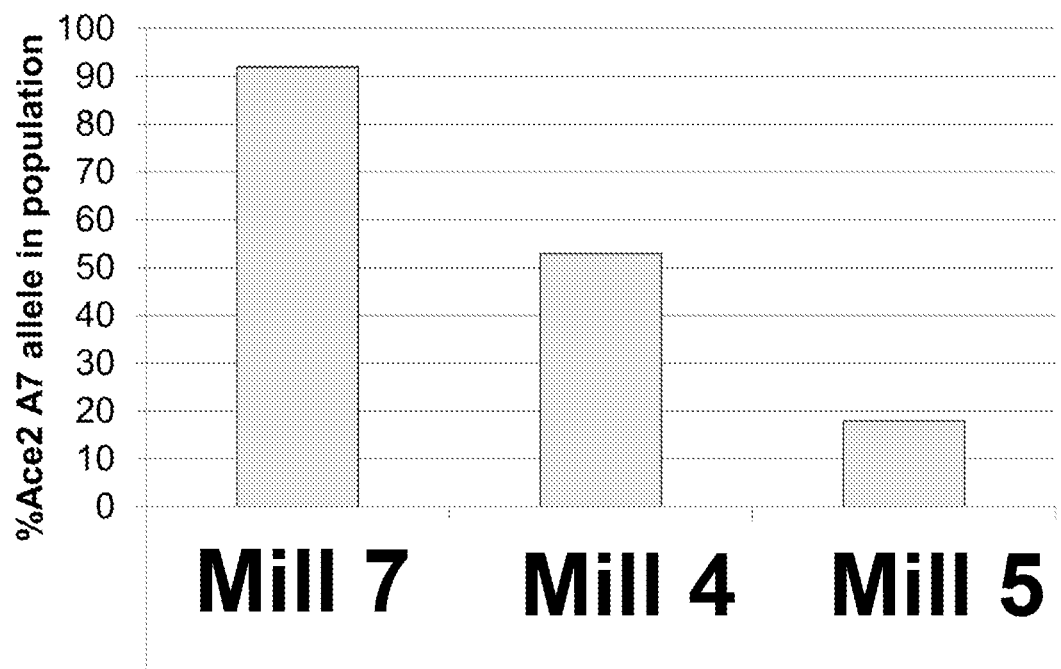
FIG. 8 provides the percentage of the A7 ACE2 mutation in three different commercial wild yeast populations (e.g., Mill 7, Mille 4 and Mill 5). Results are shown as the percentage of the A7 allele in the wild yeast population.

Additionally, when the wild population was analyzed for mutations in the ACE2 gene, it was found that there was a high percentage of the truncated Ace2, 7 A poly A tract, allele in the mill populations (FIG. 8).

Other mutations in the ACE2 gene were also identified amongst the wild yeasts that, similar to the A8 to A7, cause a premature stop codon. These mutations (presented in Table 4) can be seen in the wild population as shown in Table 5.

TABLE 4

Mutations observed in the ACE2 gene

| Mutation location in genome | Nucleotide location in Ace2 | Effect of mutation on ACE2 polypeptide | Amino acid sequence |
|---|---|---|---|
| 385, 423-385, 424: A6 > A7 insertion | 549 | Stop codon position at 169 | MDNVVDPWYINPSGFAKDTQDEEYVQHHDNVNPTIPPPDN YILNNENDDGLDNLLGMDYYNIDDLLTQELRDLDIPLVPS PKTGDGSSDKKNIDRTWNLGDENNKVSHYSKKSMSSHKRG LSGTAIFGFLGHNKTLSISSLQQSILNMSKDPQPMELINE LGNHNTVKK (SEQ ID NO: 13) |
| 385, 379: A4 > A3 deletion | 551 | Stop codon at position 186 | MDNVVDPWYINPSGFAKDTQDEEYVQHHDNVNPTIPPPDN YILNNENDDGLDNLLGMDYYNIDDLLTQELRDLDIPLVPS PKTGDGSSDKKNIDRTWNLGDENNKVSHYSKKSMSSHKRG LSGTAIFGFLGHNKTLSISSLQQSILNMSKDPQPMELINE LGNHNTVKNNNDDFDHIRENDGEIAI (SEQ ID NO: 14) |
| 385, 358: T4 > T3 deletion | 572 | Stop codon at position 191 | MDNVVDPWYINPSGFAKDTQDEEYVQHHDNVNPTIPPPDN YILNNENDDGLDNLLGMDYYNIDDLLTQELRDLDIPLVPS PKTGDGSSDKKNIDRTWNLGDENNKVSHYSKKSMSSHKRG LSGTAIFGFLGHNKTLSISSLQQSILNMSKDPQPMELINE LGNHNTVKNNNDDFDHIRENDGENSYLSQVC (SEQ ID NO: 15) |
| 384, 818: A8 > A7 deletion | 1112 | Stop codon position 389 | MDNVVDPWYINPSGFAKDTQDEEYVQHHDNVNPTIPPPDN YILNNENDDGLDNLLGMDYYNIDDLLTQELRDLDIPLVPS PKTGDGSSDKKNIDRTWNLGDENNKVSHYSKKSMSSHKRG LSGTAIFGFLGHNKTLSISSLQQSILNMSKDPQPMELINE LGNHNTVKNNNDDFDHIRENDGENSYLSQVLLKQQEELRI ALEKQKEVNEKLEKQLRDNQIQQEKLRKVLEEQEEVAQKL VSGATNSNSKPGSPVILKTPAMQNGRMKDNAIIVTTNSAN GGYQFPPPTLISPRMSNTSINGSPSRKYHRQRYPNKSPES NGLNLFSSNSGYLRDSELLSFSPQNYNLNLDGLTYNDHNN TSDKNNNDKKIVLVITYSVCSKRLPRVG (SEQ ID NO: 16) |

TABLE 5

Percentage of ACE2 mutants observed in wild populations. A = % of contaminating cells, B = % of products, C = % of Y1, D = % of Y2, E = % ACE2 A7 @384,818, F = % ACE2 T3 @385,358, G = % ACE2 A3 @385,379, H = % ACE2 A7 @385,423

| Sample | A | B | C | D | E | F | G | H |
|---|---|---|---|---|---|---|---|---|
| 1 | 0 | 100 | 100 | 0 | 49 | | | |
| 2 | 0 | 100 | 100 | 0 | 52 | | | |
| 3 | 0 | 100 | 100 | 0 | 52 | | | |
| 4 | 0 | 100 | 100 | 0 | 30 | | | |
| 5 | 0 | 100 | 100 | 0 | 57 | | | |
| 6 | 0 | 100 | 100 | 0 | 49 | | | |
| 7 | 0 | 100 | 100 | 0 | 47 | | | |
| 8 | 0 | 100 | 100 | 0 | 50 | | | |
| 9 | 0 | 100 | 100 | 0 | 62 | | | |
| 10 | 1 | 99 | 99 | 0 | 46 | | | |
| 11 | 1 | 99 | 99 | 0 | 50 | | | |
| 12 | 43 | 57 | 57 | 0 | 40 | | | |
| 13 | 94 | 6 | 6 | 0 | 64 | | | |
| 14 | 94 | 6 | 6 | 0 | 60 | | | |
| 15 | 19 | 81 | 81 | 0 | 46 | | | |
| 16 | 58 | 42 | 42 | 0 | 29 | | | |
| 17 | 0 | 100 | 74 | 26 | 60 | | | |
| 18 | 0 | 100 | 100 | 0 | 51 | | | |
| 19 | 0 | 100 | 86 | 14 | 62 | | | |
| 20 | 0 | 100 | 96 | 4 | 58 | | | |
| 21 | 0 | 100 | 86 | 14 | 71 | | | |
| 22 | 0 | 100 | 72 | 28 | 65 | | | |
| 23 | 0 | 100 | 76 | 24 | 65 | | | |
| 24 | 0 | 100 | 67 | 32 | 71 | 0 | 0 | 0 |
| 25 | 3 | 97 | 64 | 33 | 71 | 0 | 0 | 0 |
| 26 | 33 | 67 | 40 | 27 | 41 | 0 | 11 | 14 |
| 27 | 85 | 15 | 11 | 5 | 12 | 0 | 21 | 51 |
| 28 | 94 | 6 | 6 | 0 | 3 | 0 | 28 | 70 |
| 29 | 88 | 12 | 12 | 0 | 92 | | | |
| 30 | 99 | 1 | 1 | 0 | 35 | 0 | 10 | 0 |

TABLE 5-continued

Percentage of ACE2 mutants observed in wild populations. A = % of contaminating cells, B = % of products, C = % of Y1, D = % of Y2, E = % ACE2 A7 @384,818, F = % ACE2 T3 @385,358, G = % ACE2 A3 @385,379, H = % ACE2 A7 @385,423

| Sample | A | B | C | D | E | F | G | H |
|---|---|---|---|---|---|---|---|---|
| 31 | 0 | 100 | 78 | 22 | 64 | 0 | 0 | 0 |
| 32 | 0 | 100 | 64 | 36 | 68 | | | |
| 33 | 0 | 100 | 96 | 4 | 64 | | | |
| 34 | 0 | 100 | 66 | 34 | 76 | | | |
| 35 | 0 | 100 | 100 | 0 | 72 | | | |
| 36 | 0 | 100 | 80 | 20 | 54 | | | |
| 37 | 0 | 100 | 76 | 24 | 66 | | | |
| 38 | 0 | 100 | 80 | 20 | 66 | | | |
| 39 | 0 | 100 | 84 | 16 | 62 | | | |
| 40 | 0 | 100 | 74 | 26 | 70 | | | |
| 41 | 0 | 100 | 74 | 26 | 61 | | | |
| 42 | 0 | 100 | 80 | 20 | 70 | | | |
| 43 | 0 | 100 | 72 | 28 | 72 | | | |
| 44 | 0 | 100 | 92 | 8 | 71 | | | |
| 45 | 0 | 100 | 80 | 20 | 68 | 0 | 0 | 0 |
| 46 | 0 | 100 | 66 | 34 | 64 | 0 | 0 | 0 |
| 47 | 0 | 100 | 74 | 26 | 59 | 0 | 0 | 0 |
| 48 | 0 | 100 | 68 | 32 | 63 | 0 | 0 | 0 |
| 49 | 1 | 99 | 64 | 35 | 68 | 0 | 0 | 0 |
| 50 | 97 | 3 | 3 | 0 | 53 | | | |
| 51 | 99 | 1 | 1 | 0 | 55 | 23 | 28 | 0 |
| 52 | 96 | 4 | 4 | 0 | 18 | | | |
| 53 | 98 | 2 | 2 | 0 | 20 | 0 | 85 | 0 |
| 54 | 89 | 11 | 4 | 7 | 40 | | | |
| 56 | 99 | 1 | 1 | 0 | 16 | 0 | 82 | 0 |
| 57 | 7 | 93 | 90 | 3 | 39 | | | |
| 58 | 97 | 3 | 3 | 0 | 40 | | | |

Figure 9:
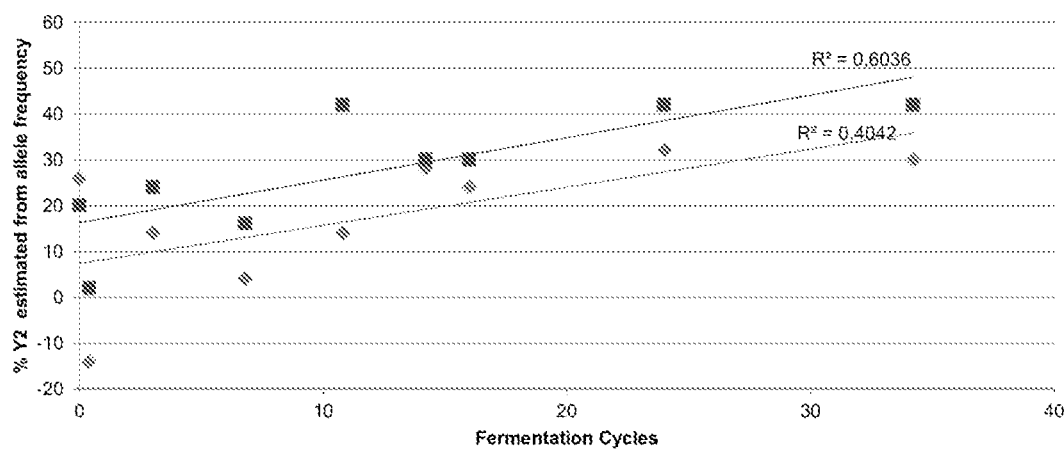
FIG. 9 shows the increase of the concentration of strain Y2 during a commercial implementation. Results are shown as the percentage of strain Y2 (estimated from the determination of allele frequency) in function of the number of fermentation cycle based on the estimation of the CDA1-2 allele (♦) or the ACE2-A7 allele (■).

The Y1 strain was run in co-inoculation with Y2 (at a 75:25 ratio) at commercial scale to determine if selection of the Y2 strain occurred in a commercial process. DNA was extracted from particular fermentation cycles throughout the implementation test and Illumina sequenced (2×126 bp read data; short reads of all DNA present). Read data was processed and aligned against the Y0 (e.g., PE-2) reference genome, computing read coverage across the genome and calling variants from each alignment. The relative abundance was determined for Y1 vs. Y2 in co-pitched fermentations. Tracking of two alleles that are present at higher levels in the Y2 background (cda1-2 A:A and Ace2 A7:A7) allowed to estimate if Y2 was increasing relative to Y1. During the implementation the level of Y2 as reported by the CDA1-2 A and Ace2 A7 alleles increase by ~2-fold over the 30 cycles of the commercial test (FIG. 9).

Invertase Activity

The acid treatment in the fed batch fermentation process is typically run at pH 2-3. After acid treatment sugarcane must is fed to the fermentation over 3-8 hours which buffers the pH of the fermentation. A typical fermentation starts at pH 2-3 and ends with a pH of 4-5.5 depending on the buffering capacity of the fed must. Sucrose is the predominate sugar in must and needs to be hydrolyzed by yeast expressed invertase to glucose and fructose. The typical pH optimum for S. cerevisiae invertase ranges over 3.5-5. It was determined if strains with increased invertase activity in the process could be more competitive. Without wishing to be bound to theory, increased invertase activity could provide an advantage during the first few hours of feeding when the pH is low coming out of acid treatment. The improved invertase activity could be derived from expressing an enzyme that has higher activity at lower pH, expressing and/or secreting higher level of an invertase (which may be more acid stable).

Invertase activity of 75 yeast isolates from a commercial mill was measured on YPD and commercial must after 48 hours of anaerobic growth. Invertase activity was measured by mixing cells and supernatant with a 40 g/L sucrose solution at pH 5 and incubated at 32° C. for 12 minutes and reducing sugar was determined using DNS and monitored by $OD_{540}$. In Table 6, the average fold increase in invertase activity vs. Y0 is ~12 fold higher on either YPD or must.

TABLE 6

Invertase activity of 75 isolates from a commercial mill compared to commercial strain Y0.

| | fold difference in invertase activity from Y0 |
|---|---|
| YPD anaerobic | 13.8 |
| Must anaerobic | 12.0 |

The invertase activity was also measured for two mill isolates on a variety of substrates after 48 h of anaerobic growth compared to yeast samples taken from the end of 15 cycles of acid treatment and fermentation. The mill isolated yeasts had invertase activity on all media tested but drastically higher activity when the activity is tested on cells directly out of the fed-batch process (Table 7).

TABLE 7

Fold change in invertase activity of engineered wild yeast vs. Y0 on various media

| | YPD | YPS | YPF | Commercial Must 1 | Commercial Must 2 | Commercial Must 3 | 15 cycles in cell recycle system |
|---|---|---|---|---|---|---|---|
| Y4 | 2.0 | 2.6 | 2.6 | 1.8 | 2.2 | 1.7 | 11.8 |
| Y6 | 2.3 | 2.5 | 2.9 | 1.9 | 2.5 | 1.7 | 7.0 |

Figure 10A:
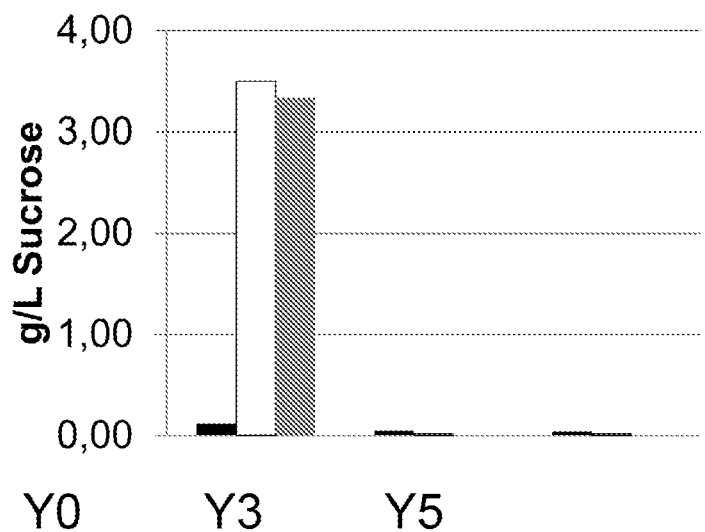
FIGS. 10A and 10B show the results of strains fermented in a cell recycle process with acid wash at 33.5° C. for 10 hours with a 7 hour feed of industrially sourced must.
Figure 10B:
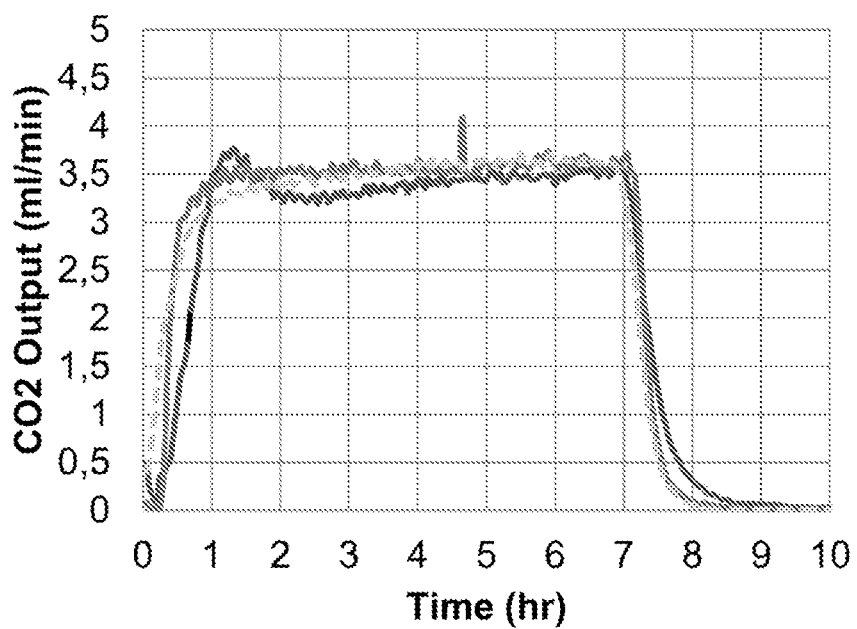

This higher level of invertase was reflected in the faster hydrolysis of sucrose of strains Y3 and Y5 during a fed-batch sucrose fermentation compared to the Y0 strain (FIG. 10A). Faster sucrose hydrolysis allowed strains Y3 and Y5 to ferment faster than strain Y0 as seen by the faster production of ethanol (FIG. 10B).

Figure 19:
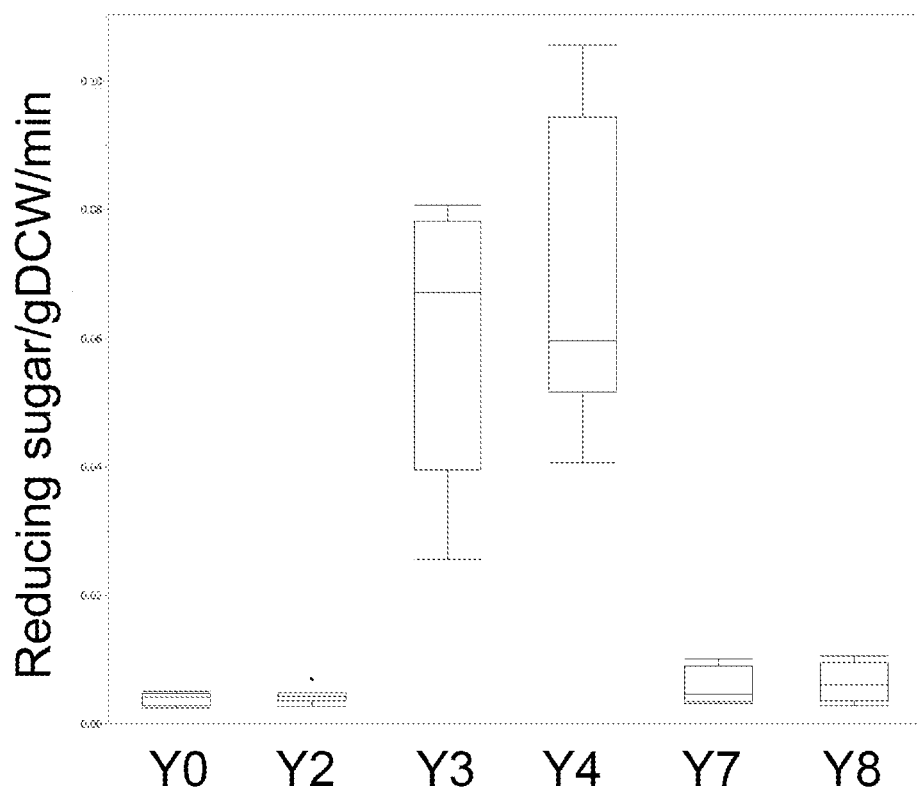
FIG. 19 provides the amount of reducing sugar per gram of dry cell weight (gDCW) per minute for yeast strains Y0, Y2, Y3, Y4, Y7 or Y8 on commercial must. The horizontal line within the box represents the median sample value. The ends of the box represent the $25^{th}$ and $75^{th}$ quantiles, also expressed as the $1^{st}$ and $3^{rd}$ quartile, respectively. The difference between the $1^{st}$ and $3^{rd}$ quartiles is referred to as the interquartile range. The whiskers extend from the ends of the box to the outermost data point that falls within the distances computed as follows: $1^{st}$ quartile−1.5*(interquartile range) and $3^{rd}$ quartile+1.5*(interquartile range). If the data points do not reach the computed ranges, then the whiskers are determined by the upper and lower data point values (not including outliers).

The rate of invertase activity associated with strains Y0, Y2, Y3, Y4, Y7 and Y8 (as the amount of reducing sugar/dry cell weight per minute) was determined on commercial must and is shown on FIG. 19 as a box and whisker plot obtained using the JMP software.

The rate of invertse activity associated with Y61 was determined to be equal to or higher than its parental strain Y3.

RAS/cAMP/PKA Activity

Strains showing normal RAS/cAMP/PKA activity (Y0 and Y1) and strains showing hyperactivated RAS/cAMP activity (Y9, Y10, Y11 and Y12) were tested on media containing 2-deoxyglucose and rapamycin. As shown in FIGS. 11B and 11C, the strains exhibiting hyperactivated Ras/cAMP activity were less sensitive to these compounds (which perturb glucose and nitrogen sensing in yeast). Without wishing to be bound to theory, these results suggests that the strains may have differential regulation of the RAS/cAMP/PKA pathway which provide them with a growth.

The ability of strains Y0, Y3 and Y13 to modulate their cAMP production was measured before and after (5 min) a 100 mM glucose spike. As shown in Table 8, strains Y3 and Y13 were not able to produce as much cAMP as strain Y0 (which does not exhibit an increase in the signaling on the RAS/cAMP/PKA pathway).

TABLE 8 cAMP production following glucose spike

| Strain | cAMP levels in basal medium | cAMP levels 5 min after a 100 mM glucose spike | Fold increase in cAMP level at 5 min following glucose spike | % change in fold increase when compared to Y0 |
|---|---|---|---|---|
| Y0 | 162.592 | 272.416 | 1.7 | N. A. |
| Y3 | 141.108 | 178.044 | 1.3 | −25% |
| Y13 | 182.816 | 155.808 | 0.9 | −49% |

The RAS/cAMP/PKA activity was specifically measured for recombinant strain Y1 as well as wild yeast strains Y3 and Y13. Strain Y1 showed almost 2 fold increase in cAMP production upon glucose spike showing a typical upregulation of the cAMP/PKA pathway (FIG. 12). Two commercial isolates, Y3 and Y13 showed no cAMP spike after the addition of glucose. This suggests that the cAMP pathway is hyperactive even at a basal state in strains Y3 and Y13.

Yeast cream samples were taken from various commercial mills (from which the Y3 and Y13 isolates were obtained) and Illumina sequencing was performed on the mixed commercial samples. The sequence of genes involved in the cAMP/PKA pathway were analyzed and a homozygous IRA2 Lys:Lys 2440/3079 at position was identified that differed from the beginning of the season where the strains were homozygous Glu:Glu (Table 9) The prevalence of this mutation in various mills suggested an adaptive advantage. Consistent with the IRA2 Lys mutation in these strain leading to derepression cAMP/PKA pathway.

TABLE 9

IRA2 mutations observed in wild populations.
A = % of contaminating cells, B = % of products, C = % of Y1,
D = % of Y2, E = % cells expressing the CDA1/2 A allele and
F = % of cells expressing an homozygous Lys:Lys mutation at
positions 2440 and 3079. The sample presented in this table
correspond to the samples presented in Table 5.

| Sample | A | B | C | D | E | F |
|---|---|---|---|---|---|---|
| 1 | 0 | 100 | 100 | 0 | 53 | 0 |
| 2 | 0 | 100 | 100 | 0 | 42 | 0 |
| 3 | 0 | 100 | 100 | 0 | 57 | 0 |
| 4 | 0 | 100 | 100 | 0 | 45 | 0 |
| 5 | 0 | 100 | 100 | 0 | 47 | 0 |
| 6 | 0 | 100 | 100 | 0 | 56 | 0 |
| 7 | 0 | 100 | 100 | 0 | 51 | 0 |
| 8 | 0 | 100 | 100 | 0 | 51 | 0 |
| 9 | 0 | 100 | 100 | 0 | 56 | 0 |
| 10 | 1 | 99 | 99 | 0 | 47 | 0 |
| 11 | 1 | 99 | 99 | 0 | 65 | 0 |
| 12 | 43 | 57 | 57 | 0 | 23 | 21 |
| 13 | 94 | 6 | 6 | 0 | 9 | 61 |
| 14 | 94 | 6 | 6 | 0 | 0 | 66 |
| 15 | 19 | 81 | 81 | 0 | 0 | 17 |
| 16 | 58 | 42 | 42 | 0 | 0 | 48 |
| 17 | 0 | 100 | 74 | 26 | 63 | 0 |
| 18 | 0 | 100 | 100 | 0 | 43 | 0 |
| 19 | 0 | 100 | 86 | 14 | 57 | 0 |
| 20 | 0 | 100 | 96 | 4 | 52 | 0 |
| 21 | 0 | 100 | 86 | 14 | 57 | 0 |
| 22 | 0 | 100 | 72 | 28 | 64 | 0 |
| 23 | 0 | 100 | 76 | 24 | 62 | 0 |
| 24 | 0 | 100 | 67 | 32 | 66 | 0 |
| 25 | 3 | 97 | 64 | 33 | 65 | 0 |
| 26 | 33 | 67 | 40 | 27 | 47 | 33 |
| 27 | 85 | 15 | 11 | 5 | 10 | 79 |
| 28 | 94 | 6 | 6 | 0 | 0 | 93 |
| 29 | 88 | 12 | 12 | 0 | 0 | 96 |
| 30 | 99 | 1 | 1 | 0 | 0 | 68 |
| 31 | 0 | 100 | 78 | 22 | 61 | 0 |
| 32 | 0 | 100 | 64 | 36 | 68 | 0 |
| 33 | 0 | 100 | 96 | 4 | 52 | 0 |
| 34 | 0 | 100 | 66 | 34 | 67 | 0 |
| 35 | 0 | 100 | 100 | 0 | 47 | 0 |
| 36 | 0 | 100 | 80 | 20 | 60 | 0 |
| 37 | 0 | 100 | 76 | 24 | 62 | 0 |
| 38 | 0 | 100 | 80 | 20 | 60 | 0 |
| 39 | 0 | 100 | 84 | 16 | 58 | 0 |
| 40 | 0 | 100 | 74 | 26 | 63 | 0 |
| 41 | 0 | 100 | 74 | 26 | 63 | 0 |
| 42 | 0 | 100 | 80 | 20 | 60 | 0 |
| 43 | 0 | 100 | 72 | 28 | 64 | 0 |
| 44 | 0 | 100 | 92 | 8 | 54 | 0 |
| 45 | 0 | 100 | 80 | 20 | 60 | 0 |
| 46 | 0 | 100 | 66 | 34 | 67 | 0 |
| 47 | 0 | 100 | 74 | 26 | 63 | 0 |
| 48 | 0 | 100 | 68 | 32 | 66 | 0 |
| 49 | 1 | 99 | 64 | 35 | 67 | 0 |
| 50 | 97 | 3 | 3 | 0 | 0 | 100 |
| 51 | 99 | 1 | 1 | 0 | 0 | 100 |
| 52 | 96 | 4 | 4 | 0 | 0 | 78 |
| 53 | 98 | 2 | 2 | 0 | 0 | 89 |
| 54 | 89 | 11 | 4 | 7 | 9 | 49 |
| 56 | 99 | 1 | 1 | 0 | 0 | 65 |
| 57 | 7 | 93 | 90 | 3 | 48 | 0 |
| 58 | 97 | 3 | 3 | 0 | 0 | |

Figure 13:
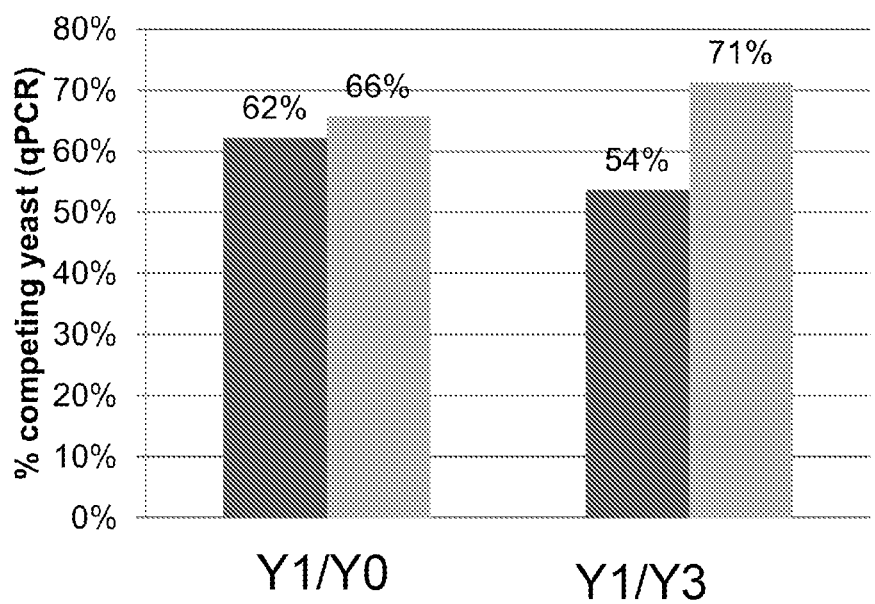
FIG. 13 shows the population monitoring of co-cultures in a lab scale cell recycling process. Results are shown as the percentage of competing yeasts (as measure by qPCR) for two different yeast strain populations (Y1/Y0 and Y1/Y3) prior to (dark grey bars) and after three recycling cycles (light gray bars).

Strain Y1 was admixed with strain Y0 or a commercial isolate bearing a IRA Lys mutation, Y3 (ratio is provided on FIG. 13). As shown on FIG. 13, isolate Y3 rapidly outcompeted Y1 in three cycles of the fed-batch lab scale system rising from 54% to 71% of the population demonstrating the competitive advantage of the wild yeast.

Triploid Phenotype

Figure 14A:
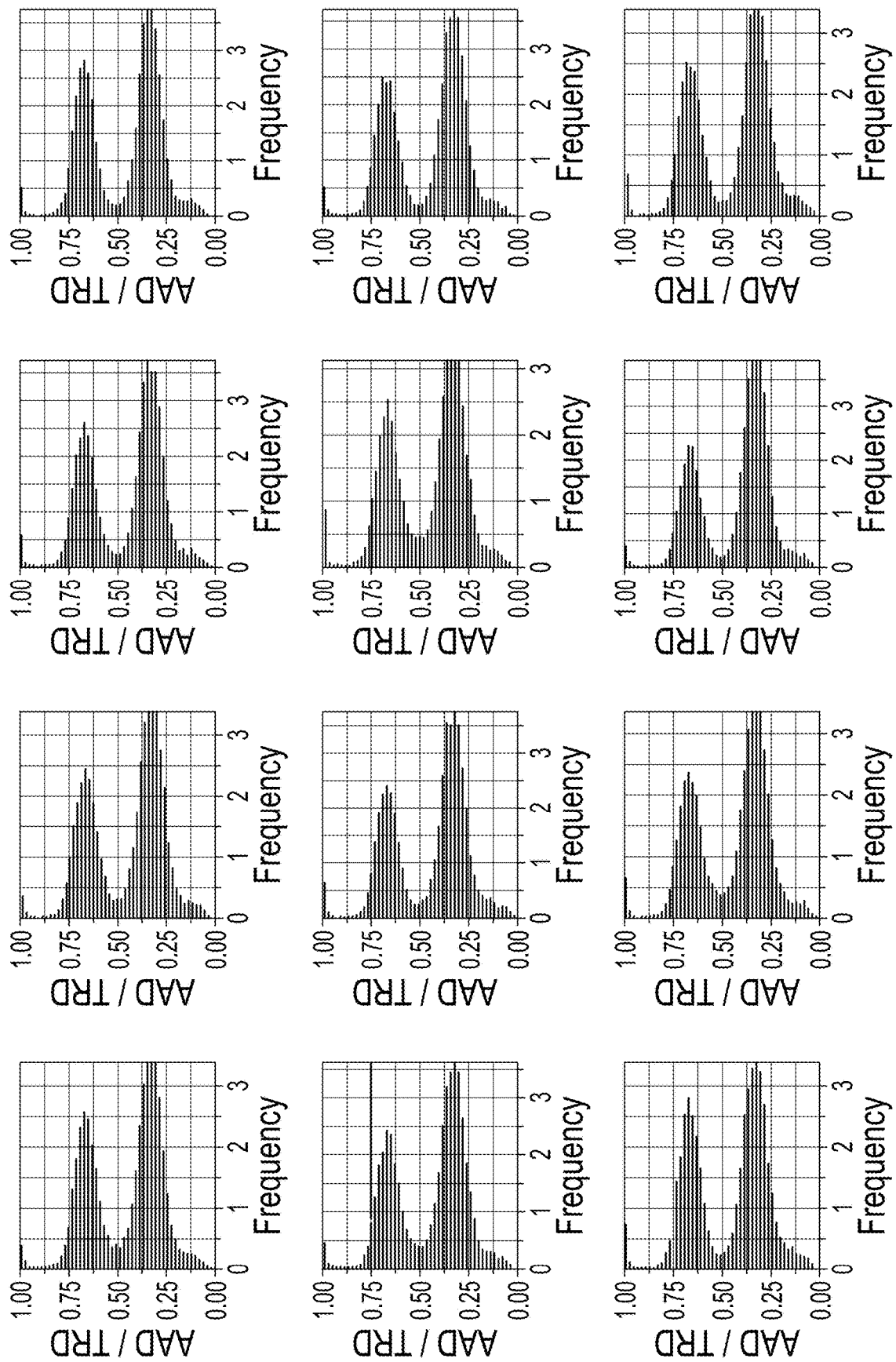
FIGS. 14A to 14C show the strain ploidy of wild yeast isolates from commercial cane ethanol facilities. Results are shown as the ratio of the alternate allele depth/total read region in function of frequency. Boxes highlight the triploid strains. Diploids are not boxed. Results are shown for the following strains (left to right, top to bottom).
Figure 14B:
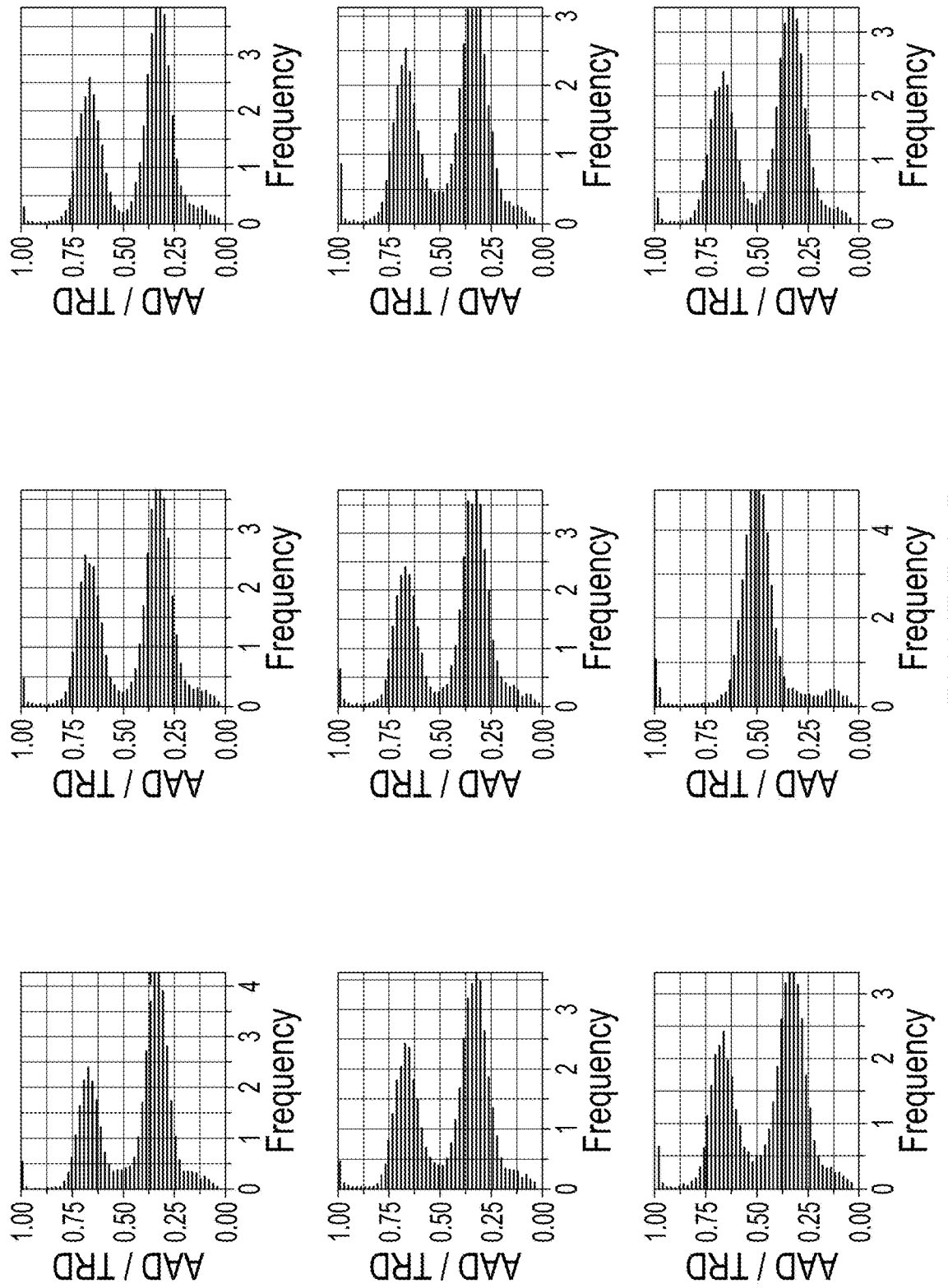
Figure 14C:
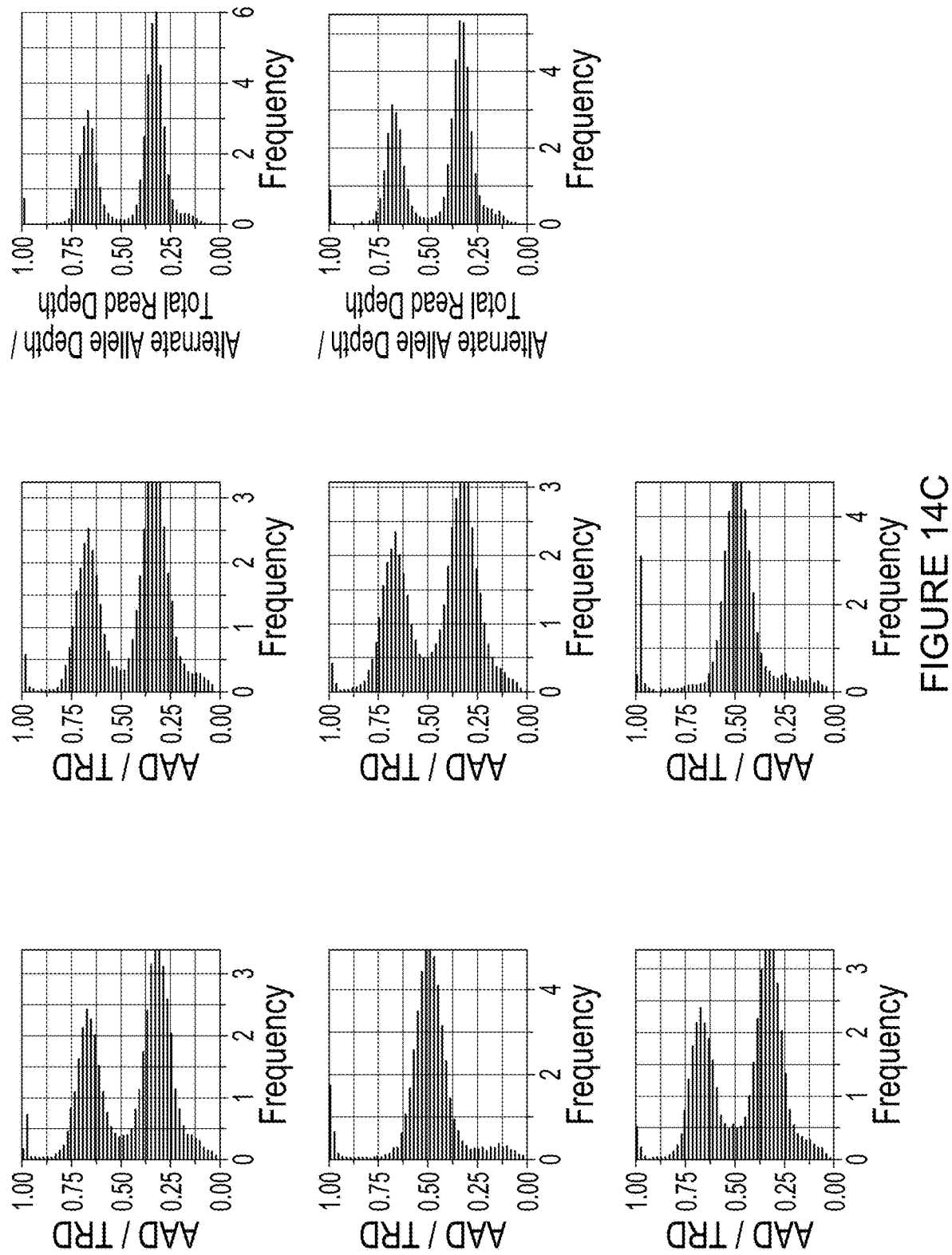

Various commercial and contaminating yeasts from mills were isolated and sequenced by Illumina sequencing. While each of the available commercial strains were found to be highly heterozygous diploid (data not shown), the majority of the strains isolated from the fermentation process in the end of the season were found to be highly heterozygous triploids (3n) (FIG. 14).

Recombinant Yeast Expressing Heterologous STL1

Figure 15:
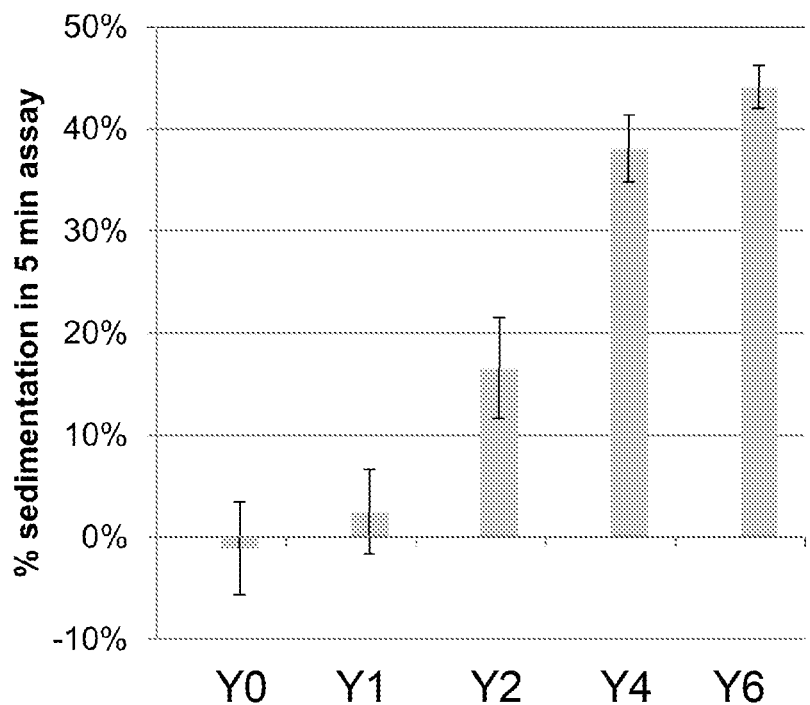
FIG. 15 compares the sedimentation rate of various yeast strains. Results are shown as the percentage of sedimentation in function of the yeast strain tested (Y0, Y1, Y2, Y4 or Y6).

Strains Y4, Y6 and Y61 were genetically engineer to express the STL1 polypeptide. Briefly, two parental yeast strains (Y3 and Y5) isolated from the fed batch process with the dominant features of rugose colony formation, fast settling, high invertase activity post-acid treatment, triploid and features of cAMP/PKA hyperactivation were selected. These parental strains were then engineered with additional copies of STL1 to reduce glycerol and increase ethanol yields (see Table 1). After engineering, the strains were tested and demonstrated that they maintained the characteristics that they were chosen for fast settling (FIG. 15 for Y4 and Y6), hyperactivation of the RAS/cAMP pathway (data not shown) and high invertase activity (data not shown).

Figure 16A:
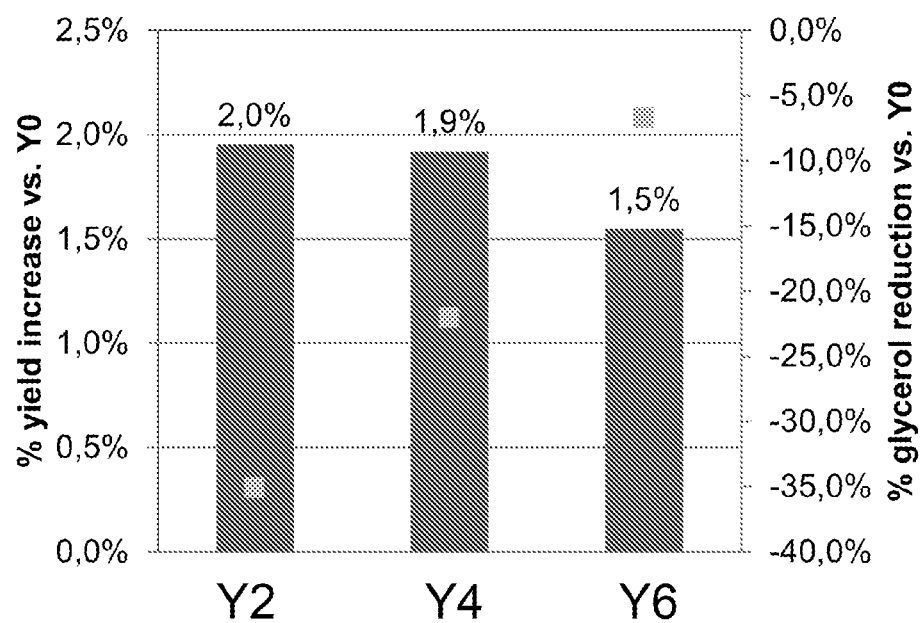
FIGS. 16A and 16B provide the yield increase and kinetics of engineered yeasts with persistence traits. Y0, Y2, Y4 and Y6 were recycled for 13 cycles of acid treatment and fermentation on commercial must.
Figure 16B:
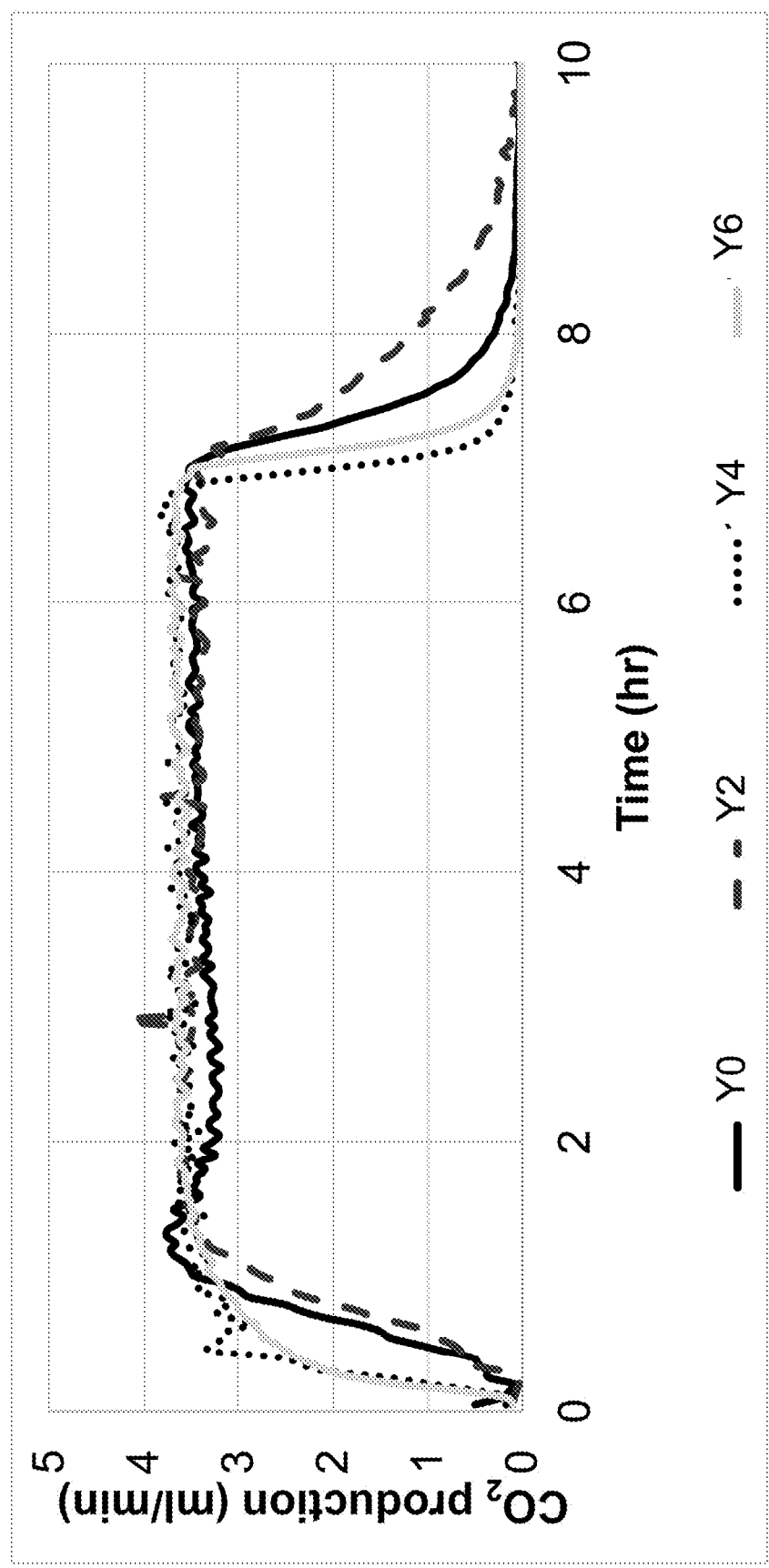

The performance of strains Y4 and Y6 was then monitored in a fed-batch high cell density fermentation with acid recycle for 13 rounds of fermentation. Over the 13 cycles, the yield of ethanol and glycerol were compared to the conventional strain Y0 and achieved a 1.9% yield increase for Y4 and a 1.5% yield increase for Y6 (FIG. 16A). These yield were close to the corresponding Y0-based strain (Y2) that is engineered and achieved a 1.9% yield increase over Y0. In addition, faster kinetics was maintained for strains Y4 and Y6 after engineering (FIG. 16B).

Figure 17A:
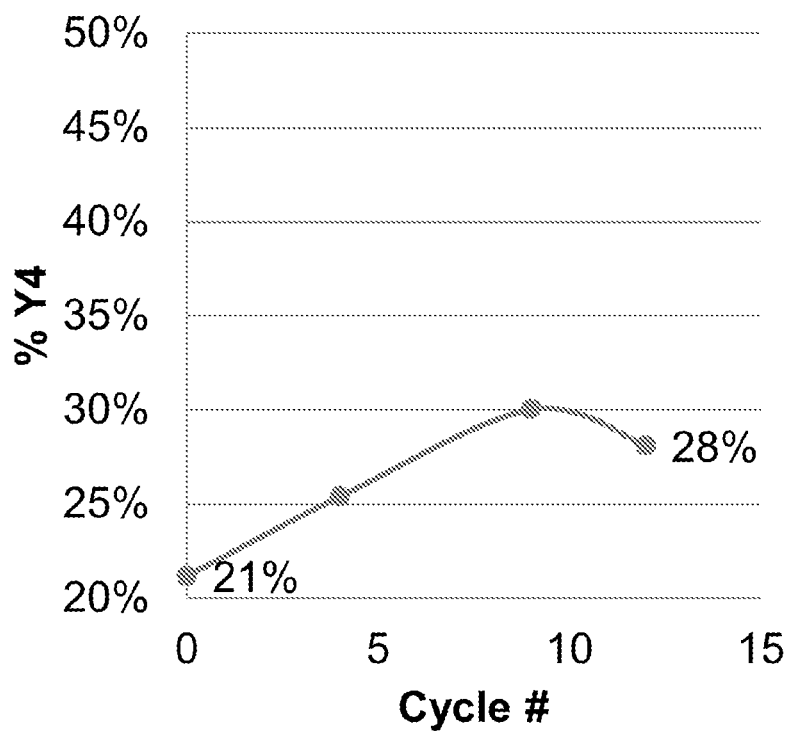
FIGS. 17A and 17B provide the population tracking of yeast strains Y2 compared with (FIG. 17A) Y4 or (FIG. 17B) Y6 over 13 cycles of acid treatment and fermentation. Results are shown as the percentage of the yeast strain in function of the number of cycles.
Figure 17B:
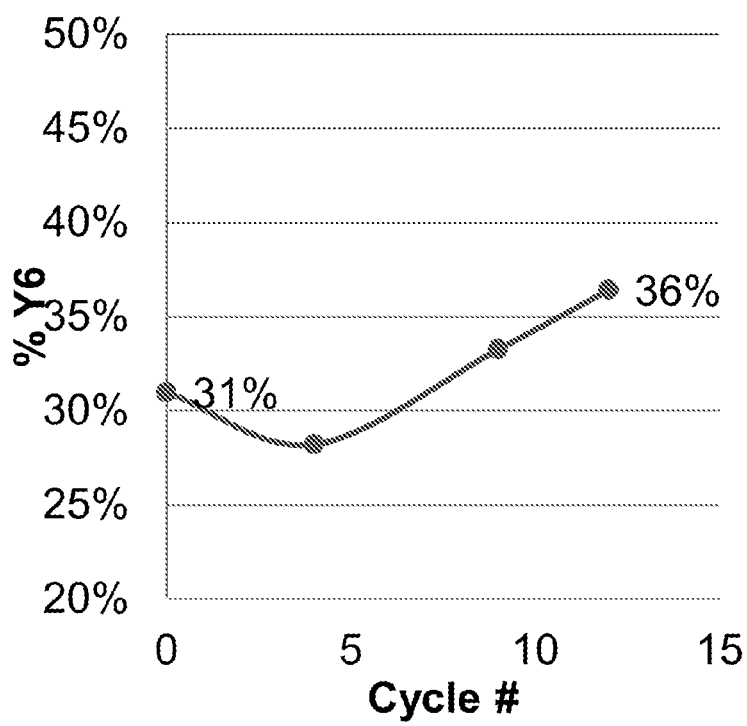

The strains Y4 and Y6 were then mixed in co-culture with Y2 to determine if they had growth advantage in co-culture and could displace the Y2 strain. A mixture of 20% Y4 to 80% Y2 and 30% Y6 to 70% Y2 were co-fermented in the fed-batch system with acid recycle. Populations were monitored using the qPCR method described above. Over the course of the 13 cycles of fermentation, both Y4 and Y6 increased within the population at an average of about 0.5% per cycle demonstrating their competitive fitness and growth advantage in this type of fermentation process (FIGS. 17A and 17B).

Figure 20A:
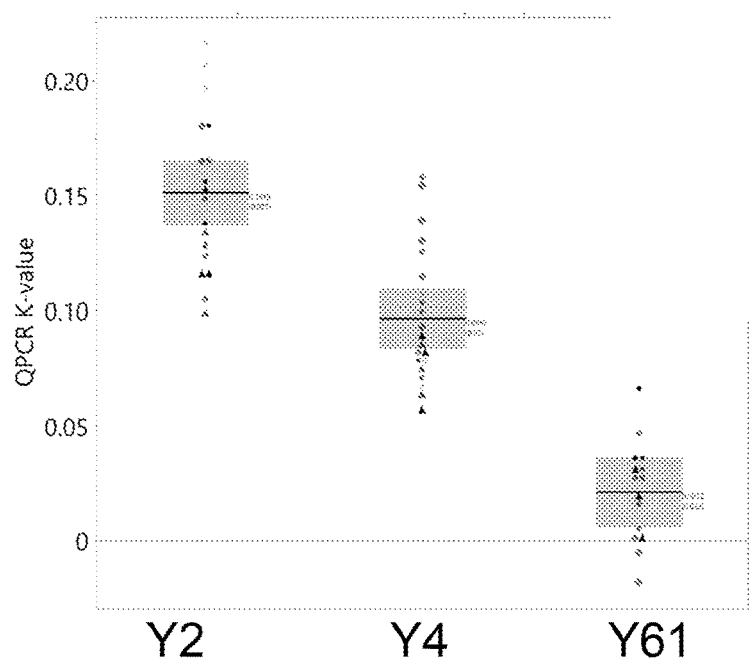
FIGS. 20A and 20B compare the performances of yeast strains Y2, Y4 and Y61 during multiple rounds of cocultures.
Figure 20B:
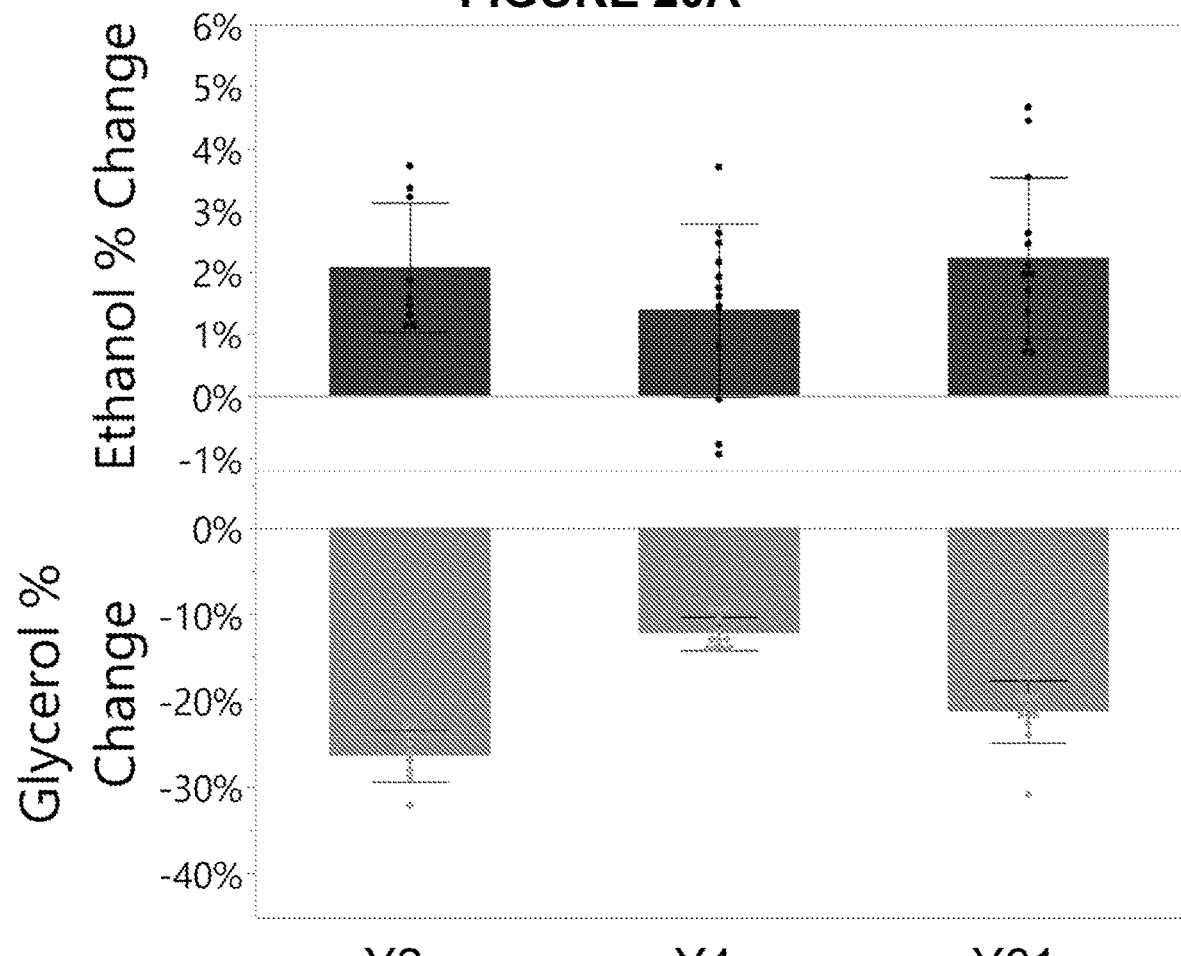

The performance of strain Y61 was monitored in co-culture fermentation experiments with strain Y3 on seven different commercial substrates and compared to the performances of strains Y2 or Y4 also in co-culture fermentation experiments with Y3. Populations were monitored using the qPCR method described above. Ethanol and glycerol levels were determined using HPLC. Over the various fermentations, the washout rate of strains Y4 and Y61 was lower than the washout rate of strain Y2 (FIG. 20A). These results indicated that the strains built in the Y3 background have improved competitive fitness during fermentation compared to the Y2 strain which was built in the Y0 background. In addition, strains Y2, Y4 and Y61 exhibited an increase in the percent in ethanol change as well as a decrease in the percent in glycerol changed when compared to strain Y0 (FIG. 20B). These results indicated that the strains with the persistent phenotypic traits maintained fermentation performances during multiple rounds of fermentation even though they included genetic modifications and expressed the heterologous STL1 gene.

Recombinant Yeast Having Inactivated GPD1

Figure 18A:
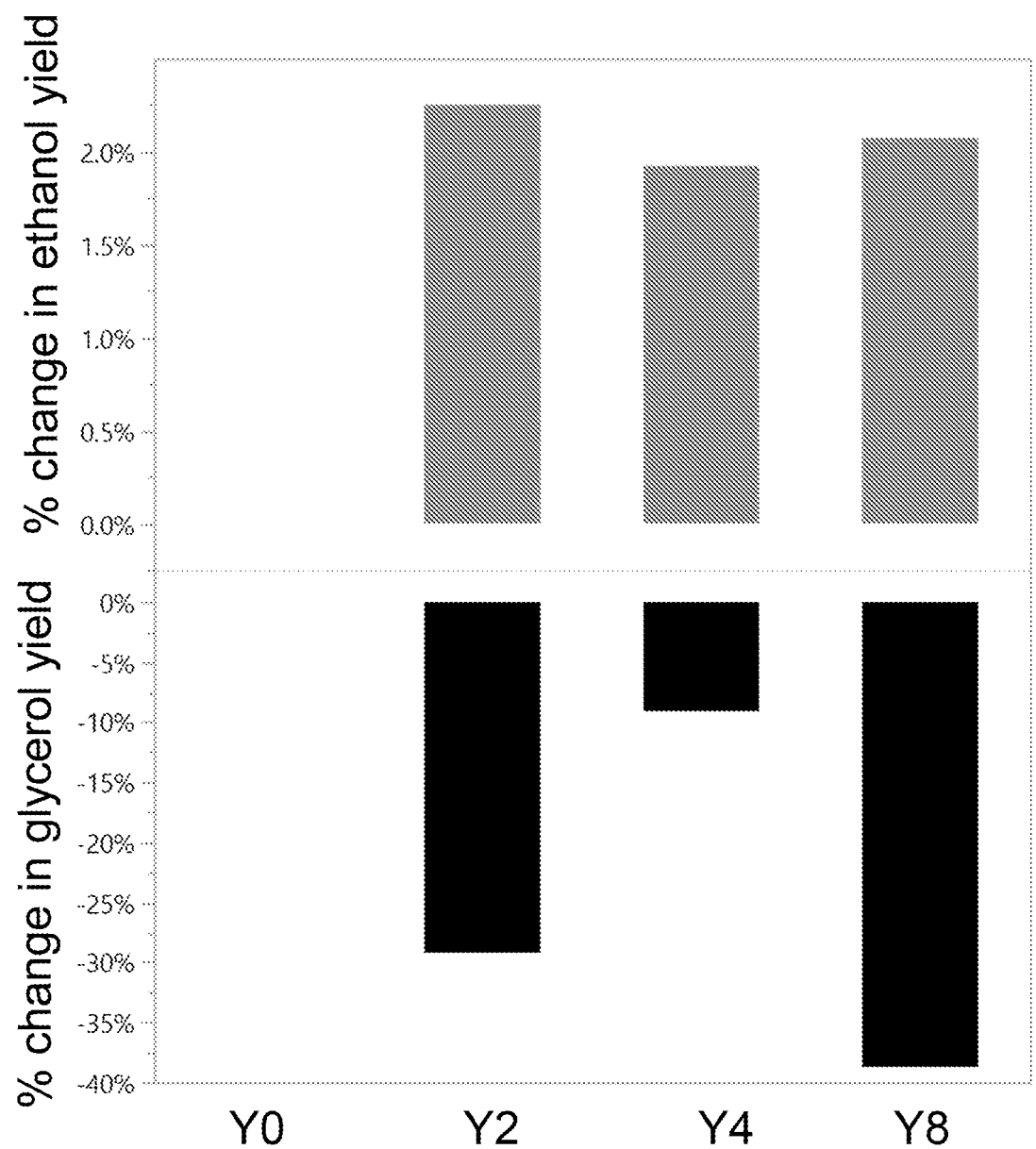
FIGS. 18A and 18B provide the fermentation yields obtained with strains Y0, Y2, Y4 and Y0.
Figure 18B:
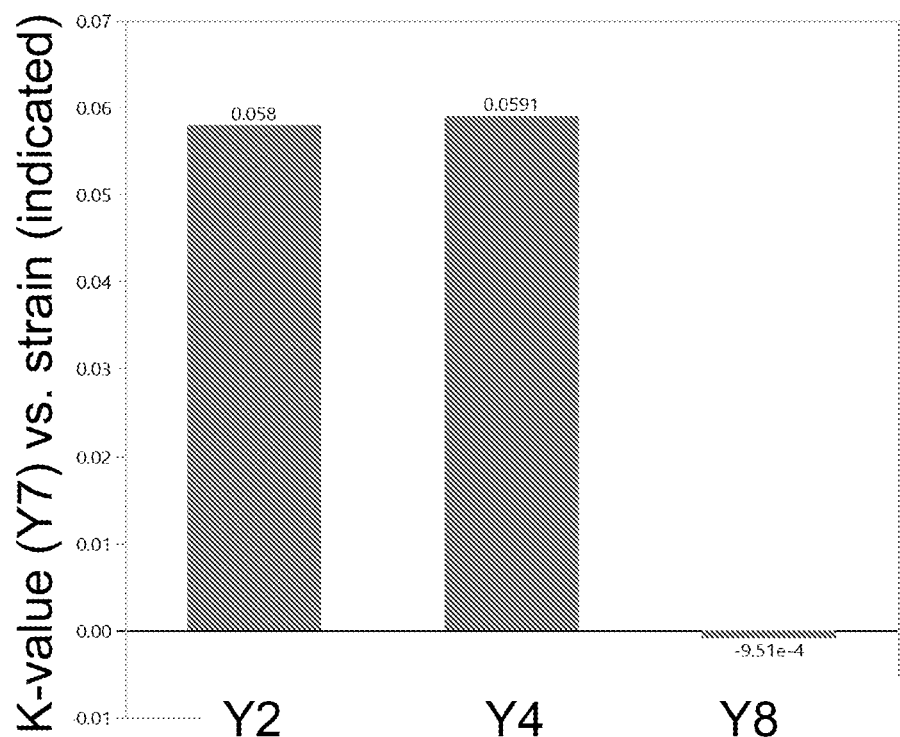

Strains Y0, Y2, Y4 and Y8 were pitched in monoculture or in co-culture with ~15% of the wild type strain Y7. As described in Table 1 above, strain Y8 contained an additional modification that is not present in Y4, a replacement of the native GPD1 gene with GPD2 (Δgpd1::gpd2) in addition to the overexpression of STL1 (Δfcy1::stl1). This additional modification lead to a 2% yield increase over Y0 as well as higher levels of glycerol reduction (>−35% vs. Y0, FIG. 18A). In addition, strain Y8 showed a high levels of persistence over the recycle testing when in co-culture with Y7 (FIG. 18B).

Improved Persistence

Several strains were submitted to commercial fermentations on cane must in which they were recycled and submitted to several consecutive cycles of fermentations. It was then determined, using quantitative PCR, the number of cycles at which the strain (or the combination of strains) represented 99%, 90% or 50% of the fermenting population. The results are presented at Table 10.

TABLE 10

Number of cycles at which the strain (or the combination of strains) represented 99% ("number of cycles to 99%), 90% ("number of cycles to 90%") or 50% ("number of cycles to 90%") of total the fermenting population in function of each mill.

| Mill Code | Strain | Number of cycles to 99% | Number of cycles to 90% | Number of cycles to 50% |
|---|---|---|---|---|
| Mill #1 | Y1 | 50 | 53 | 72 |
| Mill #2 | Y1 | 29 | 45 | 53 |
| Mill #3 | Y1 | 41 | 48 | 53 |
| Mill #4 | Y1 | 26 | 30 | 38 |
| Mill #5 | Y1 | 29 | 38 | 42 |
| Mill #6 | Y2 | 100 | 120 | NA |
| Mill #7 | Y2 | 23 | 35 | 39 |
| Mill #8 | Y2 | 42 | 58 | 80 |
| Mill #9 | Y2 | 47 | 59 | 69 |
| Mill #10 | Y2 | 64 | 73 | 90 |
| Mill #11 | Y2 | 48 | 57 | 75 |
| Mill #12 | Y2 | 37 | 47 | 58 |
| Mill #13 | Y2 | 96 | 115 | 140 |
| Mill #14 | Y2 | 60 | 65 | 82 |
| Mill #15 | Y2 | 53 | 55 | 65 |
| Mill #16 | Y2 | 56 | 60 | 70 |
| Mill #17 | Y2 | 30 | 40 | 46 |
| Mill #18 | Y2 | 60 | 72 | 83 |
| Mill #19 | Y2 | 63 | 75 | 94 |
| Mill #20 | Y4 | 124 | 160 | 170 |
| Mill #21 | Y4 | 120 | 133 | 163 |
| Mill #22 | Y4 | 160 | 190 | 200 |
| Mill #23 | Y4 | 225 | 250 | 270 |
| Mill #24 | Y2 & Y4 | 75 | 100 | 116 |
| Mill #25 | Y2 & Y4 | 110 | 135 | 160 |
| Mill #26 | Y2 & Y4 | 88 | 100 | 120 |
| Mill #27 | Y2 & Y4 | 42 | 70 | 97 |

While the invention has been described in connection with specific embodiments thereof, it will be understood that the scope of the claims should not be limited by the preferred embodiments set forth in the examples, but should be given the broadest interpretation consistent with the description as a whole.

REFERENCES

Luiz Carlos Basso, Thiago Olitta Basso and Saul Nitsche Rocha (Sep. 15, 2011). Ethanol Production in Brazil: The Industrial Process and Its Impact on Yeast Fermentation, Biofuel Production—Recent Developments and Prospects, Marco Aurelio dos Santos Bernardes, IntechOpen, DOI: 10.5772/17047.

Brociner R. E., Vollans E. C. (1973) Thickening flocculated kaolinite slurries in the nozzle discharge, multi disc, bowl centrifuge. Clay Minerals 10 (99).

Conrad M, Schothorst J, Kankipati H N, Van Zeebroeck G, Rubio-Texeira M, Thevelein J M. Nutrient sensing and signaling in the yeast *Saccharomyces cerevisiae*. FEMS Microbiol Rev. 2014; 38(2):254-299.

Danecek, Petr, Adam Auton, Goncalo Abecasis, Cornelis A. Albers, Eric Banks, Mark A. DePristo, Robert E. Handsaker, et al. "The Variant Call Format and VCFtools." Bioinformatics (Oxford, England) 27, no. 15 (Aug. 1, 2011): 2156-58.

Fisher K J, Buskirk S W, Vignogna R C, Marad D A, Lang G I. Adaptive genome duplication affects patterns of molecular evolution in *Saccharomyces cerevisiae*. PLoS Genet. 2018; 14(5):e1007396. Published 2018 May 25.

Li, Heng. "A Statistical Framework for SNP Calling, Mutation Discovery, Association Mapping and Population Genetical Parameter Estimation from Sequencing Data." *Bioinformatics* 27, no. 21 (Nov. 1, 2011): 2987-93.

Li, Heng, Bob Handsaker, Alec Wysoker, Tim Fennell, Jue Ruan, Nils Homer, Gabor Marth, Goncalo Abecasis, Richard Durbin, and 1000 Genome Project Data Processing Subgroup. "The Sequence Alignment/Map Format and SAMtools." Bioinformatics (Oxford, England) 25, no. 16 (Aug. 15, 2009): 2078-79.

Oud B, Guadalupe-Medina V, Nijkamp J F, de Ridder D, Pronk J T, van Maris A J, Daran J M. Genome duplication and mutations in ACE2 cause multicellular, fast-sedimenting phenotypes in evolved *Saccharomyces cerevisiae*. Proc Natl Acad Sci USA. 2013 Nov. 5; 110(45): E4223-31. doi: 10.1073/pnas.1305949110. Epub 2013 Oct. 21. PMID: 24145419; PMCID: PMC3831460.

Purcell, Shaun, Benjamin Neale, Kathe Todd-Brown, Lori Thomas, Manuel A. R. Ferreira, David Bender, Julian Maller, "PLINK: A Tool Set for Whole-Genome Association and Population-Based Linkage Analyses." American Journal of Human Genetics 81, no. 3 (September 2007): 559-75.

Scott A L, Richmond P A, Dowell R D, Selmecki A M. The Influence of Polyploidy on the Evolution of Yeast Grown in a Sub-Optimal Carbon Source. Mol Biol Evol. 2017; 34(10):2690-2703.

Selmecki A M, Maruvka Y E, Richmond P A, et al. Polyploidy can drive rapid adaptation in yeast. Nature. 2015; 519(7543):349-352.

Zadrag-Tecza R, Kwolek-Mirek M, Alabrudzińska M, Skoneczna A. Cell Size Influences the Reproductive Potential and Total Lifespan of the *Saccharomyces cerevisiae* Yeast as Revealed by the Analysis of Polyploid Strains. Oxid Med Cell Longev. 2018; 2018:1898421. Published 2018 Mar. 20.

Zhang, K., Fang, Y., Gao, K. et al. Effects of genome duplication on phenotypes and industrial applications of *Saccharomyces cerevisiae* strains. Appl Microbiol Biotechnol 101, 5405-5414 (2017).

What is claimed is:

1. A recombinant yeast host cell expressing a heterologous sugar transporter protein (STL1) and/or having, when compared to a parental cell, a decreased expression of a native NAD-dependent glycerol-3-phosphate dehydrogenase gene,
wherein the heterologous sugar transporter protein comprises the amino acid sequence of any one of SEQ ID NO: 8 and 31 to 69, is a variant having at least 70% identity to the amino acid sequence of any one of SEQ ID NO: 8 and 31 to 69 and glycerol transport activity, or is a fragment having at least 70% identity to the amino acid sequence of any one of SEQ ID NO: 8 and 31 to 69 and glycerol transport activity; and
wherein the recombinant yeast host cell has at least one of phenotypic trait providing persistence of the recombinant yeast host cell in a plurality of fermentation cycles, and wherein the at least one phenotypic trait is triploidy.

2. The recombinant yeast host cell of claim 1, wherein the recombinant yeast host cell expresses the heterologous sugar transporter protein (STL1).

3. The recombinant yeast host cell of claim 1, wherein the recombinant yeast host cell has decreased expression of the native NAD-dependent glycerol-3-phosphate dehydrogenase gene.

4. The recombinant yeast host cell of claim 3, wherein the native NAD-dependent glycerol-3-phosphate dehydrogenase gene is a native glycerol-3-phosphate dehydrogenase 1 (GPD1) gene and/or a native glycerol-3-phosphate dehydrogenase 2 (GPD2) gene.

5. The recombinant yeast host cell of claim 1 further exhibiting a fast settling phenotype.

6. The recombinant yeast host cell of claim 5, wherein:
(i) at least 5% of a population consisting essentially of the recombinant yeast host cells is able to sediment by gravity after 5 minutes and/or
(ii) the population consisting essentially of the recombinant yeast host cells is able to sediment by gravity in 5 minutes in a proportion equal to or higher than a control population consisting essentially of control yeast cells lacking the fast settling phenotype, and wherein the control yeast cells are from a *Saccharomyces cerevisiae* PE-2 strain.

7. The recombinant yeast host cell of claim 1 further exhibiting a rugose phenotype.

8. The recombinant yeast host cell of claim 7, wherein at least 90% of a population consisting essentially of the recombinant yeast host cells, after exponential growth in a medium inoculated at low recombinant yeast host cell density, has at least two daughter cells attached.

9. The recombinant yeast host cell of claim 7 being capable of:
reducing the transcription factor activity of an Activator of CUP1 Expression (ACE2) polypeptide; and/or
expressing a mutated ACE2 polypeptide, wherein the mutated ACE2 polypeptide has decreased activity when compared to a wild type ACE2 polypeptide.

10. The recombinant yeast host cell of claim 1 further exhibiting improved invertase activity.

11. The recombinant yeast host cell of claim 10, wherein a population consisting essentially of the recombinant yeast host cells is able to hydrolyze more than 0.05 gram of sucrose per gram of dry cell weight per minute and/or exhibits more than 1.0 times invertase activity than a control population consisting essentially of control yeast cells lacking the improved invertase activity phenotypic trait, wherein the control yeast cells are from a *Saccharomyces cerevisiae* PE-2 strain, and wherein invertase activity is measured after exponential growth of the population diluted to a concentration of 9 mg/mL on a wet cell weight in a buffer and wherein the buffer comprises 40 g/L of sucrose, is at of pH 5 and at a temperature of 35° C.

12. The recombinant yeast host cell of claim 1 being capable of increasing the enzymatic activity of at least one polypeptide having invertase activity.

13. The recombinant yeast host cell of claim 12, wherein the at least one polypeptide having invertase activity comprises SUC1, SUC2, SUC3, SUC4, SUC5, SUC6, SUC7, SUC8 or SUC9.

14. The recombinant yeast host cell of claim 1 further exhibiting increased signaling in the RAS/cAMP/PKA pathway.

15. The recombinant yeast host cell of claim 14, wherein a population consisting essentially of the recombinant yeast host cells is able to exhibit a fold increase in the production of cAMP of equal to or less than 1.7 and/or a fold increase in the production of cAMP production of less than 70% when compared a control population consisting essentially of control yeast cells lacking the increased signaling in the RAS/cAMP/PKA pathway phenotypic trait, wherein the control yeast cells are from a *Saccharomyces cerevisiae* PE-2 strain, and wherein the production of cAMP is measured in the population having been glucose depleted and at 5 minutes after a glucose spike.

16. The recombinant yeast host cell of claim 14 being capable of expressing a mutated polypeptide involved in the RAS/cAMP/PKA pathway.

17. The recombinant yeast host cell of claim 16, wherein the mutated polypeptide involved in the RAS/cAMP/PKA pathway comprises a mutated RAS2 polypeptide having increased activity when compared to a wild-type RAS2 polypeptide, a mutated IRA2 polypeptide having a reduced inhibitory activity towards a wild-type RAS1 and/or a wild-type RAS2 polypeptide when compared to a wild-type IRA2 polypeptide.

18. The recombinant yeast host cell of claim 1 being from the genus *Saccharomyces* sp. or from the species *Saccharomyces cerevisiae*.

19. The recombinant yeast host cell of claim 2 comprising a heterologous nucleic acid encoding a sugar transporter protein (STL1).

20. The recombinant yeast host cell of claim 4 having a deletion in the native glycerol-3-phosphate dehydrogenase 1 gene (GPD1).

21. The recombinant yeast host cell of claim 4 having a deletion in the native glycerol-3-phosphate dehydrogenase 2 gene (GPD2).

22. The recombinant yeast host cell of claim 1, wherein the heterologous sugar transporter protein (STL1) comprises the amino acid sequence of SEQ ID NO: 8, is the variant having at least 70% identity to the amino acid sequence of SEQ ID NO: 8 and glycerol transport activity, or is the fragment having at least 70% identity to the amino acid sequence of SEQ ID NO: 8 and glycerol transport activity.

23. The recombinant yeast host cell of claim 1, wherein the heterologous sugar transporter protein (STL1) comprises the amino acid sequence of any one of SEQ ID NO: 31 to 56, 68, or 69 is the variant having at least 70% identity to the amino acid sequence of any one of SEQ ID NO: 31 to 56, 68, and 69 and glycerol transport activity, or is the fragment having at least 70% identity to the amino acid sequence of any one of SEQ ID NO: 31 to 56, 68, and 69 and glycerol transport activity.

* * * * *

SEQUENCE LISTING

<160> NUMBER OF SEQ ID NOS: 69

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
cacgctgcct tagaagatgg        20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
gttctgcagc tgagatgagg        20

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide

<400> SEQUENCE: 3
gtttaatccg ggctggttcc at        22

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide

<400> SEQUENCE: 4
tagacccagt ggacagatag cg    22

<210> SEQ ID NO 5
<211> LENGTH: 1323
<212> TYPE: DNA
<213> ORGANISM: Saccharomyces cerevisiae

<400> SEQUENCE: 5

```
atgcttgctg tcagaagatt aacaagatac acattcctta agcgaacgca tccggtgtta    60
tatactcgtc gtgcatataa aattttgcct tcaagatcta ctttcctaag aagatcatta   120
ttacaaacac aactgcactc aaagatgact gctcatacta atatcaaaca gcacaaacac   180
tgtcatgagg accatcctat cagaagatcg gactctgccg tgtcaattgt acatttgaaa   240
cgtgcgccct tcaaggttac agtgattggt tctggtaact gggggaccac catcgccaaa   300
gtcattgcgg aaaacacaga attgcattcc catatcttcg agccagaggt gagaatgtgg   360
gttttttgatg aaaagatcgg cgacgaaaat ctgacggata tcataaatac aagacaccag   420
aacgttaaat atctacccaa tattgacctg ccccataatc tagtggccga tcctgatctt   480
ttacactcca tcaagggtgc tgacatcctt gttttcaaca tccctcatca attttttacca   540
aacatagtca acaattgca aggccacgtg gcccctcatg taagggccat ctcgtgtcta   600
aaagggttcg agttgggctc caagggtgtg caattgctat cctcctatgt tactgatgag   660
ttaggaatcc aatgtggcgc actatctggt gcaaacttgg caccggaagt ggccaaggag   720
cattggtccg aaaccaccgt ggcttaccaa ctaccaaagg attatcaagg tgatggcaag   780
gatgtagatc ataagatttt gaaattgctg ttccacagac cttacttcca cgtcaatgtc   840
atcgatgatg ttgctggtat atccattgcc ggtgccttga agaacgtcgt ggcacttgca   900
tgtggtttcg tagaaggtat gggatggggt aacaatgcct ccgcagccat tcaaaggctg   960
ggtttaggtg aaattatcaa gttcggtaga atgttttttcc cagaatccaa agtcgagacc  1020
tactatcaag aatccgctgg tgttgcagat ctgatcacca cctgctcagg cggtagaaac  1080
gtcaaggttg ccacatacat ggccaagacc ggtaagtcag ccttgaagc agaaaaggaa  1140
ttgcttaacg tcaatccgc ccaagggata atcacatgca gagaagttca cgagtggcta  1200
caaacatgtg agttgaccca agaattccca ttattcgagg cagtctacca gatagtctac  1260
aacaacgtcc gcatggaaga cctaccggag atgattgaag agctagacat cgatgacgaa  1320
tag                                                                1323
```

<210> SEQ ID NO 6
<211> LENGTH: 440
<212> TYPE: PRT
<213> ORGANISM: Saccharomyces cerevisiae

<400> SEQUENCE: 6

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

```
Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
        435                 440

<210> SEQ ID NO 7
<211> LENGTH: 1710
<212> TYPE: DNA
<213> ORGANISM: Saccharomyces cerevisiae

<400> SEQUENCE: 7
atgaaggatt taaaattatc gaatttcaaa ggcaaattta taagcagaac cagtcactgg      60
```

-continued

```
ggacttacgg gtaagaagtt gcggtatttc atcactatcg catctatgac gggcttctcc    120
ctgtttggat acgaccaagg gttgatggca agtctaatta ctggtaaaca gttcaactat    180
gaatttccag caaccaaaga aaatggcgat catgacagac acgcaactgt agtgcagggc    240
gctacaacct cctgttatga attaggttgt ttcgcaggtt ctctattcgt tatgttctgc    300
ggtgaaagaa ttggtagaaa accattaatc ctgatgggtt ccgtaataac catcattggt    360
gccgttattt ctacatgcgc atttcgtggt tactgggcat taggccagtt tatcatcgga    420
agagtcgtca ccggtgttgg aacagggttg aatacatcta ctattcccgt ttggcaatca    480
gaaatgtcaa aagctgaaaa tagagggttg ctggtcaatt tagaaggttc cacaattgct    540
tttggtacta tgattgctta ttggattgat tttgggttgt cttataccaa cagttctgtt    600
cagtggagat tccccgtgtc aatgcaaatc gttttgctc tcttcctgct tgctttcatg    660
attaaactac ctgaatcgcc acgttggctg atttctcaaa gtcgaacaga gaagctcgc    720
tacttggtag aacactaga cgacgcggat ccaaatgatg aggaagttat aacagaagtt    780
gctatgcttc acgatgctgt taacaggacc aaacacgaga acattcact gtcaagtttg    840
ttctccagag gcaggtccca aaatcttcag agggctttga ttgcagcttc aacgcaattt    900
ttccagcaat ttactggttg taacgctgcc atatactact ctactgtatt attcaacaaa    960
acaattaaat tagactatag attatcaatg atcataggtg gggtcttcgc aacaatctac    1020
gccttatcta ctattggttc attttttcta attgaaaagc taggtagacg taagctgttt    1080
ttattaggtg ccacaggtca agcagtttca ttcacaatta catttgcatg cttggtcaaa    1140
gaaaataaag aaaacgcaag aggtgctgcc gtcggcttat ttttgttcat tacattcttt    1200
ggtttgtctt tgctatcatt accatggata tacccaccag aaattgcatc aatgaaagtt    1260
cgtgcatcaa caaacgcttt ctccacatgt actaattggt tgtgtaactt tgcggttgtc    1320
atgttcaccc caatatttat tggacagtcc ggttgggtt gctacttatt ttttgctgtt    1380
atgaattatt tatacattcc agttatcttc tttttctacc ctgaaaccgc cggaagaagt    1440
ttggaggaaa tcgacatcat ctttgctaaa gcatacgagg atggcactca accatggaga    1500
gttgctaacc atttgcccaa gttatcccta caagaagtcg aagatcatgc caatgcattg    1560
ggctcttatg acgacgaaat ggaaaaagag gactttggtg aagatagagt agaagacacc    1620
tataaccaaa ttaacggcga taattcgtct agttcttcaa acatcaaaaa tgaagataca    1680
gtgaacgata agcaaatttt tgagggttga                                     1710
```

<210> SEQ ID NO 8
<211> LENGTH: 569
<212> TYPE: PRT
<213> ORGANISM: Saccharomyces cerevisiae

<400> SEQUENCE: 8

```
Met Lys Asp Leu Lys Leu Ser Asn Phe Lys Gly Lys Phe Ile Ser Arg
1               5                   10                  15

Thr Ser His Trp Gly Leu Thr Gly Lys Lys Leu Arg Tyr Phe Ile Thr
            20                  25                  30

Ile Ala Ser Met Thr Gly Phe Ser Leu Phe Gly Tyr Asp Gln Gly Leu
        35                  40                  45

Met Ala Ser Leu Ile Thr Gly Lys Gln Phe Asn Tyr Glu Phe Pro Ala
    50                  55                  60

Thr Lys Glu Asn Gly Asp His Asp Arg His Ala Thr Val Val Gln Gly
65                  70                  75                  80
```

-continued

```
Ala Thr Thr Ser Cys Tyr Glu Leu Gly Cys Phe Ala Gly Ser Leu Phe
                85              90              95

Val Met Phe Cys Gly Glu Arg Ile Gly Arg Lys Pro Leu Ile Leu Met
            100             105             110

Gly Ser Val Ile Thr Ile Ile Gly Ala Val Ile Ser Thr Cys Ala Phe
        115             120             125

Arg Gly Tyr Trp Ala Leu Gly Gln Phe Ile Ile Gly Arg Val Val Thr
    130             135             140

Gly Val Gly Thr Gly Leu Asn Thr Ser Thr Ile Pro Val Trp Gln Ser
145             150             155             160

Glu Met Ser Lys Ala Glu Asn Arg Gly Leu Leu Val Asn Leu Glu Gly
                165             170             175

Ser Thr Ile Ala Phe Gly Thr Met Ile Ala Tyr Trp Ile Asp Phe Gly
            180             185             190

Leu Ser Tyr Thr Asn Ser Ser Val Gln Trp Arg Phe Pro Val Ser Met
        195             200             205

Gln Ile Val Phe Ala Leu Phe Leu Leu Ala Phe Met Ile Lys Leu Pro
    210             215             220

Glu Ser Pro Arg Trp Leu Ile Ser Gln Ser Arg Thr Glu Glu Ala Arg
225             230             235             240

Tyr Leu Val Gly Thr Leu Asp Asp Ala Asp Pro Asn Asp Glu Glu Val
                245             250             255

Ile Thr Glu Val Ala Met Leu His Asp Ala Val Asn Arg Thr Lys His
            260             265             270

Glu Lys His Ser Leu Ser Ser Leu Phe Ser Arg Gly Arg Ser Gln Asn
        275             280             285

Leu Gln Arg Ala Leu Ile Ala Ala Ser Thr Gln Phe Phe Gln Gln Phe
    290             295             300

Thr Gly Cys Asn Ala Ala Ile Tyr Tyr Ser Thr Val Leu Phe Asn Lys
305             310             315             320

Thr Ile Lys Leu Asp Tyr Arg Leu Ser Met Ile Ile Gly Gly Val Phe
                325             330             335

Ala Thr Ile Tyr Ala Leu Ser Thr Ile Gly Ser Phe Phe Leu Ile Glu
            340             345             350

Lys Leu Gly Arg Arg Lys Leu Phe Leu Leu Gly Ala Thr Gly Gln Ala
        355             360             365

Val Ser Phe Thr Ile Thr Phe Ala Cys Leu Val Lys Glu Asn Lys Glu
    370             375             380

Asn Ala Arg Gly Ala Ala Val Gly Leu Phe Leu Phe Ile Thr Phe Phe
385             390             395             400

Gly Leu Ser Leu Leu Ser Leu Pro Trp Ile Tyr Pro Pro Glu Ile Ala
                405             410             415

Ser Met Lys Val Arg Ala Ser Thr Asn Ala Phe Ser Thr Cys Thr Asn
            420             425             430

Trp Leu Cys Asn Phe Ala Val Val Met Phe Thr Pro Ile Phe Ile Gly
        435             440             445

Gln Ser Gly Trp Gly Cys Tyr Leu Phe Phe Ala Val Met Asn Tyr Leu
    450             455             460

Tyr Ile Pro Val Ile Phe Phe Tyr Pro Glu Thr Ala Gly Arg Ser
465             470             475             480

Leu Glu Glu Ile Asp Ile Ile Phe Ala Lys Ala Tyr Glu Asp Gly Thr
                485             490             495
```

```
Gln Pro Trp Arg Val Ala Asn His Leu Pro Lys Leu Ser Leu Gln Glu
            500                 505                 510
Val Glu Asp His Ala Asn Ala Leu Gly Ser Tyr Asp Asp Glu Met Glu
        515                 520                 525
Lys Glu Asp Phe Gly Glu Asp Arg Val Glu Asp Thr Tyr Asn Gln Ile
    530                 535                 540
Asn Gly Asp Asn Ser Ser Ser Ser Asn Ile Lys Asn Glu Asp Thr
545                 550                 555                 560
Val Asn Asp Lys Ala Asn Phe Glu Gly
                565

<210> SEQ ID NO 9
<211> LENGTH: 2313
<212> TYPE: DNA
<213> ORGANISM: Saccharomyces cerevisiae

<400> SEQUENCE: 9
atggataacg ttgtagatcc gtggtatata aatccctcag gcttcgcgaa agacactcaa        60
gatgaggagt atgttcaaca tcatgataat gtcaatccta ccataccccc acccgacaat       120
tatattttga ataatgaaaa cgatgatggc ctcgataact tgttaggtat ggactactat       180
aacatcgatg acctgttgac tcaagagtta agagatctgg atattccttt agtgccttct       240
cctaagacgg gcgatggttc ttctgataaa aagaatattg atagaacttg gaaccttggt       300
gatgaaaaca caaagtctcc cactatagc aaaaaatcaa tgtcctcaca aagagaggt        360
ctaagtggca cagcgatatt tggatttctc ggccataata agacattgag tatttccagt       420
ttacagcaat ccattctaaa tatgtctaaa gatccgcaac ccatggaact cataaatgaa       480
ttgggtaatc ataatacggt aaaaaataac aatgatgact tgaccatat aagggaaaat        540
gatggtgaaa atagctattt gagccaagtt ttgttgaaac agcaggagga gttaagaatt       600
gctcttgaaa acaaaagga agtgaacgaa aaattggaga agcagttgag agacaatcaa        660
atacagcaag aaaagttgcg taaagtatta gaagagcaag aagaggtggc gcagaagttg       720
gtttctgggg ctacaaattc taattccaaa cctggatctc cagtaatact aaagacacct       780
gccatgcaaa acggtagaat gaaagataat gctataatcg tcacaacgaa ctctgcaaat       840
ggcggatatc aatttcctcc tccgacgtta atatcgcctc ggatgtcaaa tacttcaata       900
aatggttcac catccaggaa ataccatagg caacgatatc caaataaaag cccagaaagt       960
aatggattga accttttttc ctctaacagt ggttatttga gagattctga actgctttca      1020
ttttctccac aaaattataa tttaaacttg gacggcttga cttataatga ccataataac      1080
accagtgata aaaacaataa tgataaaaaa aatagtactg gtgataacat attccgtctg      1140
ttcgaaaaga cttccccggg tgggctaagt atctctccaa ggataaatgg aaatagtttg      1200
agatcgccct cctcgtcgg cacagataaa gcagggatg atcgatatgc tgctggcacg       1260
ttcacgccta gaacacagtt gtcacctatc acaagaaaaa gggaatccgt agtttccacg      1320
gtctcgacaa tatcacaact gcaggatgac actgaaccca tccacatgcg aaatacccag      1380
aacccaacat taagaaatgc aaacgcttta gcgtcatcaa gtgtactacc tcctattcct      1440
ggttccagca ataacactcc aattaagaat tctttgccac aaaaacatgt atttcaacat      1500
actcccgtca agctccacc aaagaacgga agtaacctag ctccgcttct aaatgcaccg      1560
gatttaacag atcatcagtt agaaattaag acacccatac gaaataacag tcactgtgaa      1620
gtggaaagct atccgcaagt accacctgtc acacatgata ttcacaaaag ccccactttg      1680
```

-continued

```
catagtacgt ctcctttacc agatgaaata atacctagga ctacgccaat gaaaataacc    1740
aagaaaccaa ctactctgcc tccgggtacc attgaccagt acgtcaagga actacccgac    1800
aaactattcg agtgcttata ccctaactgt aacaaagtat tcaagcgtag atacaacata    1860
aggtcgcata ttcagacaca tttgcaagat agaccgtatt catgcgactt ccccggttgc    1920
accaaggcgt tgttcgcaa tcatgattta ataagacaca aaatctccca taatgccaag    1980
aaatacatct gcccatgcgg aaagagattt aatagggagg atgctctaat ggtgcataga    2040
agtcggatga tttgcaccgg cggtaagaaa ttagaacatt cgatcaacaa gaaacttaca    2100
tctcccaaaa aaagcctgct tgacagcccg catgacacaa gtcccgtaaa agaaactatc    2160
gcccgggata agatgggag cgtcctaatg aaaatggagg aacagctgcg agatgatatg    2220
cgcaaacatg gattactgga tccacccca tccacagcag cgcacgagca aaactcgaac    2280
cgcacccttt caaacgaaac tgatgctctc tga                                 2313
```

<210> SEQ ID NO 10
<211> LENGTH: 770
<212> TYPE: PRT
<213> ORGANISM: Saccharomyces cerevisiae

<400> SEQUENCE: 10

```
Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
            20                  25                  30

Pro Thr Ile Pro Pro Pro Asp Asn Tyr Ile Leu Asn Asn Glu Asn Asp
        35                  40                  45

Asp Gly Leu Asp Asn Leu Leu Gly Met Asp Tyr Tyr Asn Ile Asp Asp
    50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
        115                 120                 125

Phe Leu Gly His Asn Lys Thr Leu Ser Ile Ser Ser Leu Gln Gln Ser
    130                 135                 140

Ile Leu Asn Met Ser Lys Asp Pro Gln Pro Met Glu Leu Ile Asn Glu
145                 150                 155                 160

Leu Gly Asn His Asn Thr Val Lys Asn Asn Asp Asp Phe Asp His
                165                 170                 175

Ile Arg Glu Asn Asp Gly Glu Asn Ser Tyr Leu Ser Gln Val Leu Leu
            180                 185                 190

Lys Gln Gln Glu Glu Leu Arg Ile Ala Leu Glu Lys Gln Lys Glu Val
        195                 200                 205

Asn Glu Lys Leu Glu Lys Gln Leu Arg Asp Asn Gln Ile Gln Gln Glu
    210                 215                 220

Lys Leu Arg Lys Val Leu Glu Gln Glu Val Ala Gln Lys Leu
225                 230                 235                 240

Val Ser Gly Ala Thr Asn Ser Asn Ser Lys Pro Gly Ser Pro Val Ile
                245                 250                 255

Leu Lys Thr Pro Ala Met Gln Asn Gly Arg Met Lys Asp Asn Ala Ile
```

-continued

```
               260                 265                 270
Ile Val Thr Thr Asn Ser Ala Asn Gly Gly Tyr Gln Phe Pro Pro
            275                 280                 285

Thr Leu Ile Ser Pro Arg Met Ser Asn Thr Ser Ile Asn Gly Ser Pro
        290                 295                 300

Ser Arg Lys Tyr His Arg Gln Arg Tyr Pro Asn Lys Ser Pro Glu Ser
305                 310                 315                 320

Asn Gly Leu Asn Leu Phe Ser Ser Asn Ser Gly Tyr Leu Arg Asp Ser
                325                 330                 335

Glu Leu Leu Ser Phe Ser Pro Gln Asn Tyr Asn Leu Asn Leu Asp Gly
            340                 345                 350

Leu Thr Tyr Asn Asp His Asn Asn Thr Ser Asp Lys Asn Asn Asn Asp
        355                 360                 365

Lys Lys Asn Ser Thr Gly Asp Asn Ile Phe Arg Leu Phe Glu Lys Thr
    370                 375                 380

Ser Pro Gly Gly Leu Ser Ile Ser Pro Arg Ile Asn Gly Asn Ser Leu
385                 390                 395                 400

Arg Ser Pro Phe Leu Val Gly Thr Asp Lys Ser Arg Asp Asp Arg Tyr
                405                 410                 415

Ala Ala Gly Thr Phe Thr Pro Arg Thr Gln Leu Ser Pro Ile His Lys
            420                 425                 430

Lys Arg Glu Ser Val Val Ser Thr Val Ser Thr Ile Ser Gln Leu Gln
        435                 440                 445

Asp Asp Thr Glu Pro Ile His Met Arg Asn Thr Gln Asn Pro Thr Leu
    450                 455                 460

Arg Asn Ala Asn Ala Leu Ala Ser Ser Ser Val Leu Pro Pro Ile Pro
465                 470                 475                 480

Gly Ser Ser Asn Asn Thr Pro Ile Lys Asn Ser Leu Pro Gln Lys His
                485                 490                 495

Val Phe Gln His Thr Pro Val Lys Ala Pro Pro Lys Asn Gly Ser Asn
            500                 505                 510

Leu Ala Pro Leu Leu Asn Ala Pro Asp Leu Thr Asp His Gln Leu Glu
        515                 520                 525

Ile Lys Thr Pro Ile Arg Asn Asn Ser His Cys Glu Val Glu Ser Tyr
    530                 535                 540

Pro Gln Val Pro Pro Val Thr His Asp Ile His Lys Ser Pro Thr Leu
545                 550                 555                 560

His Ser Thr Ser Pro Leu Pro Asp Glu Ile Ile Pro Arg Thr Thr Pro
                565                 570                 575

Met Lys Ile Thr Lys Lys Pro Thr Thr Leu Pro Pro Gly Thr Ile Asp
            580                 585                 590

Gln Tyr Val Lys Glu Leu Pro Asp Lys Leu Phe Glu Cys Leu Tyr Pro
        595                 600                 605

Asn Cys Asn Lys Val Phe Lys Arg Arg Tyr Asn Ile Arg Ser His Ile
    610                 615                 620

Gln Thr His Leu Gln Asp Arg Pro Tyr Ser Cys Asp Phe Pro Gly Cys
625                 630                 635                 640

Thr Lys Ala Phe Val Arg Asn His Asp Leu Ile Arg His Lys Ile Ser
                645                 650                 655

His Asn Ala Lys Lys Tyr Ile Cys Pro Cys Gly Lys Arg Phe Asn Arg
            660                 665                 670

Glu Asp Ala Leu Met Val His Arg Ser Arg Met Ile Cys Thr Gly Gly
        675                 680                 685
```

```
Lys Lys Leu Glu His Ser Ile Asn Lys Lys Leu Thr Ser Pro Lys Lys
        690                 695                 700

Ser Leu Leu Asp Ser Pro His Asp Thr Ser Pro Val Lys Glu Thr Ile
705                 710                 715                 720

Ala Arg Asp Lys Asp Gly Ser Val Leu Met Lys Met Glu Glu Gln Leu
                725                 730                 735

Arg Asp Asp Met Arg Lys His Gly Leu Leu Asp Pro Pro Pro Ser Thr
            740                 745                 750

Ala Ala His Glu Gln Asn Ser Asn Arg Thr Leu Ser Asn Glu Thr Asp
        755                 760                 765

Ala Leu
    770

<210> SEQ ID NO 11
<211> LENGTH: 2312
<212> TYPE: DNA
<213> ORGANISM: Saccharomyces cerevisiae

<400> SEQUENCE: 11
```

| | | | | | |
|---|---|---|---|---|---|
| atggataacg | ttgtagatcc | gtggtatata | aatccctcag | gcttcgcgaa | agacactcaa | 60 |
| gatgaggagt | atgttcaaca | tcatgataat | gtcaatccta | ccataccccc | acccgacaat | 120 |
| tatattttga | ataatgaaaa | cgatgatggc | ctcgataact | tgttaggtat | ggactactat | 180 |
| aacatcgatg | acctgttgac | tcaagagtta | agagatctgg | atattccttt | agtgccttct | 240 |
| cctaagacgg | gcgatggttc | ttctgataaa | aagaatattg | atagaacttg | gaaccttggt | 300 |
| gatgaaaaca | acaaagtctc | ccactatagc | aaaaaatcaa | tgtcctcaca | aagagaggt | 360 |
| ctaagtggca | cagcgatatt | tggatttctc | ggccataata | agacattgag | tatttccagt | 420 |
| ttacagcaat | ccattctaaa | tatgtctaaa | gatccgcaac | ccatggaact | cataaatgaa | 480 |
| ttgggtaatc | ataatacggt | aaaaaataac | aatgatgact | tgaccatat | aagggaaaat | 540 |
| gatggtgaaa | atagctattt | gagccaagtt | ttgttgaaac | agcaggagga | gttaagaatt | 600 |
| gctcttgaaa | acaaaaagga | agtgaacgaa | aaattggaga | agcagttgag | agacaatcaa | 660 |
| atacagcaag | aaaagttgcg | taaagtatta | gaagagcaag | aagaggtggc | gcagaagttg | 720 |
| gtttctgggg | ctacaaattc | taattccaaa | cctggatctc | cagtaatact | aaagacacct | 780 |
| gccatgcaaa | acggtagaat | gaaagataat | gctataatcg | tcacaacgaa | ctctgcaaat | 840 |
| ggcggatatc | aatttcctcc | tccgacgtta | atatcgcctc | ggatgtcaaa | tacttcaata | 900 |
| aatggttcac | catccaggaa | ataccatagg | caacgatatc | caaataaaag | cccagaaagt | 960 |
| aatggattga | acctttttc | ctctaacagt | ggttatttga | gagattctga | actgctttca | 1020 |
| ttttctccac | aaaattataa | tttaaacttg | gacggcttga | cttataatga | ccataataac | 1080 |
| accagtgata | aaaacaataa | tgataaaaaa | atagtactgg | tgataacata | ttccgtctgt | 1140 |
| tcgaaaagac | ttccccgggt | gggctaagta | tctctccaag | gataaatgga | atagtttga | 1200 |
| gatcgccctt | cctcgtcggc | acagataaaa | gcagggatga | tcgatatgct | gctggcacgt | 1260 |
| tcacgcctag | aacacagttg | tcacctatcc | acaagaaaag | ggaatccgta | gtttccacgg | 1320 |
| tctcgacaat | atcacaactg | caggatgaca | ctgaacccat | ccacatgcga | atacccaga | 1380 |
| acccaacatt | aagaaatgca | aacgctttag | cgtcatcaag | tgtactacct | cctattcctg | 1440 |
| gttccagcaa | taacactcca | attaagaatt | cttttgccaca | aaacatgta | tttcaacata | 1500 |
| ctcccgtcaa | agctccacca | aagaacgaa | gtaacctagc | tccgcttcta | aatgcaccgg | 1560 |

```
atttaacaga tcatcagtta gaaattaaga cacccatacg aaataacagt cactgtgaag    1620
tggaaagcta tccgcaagta ccacctgtca cacatgatat tcacaaaagc cccactttgc    1680
atagtacgtc tcctttacca gatgaaataa tacctaggac tacgccaatg aaaataacca    1740
agaaaccaac tactctgcct ccgggtacca ttgaccagta cgtcaaggaa ctacccgaca    1800
aactattcga gtgcttatac cctaactgta acaaagtatt caagcgtaga tacaacataa    1860
ggtcgcatat tcagacacat ttgcaagata gaccgtattc atgcgacttt cccggttgca    1920
ccaaggcgtt tgttcgcaat catgatttaa taagacacaa aatctcccat aatgccaaga    1980
aatacatctg cccatgcgga aagagattta atagggagga tgctctaatg gtgcatagaa    2040
gtcggatgat ttgcaccggc ggtaagaaat tagaacattc gatcaacaag aaacttacat    2100
ctcccaaaaa aagcctgctt gacagcccgc atgacacaag tcccgtaaaa gaaactatcg    2160
cccgggataa agatgggagc gtcctaatga aaatggagga acagctgcga gatgatatgc    2220
gcaaacatgg attactggat ccaccccat ccacagcagc gcacgagcaa aactcgaacc    2280
gcaccctttc aaacgaaact gatgctctct ga                                  2312
```

<210> SEQ ID NO 12
<211> LENGTH: 387
<212> TYPE: PRT
<213> ORGANISM: Saccharomyces cerevisiae

<400> SEQUENCE: 12

```
Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
            20                  25                  30

Pro Thr Ile Pro Pro Pro Asp Asn Tyr Ile Leu Asn Asn Glu Asn Asp
        35                  40                  45

Asp Gly Leu Asp Asn Leu Leu Gly Met Asp Tyr Tyr Asn Ile Asp Asp
    50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
        115                 120                 125

Phe Leu Gly His Asn Lys Thr Leu Ser Ile Ser Ser Leu Gln Gln Ser
    130                 135                 140

Ile Leu Asn Met Ser Lys Asp Pro Gln Pro Met Glu Leu Ile Asn Glu
145                 150                 155                 160

Leu Gly Asn His Asn Thr Val Lys Asn Asn Asp Asp Phe Asp His
                165                 170                 175

Ile Arg Glu Asn Asp Gly Glu Asn Ser Tyr Leu Ser Gln Val Leu Leu
            180                 185                 190

Lys Gln Gln Glu Glu Leu Arg Ile Ala Leu Glu Lys Gln Lys Glu Val
        195                 200                 205

Asn Glu Lys Leu Glu Lys Gln Leu Arg Asp Asn Gln Ile Gln Gln Glu
    210                 215                 220

Lys Leu Arg Lys Val Leu Glu Glu Gln Glu Val Ala Gln Lys Leu
225                 230                 235                 240
```

```
Val Ser Gly Ala Thr Asn Ser Asn Ser Lys Pro Gly Ser Pro Val Ile
                245                 250                 255

Leu Lys Thr Pro Ala Met Gln Asn Gly Arg Met Lys Asp Asn Ala Ile
            260                 265                 270

Ile Val Thr Thr Asn Ser Ala Asn Gly Gly Tyr Gln Phe Pro Pro Pro
            275                 280                 285

Thr Leu Ile Ser Pro Arg Met Ser Asn Thr Ser Ile Asn Gly Ser Pro
        290                 295                 300

Ser Arg Lys Tyr His Arg Gln Arg Tyr Pro Asn Lys Ser Pro Glu Ser
305                 310                 315                 320

Asn Gly Leu Asn Leu Phe Ser Ser Asn Ser Gly Tyr Leu Arg Asp Ser
                325                 330                 335

Glu Leu Leu Ser Phe Ser Pro Gln Asn Tyr Asn Leu Asn Leu Asp Gly
            340                 345                 350

Leu Thr Tyr Asn Asp His Asn Asn Thr Ser Asp Lys Asn Asn Asn Asp
        355                 360                 365

Lys Lys Ile Val Leu Val Ile Thr Tyr Ser Val Cys Ser Lys Arg Leu
370                 375                 380

Pro Arg Val
385

<210> SEQ ID NO 13
<211> LENGTH: 169
<212> TYPE: PRT
<213> ORGANISM: Saccharomyces cerevisiae

<400> SEQUENCE: 13

Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
            20                  25                  30

Pro Thr Ile Pro Pro Pro Asp Asn Tyr Ile Leu Asn Asn Glu Asn Asp
        35                  40                  45

Asp Gly Leu Asp Asn Leu Leu Gly Met Asp Tyr Tyr Asn Ile Asp Asp
    50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
        115                 120                 125

Phe Leu Gly His Asn Lys Thr Leu Ser Ile Ser Ser Leu Gln Gln Ser
    130                 135                 140

Ile Leu Asn Met Ser Lys Asp Pro Gln Pro Met Glu Leu Ile Asn Glu
145                 150                 155                 160

Leu Gly Asn His Asn Thr Val Lys Lys
                165

<210> SEQ ID NO 14
<211> LENGTH: 186
<212> TYPE: PRT
<213> ORGANISM: Saccharomyces cerevisiae

<400> SEQUENCE: 14
```

```
Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
                20                  25                  30

Pro Thr Ile Pro Pro Pro Asp Asn Tyr Ile Leu Asn Asn Glu Asn Asp
            35                  40                  45

Asp Gly Leu Asp Asn Leu Leu Gly Met Asp Tyr Tyr Asn Ile Asp Asp
        50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
            115                 120                 125

Phe Leu Gly His Asn Lys Thr Leu Ser Ile Ser Ser Leu Gln Gln Ser
        130                 135                 140

Ile Leu Asn Met Ser Lys Asp Pro Gln Pro Met Glu Leu Ile Asn Glu
145                 150                 155                 160

Leu Gly Asn His Asn Thr Val Lys Asn Asn Asp Asp Phe Asp His
                165                 170                 175

Ile Arg Glu Asn Asp Gly Glu Ile Ala Ile
            180                 185

<210> SEQ ID NO 15
<211> LENGTH: 191
<212> TYPE: PRT
<213> ORGANISM: Saccharomyces cerevisiae

<400> SEQUENCE: 15

Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
                20                  25                  30

Pro Thr Ile Pro Pro Pro Asp Asn Tyr Ile Leu Asn Asn Glu Asn Asp
            35                  40                  45

Asp Gly Leu Asp Asn Leu Leu Gly Met Asp Tyr Tyr Asn Ile Asp Asp
        50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
            115                 120                 125

Phe Leu Gly His Asn Lys Thr Leu Ser Ile Ser Ser Leu Gln Gln Ser
        130                 135                 140

Ile Leu Asn Met Ser Lys Asp Pro Gln Pro Met Glu Leu Ile Asn Glu
145                 150                 155                 160

Leu Gly Asn His Asn Thr Val Lys Asn Asn Asp Asp Phe Asp His
                165                 170                 175

Ile Arg Glu Asn Asp Gly Glu Asn Ser Tyr Leu Ser Gln Val Cys
            180                 185                 190
```

<210> SEQ ID NO 16
<211> LENGTH: 388
<212> TYPE: PRT
<213> ORGANISM: Saccharomyces cerevisiae

<400> SEQUENCE: 16

Met Asp Asn Val Val Asp Pro Trp Tyr Ile Asn Pro Ser Gly Phe Ala
1               5                   10                  15

Lys Asp Thr Gln Asp Glu Glu Tyr Val Gln His His Asp Asn Val Asn
            20                  25                  30

Pro Thr Ile Pro Pro Asp Asn Tyr Ile Leu Asn Asn Glu Asn Asp
        35                  40                  45

Asp Gly Leu Asp Asn Leu Leu Gly Met Asp Tyr Tyr Asn Ile Asp Asp
    50                  55                  60

Leu Leu Thr Gln Glu Leu Arg Asp Leu Asp Ile Pro Leu Val Pro Ser
65                  70                  75                  80

Pro Lys Thr Gly Asp Gly Ser Ser Asp Lys Lys Asn Ile Asp Arg Thr
                85                  90                  95

Trp Asn Leu Gly Asp Glu Asn Asn Lys Val Ser His Tyr Ser Lys Lys
            100                 105                 110

Ser Met Ser Ser His Lys Arg Gly Leu Ser Gly Thr Ala Ile Phe Gly
        115                 120                 125

Phe Leu Gly His Asn Lys Thr Leu Ser Ile Ser Ser Leu Gln Gln Ser
    130                 135                 140

Ile Leu Asn Met Ser Lys Asp Pro Gln Pro Met Glu Leu Ile Asn Glu
145                 150                 155                 160

Leu Gly Asn His Asn Thr Val Lys Asn Asn Asp Asp Phe Asp His
                165                 170                 175

Ile Arg Glu Asn Asp Gly Glu Asn Ser Tyr Leu Ser Gln Val Leu Leu
            180                 185                 190

Lys Gln Gln Glu Glu Leu Arg Ile Ala Leu Glu Lys Gln Lys Glu Val
        195                 200                 205

Asn Glu Lys Leu Glu Lys Gln Leu Arg Asp Asn Gln Ile Gln Gln Glu
    210                 215                 220

Lys Leu Arg Lys Val Leu Glu Glu Gln Glu Val Ala Gln Lys Leu
225                 230                 235                 240

Val Ser Gly Ala Thr Asn Ser Asn Ser Lys Pro Gly Ser Pro Val Ile
                245                 250                 255

Leu Lys Thr Pro Ala Met Gln Asn Gly Arg Met Lys Asp Asn Ala Ile
            260                 265                 270

Ile Val Thr Thr Asn Ser Ala Asn Gly Gly Tyr Gln Phe Pro Pro Pro
        275                 280                 285

Thr Leu Ile Ser Pro Arg Met Ser Asn Thr Ser Ile Asn Gly Ser Pro
    290                 295                 300

Ser Arg Lys Tyr His Arg Gln Arg Tyr Pro Asn Lys Ser Pro Glu Ser
305                 310                 315                 320

Asn Gly Leu Asn Leu Phe Ser Ser Asn Ser Gly Tyr Leu Arg Asp Ser
                325                 330                 335

Glu Leu Leu Ser Phe Ser Pro Gln Asn Tyr Asn Leu Asn Leu Asp Gly
            340                 345                 350

Leu Thr Tyr Asn Asp His Asn Asn Thr Ser Asp Lys Asn Asn Asn Asp
        355                 360                 365

Lys Lys Ile Val Leu Val Ile Thr Tyr Ser Val Cys Ser Lys Arg Leu

```
              370                 375                 380
Pro Arg Val Gly
385

<210> SEQ ID NO 17
<211> LENGTH: 322
<212> TYPE: PRT
<213> ORGANISM: Saccharomyces cerevisiae

<400> SEQUENCE: 17

Met Pro Leu Asn Lys Ser Asn Ile Arg Glu Tyr Lys Leu Val Val
1               5                   10                  15

Gly Gly Gly Gly Val Gly Lys Ser Ala Leu Thr Ile Gln Leu Thr Gln
                20                  25                  30

Ser His Phe Val Asp Glu Tyr Asp Pro Thr Ile Glu Asp Ser Tyr Arg
            35                  40                  45

Lys Gln Val Val Ile Asp Asp Glu Val Ser Ile Leu Asp Ile Leu Asp
        50                  55                  60

Thr Thr Gly Gln Glu Glu Tyr Ser Ala Met Arg Glu Gln Tyr Met Arg
65                  70                  75                  80

Asn Gly Glu Gly Phe Leu Leu Val Tyr Ser Ile Thr Ser Lys Ser Ser
                85                  90                  95

Leu Asp Glu Leu Met Thr Tyr Tyr Gln Gln Ile Leu Arg Val Lys Asp
            100                 105                 110

Thr Asp Tyr Val Pro Ile Val Val Gly Asn Lys Ser Asp Leu Glu
        115                 120                 125

Asn Glu Lys Gln Val Ser Tyr Gln Asp Gly Leu Asn Met Ala Lys Gln
    130                 135                 140

Met Asn Ala Pro Phe Leu Glu Thr Ser Ala Lys Gln Ala Ile Asn Val
145                 150                 155                 160

Glu Glu Ala Phe Tyr Thr Leu Ala Arg Leu Val Arg Asp Glu Gly Gly
                165                 170                 175

Lys Tyr Asn Lys Thr Leu Thr Glu Asn Asp Asn Ser Lys Gln Thr Ser
            180                 185                 190

Gln Asp Thr Lys Gly Ser Gly Ala Asn Ser Val Pro Arg Asn Ser Gly
        195                 200                 205

Gly His Arg Lys Met Ser Asn Ala Ala Asn Gly Lys Asn Val Asn Ser
    210                 215                 220

Ser Thr Thr Val Val Asn Ala Arg Asn Ala Ser Ile Glu Ser Lys Thr
225                 230                 235                 240

Gly Leu Ala Gly Asn Gln Ala Thr Asn Gly Lys Thr Gln Thr Asp Arg
                245                 250                 255

Thr Asn Ile Asp Asn Ser Thr Gly Gln Ala Gly Gln Ala Asn Ala Gln
            260                 265                 270

Ser Ala Asn Thr Val Asn Asn Arg Val Asn Asn Ser Lys Ala Gly
        275                 280                 285

Gln Val Ser Asn Ala Lys Gln Ala Arg Lys Gln Gln Ala Ala Pro Gly
    290                 295                 300

Gly Asn Thr Ser Glu Ala Ser Lys Ser Gly Ser Gly Gly Cys Cys Ile
305                 310                 315                 320

Ile Ser

<210> SEQ ID NO 18
<211> LENGTH: 969
<212> TYPE: DNA
```

```
<213> ORGANISM: Saccharomyces cerevisiae
<220> FEATURE:
<221> NAME/KEY: misc_feature
<222> LOCATION: (198)..(198)
<223> OTHER INFORMATION: n is a, c, g, or t

<400> SEQUENCE: 18
atgcctttga caagtcgaa cataagagag tacaagctag tcgtcgttgg tggtggtggt      60
gttggtaaat ctgctttgac catacaattg acccaatcgc actttgtaga tgaatacgat     120
cccacaattg aggattcata caggaagcaa gtggtgattg atgatgaagt gtctatattg     180
gacattttgg atactacngg gcaggaagaa tactctgcta tgagggaaca atacatgcgc     240
aacggcgaag gattcctatt ggtttactct ataacatcca agtcgtctct tgatgagctt     300
atgacttact atcaacagat attgagagtc aaagataccg actatgttcc aattgtggtt     360
gttggtaaca atctgatttt agaaaacgaa aaacaggtct cttaccagga cgggttgaac     420
atggcaaagc aaatgaacgc tcctttcttg gagacatctg ctaagcaagc aatcaacgtg     480
gaagaggcgt tttacactct agcacgttta gttagagacg aaggcggcaa gtacaacaag     540
actttgacgg aaaatgacaa ctccaagcaa acttctcaag atacaaaagg gagcggtgcc     600
aactctgtgc ctagaaatag cggtggccac aggaagatga gcaatgctgc caacggtaaa     660
aatgtgaaca gtagcacaac tgtcgtgaat gccaggaatg caagcataga gagtaagaca     720
gggttggcag gcaaccaggc gacaaatggt aagacacaaa ctgatcgcac caatatagac     780
aattccacgg gccaagctgg tcaggccaac gctcaaagcg ctaataccggt taataatcgt     840
gtaaataata atagtaaggc cggtcaagtt tcaaatgcta acaggctag gaagcagcaa     900
gctgcacccg gcggtaacac cagtgaagcc tccaagagcg gatcgggtgg ctgttgtatt     960
ataagttaa                                                             969

<210> SEQ ID NO 19
<211> LENGTH: 322
<212> TYPE: PRT
<213> ORGANISM: Saccharomyces cerevisiae

<400> SEQUENCE: 19

Met Pro Leu Asn Lys Ser Asn Ile Arg Glu Tyr Lys Leu Val Val
1               5                   10                  15

Gly Gly Gly Gly Val Gly Lys Ser Ala Leu Thr Ile Gln Leu Thr Gln
            20                  25                  30

Ser His Phe Val Asp Glu Tyr Asp Pro Thr Ile Glu Asp Ser Tyr Arg
        35                  40                  45

Lys Gln Val Val Ile Asp Asp Glu Val Ser Ile Leu Asp Ile Leu Asp
    50                  55                  60

Thr Ala Gly Gln Glu Glu Tyr Ser Ala Met Arg Glu Gln Tyr Met Arg
65                  70                  75                  80

Asn Gly Glu Gly Phe Leu Leu Val Tyr Ser Ile Thr Ser Lys Ser Ser
                85                  90                  95

Leu Asp Glu Leu Met Thr Tyr Tyr Gln Gln Ile Leu Arg Val Lys Asp
            100                 105                 110

Thr Asp Tyr Val Pro Ile Val Val Gly Asn Lys Ser Asp Leu Glu
        115                 120                 125

Asn Glu Lys Gln Val Ser Tyr Gln Asp Gly Leu Asn Met Ala Lys Gln
    130                 135                 140

Met Asn Ala Pro Phe Leu Glu Thr Ser Ala Lys Gln Ala Ile Asn Val
145                 150                 155                 160
```

-continued

```
Glu Glu Ala Phe Tyr Thr Leu Ala Arg Leu Val Arg Asp Glu Gly Gly
                165                 170                 175

Lys Tyr Asn Lys Thr Leu Thr Glu Asn Asp Asn Ser Lys Gln Thr Ser
            180                 185                 190

Gln Asp Thr Lys Gly Ser Gly Ala Asn Ser Val Pro Arg Asn Ser Gly
        195                 200                 205

Gly His Arg Lys Met Ser Asn Ala Ala Asn Gly Lys Asn Val Asn Ser
    210                 215                 220

Ser Thr Thr Val Val Asn Ala Arg Asn Ala Ser Ile Glu Ser Lys Thr
225                 230                 235                 240

Gly Leu Ala Gly Asn Gln Ala Thr Asn Gly Lys Thr Gln Thr Asp Arg
                245                 250                 255

Thr Asn Ile Asp Asn Ser Thr Gly Gln Ala Gly Gln Ala Asn Ala Gln
            260                 265                 270

Ser Ala Asn Thr Val Asn Asn Arg Val Asn Asn Ser Lys Ala Gly
        275                 280                 285

Gln Val Ser Asn Ala Lys Gln Ala Arg Lys Gln Gln Ala Ala Pro Gly
    290                 295                 300

Gly Asn Thr Ser Glu Ala Ser Lys Ser Gly Ser Gly Gly Cys Cys Ile
305                 310                 315                 320

Ile Ser
```

```
<210> SEQ ID NO 20
<211> LENGTH: 3079
<212> TYPE: PRT
<213> ORGANISM: Saccharomyces cerevisiae

<400> SEQUENCE: 20
```

```
Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60

Asn Val Thr Val Ser Arg Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Gly Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
    130                 135                 140

Pro Lys Leu His Asn Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
        195                 200                 205
```

-continued

Asn Ile Val Thr Thr Leu Ser Ser Ile Leu Pro Arg His Lys Ser
        210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
            245                 250                 255

Tyr Phe Glu Phe Ile Arg Lys Ser Val Gln Val Pro Val Thr Gln Thr
                260                 265                 270

His Thr His Ser His Ser His Ser Leu Pro Ser Ser Val Tyr
            275                 280                 285

Asn Ser Ile Val Pro His Phe Asp Leu Phe Ser Phe Ile His Leu Ser
290                 295                 300

Lys Asp Asn Phe Lys Lys Tyr Leu Glu Leu Ile Lys Asn Leu Ser Val
305                 310                 315                 320

Thr Leu Arg Lys Thr Ile Tyr His Cys Leu Leu His Tyr Ser Ala
            325                 330                 335

Lys Ala Ile Met Phe Trp Ile Met Thr Arg Pro Ala Glu Tyr Tyr Glu
                340                 345                 350

Leu Phe Asn Leu Leu Lys Asp Asn Asn Glu His Ser Lys Ser Leu
            355                 360                 365

Asn Thr Leu Asn His Thr Leu Phe Glu Glu Ile His Ser Thr Phe Asn
370                 375                 380

Val Asn Ser Met Ile Thr Thr Asn Gln Asn Ala His Gln Gly Ser Ser
385                 390                 395                 400

Ser Pro Ser Ser Ser Pro Ser Ser Pro Pro Ser Ser Ser Ser Ser
            405                 410                 415

Asp Asn Asn Asn Gln Asn Ile Ile Ala Lys Ser Leu Ser Arg Gln Leu
            420                 425                 430

Ser His His Gln Ser Tyr Ile Gln Gln Gln Ser Glu Arg Lys Leu His
            435                 440                 445

Ser Ser Trp Thr Thr Asn Ser Gln Ser Ser Thr Ser Leu Ser Ser Ser
450                 455                 460

Thr Ser Asp Ser Thr Thr Thr Asp Phe Ser Thr His Thr Gln Pro Gly
465                 470                 475                 480

Glu Tyr Asp Pro Ser Leu Pro Asp Thr Pro Thr Met Ser Asn Ile Thr
            485                 490                 495

Ile Ser Ala Ser Ser Leu Leu Ser Gln Thr Pro Thr Pro Thr Thr Gln
            500                 505                 510

Leu Gln Gln Arg Leu Asn Ser Ala Ala Ala Ala Ala Ala Ala
            515                 520                 525

Ser Pro Ser Asn Ser Thr Pro Thr Gly Tyr Thr Ala Glu Gln Gln Ser
530                 535                 540

Arg Ala Ser Tyr Asp Ala His Lys Thr Gly Thr Gly Lys Asp Tyr
545                 550                 555                 560

Asp Glu His Phe Leu Ser Ile Thr Arg Leu Asp Asn Val Leu Glu Leu
            565                 570                 575

Tyr Thr His Phe Asp Asp Thr Glu Val Leu Pro His Thr Ser Val Leu
            580                 585                 590

Lys Phe Leu Thr Thr Leu Thr Met Phe Asp Ile Asp Leu Phe Asn Glu
            595                 600                 605

Leu Asn Ala Thr Ser Phe Lys Tyr Ile Pro Asp Cys Thr Met His Arg
610                 615                 620

```
Pro Lys Glu Arg Thr Ser Ser Phe Asn Asn Thr Ala His Glu Thr Gly
625                 630                 635                 640

Ser Glu Lys Thr Ser Gly Ile Lys His Ile Thr Gln Gly Leu Lys Lys
            645                 650                 655

Leu Thr Ser Leu Pro Ser Ser Thr Lys Lys Thr Val Lys Phe Met Lys
                660                 665                 670

Met Leu Leu Arg Asn Leu Ile Gly Asn Gln Ala Val Ser Asp Val Ala
            675                 680                 685

Leu Leu Asp Thr Met Arg Ala Leu Leu Ser Phe Phe Thr Met Thr Ser
    690                 695                 700

Ala Val Phe Leu Val Asp Arg Asn Leu Pro Ser Val Leu Phe Ala Lys
705                 710                 715                 720

Arg Leu Ile Pro Ile Met Gly Thr Asn Leu Ser Val Gly Gln Asp Trp
                725                 730                 735

Asn Ser Lys Ile Asn Asn Ser Leu Met Val Cys Leu Lys Lys Asn Ser
            740                 745                 750

Thr Thr Phe Val Gln Leu Gln Leu Ile Phe Phe Ser Ser Ala Ile Gln
        755                 760                 765

Phe Asp His Glu Leu Leu Leu Ala Arg Leu Ser Ile Asp Thr Met Ala
770                 775                 780

Asn Asn Leu Asn Met Gln Lys Leu Cys Leu Tyr Thr Glu Gly Phe Arg
785                 790                 795                 800

Ile Phe Phe Asp Ile Pro Ser Lys Lys Glu Leu Arg Lys Ala Ile Ala
                805                 810                 815

Val Lys Ile Ser Lys Phe Phe Lys Thr Leu Phe Ser Ile Ile Ala Asp
            820                 825                 830

Ile Leu Leu Gln Glu Phe Pro Tyr Phe Asp Glu Gln Ile Thr Asp Ile
        835                 840                 845

Val Ala Ser Ile Leu Asp Gly Thr Ile Ile Asn Glu Tyr Gly Thr Lys
850                 855                 860

Lys His Phe Lys Gly Ser Ser Pro Ser Leu Cys Ser Thr Thr Arg Ser
865                 870                 875                 880

Arg Ser Gly Ser Thr Ser Gln Ser Ser Met Thr Pro Val Ser Pro Leu
                885                 890                 895

Gly Leu Asp Thr Asp Ile Cys Pro Met Asn Thr Leu Ser Leu Val Gly
            900                 905                 910

Ser Ser Thr Ser Arg Asn Ser Asp Asn Val Asn Ser Leu Asn Ser Ser
        915                 920                 925

Pro Lys Asn Leu Ser Ser Asp Pro Tyr Leu Ser His Leu Val Ala Pro
    930                 935                 940

Arg Ala Arg His Ala Leu Gly Gly Pro Ser Ser Ile Ile Arg Asn Lys
945                 950                 955                 960

Ile Pro Thr Thr Leu Thr Ser Pro Pro Gly Thr Glu Lys Ser Ser Pro
                965                 970                 975

Val Gln Arg Pro Gln Thr Glu Ser Ile Ser Ala Thr Pro Met Ala Ile
            980                 985                 990

Thr Asn Ser Thr Pro Leu Ser Ser  Ala Ala Phe Gly Ile  Arg Ser Pro
        995                 1000                1005

Leu Gln  Lys Ile Arg Thr Arg  Arg Tyr Ser Asp Glu  Ser Leu Gly
        1010                1015                1020

Lys Phe  Met Lys Ser Thr Asn  Asn Tyr Ile Gln Glu  His Leu Ile
        1025                1030                1035

Pro Lys  Asp Leu Asn Glu Ala  Thr Leu Gln Asp Ala  Arg Arg Ile
```

|          |          |          |          |          |          |          |          |          |          |
|----------|----------|----------|----------|----------|----------|----------|----------|----------|----------|
|          |          |          | 1040     |          |          | 1045     |          |          | 1050     |
| Met      | Ile      | Asn      | Ile      | Phe      | Ser      | Ile      | Phe      | Lys      | Arg      | Pro | Asn | Ser | Tyr | Phe |

Met Ile Asn Ile Phe Ser Ile Phe Lys Arg Pro Asn Ser Tyr Phe
        1055                1060                1065

Ile Ile Pro His Asn Ile Asn Ser Asn Leu Gln Trp Val Ser Gln
        1070                1075                1080

Asp Phe Arg Asn Ile Met Lys Pro Ile Phe Val Ala Ile Val Ser
        1085                1090                1095

Pro Asp Val Asp Leu Gln Asn Thr Ala Gln Ser Phe Met Asp Thr
        1100                1105                1110

Leu Leu Ser Asn Val Ile Thr Tyr Gly Glu Ser Asp Glu Asn Ile
        1115                1120                1125

Ser Ile Glu Gly Tyr His Leu Leu Cys Ser Tyr Thr Val Thr Leu
        1130                1135                1140

Phe Ala Met Gly Leu Phe Asp Leu Lys Ile Asn Asn Glu Lys Arg
        1145                1150                1155

Gln Ile Leu Leu Asp Ile Thr Val Lys Phe Met Lys Val Arg Ser
        1160                1165                1170

His Leu Ala Gly Ile Ala Glu Ala Ser His His Met Glu Tyr Ile
        1175                1180                1185

Ser Asp Ser Glu Lys Leu Thr Phe Pro Leu Ile Met Gly Thr Val
        1190                1195                1200

Gly Arg Ala Leu Phe Val Ser Leu Tyr Ser Ser Gln Gln Lys Ile
        1205                1210                1215

Glu Lys Thr Leu Lys Ile Ala Tyr Thr Glu Tyr Leu Ser Ala Ile
        1220                1225                1230

Asn Phe His Glu Arg Asn Ile Asp Asp Ala Asp Lys Thr Trp Val
        1235                1240                1245

His Asn Ile Glu Phe Val Glu Ala Met Cys His Asp Asn Tyr Thr
        1250                1255                1260

Thr Ser Gly Ser Ile Ala Phe Gln Arg Arg Thr Arg Asn Asn Ile
        1265                1270                1275

Leu Arg Phe Ala Thr Ile Pro Asn Ala Ile Leu Leu Asp Ser Met
        1280                1285                1290

Arg Met Ile Tyr Lys Lys Trp His Thr Tyr Thr His Ser Lys Ser
        1295                1300                1305

Leu Glu Lys Gln Glu Arg Asn Asp Phe Arg Asn Phe Ala Gly Ile
        1310                1315                1320

Leu Ala Ser Leu Ser Gly Ile Leu Phe Ile Asn Lys Lys Ile Leu
        1325                1330                1335

Gln Glu Met Tyr Pro Tyr Leu Leu Asp Thr Val Ser Glu Leu Lys
        1340                1345                1350

Lys Asn Ile Asp Ser Phe Ile Ser Lys Gln Cys Gln Trp Leu Asn
        1355                1360                1365

Tyr Pro Asp Leu Leu Thr Arg Glu Asn Ser Arg Asp Ile Leu Ser
        1370                1375                1380

Val Glu Leu His Pro Leu Ser Phe Asn Leu Leu Phe Asn Asn Leu
        1385                1390                1395

Arg Leu Lys Leu Lys Glu Leu Ala Cys Ser Asp Leu Ser Ile Pro
        1400                1405                1410

Glu Asn Glu Ser Ser Tyr Val Leu Leu Glu Gln Ile Ile Lys Met
        1415                1420                1425

Leu Arg Thr Ile Leu Gly Arg Asp Asp Asp Asn Tyr Val Met Met
        1430                1435                1440

```
Leu Phe Ser Thr Glu Ile Val Asp Leu Ile Asp Leu Leu Thr Asp
    1445                1450                1455

Glu Ile Lys Lys Ile Pro Ala Tyr Cys Pro Lys Tyr Leu Lys Ala
    1460                1465                1470

Ile Ile Gln Met Thr Lys Met Phe Ser Ala Leu Gln His Ser Glu
    1475                1480                1485

Val Asn Leu Gly Val Lys Asn His Phe His Val Lys Asn Lys Trp
    1490                1495                1500

Leu Arg Gln Val Thr Asp Trp Phe Gln Val Ser Ile Ala Arg Glu
    1505                1510                1515

Tyr Asp Phe Glu Asn Leu Ser Lys Pro Leu Lys Glu Met Asp Leu
    1520                1525                1530

Val Lys Arg Asp Met Asp Ile Leu Tyr Ile Asp Thr Ala Ile Glu
    1535                1540                1545

Ala Ser Thr Ala Ile Ala Tyr Leu Thr Arg His Thr Phe Leu Glu
    1550                1555                1560

Ile Pro Pro Ala Ala Ser Asp Pro Glu Leu Ser Arg Ser Arg Ser
    1565                1570                1575

Val Ile Phe Gly Phe Tyr Phe Asn Ile Leu Met Lys Gly Leu Glu
    1580                1585                1590

Lys Ser Ser Asp Arg Asp Asn Tyr Pro Val Phe Leu Arg His Lys
    1595                1600                1605

Met Ser Val Leu Asn Asp Asn Val Ile Leu Ser Leu Thr Asn Leu
    1610                1615                1620

Ser Asn Thr Asn Val Asp Ala Ser Leu Gln Phe Thr Leu Pro Met
    1625                1630                1635

Gly Tyr Ser Gly Asn Arg Asn Ile Arg Asn Ala Phe Leu Glu Val
    1640                1645                1650

Phe Ile Asn Ile Val Thr Asn Tyr Arg Thr Tyr Thr Ala Lys Thr
    1655                1660                1665

Asp Leu Gly Lys Leu Glu Ala Asp Lys Phe Leu Arg Tyr Thr
    1670                1675                1680

Ile Glu His Pro Gln Leu Ser Ser Phe Gly Ala Ala Val Cys Pro
    1685                1690                1695

Ala Ser Asp Ile Asp Ala Tyr Ala Ala Gly Leu Ile Asn Ala Phe
    1700                1705                1710

Glu Thr Arg Asn Ala Thr His Ile Val Val Ser Gln Leu Ile Lys
    1715                1720                1725

Asn Glu Ile Glu Asn Ser Ser Arg Pro Thr Asp Ile Leu Arg Arg
    1730                1735                1740

Asn Ser Cys Ala Thr Arg Ser Leu Ser Met Leu Ala Arg Ser Lys
    1745                1750                1755

Gly Ser Glu Tyr Leu Ile Arg Thr Leu Gln Pro Leu Leu Lys Lys
    1760                1765                1770

Ile Ile Gln Asn Arg Asp Phe Phe Glu Ile Glu Lys Leu Lys Pro
    1775                1780                1785

Glu Asp Ser Asp Ala Glu Arg Gln Ile Glu Leu Phe Val Lys Tyr
    1790                1795                1800

Met Asn Glu Leu Leu Glu Ser Ile Ser Asn Ser Val Ser Tyr Phe
    1805                1810                1815

Pro Pro Pro Leu Phe Tyr Ile Cys Gln Asn Ile Tyr Lys Val Ala
    1820                1825                1830
```

```
Cys Glu Lys Phe Pro Asp His Ala Ile Ile Ala Ala Gly Ser Phe
    1835            1840                1845

Val Phe Leu Arg Phe Phe Cys Pro Ala Leu Val Ser Pro Asp Ser
    1850            1855                1860

Glu Asn Ile Ile Asp Ile Ser His Leu Ser Glu Lys Arg Thr Phe
    1865            1870                1875

Ile Ser Leu Ala Lys Val Ile Gln Asn Ile Ala Asn Gly Ser Glu
    1880            1885                1890

Asn Phe Ser Arg Trp Pro Ala Leu Cys Ser Gln Lys Asp Phe Leu
    1895            1900                1905

Lys Glu Cys Ser Asp Arg Ile Phe Arg Phe Leu Ala Glu Leu Cys
    1910            1915                1920

Arg Thr Asp Arg Thr Ile Asp Ile Gln Val Arg Thr Asp Pro Thr
    1925            1930                1935

Pro Ile Ala Phe Asp Tyr Gln Phe Leu His Ser Phe Val Tyr Leu
    1940            1945                1950

Tyr Gly Leu Glu Val Arg Arg Asn Val Leu Asn Glu Ala Lys His
    1955            1960                1965

Asp Asp Gly Asp Ile Asp Gly Asp Asp Phe Tyr Lys Thr Thr Phe
    1970            1975                1980

Leu Leu Ile Asp Asp Val Leu Gly Gln Leu Gly Gln Pro Lys Met
    1985            1990                1995

Glu Phe Ser Asn Glu Ile Pro Ile Tyr Ile Arg Glu His Met Asp
    2000            2005                2010

Asp Tyr Pro Glu Leu Tyr Glu Phe Met Asn Arg His Ala Phe Arg
    2015            2020                2025

Asn Ile Glu Thr Ser Thr Ala Tyr Ser Pro Ser Val His Glu Ser
    2030            2035                2040

Thr Ser Ser Glu Gly Ile Pro Ile Ile Thr Leu Thr Met Ser Asn
    2045            2050                2055

Phe Ser Asp Arg His Val Asp Ile Asp Thr Val Ala Tyr Lys Phe
    2060            2065                2070

Leu Gln Ile Tyr Ala Arg Ile Trp Thr Thr Lys His Cys Leu Ile
    2075            2080                2085

Ile Asp Cys Thr Glu Phe Glu Gly Gly Leu Asp Met Arg Lys
    2090            2095                2100

Phe Ile Ser Leu Val Met Gly Leu Leu Pro Glu Val Ala Pro Lys
    2105            2110                2115

Asn Cys Ile Gly Cys Tyr Tyr Phe Asn Val Asn Glu Thr Phe Met
    2120            2125                2130

Asp Asn Tyr Gly Lys Cys Leu Asp Lys Asp Asn Val Tyr Val Ser
    2135            2140                2145

Ser Lys Ile Pro His Tyr Phe Ile Asn Ser Asn Ser Asp Glu Gly
    2150            2155                2160

Leu Met Lys Ser Val Gly Ile Thr Gly Gln Gly Leu Lys Val Leu
    2165            2170                2175

Gln Asp Ile Arg Val Ser Leu His Asp Ile Thr Leu Tyr Asp Glu
    2180            2185                2190

Lys Arg Asn Arg Phe Thr Pro Val Ser Leu Lys Ile Gly Asp Ile
    2195            2200                2205

Tyr Phe Gln Val Leu His Glu Thr Pro Arg Gln Tyr Lys Ile Arg
    2210            2215                2220

Asp Met Gly Thr Leu Phe Asp Val Lys Phe Asn Asp Val Tyr Glu
```

```
                 2225                2230                2235

Ile Ser Arg Ile Phe Glu Val His Val Ser Ser Ile Thr Gly Val
    2240                2245                2250

Ala Ala Glu Phe Thr Val Thr Phe Gln Asp Glu Arg Arg Leu Ile
    2255                2260                2265

Phe Ser Ser Pro Lys Tyr Leu Glu Ile Val Lys Met Phe Tyr Tyr
    2270                2275                2280

Ala Gln Ile Arg Leu Glu Ser Glu Tyr Glu Met Asp Asn Asn Ser
    2285                2290                2295

Ser Thr Ser Ser Pro Asn Ser Asn Asn Lys Asp Lys Gln Gln Lys
    2300                2305                2310

Glu Arg Thr Lys Leu Leu Cys His Leu Leu Val Ser Leu Ile
    2315                2320                2325

Gly Leu Phe Asp Glu Ser Lys Lys Met Lys Asn Ser Ser Tyr Asn
    2330                2335                2340

Leu Ile Ala Ala Thr Glu Ala Ser Phe Gly Leu Asn Phe Gly Ser
    2345                2350                2355

His Phe His Arg Ser Pro Glu Val Tyr Val Pro Glu Asp Thr Thr
    2360                2365                2370

Thr Phe Leu Gly Val Ile Gly Lys Ser Leu Ala Glu Ser Asn Pro
    2375                2380                2385

Glu Leu Thr Ala Tyr Met Phe Ile Tyr Val Leu Glu Ala Leu Lys
    2390                2395                2400

Asn Asn Val Ile Pro His Val Tyr Ile Pro His Thr Ile Cys Gly
    2405                2410                2415

Leu Ser Tyr Trp Ile Pro Asn Leu Tyr Gln His Val Tyr Leu Ala
    2420                2425                2430

Asp Asp Glu Glu Gly Pro Lys Asn Ile Ser His Ile Phe Arg Ile
    2435                2440                2445

Leu Ile Arg Leu Ser Val Arg Glu Thr Asp Phe Lys Ala Val Tyr
    2450                2455                2460

Met Gln Tyr Val Trp Leu Leu Leu Leu Asp Asp Gly Arg Leu Thr
    2465                2470                2475

Asp Ile Ile Val Asp Glu Val Ile Asn His Ala Leu Glu Arg Asp
    2480                2485                2490

Ser Glu Asn Arg Asp Trp Lys Lys Thr Ile Ser Leu Leu Thr Val
    2495                2500                2505

Leu Pro Thr Thr Glu Val Ala Asn Asn Ile Ile Gln Lys Ile Leu
    2510                2515                2520

Ala Lys Ile Arg Ser Phe Leu Pro Ser Leu Lys Leu Glu Ala Met
    2525                2530                2535

Thr Gln Ser Trp Ser Glu Leu Thr Ile Leu Val Lys Ile Ser Ile
    2540                2545                2550

His Val Phe Phe Glu Thr Ser Leu Leu Val Gln Met Tyr Leu Pro
    2555                2560                2565

Glu Ile Leu Phe Ile Val Ser Leu Leu Ile Asp Val Gly Pro Arg
    2570                2575                2580

Glu Leu Arg Ser Ser Leu His Gln Leu Leu Met Asn Val Cys His
    2585                2590                2595

Ser Leu Ala Ile Asn Ser Ala Leu Pro Gln Asp His Arg Asn Asn
    2600                2605                2610

Leu Asp Glu Ile Ser Asp Ile Phe Ala His Gln Lys Val Lys Phe
    2615                2620                2625
```

-continued

```
Met Phe Gly Phe Ser Glu Asp Lys Gly Arg Ile Leu Gln Ile Phe
2630                2635                2640

Ser Ala Ser Ser Phe Ala Ser Lys Phe Asn Ile Leu Asp Phe Phe
2645                2650                2655

Ile Asn Asn Ile Leu Leu Met Glu Tyr Ser Ser Thr Tyr Glu
2660                2665                2670

Ala Asn Val Trp Lys Thr Arg Tyr Lys Lys Tyr Val Leu Glu Ser
2675                2680                2685

Val Phe Thr Ser Asn Ser Phe Leu Ser Ala Arg Ser Ile Met Ile
2690                2695                2700

Val Gly Ile Met Gly Lys Ser Tyr Ile Thr Glu Gly Leu Cys Lys
2705                2710                2715

Ala Met Leu Ile Glu Thr Met Lys Val Ile Ala Glu Pro Lys Ile
2720                2725                2730

Thr Asp Glu His Leu Phe Leu Ala Ile Ser His Ile Phe Thr Tyr
2735                2740                2745

Ser Lys Ile Val Glu Gly Leu Asp Pro Asn Leu Asp Leu Met Lys
2750                2755                2760

His Leu Phe Trp Phe Ser Thr Leu Phe Leu Glu Ser Arg His Pro
2765                2770                2775

Ile Ile Phe Glu Gly Ala Leu Leu Phe Val Ser Asn Cys Ile Arg
2780                2785                2790

Arg Leu Tyr Met Ala Gln Phe Glu Asn Glu Ser Glu Thr Ser Leu
2795                2800                2805

Ile Ser Thr Leu Leu Lys Gly Arg Lys Phe Ala His Thr Phe Leu
2810                2815                2820

Ser Lys Ile Glu Asn Leu Ser Gly Ile Val Trp Asn Glu Asp Asn
2825                2830                2835

Phe Thr His Ile Leu Ile Phe Ile Ile Asn Lys Gly Leu Ser Asn
2840                2845                2850

Pro Phe Ile Lys Ser Thr Ala Phe Asp Phe Leu Lys Met Met Phe
2855                2860                2865

Arg Asn Ser Tyr Phe Glu His Gln Ile Asn Gln Lys Ser Asp His
2870                2875                2880

Tyr Leu Cys Tyr Met Phe Leu Leu Tyr Phe Val Leu Asn Cys Asn
2885                2890                2895

Gln Phe Glu Glu Leu Leu Gly Asp Val Asp Phe Glu Gly Glu Met
2900                2905                2910

Val Asn Ile Glu Asn Lys Asn Thr Ile Pro Lys Ile Leu Leu Glu
2915                2920                2925

Trp Leu Ser Ser Asp Asn Glu Asn Ala Asn Ile Thr Leu Tyr Gln
2930                2935                2940

Gly Ala Ile Leu Phe Lys Cys Ser Val Thr Asp Glu Pro Ser Arg
2945                2950                2955

Phe Arg Phe Ala Leu Ile Ile Arg His Leu Leu Thr Lys Lys Pro
2960                2965                2970

Ile Cys Ala Leu Arg Phe Tyr Ser Val Ile Arg Asn Glu Ile Arg
2975                2980                2985

Lys Ile Ser Ala Phe Glu Gln Thr Ser Asp Cys Val Pro Leu Ala
2990                2995                3000

Phe Asp Ile Leu Asn Leu Leu Val Thr His Ser Glu Ser Asn Ser
3005                3010                3015
```

```
Leu Glu Lys Leu His Glu Glu Ser Ile Glu Arg Leu Thr Lys Arg
    3020            3025                3030
Gly Leu Ser Ile Val Thr Ser Ser Gly Ile Phe Ala Lys Asn Ser
    3035            3040                3045
Asp Met Met Ile Pro Leu Asp Val Lys Pro Glu Asp Ile Tyr Glu
    3050            3055                3060
Arg Lys Arg Ile Met Thr Met Ile Leu Ser Arg Met Ser Cys Ser
    3065            3070                3075
Ala

<210> SEQ ID NO 21
<211> LENGTH: 9240
<212> TYPE: DNA
<213> ORGANISM: Saccharomyces cerevisiae

<400> SEQUENCE: 21
atgtcccagc ccactaagaa taagaagaaa gaacacggga ccgattccaa gtcatcccgc      60
atgactcgga cgttggttaa ccatattctt tttgaaagaa ttctcccgat ccttccggtg     120
gagtctaatc taagtaccta ttcagaagtg aagagtatt cctcattcat ttcatgcaga     180
tctgtgctca ttaacgttac cgtttcccga gatgcaaacg ctatggtgga aggcactttg     240
gagttgatag aatcgcttct tcaagggcac gaaatcattt cagataaggg tagcagtgac     300
gttattgaat caatactgat tatactaaga ttgttaagtg atgcgctaga gtaaattgg      360
caaaatcaag aaagccttca ttacaacgac atttcgactc acgtagaaca tgaccaagaa     420
cagaagtaca gaccaaagct tcacaatatt cttcccgact actcgtcgac tcattccaat     480
ggcaacaaac acttttttcca ccagagcaaa cctcaggcac tgataccgga actggcatcg     540
aaattgcttg agagttgcgc gaagttgaag ttcaatacaa gaactttgca aattttacaa     600
aatatgatca gtcatgttca tggaaacatt gtaacgactt tgagttcctc gattcttccc     660
cgccacaaat cctatttgac aaggcacaac catccttctc attgtaaaat gattgactct     720
actctaggcc atattctccg atttgtagcg gcttccaatc cgtccgagta ttttgaattt     780
atcagaaaga gtgtgcaagt gcccgtaaca cagacacaca cgcattcaca ctcccattca     840
cactctttgc catcttccgt ttataacagc atagtgcccc actttgatct tttcagcttc     900
atccatttaa gtaaggataa ttttaagaaa tacttggaac tcatcaaaaa cttatcggtg     960
acgttaagga aaacgattta tcattgccta cttttgcatt acagcgccaa agcaataatg    1020
ttttggataa tgactaggcc tgcggaatat tatgaactct tcaacttatt aaaagataat    1080
aacaatgaac actcgaaatc cttaaacacg ttaaccata cacttttcga ggagatccat     1140
tcgactttta atgtgaatag catgataacc accaatcaaa atgctcatca aggctcatct    1200
tccccttcgt cctcctcgcc atcgtcacca cctagctcat catcatcgga taacaacaat    1260
caaaacataa tagcaaaatc cttaagtcgt cagctttctc accaccagtc atacattcaa    1320
cagcagtctg aaagaaaact acattcttca tggactacaa actctcaatc ctctacttca    1380
ctgtcatctt caacgtctga ttcaacaaca actgatttct ctactcacac tcaaccagga    1440
gaatacgacc cttccttacc agatactccc acgatgtcta acatcactat tagtgcatct    1500
tcattattat cccaaactcc aactccaaca acacaattgc aacagcggtt gaactcagca    1560
gctgcagccg ccgccgcagc tgcttcacca tcgaattcca ccccaactgg atacacagca    1620
gagcaacaaa gtcgagcttc atacgatgca cacaaaactg gccatactgg taaggattat    1680
gatgaacatt ttttgtctat cactcgtttg gataatgttt tggagttata cacgcacttt    1740
```

```
gatgatactg aggtattacc acacacatcc gtactgaagt ttttaactac tttgacaatg    1800
ttcgatattg accttttttaa tgaattaaac gctacatcat tcaaatatat tcctgattgt    1860
actatgcatc gtccaaaaga aagaacgagt tctttcaata atactgcaca cgagacaggt    1920
tccgaaaaga cttcgggtat aaaacatatt acgcaaggct taaagaaatt aacttcttta    1980
ccttcctcaa ccaaaaaaac tgtaaaattt atgaagatgt tgctaagaaa tttaattggg    2040
aaccaagctg tatcagacgt tgccctctta gatacaatga gggccttact atcattcttc    2100
acaatgactt ctgcggtctt tctcgtggat aggaacttac cctcagtact ttttgccaag    2160
agactcatcc ccataatggg gacaaattta agcgtcggtc aagactggaa ttcaaaaata    2220
aataacagtt tgatggtttg tttgaaaaaa aactccacca cgtttgttca attacaatta    2280
atattcttct cttcagctat tcaattcgat catgaattat tgctggcacg tctgagcatc    2340
gatacaatgg ccaacaattt aaacatgcag aagctatgcc tttatactga aggattcagg    2400
atattcttcg acataccaag taagaaggaa ttgcggaagg caattgcggt taaaatttct    2460 aaattttttca aaacattatt ctccattata gcagatattc ttttacaaga atttccgtat    2520
tttgatgagc aaatcaccga catagttgct tccattcttg acggtacaat tatcaatgag    2580
tatggtacga agaaacattt caaggggagc tcaccctctt tatgttcgac aacccggtca    2640
agatcaggat ctacatctca aagttcaatg acaccagttt ctccgctggg actggatact    2700
gatatatgtc caatgaacac cctgtcttta gttggttcaa gtacttcaag aaattctgac    2760
aacgttaatt cattaaacag ttcaccaaag aacttgtctt ctgatccata cttgtcacat    2820
cttgtggccc caagagcacg tcatgcttta ggtgggccat ctagtattat aaggaataaa    2880
ataccgacta cattgacttc acctccagga acggaaaaat cttcaccagt acaacgtccg    2940
caaacggaaa gcatcagtgc cacaccaatg gccataacaa attctactcc attatcgtcg    3000
gcagcattcg gaattcgatc cccttttgcag aaaataagaa cgaggcgtta ttccgatgaa    3060
agtttaggaa aattcatgaa atcaacaaat aattacattc aagaacattt gataccaaaa    3120
gatttgaatg aggcaactct tcaagatgct agaagaataa tgattaatat tttcagtatt    3180
tttaagagac cgaatagtta cttcatcatt cctcacaata taaactcgaa tttacaatgg    3240
gtttcgcagg atttcagaaa tattatgaaa ccgattttcg tcgccatcgt aagtccggat    3300
gtagatttac agaatactgc tcaatcattc atggatacct tattatcgaa tgttattact    3360
tatggtgaat cagatgagaa tatcagtatt gaaggttatc atcttctttg cagttacact    3420
gtaacattat ttgcaatggg ccttttcgat ttgaaaatta ataatgaaaa gcgtcaaatt    3480
ctcttggata taactgtcaa gtttatgaag gttagatcac atttagcagg gatcgcggag    3540
gcctcacacc acatggaata cataagtgat tctgaaaaac tcacctttcc gctgattatg    3600
gggaccgttg gtagggccct atttgtttca ttatactcta gtcaacaaaa aattgaaaag    3660
actttaaaga ttgcttacac agagtatctt tctgcaatca atttttcatga gaggaatatt    3720 gatgatgctg ataaaacttg ggttcataat attgagtttg tagaagcgat gtgtcatgac    3780
aactacacaa cttctggttc aattgctttc caaaggagga caagaaataa tattttacga    3840
tttgctacta ttcctaacgc tatcttactt gattctatga ggatgatcta taagaagtgg    3900
catacttaca cacacagtaa aagtttagaa aaacaagaac ggaacgactt cagaaatttc    3960
gcgggtattt tagcctcttt gtcgggtatc ctattcatca ataaaaagat attgcaagaa    4020
atgtatccat acctactcga caccgtttca gaattgaaaa aaaatataga ctcttttatc    4080
```

```
tcaaaacaat gccaatggtt aaactatccg gatttattaa cgagagaaaa ttcaagagat    4140
attctaagtg tagaactgca tcctttgtct tttaacttac tttttaataa tttgaggctc    4200
aagttaaaag aacttgcttg ttcagactta tcaataccag aaaatgaaag ttcctatgtt    4260
ttattagaac aaataatcaa aatgctgcgg acaatcctag gtcgtgatga tgacaattat    4320
gtaatgatgc ttttttccac agagattgta gatcttattg atttattgac agatgaaata    4380
aaaaaaatac cagcctattg tccaaaatat ctcaaggcaa ttattcaaat gaccaaaatg    4440
tttagtgcct tgcagcactc agaggttaat ttaggtgtca aaaatcattt tcacgttaaa    4500
aataaatggt tgagacaagt cactgattgg tttcaagtga gtattgcgag agagtacgat    4560
ttcgaaaact tgtcaaaacc tctaaaagaa atggatttgg taaaaagaga catggatatt    4620
ctatacatag atacggcaat cgaagcttca accgctattg cgtacctcac gagacatact    4680
ttcttagaga ttccacctgc cgcgtcagat cccgaactat ctcgatctag gtctgtgata    4740
tttggctttt atttcaacat cttaatgaaa ggccttgaaa aaagtagtga tcgtgacaat    4800
tacccagtat tcttgaggca caaaatgagt gtcctcaacg acaatgtaat actttcatta    4860
acaaatcttt ctaacaccaa tgttgatgcg agtttgcagt tcaccttacc gatgggctat    4920
tccggaaatc gaaacattag gaatgcattt ttggaggtct tcattaatat cgttacgaac    4980
tatcggacat acacggctaa aactgacctt ggaaaattag aagcagcaga caaatttttg    5040
cgatatacga ttgaacatcc ccagctatcg tcctttggag cagcggtttg tcccgctagc    5100
gatattgatg cttatgctgc tggcttaata aatgcatttg aaacgagaaa tgccacccac    5160
attgtagtgt cacagttgat taaaaatgaa attgaaaatt cttccagacc tacgatatc     5220
cttagaagga atagctgtgc tacgagatca ttatctatgc tagccaggtc caagggtagc    5280
gaatatttga ttcgcacttt gcaaccatta ctaaaaaaaa ttatccagaa cagagatttt    5340
tttgaaattg agaaattaaa accggaagat tcagatgctg aacgtcaaat agagcttttt    5400
gttaaataca tgaatgaatt attggaatcc atatccaact ccgtatctta ttttccccct    5460
cctttatttt atatttgtca aaacatttat aaagttgcgt gtgaaaaatt tccggatcac    5520
gcaattatcg ccgctgggtc tttcgtattt ttacggtttt tttgtcctgc tttagtcagc    5580
cctgattctg aaaatatcat agatatttct cacttgagcg aaaagcgtac cttcatcagc    5640
ttggctaaag ttatccaaaa tattgccaat ggctcagaaa attttctccag atggccagct    5700
ttgtgttccc aaaaggattt tcttaaggaa tgtagcgata gaattttcag attcctagct    5760
gaactttgta gaacagatcg cacgatagac atccaagtga gaacagaccc aacgccaatt    5820
gcatttgact atcaattcct tcattccttt gtttacctttacggtcttga agtgagaagg    5880
aatgtgctaa atgaagcaaa acatgatgat ggtgacattg atggtgacga tttctataag    5940
accacgtttt tacttattga tgatgttctt ggccaattag gccaacctaa aatggaattt    6000
tccaatgaaa taccaatata cataagagaa catatggacg actatccgga actgtatgag    6060
ttcatgaata ggcacgcgtt cagaaacatt gagacttcaa cagcgtacag cccaagcgtt    6120
cacgagtcca cctcaagtga aggcattcca attattacgt taacaatgtc aaatttctca    6180
gacagacatg tggacattga tacagttgct tacaagttct tgcaaatttta tgctcgaatc    6240
tggaccacca aacactgttt aataatcgac tgtacagaat ttgacgaggg agggcttgat    6300
atgaggaaat ttatttcttt ggttatggga ctattaccag aagttgcacc caaaaattgt    6360
ataggctgtt actactttaa cgtaaacgag acatttatgg ataattatgg aaaatgtttg    6420
gacaaggaca acgtatatgt ttcctcgaaa attcctcatt atttcattaa tagtaactct    6480
```

```
gatgaaggac ttatgaaatc tgtgggtata actggacaag ggttgaaggt tctgcaagat    6540
attcgtgtct ctctgcatga tatcacgctt tatgacgaaa aaagaaatag atttacgccg    6600
gtatcgttga aaataggcga tatttacttt caagtcttgc atgaaactcc taggcaatat    6660
aaaataagag acatgggtac tttattcgac gtaaaattca atgatgtcta cgaaattagc    6720
cgaatattcg aagtacatgt ttcgtcaata actggagtgg cagctgaatt tacagtaact    6780
tttcaggacg agagaaggtt gattttagt agtccgaaat accttgaaat tgtgaagatg    6840
ttctattacg cacagatccg gttagaaagt gaatatgaaa tggataataa ttcgagtacc    6900
tcctccccaa attcaaacaa caaggacaaa cagcagaaag agaaacaaa attattgtgc    6960 cacctactgt tagtatctct tattggtctg tttgatgaga gtaaaaaaat gaaaaacagt    7020
tcgtataacc taatagctgc cactgaggcg tcatttggtt tgaactttgg ctcccatttt    7080
catcgctctc ccgaggtgta cgtccccgaa gatactacaa cattttagg tgttattgga    7140 aagtctcttg cagagtctaa tccagaactc acagcctata tgtttatcta tgttttggag    7200
gcattgaaga acaacgtgat tcctcatgtt tacatccctc ataccatttg cggtttgtct    7260
tattggatcc ctaatttata ccaacatgtg tatttggctg atgatgaaga aggccccaaa    7320
aacatatctc acattttccg aattcttatc aggctctctg tgagagagac tgactttaaa    7380
gccgtataca tgcaatatgt ttggctgcta cttttagatg atggccgctt aactgacatt    7440
atcgttgatg aagttattaa tcatgcgtta gaaagagact ccgaaaaccg cgattggaag    7500
aaaacaatat cgttactaac tgtcctaccc actactgagg ttgctaataa tattattcaa    7560
aaaatattgg caaaaattag atcattttta ccgtcattga agttagaagc tatgacccaa    7620
agttggtctg aactaacaat attagttaag ataagcatcc atgtttttt tgaaacttct    7680 ttgctggtac agatgtactt accagagatc ctgtttatcg tatccttatt aattgatgtt    7740
ggtccaaggg aactcagatc atcactacac cagctattaa tgaatgtatg ccattccttg    7800
gctattaact cagctttacc acaagatcat agaaataatc tagatgaaat aagtgatata    7860
tttgcacatc aaaaggtgaa gtttatgttt gggttcagcg aggacaaagg acgaattta    7920 cagatttta gcgcttcttc ttttgcaagc aagtttaata tcctggattt cttcatcaat    7980
aatatattat tgctgatgga atattcttca acgtacgaag caaacgtgtg aagacaaga    8040 tacaagaaat atgtcttgga atctgtgttt acaagtaatt cttttctttc ggcacgttca    8100
atcatgattg ttggtataat gggtaaatct tacataactg aagggttatg caaggctatg    8160
ttaattgaaa ccatgaaagt tatcgccgaa ccaaagatta ctgacgagca tcttttctta    8220
gccatatctc atattttac ttattccaaa attgttgaag gtttggatcc caaccttgac    8280
ttaatgaagc acttattttg gttttcaaca ctcttccttg aatcacgtca cccgataatt    8340
tttgagggtg cccttctctt tgtgtcaaac tgtataaggc gcctatacat ggcccagttt    8400
gaaaatgaaa gtgaaacatc attgataagt actttactta aggggagaaa gtttgctcat    8460
acctttttaa gcaagataga gaatcttagt ggtattgttt ggaatgaaga taatttaca    8520 cacattctga ttttcatcat taataaagga ctatccaatc ctttcattaa gagtacggct    8580
tttgatttct tgaagatgat gtttagaaac tcctactttg agcatcaaat caatcagaaa    8640
tctgatcatt atttgtgcta tatgttccta ttgtattttg ttttaaactg taatcaattt    8700
gaggaacttt taggtgacgt tgattttgaa ggagaaatgg ttaacattga aaacaagaac    8760
accattccta aaatttttgtt ggagtggttg agttcggata acgaaaatgc aaacattacc    8820
```

```
ctctatcaag gtgcgatact gttcaaatgt tcagttacgg atgaaccaag tagatttagg    8880
tttgcgttga ttattaggca tctattgaca agaaaccca tttgtgcatt gcgttttac     8940 agtgttattc gtaacgaaat aagaaaaata tcagcatttg agcaaacttc ggattgtgtt   9000
ccacttgctt tcgatatttt aaacttatta gtgacgcatt cagagtctaa ttccttagaa   9060
aaacttcacg aagaatccat tgaacgtctg accaaaagag gtttatcaat tgtgacttct   9120
tctggtatat ttgcgaagaa ttccgacatg atgataccgt tagatgtaaa acctgaagat   9180
atctatgaac gtaagagaat aatgacaatg atttatcaa ggatgtcatg ttctgcttag    9240
```

<210> SEQ ID NO 22
<211> LENGTH: 3079
<212> TYPE: PRT
<213> ORGANISM: Saccharomyces cerevisiae

<400> SEQUENCE: 22

```
Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60

Asn Val Thr Val Ser Arg Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Gly Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
    130                 135                 140

Pro Lys Leu His Asn Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Ser Met Ile Ser His Val His Gly
        195                 200                 205

Asn Ile Leu Thr Thr Leu Ser Ser Ser Ile Leu Pro Arg His Lys Ser
    210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
            260                 265                 270

His Thr His Ser His Ser His Ser Leu Pro Ser Ser Val Tyr
        275                 280                 285

Asn Ser Ile Val Pro His Phe Asp Leu Phe Ser Phe Ile His Leu Ser
    290                 295                 300
```

```
Lys Asp Asn Phe Lys Lys Tyr Leu Glu Leu Ile Lys Asn Leu Ser Val
305                 310                 315                 320

Thr Leu Arg Lys Thr Ile Tyr His Cys Leu Leu Leu His Tyr Ser Ala
            325                 330                 335

Lys Ala Ile Met Phe Trp Ile Met Thr Arg Pro Ala Glu Tyr Tyr Glu
                340                 345                 350

Leu Phe Asn Leu Leu Lys Asp Asn Asn Asn Glu His Ser Lys Ser Leu
                355                 360                 365

Asn Thr Leu Asn His Thr Leu Phe Glu Glu Ile His Ser Thr Phe Asn
370                 375                 380

Val Asn Ser Met Ile Thr Thr Asn Gln Asn Val His Gln Gly Ser Ser
385                 390                 395                 400

Ser Pro Ser Ser Ser Ser Pro Ser Ser Pro Pro Ser Ser Ser Ser Ser
                405                 410                 415

Asp Asn Asn Asn Gln Asn Ile Ile Ala Lys Ser Leu Ser Arg Gln His
                420                 425                 430

Ser His His Gln Ser Tyr Ile Gln Gln Gln Ser Glu Arg Lys Leu His
                435                 440                 445

Ser Ser Trp Thr Thr Asn Ser Gln Ser Ser Thr Ser Leu Ser Ser Ser
450                 455                 460

Thr Ser Asn Ser Thr Thr Thr Asp Phe Ser Thr His Thr Gln Pro Gly
465                 470                 475                 480

Glu Tyr Asp Pro Ser Leu Pro Asp Thr Pro Thr Met Ser Asn Ile Thr
                485                 490                 495

Ile Ser Ala Ser Ser Leu Leu Ser Gln Thr Pro Thr Pro Thr Thr Gln
                500                 505                 510

Leu Gln Gln Arg Leu Asn Ser Ala Ala Ala Ala Ala Ala Ala Ala Ala
                515                 520                 525

Ser Pro Ser Asn Ser Thr Pro Thr Gly Tyr Thr Ala Glu Gln Gln Ser
                530                 535                 540

Arg Ala Ser Tyr Asp Ala His Lys Thr Gly His Thr Gly Lys Asp Tyr
545                 550                 555                 560

Asp Glu His Phe Leu Ser Ile Thr Arg Leu Asp Asn Val Leu Glu Leu
                565                 570                 575

Tyr Thr His Phe Asp Asp Thr Glu Val Leu Pro His Thr Ser Val Leu
                580                 585                 590

Lys Phe Leu Thr Thr Leu Thr Met Phe Asp Ile Asp Leu Phe Asn Glu
                595                 600                 605

Leu Asn Ala Thr Ser Phe Lys Tyr Ile Pro Asp Cys Thr Met His Arg
                610                 615                 620

Pro Lys Glu Arg Thr Ser Ser Phe Asn Asn Thr Ala His Glu Thr Gly
625                 630                 635                 640

Ser Glu Lys Thr Ser Gly Ile Lys His Ile Thr Gln Gly Leu Lys Lys
                645                 650                 655

Leu Thr Ser Leu Pro Ser Ser Thr Lys Lys Thr Val Lys Phe Met Lys
                660                 665                 670

Met Leu Leu Arg Asn Leu Ile Gly Asn Gln Ala Val Ser Asp Val Ala
                675                 680                 685

Leu Leu Asp Thr Met Arg Ala Leu Leu Ser Phe Phe Thr Met Thr Ser
                690                 695                 700

Ala Val Phe Leu Val Asp Arg Asn Leu Pro Ser Val Leu Phe Ala Lys
705                 710                 715                 720

Arg Leu Ile Pro Ile Met Gly Thr Asn Leu Ser Val Gly Gln Asp Trp
```

```
                725                 730                 735
Asn Ser Lys Ile Asn Ser Leu Met Val Cys Leu Lys Lys Asn Ser
            740                 745                 750
Thr Thr Phe Val Gln Leu Gln Leu Ile Phe Phe Ser Ser Ala Ile Gln
            755                 760                 765
Phe Asp His Glu Leu Leu Leu Ala Arg Leu Ser Ile Asp Thr Met Ala
    770                 775                 780
Asn Asn Leu Asn Met Gln Lys Leu Cys Leu Tyr Thr Glu Gly Phe Arg
785                 790                 795                 800
Ile Phe Phe Asp Ile Pro Ser Lys Lys Glu Leu Arg Lys Ala Ile Ala
                805                 810                 815
Val Lys Ile Ser Lys Phe Phe Lys Thr Leu Phe Ser Ile Ile Ala Asp
                820                 825                 830
Ile Leu Leu Gln Glu Phe Pro Tyr Phe Asp Glu Gln Ile Thr Asp Ile
                835                 840                 845
Val Ala Ser Ile Leu Asp Gly Thr Ile Ile Asn Glu Tyr Gly Thr Lys
            850                 855                 860
Lys His Phe Lys Gly Ser Ser Pro Ser Leu Cys Ser Thr Thr Arg Ser
865                 870                 875                 880
Arg Ser Gly Ser Thr Ser Gln Ser Ser Met Thr Pro Val Ser Pro Leu
                        885                 890                 895
Gly Leu Asp Thr Asp Ile Cys Pro Met Asn Thr Leu Ser Leu Val Gly
                    900                 905                 910
Ser Ser Thr Ser Arg Asn Ser Asp Asn Val Asn Ser Leu Asn Ser Ser
            915                 920                 925
Pro Lys Asn Leu Ser Ser Asp Pro Tyr Leu Ser His Leu Val Ala Pro
930                 935                 940
Arg Ala Arg His Ala Leu Gly Gly Pro Ser Ser Ile Ile Arg Asn Lys
945                 950                 955                 960
Ile Pro Thr Thr Leu Thr Ser Pro Pro Gly Thr Glu Lys Ser Ser Pro
                965                 970                 975
Val Gln Arg Pro Gln Thr Glu Ser Ile Ser Ala Thr Pro Met Ala Ile
                980                 985                 990
Thr Asn Ser Thr Pro Leu Ser Ser  Ala Ala Phe Gly Ile  Arg Ser Pro
            995                 1000                1005
Leu Gln  Lys Ile Arg Thr  Arg Tyr Ser Asp Glu  Ser Leu Gly
            1010                1015                1020
Lys Phe  Met Lys Ser Thr Asn  Asn Tyr Ile Gln Glu  His Leu Ile
            1025                1030                1035
Pro Lys  Asp Leu Asn Glu Ala  Thr Leu Gln Asp Ala  Arg Arg Ile
            1040                1045                1050
Met Ile  Asn Ile Phe Ser Ile  Phe Lys Arg Pro Asn  Ser Tyr Phe
            1055                1060                1065
Ile Ile  Pro His Asn Ile Asn  Ser Asn Leu Gln Trp  Val Ser Gln
            1070                1075                1080
Asp Phe  Arg Asn Ile Met Lys  Pro Ile Phe Val Ala  Ile Val Ser
            1085                1090                1095
Pro Asp  Val Asp Leu Gln Asn  Thr Ala Gln Ser Phe  Met Asp Thr
            1100                1105                1110
Leu Leu  Ser Asn Val Ile Thr  Tyr Gly Glu Ser Asp  Glu Asn Ile
            1115                1120                1125
Ser Ile  Glu Gly Tyr His Leu  Leu Cys Ser Tyr Thr  Val Thr Leu
            1130                1135                1140
```

```
Phe Ala Met Gly Leu Phe Asp Leu Lys Ile Asn Asn Glu Lys Arg
1145                1150                1155

Gln Ile Leu Leu Asp Ile Thr Val Lys Phe Met Lys Val Arg Ser
1160                1165                1170

His Leu Ala Gly Ile Ala Glu Ala Ser His His Met Glu Tyr Ile
1175                1180                1185

Ser Asp Ser Glu Lys Leu Thr Phe Pro Leu Ile Met Gly Thr Val
1190                1195                1200

Gly Arg Ala Leu Phe Val Ser Leu Tyr Ser Ser Gln Gln Lys Ile
1205                1210                1215

Glu Lys Thr Leu Lys Ile Ala Tyr Thr Glu Tyr Leu Ser Ala Ile
1220                1225                1230

Asn Phe His Glu Arg Asn Ile Asp Asp Ala Asp Lys Thr Trp Val
1235                1240                1245

His Asn Ile Glu Phe Val Glu Ala Met Cys His Asp Asn Tyr Thr
1250                1255                1260

Thr Ser Gly Ser Ile Ala Phe Gln Arg Arg Thr Arg Asn Asn Ile
1265                1270                1275

Leu Arg Phe Ala Thr Ile Pro Asn Ala Ile Leu Leu Asp Ser Met
1280                1285                1290

Arg Met Ile Tyr Lys Lys Trp His Thr Tyr Thr His Ser Lys Ser
1295                1300                1305

Leu Glu Lys Gln Glu Arg Asn Asp Phe Arg Asn Phe Ala Gly Ile
1310                1315                1320

Leu Ala Ser Leu Ser Gly Ile Leu Phe Ile Asn Lys Lys Ile Leu
1325                1330                1335

Gln Glu Met Tyr Pro Tyr Leu Leu Asp Thr Val Ser Glu Leu Lys
1340                1345                1350

Lys Asn Ile Asp Ser Phe Ile Ser Lys Gln Cys Gln Trp Leu Asn
1355                1360                1365

Tyr Pro Asp Leu Leu Thr Arg Glu Asn Ser Arg Asp Ile Leu Ser
1370                1375                1380

Val Glu Leu His Pro Leu Ser Phe Asn Leu Leu Phe Asn Asn Leu
1385                1390                1395

Arg Leu Lys Leu Lys Glu Leu Ala Cys Ser Asp Leu Ser Ile Pro
1400                1405                1410

Glu Asn Glu Ser Ser Tyr Val Leu Leu Glu Gln Ile Ile Lys Met
1415                1420                1425

Leu Arg Thr Ile Leu Gly Arg Asp Asp Asp Asn Tyr Val Met Met
1430                1435                1440

Leu Phe Ser Thr Glu Ile Val Asp Leu Ile Asp Leu Leu Thr Asp
1445                1450                1455

Glu Ile Lys Lys Ile Pro Ala Tyr Cys Pro Lys Tyr Leu Lys Ala
1460                1465                1470

Ile Ile Gln Met Thr Lys Met Phe Ser Ala Leu Gln His Ser Glu
1475                1480                1485

Val Asn Leu Gly Val Lys Asn His Phe His Val Lys Asn Lys Trp
1490                1495                1500

Leu Arg Gln Val Thr Asp Trp Phe Gln Val Ser Ile Ala Arg Glu
1505                1510                1515

Tyr Asp Phe Glu Asn Leu Ser Lys Pro Leu Lys Glu Met Asp Leu
1520                1525                1530
```

Val Lys Arg Asp Met Asp Ile Leu Tyr Ile Asp Thr Ala Ile Glu
1535                1540                1545

Ala Ser Thr Ala Ile Ala Tyr Leu Thr Arg His Thr Phe Leu Glu
1550                1555                1560

Ile Pro Pro Ala Ala Ser Asp Pro Glu Leu Ser Arg Ser Arg Ser
1565                1570                1575

Val Ile Phe Gly Phe Tyr Phe Asn Ile Leu Met Lys Gly Leu Glu
1580                1585                1590

Lys Ser Ser Asp Arg Asp Asn Tyr Pro Val Phe Leu Arg His Lys
1595                1600                1605

Met Ser Val Leu Asn Asp Asn Val Ile Leu Ser Leu Thr Asn Leu
1610                1615                1620

Ser Asn Thr Asn Val Asp Ala Ser Leu Gln Phe Thr Leu Pro Met
1625                1630                1635

Gly Tyr Ser Gly Asn Arg Asn Ile Arg Asn Ala Phe Leu Glu Val
1640                1645                1650

Phe Ile Asn Ile Val Thr Asn Tyr Arg Thr Tyr Thr Ala Lys Thr
1655                1660                1665

Asp Leu Gly Lys Leu Glu Ala Ala Asp Lys Phe Leu Arg Tyr Thr
1670                1675                1680

Ile Glu His Pro Gln Leu Ser Ser Phe Gly Ala Ala Val Cys Pro
1685                1690                1695

Ala Ser Asp Ile Asp Ala Tyr Ala Ala Gly Leu Ile Asn Ala Phe
1700                1705                1710

Glu Thr Arg Asn Ala Thr His Ile Val Val Ser Gln Leu Ile Lys
1715                1720                1725

Asn Glu Ile Glu Asn Ser Ser Arg Pro Thr Asp Ile Leu Arg Arg
1730                1735                1740

Asn Ser Cys Ala Thr Arg Ser Leu Ser Met Leu Ala Arg Ser Lys
1745                1750                1755

Gly Ser Glu Tyr Leu Ile Arg Thr Leu Gln Pro Leu Leu Lys Lys
1760                1765                1770

Ile Ile Gln Asn Arg Asp Phe Phe Glu Ile Glu Lys Leu Lys Pro
1775                1780                1785

Glu Asp Ser Asp Ala Glu Arg Gln Ile Glu Leu Phe Val Lys Tyr
1790                1795                1800

Met Asn Glu Leu Leu Glu Ser Ile Ser Asn Ser Val Ser Tyr Phe
1805                1810                1815

Pro Pro Pro Leu Phe Tyr Ile Cys Gln Asn Ile Tyr Lys Val Ala
1820                1825                1830

Cys Glu Lys Phe Pro Asp His Ala Ile Ile Ala Ala Gly Ser Phe
1835                1840                1845

Val Phe Leu Arg Phe Phe Cys Pro Ala Leu Val Ser Pro Asp Ser
1850                1855                1860

Glu Asn Ile Ile Asp Ile Ser His Leu Ser Glu Lys Arg Thr Phe
1865                1870                1875

Ile Ser Leu Ala Lys Val Ile Gln Asn Ile Ala Asn Gly Ser Glu
1880                1885                1890

Asn Phe Ser Arg Trp Pro Ala Leu Cys Ser Gln Lys Asp Phe Leu
1895                1900                1905

Lys Glu Cys Ser Asp Arg Ile Phe Arg Phe Leu Ala Glu Leu Cys
1910                1915                1920

Arg Thr Asp Arg Thr Ile Asp Ile Gln Val Arg Thr Asp Pro Thr

-continued

```
                1925                1930                1935
Pro Ile Ala Phe Asp Tyr Gln Phe Leu His Ser Phe Val Tyr Leu
                1940                1945                1950

Tyr Gly Leu Glu Val Arg Arg Asn Val Leu Asn Glu Ala Lys His
                1955                1960                1965

Asp Asp Gly Asp Ile Asp Gly Asp Asp Phe Tyr Lys Thr Thr Phe
                1970                1975                1980

Leu Leu Ile Asp Asp Val Leu Gly Gln Leu Gly Gln Pro Lys Met
                1985                1990                1995

Glu Phe Ser Asn Glu Ile Pro Ile Tyr Ile Arg Glu His Met Asp
                2000                2005                2010

Asp Tyr Pro Glu Leu Tyr Glu Phe Met Asn Arg His Ala Phe Arg
                2015                2020                2025

Asn Ile Glu Thr Ser Thr Ala Tyr Ser Pro Ser Val His Glu Ser
                2030                2035                2040

Thr Ser Ser Glu Gly Ile Pro Ile Ile Thr Leu Thr Met Ser Asn
                2045                2050                2055

Phe Ser Asp Arg His Val Asp Ile Asp Thr Val Ala Tyr Lys Phe
                2060                2065                2070

Leu Gln Ile Tyr Ala Arg Ile Trp Thr Thr Lys His Cys Leu Ile
                2075                2080                2085

Ile Asp Cys Thr Glu Phe Asp Glu Gly Gly Leu Asp Met Arg Lys
                2090                2095                2100

Phe Ile Ser Leu Val Met Gly Leu Leu Pro Glu Val Ala Pro Lys
                2105                2110                2115

Asn Cys Ile Gly Cys Tyr Tyr Phe Asn Val Asn Glu Thr Phe Met
                2120                2125                2130

Asp Asn Tyr Gly Lys Cys Leu Asp Lys Asp Asn Val Tyr Val Ser
                2135                2140                2145

Ser Lys Ile Pro His Tyr Phe Ile Asn Ser Asn Ser Asp Glu Gly
                2150                2155                2160

Leu Met Lys Ser Val Gly Ile Thr Gly Gln Gly Leu Lys Val Leu
                2165                2170                2175

Gln Asp Ile Arg Val Ser Leu His Asp Ile Thr Leu Tyr Asp Glu
                2180                2185                2190

Lys Arg Asn Arg Phe Thr Pro Val Ser Leu Lys Ile Gly Asp Ile
                2195                2200                2205

Tyr Phe Gln Val Leu His Glu Thr Pro Arg Gln Tyr Lys Ile Arg
                2210                2215                2220

Asp Met Gly Thr Leu Phe Asp Val Lys Phe Asn Asp Val Tyr Glu
                2225                2230                2235

Ile Ser Arg Ile Phe Glu Val His Val Ser Ser Ile Thr Gly Val
                2240                2245                2250

Ala Ala Glu Phe Thr Val Thr Phe Gln Asp Glu Arg Arg Leu Ile
                2255                2260                2265

Phe Ser Ser Pro Lys Tyr Leu Glu Ile Val Lys Met Phe Tyr Tyr
                2270                2275                2280

Ala Gln Ile Arg Leu Glu Ser Glu Tyr Glu Met Asp Asn Asn Ser
                2285                2290                2295

Ser Thr Ser Ser Pro Asn Ser Asn Asn Lys Asp Lys Gln Gln Lys
                2300                2305                2310

Glu Arg Thr Lys Leu Leu Cys His Leu Leu Leu Val Ser Leu Ile
                2315                2320                2325
```

-continued

```
Gly Leu Phe Asp Glu Ser Lys Lys Met Lys Asn Ser Ser Tyr Asn
2330                2335                2340

Leu Ile Ala Ala Thr Glu Ala Ser Phe Gly Leu Asn Phe Gly Ser
2345                2350                2355

His Phe His Arg Ser Pro Glu Val Tyr Val Pro Glu Asp Thr Thr
2360                2365                2370

Thr Phe Leu Gly Val Ile Gly Lys Ser Leu Ala Glu Ser Asn Pro
2375                2380                2385

Glu Leu Thr Ala Tyr Met Phe Ile Tyr Val Leu Glu Ala Leu Lys
2390                2395                2400

Asn Asn Val Ile Pro His Val Tyr Ile Pro His Thr Ile Cys Gly
2405                2410                2415

Leu Ser Tyr Trp Ile Pro Asn Leu Tyr Gln His Val Tyr Leu Ala
2420                2425                2430

Asp Asp Glu Glu Gly Pro Glu Asn Ile Ser His Ile Phe Arg Ile
2435                2440                2445

Leu Ile Arg Leu Ser Val Arg Glu Thr Asp Phe Lys Ala Val Tyr
2450                2455                2460

Met Gln Tyr Val Trp Leu Leu Leu Leu Asp Gly Arg Leu Thr
2465                2470                2475

Asp Ile Ile Val Asp Glu Val Ile Asn His Ala Leu Glu Arg Asp
2480                2485                2490

Ser Glu Asn Arg Asp Trp Lys Lys Thr Ile Ser Leu Leu Thr Val
2495                2500                2505

Leu Pro Thr Thr Glu Val Ala Asn Asn Ile Ile Gln Lys Ile Leu
2510                2515                2520

Ala Lys Ile Arg Ser Phe Leu Pro Ser Leu Lys Leu Glu Ala Met
2525                2530                2535

Thr Gln Ser Trp Ser Glu Leu Thr Ile Leu Val Lys Ile Ser Ile
2540                2545                2550

His Val Phe Phe Glu Thr Ser Leu Leu Val Gln Met Tyr Leu Pro
2555                2560                2565

Glu Ile Leu Phe Ile Val Ser Leu Leu Ile Asp Val Gly Pro Arg
2570                2575                2580

Glu Leu Arg Ser Ser Leu His Gln Leu Leu Met Asn Val Cys His
2585                2590                2595

Ser Leu Ala Ile Asn Ser Ala Leu Pro Gln Asp His Arg Asn Asn
2600                2605                2610

Leu Asp Glu Ile Ser Asp Ile Phe Ala His Gln Lys Val Lys Phe
2615                2620                2625

Met Phe Gly Phe Ser Glu Asp Lys Gly Arg Ile Leu Gln Ile Phe
2630                2635                2640

Ser Ala Ser Ser Phe Ala Ser Lys Phe Asn Ile Leu Asp Phe Phe
2645                2650                2655

Ile Asn Asn Ile Leu Leu Leu Met Glu Tyr Ser Ser Thr Tyr Glu
2660                2665                2670

Ala Asn Val Trp Lys Thr Arg Tyr Lys Lys Tyr Val Leu Glu Ser
2675                2680                2685

Val Phe Thr Ser Asn Ser Phe Leu Ser Ala Arg Ser Ile Met Ile
2690                2695                2700

Val Gly Ile Met Gly Lys Ser Tyr Ile Thr Glu Gly Leu Cys Lys
2705                2710                2715
```

Ala Met Leu Ile Glu Thr Met Lys Val Ile Ala Glu Pro Lys Ile
2720                2725                2730

Thr Asp Glu His Leu Phe Leu Ala Ile Ser His Ile Phe Thr Tyr
2735                2740                2745

Ser Lys Ile Val Glu Gly Leu Asp Pro Asn Leu Asp Leu Met Lys
2750                2755                2760

His Leu Phe Trp Phe Ser Thr Leu Phe Leu Glu Ser Arg His Pro
2765                2770                2775

Ile Ile Phe Glu Gly Ala Leu Leu Phe Val Ser Asn Cys Ile Arg
2780                2785                2790

Arg Leu Tyr Met Ala Gln Phe Glu Asn Glu Ser Glu Thr Ser Leu
2795                2800                2805

Ile Ser Thr Leu Leu Lys Gly Arg Lys Phe Ala His Thr Phe Leu
2810                2815                2820

Ser Lys Ile Glu Asn Leu Ser Gly Ile Val Trp Asn Glu Asp Asn
2825                2830                2835

Phe Thr His Ile Leu Ile Phe Ile Ile Asn Lys Gly Leu Ser Asn
2840                2845                2850

Pro Phe Ile Lys Ser Thr Ala Phe Asp Phe Leu Lys Met Met Phe
2855                2860                2865

Arg Asn Ser Tyr Phe Glu His Gln Ile Asn Gln Lys Ser Asp His
2870                2875                2880

Tyr Leu Cys Tyr Met Phe Leu Leu Tyr Phe Val Leu Asn Cys Asn
2885                2890                2895

Gln Phe Glu Glu Leu Leu Gly Asp Val Asp Phe Glu Gly Glu Met
2900                2905                2910

Val Asn Ile Glu Asn Lys Asn Thr Ile Pro Lys Ile Leu Leu Glu
2915                2920                2925

Trp Leu Ser Ser Asp Asn Glu Asn Ala Asn Ile Thr Leu Tyr Gln
2930                2935                2940

Gly Ala Ile Leu Phe Lys Cys Ser Val Thr Asp Glu Pro Ser Arg
2945                2950                2955

Phe Arg Phe Ala Leu Ile Ile Arg His Leu Leu Thr Lys Lys Pro
2960                2965                2970

Ile Cys Ala Leu Arg Phe Tyr Ser Val Ile Arg Asn Glu Ile Arg
2975                2980                2985

Lys Ile Ser Ala Phe Glu Gln Thr Ser Asp Cys Val Pro Leu Ala
2990                2995                3000

Phe Asp Ile Leu Asn Leu Leu Val Thr His Ser Glu Ser Asn Ser
3005                3010                3015

Leu Glu Lys Leu His Glu Glu Ser Ile Glu Arg Leu Thr Lys Arg
3020                3025                3030

Gly Leu Ser Ile Val Thr Ser Ser Gly Ile Phe Ala Lys Asn Ser
3035                3040                3045

Asp Met Met Ile Pro Leu Asp Val Lys Pro Glu Asp Ile Tyr Glu
3050                3055                3060

Arg Lys Arg Ile Met Thr Met Ile Leu Ser Arg Met Ser Cys Ser
3065                3070                3075

Ala

<210> SEQ ID NO 23
<211> LENGTH: 3079
<212> TYPE: PRT
<213> ORGANISM: Artificial Sequence

```
<220> FEATURE:
<223> OTHER INFORMATION: Consensus IRA2 sequence

<400> SEQUENCE: 23

Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
                20                  25                  30

Arg Ile Leu Pro Ile Leu Pro Val Glu Ser Asn Leu Ser Thr Tyr Ser
                35                  40                  45

Glu Val Glu Glu Tyr Ser Ser Phe Ile Ser Cys Arg Ser Val Leu Ile
        50                  55                  60

Asn Val Thr Val Ser Arg Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Gly Ser Ser Asp Val Ile Glu Ser Ile Leu Ile Ile Leu Arg Leu Leu
                100                 105                 110

Ser Asp Ala Leu Glu Tyr Asn Trp Gln Asn Gln Glu Ser Leu His Tyr
                115                 120                 125

Asn Asp Ile Ser Thr His Val Glu His Asp Gln Glu Gln Lys Tyr Arg
                130                 135                 140

Pro Lys Leu Asn Ser Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
                180                 185                 190

Thr Arg Thr Leu Gln Ile Leu Gln Asn Met Ile Ser His Val His Gly
                195                 200                 205

Asn Ile Leu Thr Thr Leu Ser Ser Ser Ile Leu Pro Arg His Lys Ser
                210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
                260                 265                 270

His Thr His Ser His Ser His Ser His Ser Leu Pro Ser Ser Val Tyr
                275                 280                 285

Asn Ser Ile Val Pro His Phe Asp Leu Phe Ser Phe Ile Tyr Leu Ser
                290                 295                 300

Lys His Asn Phe Lys Lys Tyr Leu Glu Leu Ile Lys Asn Leu Ser Val
305                 310                 315                 320

Thr Leu Arg Lys Thr Ile Tyr His Cys Leu Leu Leu His Tyr Ser Ala
                325                 330                 335

Lys Ala Ile Met Phe Trp Ile Met Ala Arg Pro Ala Glu Tyr Tyr Glu
                340                 345                 350

Leu Phe Asn Leu Leu Lys Asp Asn Asn Glu His Ser Lys Ser Leu
                355                 360                 365

Asn Thr Leu Asn His Thr Leu Phe Glu Glu Ile His Ser Thr Phe Asn
                370                 375                 380

Val Asn Ser Met Ile Thr Thr Asn Gln Asn Ala His Gln Gly Ser Ser
385                 390                 395                 400
```

```
Ser Pro Ser Ser Ser Pro Ser Ser Pro Pro Ser Ser Ser Ser
            405                 410                 415

Asp Asn Asn Asn Gln Asn Ile Ile Ala Lys Ser Leu Ser Arg Gln Leu
                420                 425                 430

Ser His His Gln Ser Tyr Ile Gln Gln Gln Ser Glu Arg Lys Leu His
        435                 440                 445

Ser Ser Trp Thr Thr Asn Ser Gln Ser Ser Thr Ser Leu Ser Ser Ser
450                 455                 460

Thr Ser Asn Ser Thr Thr Thr Asp Phe Ser Thr His Thr Gln Pro Gly
465                 470                 475                 480

Glu Tyr Asp Pro Ser Leu Pro Asp Thr Pro Thr Met Ser Asn Ile Thr
                485                 490                 495

Ile Ser Ala Ser Ser Leu Leu Ser Gln Thr Pro Thr Pro Thr Thr Gln
                500                 505                 510

Leu Gln Gln Arg Leu Asn Ser Ala Ala Ala Ala Ala Ala Ala Ala
        515                 520                 525

Ser Pro Ser Asn Ser Thr Pro Thr Gly Tyr Thr Ala Glu Gln Gln Ser
        530                 535                 540

Arg Ala Ser Tyr Asp Ala His Lys Thr Gly His Thr Gly Lys Asp Tyr
545                 550                 555                 560

Asp Glu His Phe Leu Ser Val Thr Arg Leu Asp Asn Val Leu Glu Leu
                565                 570                 575

Tyr Thr His Phe Asp Asp Thr Glu Val Leu Pro His Thr Ser Val Leu
                580                 585                 590

Lys Phe Leu Thr Thr Leu Thr Met Phe Asp Ile Asp Leu Phe Asn Glu
        595                 600                 605

Leu Asn Ala Thr Ser Phe Lys Tyr Ile Pro Asp Cys Thr Met His Arg
610                 615                 620

Pro Lys Glu Arg Thr Ser Ser Phe Asn Asn Thr Ala His Glu Thr Gly
625                 630                 635                 640

Ser Glu Lys Thr Ser Gly Ile Lys His Ile Thr Gln Gly Leu Lys Lys
                645                 650                 655

Leu Thr Ser Leu Pro Ser Ser Thr Lys Lys Thr Val Lys Phe Val Lys
                660                 665                 670

Met Leu Leu Arg Asn Leu Asn Gly Asn Gln Ala Val Ser Asp Val Ala
        675                 680                 685

Leu Leu Asp Thr Met Arg Ala Leu Leu Ser Phe Phe Thr Met Thr Ser
        690                 695                 700

Ala Val Phe Leu Val Asp Arg Asn Leu Pro Ser Val Leu Phe Ala Lys
705                 710                 715                 720

Arg Leu Ile Pro Ile Met Gly Thr Asn Leu Ser Val Gly Gln Asp Trp
                725                 730                 735

Asn Ser Lys Ile Asn Asn Ser Leu Met Val Cys Leu Lys Lys Asn Ser
                740                 745                 750

Thr Thr Phe Val Gln Leu Gln Leu Ile Phe Ser Ser Ala Ile Gln
        755                 760                 765

Phe Asp His Glu Leu Leu Leu Ala Arg Leu Ser Ile Asp Thr Met Ala
770                 775                 780

Asn Asn Leu Asn Met Gln Lys Leu Cys Leu Tyr Thr Glu Gly Phe Arg
785                 790                 795                 800

Ile Phe Phe Asp Ile Pro Ser Lys Lys Glu Leu Arg Lys Ala Ile Ala
                805                 810                 815
```

```
Val Lys Ile Ser Lys Phe Phe Lys Thr Leu Phe Ser Ile Ile Ala Asp
            820                 825                 830

Ile Leu Leu Gln Glu Phe Pro Tyr Phe Asp Glu Gln Ile Thr Asp Ile
            835                 840                 845

Val Ala Ser Ile Leu Asp Gly Thr Ile Ile Asn Glu Tyr Gly Thr Lys
            850                 855                 860

Lys His Phe Lys Gly Ser Ser Pro Ser Leu Cys Ser Thr Thr Arg Ser
865                 870                 875                 880

Arg Ser Gly Ser Thr Ser Gln Ser Ser Met Thr Pro Val Ser Pro Leu
                    885                 890                 895

Gly Leu Asp Thr Asp Ile Cys Pro Met Asn Thr Leu Ser Leu Val Gly
            900                 905                 910

Ser Ser Thr Ser Arg Asn Ser Asp Asn Val Asn Ser Leu Asn Ser Ser
            915                 920                 925

Pro Lys Asn Leu Ser Ser Asp Pro Tyr Leu Ser His Leu Val Ala Pro
            930                 935                 940

Arg Ala Arg His Ala Leu Gly Gly Pro Ser Ser Ile Ile Arg Asn Lys
945                 950                 955                 960

Ile Pro Thr Thr Leu Thr Ser Pro Pro Gly Thr Glu Lys Ser Ser Pro
            965                 970                 975

Val Gln Arg Pro Gln Thr Glu Ser Ile Ser Ala Thr Pro Met Ala Ile
            980                 985                 990

Thr Asn Ser Thr Pro Leu Ser Ser  Ala Ala Phe Gly Ile  Arg Ser Pro
            995                 1000                1005

Leu Gln Lys Ile Arg Thr Arg  Arg Tyr Ser Asp Glu  Ser Leu Gly
    1010                1015                1020

Lys Phe Met Lys Ser Thr Asn  Asn Tyr Ile Gln Glu  His Leu Ile
    1025                1030                1035

Pro Lys Asp Leu Asn Glu Ala  Thr Leu Gln Asp Ala  Arg Arg Ile
    1040                1045                1050

Met Ile Asn Ile Phe Ser Ile  Phe Lys Arg Pro Asn  Ser Tyr Phe
    1055                1060                1065

Ile Ile Pro His Asn Ile Asn  Ser Asn Leu Gln Trp  Val Ser Gln
    1070                1075                1080

Asp Phe Arg Asn Ile Met Lys  Pro Ile Phe Val Ala  Ile Val Ser
    1085                1090                1095

Pro Asp Val Asp Leu Gln Asn  Thr Ala Gln Ser Phe  Met Asp Thr
    1100                1105                1110

Leu Leu Ser Asn Val Ile Thr  Tyr Gly Glu Ser Asp  Glu Asn Ile
    1115                1120                1125

Ser Ile Glu Gly Tyr His Leu  Leu Cys Ser Tyr Thr  Val Thr Leu
    1130                1135                1140

Phe Ala Met Gly Leu Phe Asp  Leu Lys Ile Asn Asn  Glu Lys Arg
    1145                1150                1155

Gln Ile Leu Leu Asp Ile Thr  Val Lys Phe Met Lys  Val Arg Ser
    1160                1165                1170

His Leu Ala Gly Ile Ala Glu  Ala Ser His His Met  Glu Tyr Ile
    1175                1180                1185

Ser Asp Ser Glu Lys Leu Thr  Phe Pro Leu Ile Met  Gly Thr Val
    1190                1195                1200

Gly Arg Ala Leu Phe Val Ser  Leu Tyr Ser Ser Gln  Gln Lys Ile
    1205                1210                1215

Glu Lys Thr Leu Lys Ile Ala  Tyr Thr Glu Tyr Leu  Ser Ala Ile
```

```
           1220                1225                1230
Asn Phe His Glu Arg Asn Ile Asp Asp Ala Asp Lys Thr Trp Val
    1235                1240                1245

His Asn Ile Glu Phe Val Glu Ala Met Cys His Asp Asn Tyr Thr
    1250                1255                1260

Thr Ser Gly Ser Ile Ala Phe Gln Arg Arg Thr Arg Asn Asn Ile
    1265                1270                1275

Leu Arg Phe Ala Thr Ile Pro Asn Ala Ile Leu Leu Asp Ser Met
    1280                1285                1290

Arg Met Ile Tyr Lys Lys Trp His Thr Tyr Thr His Ser Lys Ser
    1295                1300                1305

Leu Glu Lys Gln Glu Arg Asn Asp Phe Arg Asn Phe Ala Gly Ile
    1310                1315                1320

Leu Ala Ser Leu Ser Gly Ile Leu Phe Ile Asn Lys Lys Ile Leu
    1325                1330                1335

Gln Glu Met Tyr Pro Tyr Leu Leu Asp Thr Val Ser Glu Leu Lys
    1340                1345                1350

Lys Asn Ile Asp Ser Phe Ile Ser Lys Gln Cys Gln Trp Leu Asn
    1355                1360                1365

Tyr Pro Asp Leu Leu Thr Arg Glu Asn Ser Arg Asp Ile Leu Ser
    1370                1375                1380

Val Glu Leu His Pro Leu Ser Phe Asn Leu Leu Phe Asn Asn Leu
    1385                1390                1395

Arg Leu Lys Leu Lys Glu Leu Ala Cys Ser Asp Leu Ser Ile Pro
    1400                1405                1410

Glu Asn Glu Ser Ser Tyr Val Leu Leu Glu Gln Ile Ile Lys Met
    1415                1420                1425

Leu Arg Thr Ile Leu Gly Arg Asp Asp Asp Asn Tyr Val Met Met
    1430                1435                1440

Leu Phe Ser Thr Glu Ile Val Asp Leu Ile Asp Leu Leu Thr Asp
    1445                1450                1455

Glu Ile Lys Lys Ile Pro Ala Tyr Cys Pro Lys Tyr Leu Lys Ala
    1460                1465                1470

Ile Ile Gln Met Thr Lys Met Phe Ser Ala Leu Gln His Ser Glu
    1475                1480                1485

Val Asn Leu Gly Val Lys Asn His Phe His Val Lys Asn Lys Trp
    1490                1495                1500

Leu Arg Gln Ile Thr Asp Trp Phe Gln Val Ser Ile Ala Arg Glu
    1505                1510                1515

Tyr Asp Phe Glu Asn Leu Ser Lys Pro Leu Lys Glu Met Asp Leu
    1520                1525                1530

Val Lys Arg Asp Met Asp Ile Leu Tyr Ile Asp Thr Ala Ile Glu
    1535                1540                1545

Ala Ser Thr Ala Ile Ala Tyr Leu Thr Arg His Thr Phe Leu Glu
    1550                1555                1560

Ile Pro Pro Ala Ala Ser Asp Pro Glu Leu Ser Arg Ser Arg Ser
    1565                1570                1575

Val Ile Phe Gly Phe Tyr Phe Asn Ile Leu Met Lys Gly Leu Glu
    1580                1585                1590

Lys Ser Ser Asp Arg Asp Asn Tyr Pro Val Phe Leu Arg His Lys
    1595                1600                1605

Met Ser Val Leu Asn Asp Asn Val Ile Leu Ser Leu Thr Asn Leu
    1610                1615                1620
```

-continued

Ser Asn Thr Asn Val Asp Ala Ser Leu Gln Phe Thr Leu Pro Met
1625                1630                1635

Gly Tyr Ser Gly Asn Arg Asn Ile Arg Asn Ala Phe Leu Glu Val
1640                1645                1650

Phe Ile Asn Ile Val Thr Asn Tyr Arg Thr Tyr Thr Ala Lys Thr
1655                1660                1665

Asp Leu Gly Lys Leu Glu Ala Ala Asp Lys Phe Leu Arg Tyr Thr
1670                1675                1680

Ile Glu His Pro Gln Leu Ser Ser Phe Gly Ala Ala Val Cys Pro
1685                1690                1695

Ala Ser Asp Ile Asp Ala Tyr Ala Ala Gly Leu Ile Asn Ala Phe
1700                1705                1710

Glu Thr Arg Asn Ala Thr His Ile Val Val Ala Gln Leu Ile Lys
1715                1720                1725

Asn Glu Ile Glu Lys Ser Ser Arg Pro Thr Asp Ile Leu Arg Arg
1730                1735                1740

Asn Ser Cys Ala Thr Arg Ser Leu Ser Met Leu Ala Arg Ser Lys
1745                1750                1755

Gly Asn Glu Tyr Leu Ile Arg Thr Leu Gln Pro Leu Leu Lys Lys
1760                1765                1770

Ile Ile Gln Asn Arg Asp Phe Phe Glu Ile Glu Lys Leu Lys Pro
1775                1780                1785

Glu Asp Ser Asp Ala Glu Arg Gln Ile Glu Leu Phe Val Lys Tyr
1790                1795                1800

Met Asn Glu Leu Leu Glu Ser Ile Ser Asn Ser Val Ser Tyr Phe
1805                1810                1815

Pro Pro Pro Leu Phe Tyr Ile Cys Gln Asn Ile Tyr Lys Val Ala
1820                1825                1830

Cys Glu Lys Phe Pro Asp His Ala Ile Ile Ala Ala Gly Ser Phe
1835                1840                1845

Val Phe Leu Arg Phe Phe Cys Pro Ala Leu Val Ser Pro Asp Ser
1850                1855                1860

Glu Asn Ile Ile Asp Ile Ser His Leu Ser Glu Lys Arg Thr Phe
1865                1870                1875

Ile Ser Leu Ala Lys Val Ile Gln Asn Ile Ala Asn Gly Ser Glu
1880                1885                1890

Asn Phe Ser Arg Trp Pro Ala Leu Cys Ser Gln Lys Asp Phe Leu
1895                1900                1905

Lys Glu Cys Ser Asp Arg Ile Phe Arg Phe Leu Ala Glu Leu Cys
1910                1915                1920

Arg Thr Asp Arg Thr Ile Asp Ile Gln Val Arg Thr Asp Pro Thr
1925                1930                1935

Pro Ile Ala Phe Asp Tyr Gln Phe Leu His Ser Phe Val Tyr Leu
1940                1945                1950

Tyr Gly Leu Glu Val Arg Arg Asn Val Leu Asn Glu Ala Lys His
1955                1960                1965

Asp Asp Gly Asp Ile Asp Gly Asp Asp Phe Tyr Lys Thr Thr Phe
1970                1975                1980

Leu Leu Ile Asp Asp Val Leu Gly Gln Leu Gly Gln Pro Lys Met
1985                1990                1995

Glu Phe Ser Asn Glu Ile Pro Ile Tyr Ile Arg Glu His Met Asp
2000                2005                2010

-continued

Asp Tyr Pro Glu Leu Tyr Glu Phe Met Asn Arg His Ala Phe Arg
    2015                2020                2025

Asn Ile Glu Thr Ser Thr Ala Tyr Ser Pro Ser Val His Glu Ser
    2030                2035                2040

Thr Ser Ser Glu Gly Ile Pro Ile Ile Thr Leu Thr Met Ser Asn
    2045                2050                2055

Phe Ser Asp Arg His Val Asp Ile Asp Thr Val Ala Tyr Lys Phe
    2060                2065                2070

Leu Gln Ile Tyr Ala Arg Ile Trp Thr Thr Lys His Cys Leu Ile
    2075                2080                2085

Ile Asp Cys Thr Glu Phe Asp Glu Gly Gly Leu Asp Met Arg Lys
    2090                2095                2100

Phe Ile Ser Leu Val Met Gly Leu Leu Pro Glu Val Ala Pro Lys
    2105                2110                2115

Asn Cys Ile Gly Cys Tyr Tyr Phe Asn Val Asn Glu Thr Phe Met
    2120                2125                2130

Asp Asn Tyr Gly Lys Cys Leu Asp Lys Asp Asn Val Tyr Val Ser
    2135                2140                2145

Ser Lys Ile Pro His Tyr Phe Ile Asn Ser Asn Ser Asp Glu Gly
    2150                2155                2160

Leu Met Lys Ser Val Gly Ile Thr Gly Gln Gly Leu Lys Val Leu
    2165                2170                2175

Gln Asp Ile Arg Val Ser Leu His Asp Ile Thr Leu Tyr Asp Glu
    2180                2185                2190

Lys Arg Asn Arg Phe Thr Pro Val Ser Leu Lys Ile Gly Asp Ile
    2195                2200                2205

Tyr Phe Gln Val Leu His Glu Thr Pro Arg Gln Tyr Lys Ile Arg
    2210                2215                2220

Asp Met Gly Thr Leu Phe Asp Val Lys Phe Asn Asp Val Tyr Glu
    2225                2230                2235

Ile Ser Arg Ile Phe Glu Val His Val Ser Ser Ile Thr Gly Val
    2240                2245                2250

Ala Ala Glu Phe Thr Val Thr Phe Gln Asp Glu Arg Arg Leu Ile
    2255                2260                2265

Phe Ser Ser Pro Lys Tyr Leu Glu Ile Val Lys Met Phe Tyr Tyr
    2270                2275                2280

Ala Gln Ile Arg Leu Glu Ser Glu Tyr Glu Met Asp Asn Asn Ser
    2285                2290                2295

Ser Thr Ser Ser Pro Asn Ser Asn Asn Lys Asp Lys Gln Gln Lys
    2300                2305                2310

Glu Arg Thr Lys Leu Leu Cys His Leu Leu Val Ser Leu Ile
    2315                2320                2325

Gly Leu Phe Asp Glu Ser Lys Lys Met Lys Asn Ser Ser Tyr Asn
    2330                2335                2340

Leu Ile Ala Ala Thr Glu Ala Ser Phe Gly Leu Asn Phe Gly Ser
    2345                2350                2355

His Phe His Arg Ser Pro Glu Val Tyr Val Pro Glu Asp Thr Thr
    2360                2365                2370

Thr Phe Leu Gly Val Ile Gly Lys Ser Leu Ala Glu Ser Asn Pro
    2375                2380                2385

Glu Leu Thr Ala Tyr Met Phe Ile Tyr Val Leu Glu Ala Leu Lys
    2390                2395                2400

Asn Asn Val Ile Pro His Val Tyr Ile Pro His Thr Ile Cys Gly

```
            2405                2410                2415

Leu Ser Tyr Trp Ile Pro Asn Leu Tyr Gln His Val Tyr Leu Ala
    2420                2425                2430

Asp Asp Glu Glu Gly Pro Lys Asn Ile Ser His Ile Phe Arg Ile
    2435                2440                2445

Leu Ile Arg Leu Ser Val Arg Glu Thr Asp Phe Lys Ala Val Tyr
    2450                2455                2460

Met Gln Tyr Val Trp Leu Leu Leu Asp Asp Gly Arg Leu Thr
    2465                2470                2475

Asp Ile Ile Val Asp Glu Val Ile Asn His Ala Leu Glu Arg Asp
    2480                2485                2490

Ser Glu Asn Arg Asp Trp Lys Lys Thr Ile Ser Leu Leu Thr Val
    2495                2500                2505

Leu Pro Thr Thr Glu Val Ala Asn Asn Ile Ile Gln Lys Ile Leu
    2510                2515                2520

Ala Lys Ile Arg Ser Phe Leu Pro Ser Leu Lys Leu Glu Ala Met
    2525                2530                2535

Thr Gln Ser Trp Ser Glu Leu Thr Ile Leu Val Lys Ile Ser Ile
    2540                2545                2550

His Val Phe Phe Glu Thr Ser Leu Leu Val Gln Met Tyr Leu Pro
    2555                2560                2565

Glu Ile Leu Phe Ile Val Ser Leu Leu Ile Asp Val Gly Pro Arg
    2570                2575                2580

Glu Leu Arg Ser Ser Leu His Gln Leu Leu Met Asn Val Cys His
    2585                2590                2595

Ser Leu Ala Ile Asn Ser Ala Leu Pro Gln Asp His Arg Asn Asn
    2600                2605                2610

Leu Asp Glu Ile Ser Asp Ile Phe Ala His Gln Lys Val Lys Phe
    2615                2620                2625

Met Phe Gly Phe Ser Glu Asp Lys Gly Arg Ile Leu Gln Ile Phe
    2630                2635                2640

Ser Ala Ser Ser Phe Ala Ser Lys Phe Asn Ile Leu Asp Phe Phe
    2645                2650                2655

Ile Asn Asn Ile Leu Leu Leu Met Glu Tyr Ser Ser Thr Tyr Glu
    2660                2665                2670

Ala Asn Val Trp Lys Thr Arg Tyr Lys Lys Tyr Val Leu Glu Ser
    2675                2680                2685

Val Phe Thr Ser Asn Ser Phe Leu Ser Ala Arg Ser Ile Met Ile
    2690                2695                2700

Val Gly Ile Met Gly Lys Ser Tyr Ile Thr Glu Gly Leu Cys Lys
    2705                2710                2715

Ala Met Leu Ile Glu Thr Met Lys Val Ile Ala Glu Pro Lys Ile
    2720                2725                2730

Thr Asp Glu His Leu Phe Leu Ala Ile Ser His Ile Phe Thr Tyr
    2735                2740                2745

Ser Lys Ile Val Glu Gly Leu Asp Pro Asn Leu Asp Leu Met Lys
    2750                2755                2760

His Leu Phe Trp Phe Ser Thr Leu Phe Leu Glu Ser Arg His Pro
    2765                2770                2775

Ile Ile Phe Glu Gly Ala Leu Leu Phe Val Ser Asn Cys Ile Arg
    2780                2785                2790

Arg Leu Tyr Met Ala Gln Phe Glu Asn Glu Ser Glu Thr Ser Leu
    2795                2800                2805
```

```
Ile Ser Thr Leu Leu Lys Gly Arg Lys Phe Ala His Thr Phe Leu
2810                2815                2820

Ser Lys Ile Glu Asn Leu Ser Gly Ile Val Trp Asn Glu Asp Asn
    2825                2830                2835

Phe Thr His Ile Leu Ile Phe Ile Ile Asn Lys Gly Leu Ser Asn
2840                2845                2850

Pro Phe Ile Lys Ser Thr Ala Phe Asp Phe Leu Lys Met Met Phe
    2855                2860                2865

Arg Asn Ser Tyr Phe Glu His Gln Ile Asn Gln Lys Ser Asp His
2870                2875                2880

Tyr Leu Cys Tyr Met Phe Leu Leu Tyr Phe Val Leu Asn Cys Asn
    2885                2890                2895

Gln Phe Glu Glu Leu Leu Gly Asp Val Asp Phe Glu Gly Glu Met
2900                2905                2910

Val Asn Ile Glu Asn Lys Asn Thr Ile Pro Lys Ile Leu Leu Glu
    2915                2920                2925

Trp Leu Ser Ser Asp Asn Glu Asn Ala Asn Ile Thr Leu Tyr Gln
2930                2935                2940

Gly Ala Ile Leu Phe Lys Cys Ser Val Thr Asp Glu Pro Ser Arg
    2945                2950                2955

Phe Arg Phe Ala Leu Ile Ile Arg His Leu Leu Thr Lys Lys Pro
2960                2965                2970

Ile Cys Ala Leu Arg Phe Tyr Ser Val Ile Arg Asn Glu Ile Arg
    2975                2980                2985

Lys Ile Ser Ala Phe Glu Gln Asn Ser Asp Cys Val Pro Leu Ala
2990                2995                3000

Phe Asp Ile Leu Asn Leu Leu Val Thr His Ser Glu Ser Asn Ser
    3005                3010                3015

Leu Glu Lys Leu His Glu Glu Ser Ile Glu Arg Leu Thr Lys Arg
3020                3025                3030

Gly Leu Ser Ile Val Thr Ser Ser Gly Ile Phe Ala Lys Asn Ser
    3035                3040                3045

Asp Met Met Ile Pro Leu Asp Val Lys Pro Glu Asp Ile Tyr Glu
3050                3055                3060

Arg Lys Arg Ile Met Thr Met Ile Leu Ser Arg Met Ser Cys Ser
    3065                3070                3075

Ala
```

<210> SEQ ID NO 24
<211> LENGTH: 293
<212> TYPE: PRT
<213> ORGANISM: Saccharomyces cerevisiae

<400> SEQUENCE: 24

```
Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
                20                  25                  30

Arg Ile Leu Pro Ile Leu Pro Val Glu Ser Asn Leu Ser Thr Tyr Ser
            35                  40                  45

Glu Val Glu Glu Tyr Ser Ser Phe Ile Ser Cys Arg Ser Val Leu Ile
        50                  55                  60

Asn Val Thr Val Ser Gln Asp Ala Asn Ala Met Val Glu Gly Thr Leu
65                  70                  75                  80
```

```
Glu Leu Ile Glu Ser Leu Leu Gln Gly His Glu Ile Ile Ser Asp Lys
                85                  90                  95

Cys Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
    130                 135                 140

Pro Lys Leu Asn Ser Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
        195                 200                 205

Asn Ile Leu Thr Thr Leu Ser Ser Ile Leu Pro Arg His Lys Ser
    210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
            260                 265                 270

His Thr His Thr Arg Ile His Thr Pro Ile His Thr Leu Cys His Leu
        275                 280                 285

Pro Phe Ile Thr Ala
        290

<210> SEQ ID NO 25
<211> LENGTH: 3081
<212> TYPE: PRT
<213> ORGANISM: Saccharomyces cerevisiae

<400> SEQUENCE: 25

Met Ser Gln Pro Thr Lys Asn Lys Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60

Asn Val Thr Val Ser Gln Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Cys Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
    130                 135                 140

Pro Lys Leu Asn Ser Ile Leu Pro Asp Tyr Ser Ser Thr His Ser Asn
```

```
                145                 150                 155                 160
        Gly Asn Lys His Phe Phe His Gln Ser Lys Pro Gln Ala Leu Ile Pro
                            165                 170                 175

Glu Leu Ala Ser Lys Leu Leu Glu Ser Cys Ala Lys Leu Lys Phe Asn
                            180                 185                 190

Thr Arg Thr Leu Gln Ile Leu Gln Asn Met Ile Ser His Val His Gly
                            195                 200                 205

Asn Ile Leu Thr Thr Leu Ser Ser Ser Ile Leu Pro Arg His Lys Ser
        210                 215                 220

Tyr Leu Thr Arg His Asn His Pro Ser His Cys Lys Met Ile Asp Ser
        225                 230                 235                 240

Thr Leu Gly His Ile Leu Arg Phe Val Ala Ser Asn Pro Ser Glu
                            245                 250                 255

Tyr Phe Glu Phe Ile Arg Lys Ser Val Gln Val Pro Val Thr Gln Thr
                            260                 265                 270

His Thr His Thr His Ser His Ser His Ser His Ser Leu Pro Ser Ser
                            275                 280                 285

Val Tyr Asn Ser Ile Val Pro His Phe Asp Leu Phe Ser Phe Ile Tyr
                            290                 295                 300

Leu Ser Lys His Asn Phe Lys Lys Tyr Leu Glu Leu Ile Lys Asn Leu
        305                 310                 315                 320

Ser Val Thr Leu Arg Lys Thr Ile Tyr His Cys Leu Leu Leu His Tyr
                            325                 330                 335

Ser Ala Lys Ala Ile Met Phe Trp Ile Met Ala Arg Pro Ala Glu Tyr
                            340                 345                 350

Tyr Glu Leu Phe Asn Leu Leu Lys Asp Asn Asn Glu His Ser Lys
                            355                 360                 365

Ser Leu Asn Thr Leu Asn His Thr Leu Phe Glu Glu Ile His Ser Thr
                            370                 375                 380

Phe Asn Val Asn Ser Met Ile Thr Thr Asn Gln Asn Ala His Gln Gly
        385                 390                 395                 400

Ser Ser Ser Pro Ser Ser Ser Pro Ser Ser Pro Pro Ser Ser Ser
                            405                 410                 415

Ser Ser Asp Asn Asn Asn Gln Asn Ile Ile Ala Lys Ser Leu Ser Arg
                            420                 425                 430

Gln Leu Ser His His Gln Ser Tyr Ile Gln Gln Ser Glu Arg Lys
                            435                 440                 445

Leu His Ser Ser Trp Thr Thr Asn Ser Gln Ser Ser Thr Ser Leu Ser
        450                 455                 460

Ser Ser Thr Ser Asn Ser Thr Thr Asp Phe Ser Thr His Thr Gln
        465                 470                 475                 480

Pro Gly Glu Tyr Asp Pro Ser Leu Pro Asp Thr Pro Thr Met Ser Asn
                            485                 490                 495

Ile Thr Ile Ser Ala Ser Ser Leu Leu Ser Gln Thr Pro Thr Pro Thr
                            500                 505                 510

Thr Gln Leu Gln Gln Arg Leu Asn Ser Ala Ala Ala Ala Ala Ala
                            515                 520                 525

Ala Ala Ser Pro Ser Asn Ser Thr Pro Thr Gly Tyr Thr Ala Glu Gln
                            530                 535                 540

Gln Ser Arg Ala Ser Tyr Asp Ala His Lys Thr Gly His Thr Gly Lys
        545                 550                 555                 560

Asp Tyr Asp Glu His Phe Leu Ser Val Thr Arg Leu Asp Asn Val Leu
                            565                 570                 575
```

```
Glu Leu Tyr Thr His Phe Asp Asp Thr Glu Val Leu Pro His Thr Ser
            580                 585                 590

Val Leu Lys Phe Leu Thr Thr Leu Thr Met Phe Asp Ile Asp Leu Phe
        595                 600                 605

Asn Glu Leu Asn Ala Thr Ser Phe Lys Tyr Ile Pro Asp Cys Thr Met
    610                 615                 620

His Arg Pro Lys Glu Arg Thr Ser Ser Phe Asn Asn Thr Ala His Glu
625                 630                 635                 640

Thr Gly Ser Glu Lys Thr Ser Gly Ile Lys His Ile Thr Gln Gly Leu
                645                 650                 655

Lys Lys Leu Thr Ser Leu Pro Ser Ser Thr Lys Lys Thr Val Lys Phe
            660                 665                 670

Met Lys Met Leu Leu Arg Asn Leu Asn Gly Asn Gln Ala Val Ser Asp
        675                 680                 685

Val Ala Leu Leu Asp Thr Met Arg Ala Leu Leu Ser Phe Phe Thr Met
    690                 695                 700

Thr Ser Ala Val Phe Leu Val Asp Arg Asn Leu Pro Ser Val Leu Phe
705                 710                 715                 720

Ala Lys Arg Leu Ile Pro Ile Met Gly Thr Asn Leu Ser Val Gly Gln
                725                 730                 735

Asp Trp Asn Ser Lys Ile Asn Asn Ser Leu Met Val Cys Leu Lys Lys
            740                 745                 750

Asn Ser Thr Thr Phe Val Gln Leu Gln Leu Ile Phe Phe Ser Ser Ala
        755                 760                 765

Ile Gln Phe Asp His Glu Leu Leu Ala Arg Leu Ser Ile Asp Thr
    770                 775                 780

Met Ala Asn Asn Leu Asn Met Gln Lys Leu Cys Leu Tyr Thr Glu Gly
785                 790                 795                 800

Phe Arg Ile Phe Phe Asp Ile Pro Ser Lys Lys Glu Leu Arg Lys Ala
                805                 810                 815

Ile Ala Val Lys Ile Ser Lys Phe Phe Lys Thr Leu Phe Ser Ile Ile
            820                 825                 830

Ala Asp Ile Leu Leu Gln Glu Phe Pro Tyr Phe Asp Glu Gln Ile Thr
        835                 840                 845

Asp Ile Val Ala Ser Ile Leu Asp Gly Thr Ile Ile Asn Glu Tyr Gly
    850                 855                 860

Thr Lys Lys His Phe Lys Gly Ser Ser Pro Ser Leu Cys Ser Thr Thr
865                 870                 875                 880

Arg Ser Arg Ser Gly Ser Thr Ser Gln Ser Ser Met Thr Pro Val Ser
                885                 890                 895

Pro Leu Gly Leu Asp Thr Asp Ile Arg Pro Met Asn Thr Leu Ser Leu
            900                 905                 910

Val Gly Ser Ser Thr Ser Arg Asn Ser Asp Asn Val Asn Ser Leu Asn
        915                 920                 925

Ser Ser Pro Lys Asn Leu Ser Ser Asp Pro Tyr Leu Ser His Leu Val
    930                 935                 940

Ala Pro Arg Ala Arg His Ala Leu Gly Gly Pro Ser Ser Ile Ile Arg
945                 950                 955                 960

Asn Lys Ile Pro Thr Thr Leu Thr Ser Pro Pro Gly Thr Glu Lys Ser
                965                 970                 975

Ser Pro Val Gln Arg Pro Gln Thr Glu Ser Ile Ser Ala Thr Pro Met
            980                 985                 990
```

-continued

Ala Ile Thr Asn Ser Thr Pro Leu Ser Ser Ala Ala Phe Gly Ile Arg
              995                 1000                1005

Ser Pro Leu Gln Lys Ile Arg Thr Arg Arg Tyr Ser Asp Glu Ser
    1010                1015                1020

Leu Gly Lys Phe Met Lys Ser Thr Asn Asn Tyr Ile Gln Glu His
    1025                1030                1035

Leu Ile Pro Lys Asp Leu Asn Glu Ala Thr Leu Gln Asp Ala Arg
    1040                1045                1050

Arg Ile Met Ile Asn Ile Phe Ser Ile Phe Lys Arg Pro Asn Ser
    1055                1060                1065

Tyr Phe Ile Ile Pro His Asn Ile Asn Ser Asn Leu Gln Trp Val
    1070                1075                1080

Ser Gln Asp Phe Arg Asn Ile Met Lys Pro Ile Phe Val Ala Ile
    1085                1090                1095

Val Ser Pro Asp Val Asp Leu Gln Asn Thr Ala Gln Ser Phe Met
    1100                1105                1110

Asp Thr Leu Leu Ser Asn Val Ile Thr Tyr Gly Glu Ser Asp Glu
    1115                1120                1125

Asn Ile Ser Ile Glu Gly Tyr His Leu Leu Cys Ser Tyr Thr Val
    1130                1135                1140

Thr Leu Phe Ala Met Gly Leu Phe Asp Leu Lys Ile Asn Asn Glu
    1145                1150                1155

Lys Arg Gln Ile Leu Leu Asp Ile Thr Val Lys Phe Met Lys Val
    1160                1165                1170

Arg Ser His Leu Ala Gly Ile Ala Glu Ala Ser His His Met Glu
    1175                1180                1185

Tyr Ile Ser Asp Ser Glu Lys Leu Thr Phe Pro Leu Ile Met Gly
    1190                1195                1200

Thr Val Gly Arg Ala Leu Phe Val Ser Leu Tyr Ser Ser Gln Gln
    1205                1210                1215

Lys Ile Glu Lys Thr Leu Asn Ile Ala Tyr Thr Glu Tyr Leu Ser
    1220                1225                1230

Ala Ile Asn Phe His Glu Arg Asn Ile Asp Asp Ala Asp Lys Thr
    1235                1240                1245

Trp Val His Asn Ile Glu Phe Val Glu Ala Met Cys His Asp Asn
    1250                1255                1260

Tyr Thr Thr Ser Gly Ser Ile Ala Phe Gln Arg Arg Thr Arg Asn
    1265                1270                1275

Asn Ile Leu Arg Phe Ala Thr Ile Pro Asn Ala Ile Leu Leu Asp
    1280                1285                1290

Ser Met Arg Met Ile Tyr Lys Lys Trp His Thr Tyr Thr His Ser
    1295                1300                1305

Lys Ser Leu Glu Lys Gln Glu Arg Asn Asp Phe Arg Asn Phe Ala
    1310                1315                1320

Gly Ile Leu Ala Ser Leu Ser Gly Ile Leu Phe Ile Asn Lys Lys
    1325                1330                1335

Ile Leu Gln Glu Met Tyr Pro Tyr Leu Leu Asp Thr Val Ser Glu
    1340                1345                1350

Leu Lys Lys Asn Ile Asp Ser Phe Ile Ser Lys Gln Cys Gln Trp
    1355                1360                1365

Leu Asn Tyr Pro Asp Leu Leu Thr Arg Glu Asn Ser Arg Asp Ile
    1370                1375                1380

Leu Ser Val Glu Leu His Pro Leu Ser Phe Asn Leu Leu Phe Asn

```
                 1385                1390                1395
Asn Leu Arg Leu Lys Leu Lys Glu Leu Ala Cys Ser Asp Leu Ser
    1400                1405                1410
Ile Pro Glu Asn Glu Ser Ser Tyr Val Leu Leu Glu Gln Ile Ile
    1415                1420                1425
Lys Met Leu Arg Thr Ile Leu Gly Arg Asp Asp Asp Asn Tyr Val
    1430                1435                1440
Met Met Leu Phe Ser Thr Glu Ile Val Asp Leu Ile Asp Leu Leu
    1445                1450                1455
Thr Asp Glu Ile Lys Lys Ile Pro Ala Tyr Cys Pro Lys Tyr Leu
    1460                1465                1470
Lys Ala Ile Ile Gln Met Thr Lys Met Phe Ser Ala Leu Gln His
    1475                1480                1485
Ser Glu Val Asn Leu Gly Val Lys Asn His Phe His Val Lys Asn
    1490                1495                1500
Lys Trp Leu Arg Gln Ile Thr Asp Trp Phe Gln Val Ser Ile Ala
    1505                1510                1515
Arg Glu Tyr Asp Phe Glu Asn Leu Ser Lys Pro Leu Lys Glu Met
    1520                1525                1530
Asp Leu Val Lys Arg Asp Met Asp Ile Leu Tyr Ile Asp Thr Ala
    1535                1540                1545
Ile Glu Ala Ser Thr Ala Ile Ala Tyr Leu Thr Arg His Thr Phe
    1550                1555                1560
Leu Glu Ile Pro Pro Ala Ala Ser Asp Pro Glu Leu Ser Arg Ser
    1565                1570                1575
Arg Ser Val Ile Phe Gly Phe Tyr Phe Asn Ile Leu Met Lys Gly
    1580                1585                1590
Leu Glu Lys Ser Ser Asp Arg Asp Asn Tyr Pro Val Phe Leu Arg
    1595                1600                1605
His Lys Met Ser Val Leu Asn Asp Asn Val Ile Leu Ser Leu Thr
    1610                1615                1620
Asn Leu Ser Asn Thr Asn Val Asp Ala Ser Leu Gln Phe Thr Leu
    1625                1630                1635
Pro Met Gly Tyr Ser Gly Asn Arg Asn Ile Arg Asn Ala Phe Leu
    1640                1645                1650
Glu Val Phe Ile Asn Ile Val Thr Asn Tyr Arg Thr Tyr Thr Ala
    1655                1660                1665
Lys Thr Asp Leu Gly Lys Leu Glu Ala Ala Asp Lys Phe Leu Arg
    1670                1675                1680
Tyr Thr Ile Glu His Pro Gln Leu Ser Ser Phe Gly Ala Ala Val
    1685                1690                1695
Cys Pro Ala Ser Asp Ile Asp Ala Tyr Ala Ala Gly Leu Ile Asn
    1700                1705                1710
Ala Phe Glu Thr Arg Asn Ala Thr His Ile Val Val Ala Gln Leu
    1715                1720                1725
Ile Lys Asn Glu Ile Glu Lys Ser Ser Arg Pro Thr Asp Ile Leu
    1730                1735                1740
Arg Arg Asn Ser Cys Ala Thr Arg Ser Leu Ser Met Leu Ala Arg
    1745                1750                1755
Ser Lys Gly Asn Glu Tyr Leu Ile Arg Thr Leu Gln Pro Leu Leu
    1760                1765                1770
Lys Lys Ile Ile Gln Asn Arg Asp Phe Phe Glu Ile Glu Lys Leu
    1775                1780                1785
```

```
Lys Pro Glu Asp Ser Asp Ala Glu Arg Gln Ile Glu Leu Phe Val
    1790            1795            1800

Lys Tyr Met Asn Glu Leu Leu Glu Ser Ile Ser Asn Ser Val Ser
    1805            1810            1815

Tyr Phe Pro Pro Pro Leu Phe Tyr Ile Cys Gln Asn Ile Tyr Lys
    1820            1825            1830

Val Ala Cys Glu Lys Phe Pro Asp His Ala Ile Ile Ala Ala Gly
    1835            1840            1845

Ser Phe Val Phe Leu Arg Phe Phe Cys Pro Ala Leu Val Ser Pro
    1850            1855            1860

Asp Ser Glu Asn Ile Ile Asp Ile Ser His Leu Ser Glu Lys Arg
    1865            1870            1875

Thr Phe Ile Ser Leu Ala Lys Val Ile Gln Asn Ile Ala Asn Gly
    1880            1885            1890

Ser Glu Asn Phe Ser Arg Trp Pro Ala Leu Cys Ser Gln Lys Asp
    1895            1900            1905

Phe Leu Lys Glu Cys Ser Asp Arg Ile Phe Arg Phe Leu Ala Glu
    1910            1915            1920

Leu Cys Arg Thr Asp Arg Thr Ile Asp Ile Gln Val Arg Thr Asp
    1925            1930            1935

Pro Thr Pro Ile Ala Phe Asp Tyr Gln Phe Leu His Ser Phe Val
    1940            1945            1950

Tyr Leu Tyr Gly Leu Glu Val Arg Arg Asn Val Leu Asn Glu Ala
    1955            1960            1965

Lys His Asp Asp Gly Asp Ile Asp Gly Asp Phe Tyr Lys Thr
    1970            1975            1980

Thr Phe Leu Leu Ile Asp Asp Val Leu Gly Gln Leu Gly Gln Pro
    1985            1990            1995

Lys Met Glu Phe Ser Asn Glu Ile Pro Ile Tyr Ile Arg Glu His
    2000            2005            2010

Met Asp Asp Tyr Pro Glu Leu Tyr Glu Phe Met Asn Arg His Ala
    2015            2020            2025

Phe Arg Asn Ile Glu Thr Ser Thr Ala Tyr Ser Pro Ser Val His
    2030            2035            2040

Glu Ser Thr Ser Ser Glu Gly Ile Pro Ile Ile Thr Leu Thr Met
    2045            2050            2055

Ser Asn Phe Ser Asp Arg His Val Asp Ile Asp Thr Val Ala Tyr
    2060            2065            2070

Lys Phe Leu Gln Ile Tyr Ala Arg Ile Trp Thr Thr Lys His Cys
    2075            2080            2085

Leu Ile Ile Asp Cys Thr Glu Phe Asp Glu Gly Gly Leu Asp Met
    2090            2095            2100

Arg Lys Phe Ile Ser Leu Val Met Gly Leu Leu Pro Glu Val Ala
    2105            2110            2115

Pro Lys Asn Cys Ile Gly Cys Tyr Tyr Phe Asn Val Asn Glu Thr
    2120            2125            2130

Phe Met Asp Asn Tyr Gly Lys Cys Leu Asp Lys Asp Asn Val Tyr
    2135            2140            2145

Val Ser Ser Lys Ile Pro His Tyr Phe Ile Asn Ser Asn Ser Asp
    2150            2155            2160

Glu Gly Leu Met Lys Ser Val Gly Ile Thr Gly Gln Gly Leu Lys
    2165            2170            2175
```

```
Val Leu Gln Asp Ile Arg Val Ser Leu His Asp Ile Thr Leu Tyr
    2180                2185                2190

Asp Glu Lys Arg Asn Arg Phe Thr Pro Val Ser Leu Lys Ile Gly
    2195                2200                2205

Asp Ile Tyr Phe Gln Val Leu His Glu Thr Pro Arg Gln Tyr Lys
    2210                2215                2220

Ile Arg Asp Met Gly Thr Leu Phe Asp Val Lys Phe Asn Asp Val
    2225                2230                2235

Tyr Glu Ile Ser Arg Ile Phe Glu Val His Val Ser Ser Ile Thr
    2240                2245                2250

Gly Val Ala Ala Glu Phe Thr Val Thr Phe Gln Asp Glu Arg Arg
    2255                2260                2265

Leu Ile Phe Ser Ser Pro Lys Tyr Leu Glu Ile Val Lys Met Phe
    2270                2275                2280

Tyr Tyr Ala Gln Ile Arg Leu Glu Ser Glu Tyr Glu Met Asp Asn
    2285                2290                2295

Asn Ser Ser Thr Ser Ser Pro Asn Ser Asn Asn Lys Asp Lys Gln
    2300                2305                2310

Gln Lys Glu Arg Thr Lys Leu Leu Cys His Leu Leu Val Ser
    2315                2320                2325

Leu Ile Gly Leu Phe Asp Glu Ser Lys Lys Met Lys Asn Ser Ser
    2330                2335                2340

Tyr Asn Leu Ile Ala Ala Thr Glu Ala Ser Phe Gly Leu Asn Phe
    2345                2350                2355

Gly Ser His Phe His Arg Ser Pro Glu Val Tyr Val Pro Glu Tyr
    2360                2365                2370

Thr Thr Thr Phe Leu Gly Val Ile Gly Lys Ser Leu Ala Glu Ser
    2375                2380                2385

Asn Pro Glu Leu Thr Ala Tyr Met Phe Ile Tyr Val Leu Glu Ala
    2390                2395                2400

Leu Lys Asn Asn Val Ile Pro His Val Tyr Ile Pro His Thr Ile
    2405                2410                2415

Cys Gly Leu Ser Tyr Trp Ile Pro Asn Leu Tyr Gln His Val Tyr
    2420                2425                2430

Leu Ala Asp Asp Glu Glu Gly Pro Glu Asn Ile Ser His Ile Phe
    2435                2440                2445

Arg Ile Leu Ile Arg Leu Ser Val Arg Glu Thr Asp Phe Lys Ala
    2450                2455                2460

Val Tyr Met Gln Tyr Val Trp Leu Leu Leu Leu Asp Asp Gly Arg
    2465                2470                2475

Leu Thr Asp Ile Ile Val Asp Glu Val Ile Asn His Ala Leu Glu
    2480                2485                2490

Arg Asp Ser Glu Asn Arg Asp Trp Lys Lys Thr Ile Ser Leu Leu
    2495                2500                2505

Thr Val Leu Pro Thr Thr Glu Val Ala Asn Asn Ile Ile Gln Lys
    2510                2515                2520

Ile Leu Ala Lys Ile Arg Ser Phe Leu Pro Ser Leu Lys Leu Glu
    2525                2530                2535

Ala Met Thr Gln Ser Trp Ser Glu Leu Thr Ile Leu Val Lys Ile
    2540                2545                2550

Ser Ile His Val Phe Phe Glu Thr Ser Leu Leu Val Gln Met Tyr
    2555                2560                2565

Leu Pro Glu Ile Leu Phe Ile Val Ser Leu Leu Ile Asp Val Gly
```

-continued

| | | | | | | | | | | | |
|---|---|---|---|---|---|---|---|---|---|---|---|
| | | 2570 | | | 2575 | | | 2580 | | | |
| Pro | Arg | Glu | Leu | Arg | Ser | Ser | Leu | His | Gln | Leu | Leu | Met | Asn | Val |
| | 2585 | | | | 2590 | | | | 2595 | | |
| Cys | His | Ser | Leu | Ala | Ile | Asp | Ser | Ala | Leu | Ser | Gln | Asp | His | Arg |
| 2600 | | | | | 2605 | | | | 2610 | | |
| Asn | Asn | Leu | Asp | Glu | Ile | Ser | Asp | Ile | Phe | Ala | His | Gln | Lys | Val |
| 2615 | | | | | 2620 | | | | 2625 | | |
| Lys | Phe | Met | Phe | Gly | Phe | Ser | Glu | Asp | Lys | Gly | Arg | Ile | Leu | Gln |
| 2630 | | | | | 2635 | | | | 2640 | | |
| Ile | Phe | Ser | Ala | Ser | Ser | Phe | Ala | Ser | Lys | Phe | Asn | Ile | Leu | Asp |
| 2645 | | | | | 2650 | | | | 2655 | | |
| Phe | Phe | Ile | Asn | Asn | Ile | Leu | Leu | Leu | Met | Glu | Tyr | Ser | Ser | Thr |
| 2660 | | | | | 2665 | | | | 2670 | | |
| Tyr | Glu | Ala | Asn | Val | Trp | Lys | Thr | Arg | Tyr | Lys | Lys | Tyr | Val | Leu |
| 2675 | | | | | 2680 | | | | 2685 | | |
| Glu | Ser | Val | Phe | Thr | Ser | Asn | Ser | Phe | Leu | Ser | Ala | Arg | Ser | Ile |
| 2690 | | | | | 2695 | | | | 2700 | | |
| Met | Ile | Val | Gly | Ile | Met | Gly | Lys | Ser | Tyr | Ile | Thr | Glu | Gly | Leu |
| 2705 | | | | | 2710 | | | | 2715 | | |
| Cys | Lys | Ala | Met | Leu | Ile | Glu | Thr | Met | Lys | Val | Ile | Ala | Glu | Pro |
| 2720 | | | | | 2725 | | | | 2730 | | |
| Lys | Ile | Thr | Asp | Glu | His | Leu | Phe | Leu | Ala | Ile | Ser | His | Ile | Phe |
| 2735 | | | | | 2740 | | | | 2745 | | |
| Thr | Tyr | Ser | Lys | Ile | Val | Glu | Gly | Leu | Asp | Pro | Asn | Leu | Asp | Leu |
| 2750 | | | | | 2755 | | | | 2760 | | |
| Met | Lys | His | Leu | Phe | Trp | Phe | Ser | Thr | Leu | Phe | Leu | Glu | Ser | Arg |
| 2765 | | | | | 2770 | | | | 2775 | | |
| His | Pro | Ile | Ile | Phe | Glu | Gly | Ala | Leu | Leu | Phe | Val | Ser | Asn | Cys |
| 2780 | | | | | 2785 | | | | 2790 | | |
| Ile | Arg | Arg | Leu | Tyr | Met | Ala | Gln | Phe | Glu | Asn | Glu | Ser | Glu | Thr |
| 2795 | | | | | 2800 | | | | 2805 | | |
| Ser | Leu | Ile | Ser | Thr | Leu | Leu | Lys | Gly | Arg | Lys | Phe | Ala | His | Thr |
| 2810 | | | | | 2815 | | | | 2820 | | |
| Phe | Leu | Ser | Lys | Ile | Glu | Asn | Leu | Ser | Gly | Ile | Val | Trp | Asn | Glu |
| 2825 | | | | | 2830 | | | | 2835 | | |
| Asp | Asn | Phe | Thr | His | Ile | Leu | Ile | Phe | Ile | Ile | Asn | Lys | Gly | Leu |
| 2840 | | | | | 2845 | | | | 2850 | | |
| Ser | Asn | Pro | Phe | Ile | Lys | Ser | Thr | Ala | Phe | Asp | Phe | Leu | Lys | Met |
| 2855 | | | | | 2860 | | | | 2865 | | |
| Met | Phe | Arg | Asn | Ser | Tyr | Phe | Glu | His | Gln | Ile | Asn | Gln | Lys | Ser |
| 2870 | | | | | 2875 | | | | 2880 | | |
| Asp | His | Tyr | Leu | Cys | Tyr | Met | Phe | Leu | Leu | Tyr | Phe | Val | Leu | Asn |
| 2885 | | | | | 2890 | | | | 2895 | | |
| Cys | Asn | Gln | Phe | Glu | Glu | Leu | Leu | Gly | Asp | Val | Asp | Phe | Glu | Gly |
| 2900 | | | | | 2905 | | | | 2910 | | |
| Glu | Met | Val | Asn | Ile | Glu | Asn | Lys | Asn | Thr | Ile | Pro | Lys | Ile | Leu |
| 2915 | | | | | 2920 | | | | 2925 | | |
| Leu | Glu | Trp | Leu | Ser | Ser | Asp | Asn | Glu | Asn | Ala | Asn | Ile | Thr | Leu |
| 2930 | | | | | 2935 | | | | 2940 | | |
| Tyr | Gln | Gly | Ala | Ile | Leu | Phe | Lys | Cys | Ser | Val | Thr | Asp | Glu | Pro |
| 2945 | | | | | 2950 | | | | 2955 | | |
| Ser | Lys | Phe | Arg | Phe | Ala | Leu | Ile | Ile | Arg | His | Leu | Leu | Thr | Lys |
| 2960 | | | | | 2965 | | | | 2970 | | |

```
Lys Pro Ile Cys Ala Leu Arg Phe Tyr Ser Val Ile Arg Asn Glu
    2975                2980                2985

Ile Arg Lys Ile Ser Ala Phe Glu Gln Asn Ser Asp Cys Val Pro
    2990                2995                3000

Leu Ala Phe Asp Ile Leu Asn Leu Leu Val Thr His Ser Glu Ser
    3005                3010                3015

Asn Ser Leu Glu Lys Leu His Glu Glu Ser Ile Glu Arg Leu Thr
    3020                3025                3030

Lys Arg Gly Leu Ser Ile Val Thr Ser Ser Gly Ile Phe Ala Lys
    3035                3040                3045

Asn Ser Asp Met Met Ile Pro Leu Asp Val Lys Pro Glu Asp Ile
    3050                3055                3060

Tyr Glu Arg Lys Arg Ile Met Thr Met Ile Leu Ser Arg Met Ser
    3065                3070                3075

Cys Ser Ala
    3080

<210> SEQ ID NO 26
<211> LENGTH: 309
<212> TYPE: PRT
<213> ORGANISM: Saccharomyces cerevisiae

<400> SEQUENCE: 26

Met Gln Gly Asn Lys Ser Thr Ile Arg Glu Tyr Lys Ile Val Val
1               5                   10                  15

Gly Gly Gly Gly Val Gly Lys Ser Ala Leu Thr Ile Gln Phe Ile Gln
            20                  25                  30

Ser Tyr Phe Val Asp Glu Tyr Asp Pro Thr Ile Glu Asp Ser Tyr Arg
            35                  40                  45

Lys Gln Val Val Ile Asp Asp Lys Val Ser Ile Leu Asp Ile Leu Asp
        50                  55                  60

Thr Ala Gly Gln Glu Glu Tyr Ser Ala Met Arg Glu Gln Tyr Met Arg
65                  70                  75                  80

Thr Gly Glu Gly Phe Leu Leu Val Tyr Ser Val Thr Ser Arg Asn Ser
                85                  90                  95

Phe Asp Glu Leu Leu Ser Tyr Tyr Gln Gln Ile Gln Arg Val Lys Asp
            100                 105                 110

Ser Asp Tyr Ile Pro Val Val Val Gly Asn Lys Leu Asp Leu Glu
            115                 120                 125

Asn Glu Arg Gln Val Ser Tyr Glu Asp Gly Leu Arg Leu Ala Lys Gln
    130                 135                 140

Leu Asn Ala Pro Phe Leu Glu Thr Ser Ala Lys Gln Ala Ile Asn Val
145                 150                 155                 160

Asp Glu Ala Phe Tyr Ser Leu Ile Arg Leu Val Arg Asp Asp Gly Gly
                165                 170                 175

Lys Tyr Asn Ser Met Asn Arg Gln Leu Asp Asn Thr Asn Glu Ile Arg
            180                 185                 190

Asp Ser Glu Leu Thr Ser Ser Ala Thr Ala Asp Arg Glu Lys Lys Asn
            195                 200                 205

Asn Gly Ser Tyr Val Leu Asp Asn Ser Leu Thr Asn Ala Gly Thr Gly
            210                 215                 220

Ser Ser Ser Lys Ser Ala Val Asn His Asn Gly Glu Thr Thr Lys Arg
225                 230                 235                 240

Thr Asp Glu Lys Asn Tyr Val Asn Gln Asn Asn Asn Asn Glu Gly Asn
```

```
                    245                 250                 255
Thr Lys Tyr Ser Ser Asn Gly Asn Gly Asn Arg Ser Asp Ile Ser Arg
            260                 265                 270
Gly Asn Gln Asn Asn Ala Leu Asn Ser Arg Ser Lys Gln Ser Ala Glu
            275                 280                 285
Pro Gln Lys Asn Ser Ser Ala Asn Ala Arg Lys Glu Ser Ser Gly Gly
            290                 295                 300
Cys Cys Ile Ile Cys
305

<210> SEQ ID NO 27
<211> LENGTH: 309
<212> TYPE: PRT
<213> ORGANISM: Saccharomyces cerevisiae

<400> SEQUENCE: 27

Met Gln Gly Asn Lys Ser Thr Ile Arg Glu Tyr Lys Ile Val Val Val
1               5                   10                  15
Gly Gly Gly Gly Val Gly Lys Ser Ala Leu Thr Ile Gln Phe Ile Gln
            20                  25                  30
Ser Tyr Phe Val Asp Glu Tyr Asp Pro Thr Ile Glu Asp Ser Tyr Arg
        35                  40                  45
Lys Gln Val Val Ile Asp Asp Lys Val Ser Ile Leu Asp Ile Leu Asp
    50                  55                  60
Thr Thr Gly Gln Glu Glu Tyr Ser Ala Met Arg Glu Gln Tyr Met Arg
65                  70                  75                  80
Thr Gly Glu Gly Phe Leu Leu Val Tyr Ser Val Thr Ser Arg Asn Ser
                85                  90                  95
Phe Asp Glu Leu Leu Ser Tyr Tyr Gln Gln Ile Gln Arg Val Lys Asp
            100                 105                 110
Ser Asp Tyr Ile Pro Val Val Val Val Gly Asn Lys Leu Asp Leu Glu
        115                 120                 125
Asn Glu Arg Gln Val Ser Tyr Glu Asp Gly Leu Arg Leu Ala Lys Gln
    130                 135                 140
Leu Asn Ala Pro Phe Leu Glu Thr Ser Ala Lys Gln Ala Ile Asn Val
145                 150                 155                 160
Asp Glu Ala Phe Tyr Ser Leu Ile Arg Leu Val Arg Asp Asp Gly Gly
                165                 170                 175
Lys Tyr Asn Ser Met Asn Arg Gln Leu Asp Asn Thr Asn Glu Ile Arg
            180                 185                 190
Asp Ser Glu Leu Thr Ser Ser Ala Thr Ala Asp Arg Glu Lys Lys Asn
        195                 200                 205
Asn Gly Ser Tyr Val Leu Asp Asn Ser Leu Thr Asn Ala Gly Thr Gly
    210                 215                 220
Ser Ser Ser Lys Ser Ala Val Asn His Asn Gly Glu Thr Thr Lys Arg
225                 230                 235                 240
Thr Asp Glu Lys Asn Tyr Val Asn Gln Asn Asn Asn Glu Gly Asn
                245                 250                 255
Thr Lys Tyr Ser Ser Asn Gly Asn Gly Asn Arg Ser Asp Ile Ser Arg
            260                 265                 270
Gly Asn Gln Asn Asn Ala Leu Asn Ser Arg Ser Lys Gln Ser Ala Glu
            275                 280                 285
Pro Gln Lys Asn Ser Ser Ala Asn Ala Arg Lys Glu Ser Ser Gly Gly
            290                 295                 300
```

Cys Cys Ile Ile Cys
305

<210> SEQ ID NO 28
<211> LENGTH: 9240
<212> TYPE: DNA
<213> ORGANISM: Saccharomyces cerevisiae

<400> SEQUENCE: 28

| | | | | | |
|---|---|---|---|---|---|
| atgtcccagc | ccactaagaa | taagaagaaa | gaacacggga | ccgattccaa | gtcatcccgc | 60 |
| atgactcgga | cgttggttaa | ccatattctt | tttgaaagaa | ttctcccgat | ccttccggtg | 120 |
| gagtctaatc | taagtaccta | ttcagaagtg | gaagagtatt | cctcattcat | ttcatgcaga | 180 |
| tctgtgctca | ttaacgttac | cgtttcccga | gatgcaaacg | ctatggtgga | aggcactttg | 240 |
| gagttgatag | aatcgcttct | tcaagggcac | gaaatcattt | cagataaggg | tagcagtgac | 300 |
| gttattgaat | caatactgat | tatactaaga | ttgttaagtg | atgcgctaga | gtataattgg | 360 |
| caaaatcaag | aaagccttca | ttacaacgac | atttcgactc | acgtagaaca | tgaccaagaa | 420 |
| cagaagtaca | gaccaaagct | tcacaatatt | cttcccgact | actcgtcgac | tcattccaat | 480 |
| ggcaacaaac | acttttttcca | ccagagcaaa | cctcaggcac | tgataccgga | actggcatcg | 540 |
| aaattgcttg | agagttgcgc | gaagttgaag | ttcaatacaa | gaactttgca | aattttacaa | 600 |
| agtatgatca | gtcatgttca | tggaaacatt | ctaacgactt | tgagttcctc | gattcttccc | 660 |
| cgccacaaat | cctatttgac | aaggcacaac | catccttctc | attgtaaaat | gattgactct | 720 |
| actctaggcc | atattctccg | atttgtagcg | gcttccaatc | cgtccgagta | ttttgaattt | 780 |
| atcagaaaga | gtgtgcaagt | gcccgtaaca | cagacacaca | cgcattcaca | ctcccattca | 840 |
| cactctttgc | catcttccgt | ttataacagc | atagtgcccc | actttgatct | tttcagcttc | 900 |
| atccatttaa | gtaaggataa | ttttaagaaa | tacttggaac | tcatcaaaaa | cttatcggtg | 960 |
| acgttaagga | aaacgattta | tcattgccta | cttttgcatt | acagcgccaa | agcaataatg | 1020 |
| ttttggataa | tgactaggcc | tgcggaatat | tatgaactct | tcaacttatt | aaaagataat | 1080 |
| aacaatgaac | actcgaaatc | cttaaacacg | ttaaaccata | cacttttcga | ggagatccat | 1140 |
| tcgactttta | atgtgaatag | catgataacc | accaatcaaa | atgttcatca | aggctcatct | 1200 |
| tccccttcgt | cctcctcgcc | atcgtcacca | cctagctcat | catcatcgga | taacaacaat | 1260 |
| caaaacataa | tagcaaaatc | cttaagtcgt | cagcattctc | accaccagtc | atacattcaa | 1320 |
| cagcagtctg | aaagaaaact | acattcttca | tggactacaa | actctcaatc | ctctacttca | 1380 |
| ctgtcatctt | caacgtctaa | ttcaacaaca | actgatttct | ctactcacac | tcaaccagga | 1440 |
| gaatacgacc | cttccttacc | agatactccc | acgatgtcta | acatcactat | tagtgcatct | 1500 |
| tcattattat | cccaaactcc | aactccaaca | acacaattgc | aacagcggtt | gaactcagca | 1560 |
| gctgcagccg | ccgccgcagc | tgcttcacca | tcgaattcca | ccccaactgg | atacacagca | 1620 |
| gagcaacaaa | gtcgagcttc | atacgatgca | cacaaaactg | gccatactgg | taaggattat | 1680 |
| gatgaacatt | ttttgtctat | cactcgtttg | gataatgttt | tggagttata | cacgcacttt | 1740 |
| gatgatacag | aggtactacc | acacacatcc | gtactgaagt | ttttaactac | tttgacaatg | 1800 |
| ttcgatattg | accttttttaa | tgaattaaac | gctacatcat | tcaaatatat | tcctgactgt | 1860 |
| actatgcatc | gtccaaaaga | aagaacaagt | tctttcaata | atactgcaca | cgagacaggt | 1920 |
| tccgaaaaga | cttcgggtat | aaaacatatt | acgcaaggct | taagaaaatt | aacttctttta | 1980 |
| ccttcctcaa | ccaaaaaaac | tgtaaaattt | atgaagatgt | tgctaagaaa | tttaattggg | 2040 |

```
aaccaagctg tatcagacgt tgccctctta gatacaatga gggccttact atcattcttc    2100
acaatgactt ctgcggtctt tctcgtggat aggaacttac cctcagtact ttttgccaag    2160
agactcatcc ccataatggg gacaaattta agcgtcggtc aagactggaa ttcaaaaata    2220
aataacagtt tgatggtttg tttgaaaaaa aactccacca cgtttgttca attacaatta    2280
atattcttct cttcagctat tcaattcgat catgaattat tgctggcacg tctgagcatc    2340
gatacaatgg ccaacaattt aaacatgcag aagctatgcc tttatactga aggattcagg    2400
atattcttcg acataccaag taagaaggaa ttgcggaagg caattgcggt taaaatttct    2460 aaattttttca aaacattatt ctccattata gcagatattc ttttacaaga atttccgtat    2520
tttgatgagc aaatcaccga catagttgct tccattcttg acggtacaat tatcaatgag    2580
tatggtacga agaaacattt caaggggagc tcaccctctt tatgttcgac aacccggtca    2640
agatcaggat ctacatctca aagttcaatg acaccagttt ctccgctggg actggatact    2700
gatatatgtc caatgaacac cctgtcttta gttggttcaa gtacttcaag aaattctgac    2760
aacgttaatt cattaaacag ttcaccaaag aacttgtctt ctgatccata cttgtcacat    2820
cttgtggccc caagagcacg tcatgcttta ggtgggccat ctagtattat aaggaataaa    2880
ataccgacta cattgacttc acctccagga acggaaaaat cttcaccagt acaacgtccg    2940
caaacggaaa gcatcagtgc cacaccaatg gccataacaa attctactcc attatcgtcg    3000
gcagcattcg gaattcgatc ccctttgcag aaaataagaa cgaggcgtta ttccgatgaa    3060
agtttaggaa aattcatgaa atcaacaaat aattacattc aagaacattt gataccaaaa    3120
gatttgaatg aggcaactct tcaagatgct agaagaataa tgattaatat tttcagtatt    3180
tttaagagac cgaatagtta cttcatcatt cctcacaata taaactcgaa tttacaatgg    3240
gtttcgcagg atttcagaaa tattatgaaa ccgattttcg tcgccatcgt aagtccggat    3300
gtagatttac agaatactgc tcaatcattc atggatacct tattatcgaa tgttattact    3360
tatggtgaat cagatgagaa tatcagtatt gaaggttatc atcttctttg cagttacact    3420
gtaacattat ttgcaatggg cctttttcgat ttgaaaatta ataatgaaaa gcgtcaaatt    3480
ctcttggata taactgtcaa gtttatgaag gttagatcac atttagcagg gatcgcggag    3540
gcctcacacc acatggaata cataagtgat tctgaaaaac tcacctttcc gctgattatg    3600
gggaccgttg gtagggccct atttgtttca ttatactcta gtcaacaaaa aattgaaaag    3660
actttaaaga ttgcttacac agagtatctt tctgcaatca attttcatga gaggaatatt    3720
gatgatgctg ataaaacttg ggttcataat attgagtttg tagaagcgat gtgtcatgac    3780
aactacacaa cttctggttc aattgctttc caaaggagga caagaaataa tattttacga    3840
tttgctacta ttcctaacgc tatcttactt gattctatga ggatgatcta taagaagtgg    3900
catacttaca cacacagtaa aagtttagaa aaacaagaac ggaacgactt cagaaatttc    3960
gcgggtattt tagcctcttt gtcgggtatc ctattcatca ataaaaagat attgcaagaa    4020
atgtatccat acctactcga caccgtttca gaattgaaaa aaaatataga ctctttatc     4080 tcaaaacaat gccaatggtt aaactatccg gatttattaa cgagagaaaa ttcaagagat    4140
attctaagtg tagaactgca tcctttgtct tttaacttac ttttttaataa tttgaggctc    4200 aagttaaaag aacttgcttg ttcagactta tcaataccag aaaatgaaag ttcctatgtt    4260
ttattagaac aaataatcaa aatgctgcgg acaatcctag gtcgtgatga tgacaattat    4320
gtaatgatgc ttttttccac agagattgta gatcttattg atttattgac agatgaaata    4380
aaaaaaatac cagcctattg tccaaaatat ctcaaggcaa ttattcaaat gaccaaaatg    4440
```

-continued

```
tttagtgcct tgcagcactc agaggttaat ttaggtgtca aaaatcattt tcacgttaaa    4500
aataaatggt tgagacaagt cactgattgg tttcaagtga gtattgcgag agagtacgat    4560
ttcgaaaact tgtcaaaacc tctaaaagaa atggatttgg taaaaagaga catggatatt    4620
ctatacatag atacggcaat cgaagcttca accgctattg cgtacctcac gagacatact    4680
ttcttagaga ttccacctgc cgcgtcagat cccgaactat ctcgatctag gtctgtgata    4740
tttggctttt atttcaacat cttaatgaaa ggccttgaaa aaagtagtga tcgtgacaat    4800
tacccagtat tcttgaggca caaaatgagt gtcctcaacg acaatgtaat actttcatta    4860
acaaatcttt ctaacaccaa tgttgatgcg agtttgcagt tcaccttacc gatgggctat    4920
tccggaaatc gaaacattag gaatgcattt ttggaggtct tcattaatat cgttacgaac    4980
tatcggacat acacggctaa aactgacctt ggaaaattag aagcagcaga caaattttg    5040 cgatatacga ttgaacatcc ccagctatcg tcctttggag cagcggtttg tcccgctagc    5100
gatattgatg cttatgctgc tggcttaata aatgcatttg aaacgagaaa tgccacccac    5160
attgtagtgt cacagttgat taaaaatgaa attgaaaatt cttccagacc tacggatatc    5220
cttagaagga atagctgtgc tacgagatca ttatctatgc tagccaggtc caagggtagc    5280
gaatatttga ttcgcacttt gcaaccatta ctaaaaaaaa ttatccagaa cagagatttt    5340
tttgaaattg agaaattaaa accggaagat tcagatgctg aacgtcaaat agagcttttt    5400
gttaaataca tgaatgaatt attggaatcc atatccaact ccgtatctta ttttccccct    5460
cctttatttt atatttgtca aaacatttat aaagttgcgt gtgaaaaatt tccggatcac    5520
gcaattatcg ccgctgggtc tttcgtattt ttacggtttt tttgtcctgc tttagtcagc    5580
cctgattctg aaaatatcat agatatttct cacttgagcg aaaagcgtac cttcatcagc    5640
ttggctaaag ttatccaaaa tattgccaat ggctcagaaa atttctccag atggccagct    5700
ttgtgttccc aaaaggattt tcttaaggaa tgtagcgata gaattttcag attcctagct    5760
gaactttgta gaacagatcg cacgatagac atccaagtga gaacagaccc aacgccaatt    5820
gcatttgact atcaattcct tcattccttt gtttaccttt acggtcttga agtgagaagg    5880
aatgtgctaa atgaagcaaa acatgatgat ggtgacatta atggtgacga tttctataag    5940
accacgtttt tacttattga tgatgttctt ggccaattag gccaacctaa aatggaattt    6000
tccaatgaaa taccaatata cataagagaa catatgacg actatccgga actgtatgag    6060
ttcatgaata ggcacgcgtt cagaaacatt gagacttcaa cagcgtacag cccaagcgtt    6120
cacgagtcca cctcaagtga aggcattcca attattacgt taacaatgtc aaatttctca    6180
gacagacatg tggacattga tacagttgct tacaagttct tgcaaattta tgctcgaatc    6240
tggaccacca aacactgttt aataatcgac tgtacagaat ttgacgaggg agggcttgat    6300
atgaggaaat ttatttcttt ggttatggga ctattaccag aagttgcacc caaaaattgt    6360
ataggctgtt actactttaa cgtaaacgag acatttatgg ataattatgg aaaatgtttg    6420
gacaaggaca acgtatatgt ttcctcgaaa attcctcatt atttcattaa tagtaactct    6480
gatgaaggac ttatgaaatc tgtgggtata actggacaag ggttgaaggt tctgcaagat    6540
attcgtgtct ctctgcatga tatcacgctt tatgacgaaa aagaaaatag atttacgccg    6600
gtatcgttga aaataggcga tatttacttt caagtcttgc atgaaactcc taggcaatat    6660
aaaataagag acatgggtac tttattcgac gtaaaattca atgatgtcta cgaaattagc    6720
cgaatattcg aagtacatgt ttcgtcaata actggagtgg cagctgaatt tacagtaact    6780
```

```
tttcaggacg agagaaggtt gattttagt agtccgaaat accttgaaat tgtgaagatg    6840
ttctattacg cacagatccg gttagaaagt gaatatgaaa tggataataa ttcgagtacc    6900
tcctccccaa attcaaacaa caaggacaaa cagcagaaag agagaacaaa attattgtgc    6960
cacctactgt tagtatctct tattggtctg tttgatgaga gtaaaaaaat gaaaaacagt    7020
tcgtataacc taatagctgc cactgaggcg tcatttggtt tgaactttgg ctcccatttt    7080
catcgctctc ccgaggtgta cgtccccgaa gatactacaa catttttagg tgttattgga    7140
aagtctcttg cagagtctaa tccagaactc acagcctata tgtttatcta tgttttggag    7200
gcattgaaga acaacgtgat tcctcatgtt tacatccctc ataccatttg cggtttgtct    7260
tattggatcc ctaatttata ccaacatgtg tatttggctg atgatgaaga aggccccgaa    7320
aacatatctc acattttccg aattcttatc aggctctctg tgagagagac tgactttaaa    7380
gccgtataca tgcaatatgt ttggctgcta cttttagatg atggccgctt aactgacatt    7440
atcgttgatg aagttattaa tcatgcgtta gaaagagact ccgaaaaccg cgattggaag    7500
aaaacaatat cgttactaac tgtcctaccc actactgagg ttgctaataa tattattcaa    7560
aaaatattgg caaaaattag atcatttttta ccgtcattga agttagaagc tatgacccaa    7620
agttggtctg aactaacaat attagttaag ataagcatcc atgtttttt tgaaacttct    7680
ttgctggtac agatgtactt accagagatc ctgtttatcg tatccttatt aattgatgtt    7740
ggtccaaggg aactcagatc atcactacac cagctattaa tgaatgtatg ccattccttg    7800
gctattaact cagctttacc acaagatcat agaaataatc tagatgaaat aagtgatata    7860
tttgcacatc aaaaggtgaa gtttatgttt gggttcagcg aggacaaagg acgaattta    7920
cagattttta gcgcttcttc tttttgcaagc aagtttaata tcctggattt cttcatcaat    7980
aatatattat tgctgatgga atattcttca acgtacgaag caaacgtgtg gaagacaaga    8040
tacaagaaat atgtcttgga atctgtgttt acaagtaatt cttttctttc ggcacgttca    8100
atcatgattg ttggtataat gggtaaatct tacataactg aagggttatg caaggctatg    8160
ttaattgaaa ccatgaaagt tatcgccgaa ccaaagatta ctgacgagca tcttttctta    8220
gccatatctc atatttttac ttattccaaa attgttgaag gtttggatcc caaccttgac    8280
ttaatgaagc acttatttttg gttttcaaca ctcttccttg aatcacgtca cccgataatt    8340
tttgagggtg cccttctctt tgtgtcaaac tgtataaggc gcctatacat ggcccagttt    8400
gaaaatgaaa gtgaaacatc attgataagt acttactta aggggagaaa gtttgctcat    8460
accttttaa gcaagataga gaatcttagt ggtattgttt ggaatgaaga taatttaca    8520
cacattctga ttttcatcat taataaagga ctatccaatc ctttcattaa gagtacggct    8580
tttgattct tgaagatgat gtttagaaac tcctactttg agcatcaaat caatcagaaa    8640
tctgatcatt atttgtgcta tatgttccta ttgtatttg ttttaaactg taatcaattt    8700
gaggaacttt taggtgacgt tgatttttgaa ggagaaatgg ttaacattga aaacaagaac    8760
accattccta aaattttgtt ggagtggttg agttcggata acgaaaatgc aaacattacc    8820
ctctatcaag gtgcgatact gttcaaatgt tcagttacgg atgaaccaag tagatttagg    8880
tttgcgttga ttattaggca tctattgaca agaaaaccca tttgtgcatt gcgttttac    8940
agtgttattc gtaacgaaat aagaaaaata tcagcatttg agcaaacttc ggattgtgtt    9000
ccacttgctt tcgatatttt aaacttatta gtgacgcatt cagagtctaa ttccttagaa    9060
aaacttcacg aagaatccat tgaacgtctg accaaaagag gttatcaat tgtgacttct    9120
tctggtatat ttgcgaagaa ttccgacatg atgataccgt tagatgtaaa acctgaagat    9180
```

```
atctatgaac gtaagagaat aatgacaatg attttatcaa ggatgtcatg ttctgcttag    9240
```

<210> SEQ ID NO 29
<211> LENGTH: 475
<212> TYPE: PRT
<213> ORGANISM: Streptococcus mutans

<400> SEQUENCE: 29

| | | | | | | | | | | | | | | |
|---|---|---|---|---|---|---|---|---|---|---|---|---|---|---|
| Met | Thr | Lys | Gln | Tyr | Lys | Asn | Tyr | Val | Asn | Gly | Glu | Trp | Lys | Leu | Ser |
| 1 | | | | 5 | | | | | 10 | | | | | 15 | |
| Glu | Asn | Glu | Ile | Lys | Ile | Tyr | Glu | Pro | Ala | Ser | Gly | Ala | Glu | Leu | Gly |
| | | | 20 | | | | | 25 | | | | | 30 | | |
| Ser | Val | Pro | Ala | Met | Ser | Thr | Glu | Glu | Val | Asp | Tyr | Val | Tyr | Ala | Ser |
| | | | 35 | | | | | 40 | | | | | 45 | | |
| Ala | Lys | Lys | Ala | Gln | Pro | Ala | Trp | Arg | Ser | Leu | Ser | Tyr | Ile | Glu | Arg |
| | 50 | | | | | 55 | | | | | 60 | | | | |
| Ala | Ala | Tyr | Leu | His | Lys | Val | Ala | Asp | Ile | Leu | Met | Arg | Asp | Lys | Glu |
| 65 | | | | | 70 | | | | | 75 | | | | | 80 |
| Lys | Ile | Gly | Ala | Val | Leu | Ser | Lys | Glu | Val | Ala | Lys | Gly | Tyr | Lys | Ser |
| | | | | 85 | | | | | 90 | | | | | 95 | |
| Ala | Val | Ser | Glu | Val | Val | Arg | Thr | Ala | Glu | Ile | Ile | Asn | Tyr | Ala | Ala |
| | | | 100 | | | | | 105 | | | | | 110 | | |
| Glu | Glu | Gly | Leu | Arg | Met | Glu | Gly | Glu | Val | Leu | Glu | Gly | Gly | Ser | Phe |
| | | | 115 | | | | | 120 | | | | | 125 | | |
| Glu | Ala | Ala | Ser | Lys | Lys | Lys | Ile | Ala | Val | Val | Arg | Arg | Glu | Pro | Val |
| | 130 | | | | | 135 | | | | | 140 | | | | |
| Gly | Leu | Val | Leu | Ala | Ile | Ser | Pro | Phe | Asn | Tyr | Pro | Val | Asn | Leu | Ala |
| 145 | | | | | 150 | | | | | 155 | | | | | 160 |
| Gly | Ser | Lys | Ile | Ala | Pro | Ala | Leu | Ile | Ala | Gly | Asn | Val | Ile | Ala | Phe |
| | | | | 165 | | | | | 170 | | | | | 175 | |
| Lys | Pro | Pro | Thr | Gln | Gly | Ser | Ile | Ser | Gly | Leu | Leu | Leu | Ala | Glu | Ala |
| | | | 180 | | | | | 185 | | | | | 190 | | |
| Phe | Ala | Glu | Ala | Gly | Leu | Pro | Ala | Gly | Val | Phe | Asn | Thr | Ile | Thr | Gly |
| | | | 195 | | | | | 200 | | | | | 205 | | |
| Arg | Gly | Ser | Glu | Ile | Gly | Asp | Tyr | Ile | Val | Glu | His | Gln | Ala | Val | Asn |
| | 210 | | | | | 215 | | | | | 220 | | | | |
| Phe | Ile | Asn | Phe | Thr | Gly | Ser | Thr | Gly | Ile | Gly | Glu | Arg | Ile | Gly | Lys |
| 225 | | | | | 230 | | | | | 235 | | | | | 240 |
| Met | Ala | Gly | Met | Arg | Pro | Ile | Met | Leu | Glu | Leu | Gly | Gly | Lys | Asp | Ser |
| | | | | 245 | | | | | 250 | | | | | 255 | |
| Ala | Ile | Val | Leu | Glu | Asp | Ala | Asp | Leu | Glu | Leu | Thr | Ala | Lys | Asn | Ile |
| | | | 260 | | | | | 265 | | | | | 270 | | |
| Ile | Ala | Gly | Ala | Phe | Gly | Tyr | Ser | Gly | Gln | Arg | Cys | Thr | Ala | Val | Lys |
| | | | 275 | | | | | 280 | | | | | 285 | | |
| Arg | Val | Leu | Val | Met | Glu | Ser | Val | Ala | Asp | Glu | Leu | Val | Glu | Lys | Ile |
| | 290 | | | | | 295 | | | | | 300 | | | | |
| Arg | Glu | Lys | Val | Leu | Ala | Leu | Thr | Ile | Gly | Asn | Pro | Glu | Asp | Asp | Ala |
| 305 | | | | | 310 | | | | | 315 | | | | | 320 |
| Asp | Ile | Thr | Pro | Leu | Ile | Asp | Thr | Lys | Ser | Ala | Asp | Tyr | Val | Glu | Gly |
| | | | | 325 | | | | | 330 | | | | | 335 | |
| Leu | Ile | Asn | Asp | Ala | Asn | Asp | Lys | Gly | Ala | Ala | Ala | Leu | Thr | Glu | Ile |
| | | | 340 | | | | | 345 | | | | | 350 | | |
| Lys | Arg | Glu | Gly | Asn | Leu | Ile | Cys | Pro | Ile | Leu | Phe | Asp | Lys | Val | Thr |
| | | | 355 | | | | | 360 | | | | | 365 | | |

```
Thr Asp Met Arg Leu Ala Trp Glu Glu Pro Phe Gly Pro Val Leu Pro
    370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                405                 410                 415

Ala Phe Gly Ile Ala Glu Gln Leu Glu Val Gly Thr Val His Ile Asn
            420                 425                 430

Asn Lys Thr Gln Arg Gly Thr Asp Asn Phe Pro Phe Leu Gly Ala Lys
        435                 440                 445

Lys Ser Gly Ala Gly Ile Gln Gly Val Lys Tyr Ser Ile Glu Ala Met
    450                 455                 460

Thr Thr Val Lys Ser Val Val Phe Asp Ile Lys
465                 470                 475
```

<210> SEQ ID NO 30
<211> LENGTH: 1428
<212> TYPE: DNA
<213> ORGANISM: Artificial Sequence
<220> FEATURE:
<223> OTHER INFORMATION: Encoding SEQ ID NO: 29 and codon-optimized for expression in Saccharomyces cerevisiae

<400> SEQUENCE: 30

```
atgacaaaac aatataaaaa ttatgtcaat ggcgagtgga agctttcaga aaatgaaatt      60
aaaatctacg aaccggccag tggagctgaa ttgggttcag ttccagcaat gagtactgaa     120
gaagtagatt atgtttatgc ttcagccaag aaagctcaac cagcttggcg atcactttca     180
tacatagaac gtgctgccta ccttcataag gtagcagata ttttgatgcg tgataaagaa     240
aaaataggtg ctgttctttc caagagaggtt gctaaaggtt ataaatcagc agtcagcgaa     300
gttgttcgta ctgcagaaat cattaattat gcagctgaag aaggccttcg tatggaaggt     360
gaagtccttg aaggcggcag ttttgaagca gccagcaaga aaaaaattgc cgttgttcgt     420
cgtgaaccag taggtcttgt attagctatt tcaccattta actacccctgt taacttggca     480
ggttcgaaaa ttgcaccggc tcttattgcg ggaaatgtta ttgcttttaa accaccgacg     540
caaggatcaa tctcagggct cttacttgct gaagcatttg ctgaagctgg acttcctgca     600
ggtgtcttta taccattac aggtcgtggt tctgaaattg gagactatat gtagaacat      660
caagccgtta actttatcaa tttcactggt tcaacaggaa ttggggaacg tattggcaaa     720
atggctggta tgcgtccgat tatgcttgaa ctcggtggaa agattcagc catcgttctt     780
gaagatgcag accttgaatt gactgctaaa aatattattg caggtgcttt tggttattca     840
ggtcaacgct gtacagcagt taacgtgtt cttgtgatgg aaagtgttgc tgatgaactg     900
gtcgaaaaaa tccgtgaaaa agttcttgca ttaacaattg gtaatccaga agacgatgca     960
gatattacac gcttgattga tacaaaatca gctgattatg tagaaggtct tattaatgat    1020
gccaatgata aaggagccgc tgcccttact gaaatcaaac gtgaaggtaa tcttatctgt    1080
ccaatcctct ttgataaggt aacgacagat atgcgtcttg cttgggaaga accatttggt    1140
cctgttcttc cgatcattcg tgtgacatct gtagaagaag ccattgaaat ttctaacaaa    1200
tcggaatatg gacttcaggc ttctatcttt acaaatgatt tcccacgcgc ttttggtatt    1260
gctgagcagc ttgaagttgg tacagttcat atcaataata agacacagcg cggtacggac    1320
aacttcccat tcttaggggc taaaaaatca ggtgcaggta ttcaagggct aaaatattct    1380
```
attgaagcta tgacaactgt taaatccgtc gtatttgata tcaaataa                1428

<210> SEQ ID NO 31
<211> LENGTH: 535
<212> TYPE: PRT
<213> ORGANISM: Alternaria alternata

<400> SEQUENCE: 31

Met Asp Lys Ile Ser Lys Tyr Asn Val His Arg Tyr Glu Lys Arg
1               5                   10                  15

Ser Leu Leu Ile Ala Ile Asn Cys Ile Ala Gly Leu Ser Ile Leu Phe
            20                  25                  30

Phe Gly Tyr Asp Gln Gly Met Met Gly Gly Val Asn Thr Ala Tyr Asp
        35                  40                  45

Tyr Tyr Thr Leu Met Gly Phe Gly His Lys Gly Ala Asp Gly Gly Pro
    50                  55                  60

Val Val Asp Asp Thr Leu Leu Gln Gly Gly Ile Val Ser Val Tyr Tyr
65                  70                  75                  80

Leu Gly Thr Leu Val Gly Cys Leu Val Gly Gly Ser Ile Gly Asp Arg
                85                  90                  95

Phe Gly Arg Ile Lys Thr Ile Phe Val Gly Ala Ala Val Ala Thr Val
            100                 105                 110

Gly Ala Cys Leu Gln Cys Ser Ala Met Asn His Glu Trp Met Ile Cys
        115                 120                 125

Ala Arg Leu Val Asn Gly Trp Gly Thr Gly Ile Leu Asn Ser Ile Ile
    130                 135                 140

Pro Val Trp Ala Thr Glu Thr Ala Glu His Thr Ser Arg Gly Gln Phe
145                 150                 155                 160

Ile Ala Ile Glu Phe Thr Leu Asn Ile Leu Gly Val Val Ile Ala Tyr
                165                 170                 175

Trp Leu Glu Tyr Ala Cys Ser Phe Tyr Gly Asp Gly Thr Ser Ser Phe
            180                 185                 190

Ile Trp Arg Phe Pro Ile Ala Phe Gln Ile Pro Met Leu Met Ile Leu
        195                 200                 205

Met Ala Ala Val Met Phe Phe Pro Glu Ser Pro Arg Trp Leu Val Lys
    210                 215                 220

Val Gly Arg Glu Ala Glu Gly Arg Tyr Val Leu Ser Arg Leu Arg Gly
225                 230                 235                 240

Asp Ala Gly Glu Asp Arg Glu Arg Ala Glu Thr Glu Phe Gln Glu Ile
                245                 250                 255

Val Ala Ser Cys Glu Leu Glu Arg Ser Asn Phe Arg Lys Gln Ser Tyr
            260                 265                 270

Phe His Met Leu Phe Gly Ile Gly Ser Gly Lys Leu His Thr Gly Arg
        275                 280                 285

Arg Val Gln Leu Val Ile Trp Leu Gln Ile Met Gln Glu Trp Val Gly
    290                 295                 300

Ile Ala Gly Val Thr Ile Tyr Ala Pro Thr Ile Phe Gly Ile Ala Gly
305                 310                 315                 320

Met Ser Pro Ala Lys Arg Gln Trp Ile Ser Gly Leu Asn Asn Ile Phe
                325                 330                 335

Tyr Met Phe Ala Thr Leu Ile Cys Val Phe Thr Leu Asp Arg Ile Gly
            340                 345                 350

Arg Arg Trp Thr Cys Tyr Trp Gly Ser Ala Gly Gln Gly Ile Ala Met
        355                 360                 365

Ala Leu Ala Gly Gly Phe Ser Tyr Leu Gly Gln Glu Ala Thr Lys Arg
370                 375                 380

Gly Asp Thr Ser Ala Ala Ser Ser Tyr Gly Asn Ala Ala Val Ser Met
385                 390                 395                 400

Val Phe Ile Phe Thr Ala Ile Phe Gly Ala Thr Trp Leu Thr Val Pro
            405                 410                 415

Trp Leu Tyr Pro Ala Glu Ile Phe Pro Leu Glu Val Arg Ala Lys Gly
            420                 425                 430

Asn Ala Trp Gly Val Val Gly Trp Ser Ile Gly Asn Gly Trp Leu Thr
            435                 440                 445

Leu Leu Cys Pro Ile Met Phe Glu Ala Leu Gly Glu Lys Thr Leu Tyr
450                 455                 460

Ile Phe Ala Ala Cys Asn Ala Ile Thr Ile Pro Met Val Trp Ala Leu
465                 470                 475                 480

Tyr Pro Glu Thr Asn Gln Arg Thr Leu Glu Glu Ile Asp Leu Leu Phe
            485                 490                 495

Ala Ser Asp Ser Ile Trp Asn Trp Glu Ala Glu Lys Asn Phe Ala Ala
            500                 505                 510

Leu Gln Glu Thr Leu Pro Phe Glu Ala Thr Ser His Ala Ala Lys Asn
            515                 520                 525

Asp Ile Glu Arg Val Ser Leu
530                 535

<210> SEQ ID NO 32
<211> LENGTH: 542
<212> TYPE: PRT
<213> ORGANISM: Aspergillus fumigatus

<400> SEQUENCE: 32

Met Trp Thr Thr Thr Ser Gly Leu Ser Gly Arg Ser Leu Arg Leu Ser
1               5                   10                  15

Ile Thr Phe Ala Ala Val Val Gly Phe Ser Leu Phe Gly Tyr Asn Gln
            20                  25                  30

Gly Met Met Ala Gly Leu Leu Asn Gly Asp Glu Phe Val Asn Ser Phe
        35                  40                  45

Pro Ile Leu Lys Met Pro Asp Asn Pro Thr Ala Gly Glu Lys His Tyr
50                  55                  60

Ile Asp Val Ile Arg Gly Ala Val Thr Ser Cys Tyr Glu Leu Gly Cys
65                  70                  75                  80

Phe Phe Gly Ala Leu Phe Ser Met Phe Cys Gly Asn Arg Leu Gly Arg
                85                  90                  95

Thr Arg Leu Ile Phe Met Gly Ala Ser Ile Leu Ile Val Gly Ala Leu
            100                 105                 110

Leu Thr Thr Val Cys Tyr Thr Gly Lys Trp Glu Val Gly Gln Phe Val
            115                 120                 125

Ile Gly Arg Val Val Ser Gly Ile Gly Asn Gly Met Asn Thr Ala Thr
        130                 135                 140

Ile Pro Val Trp Gln Ser Glu Cys Ser Gly Ala His Asn Arg Gly Phe
145                 150                 155                 160

Leu Val Cys Phe Glu Gly Ala Met Ile Ala Gly Gly Thr Phe Ile Ala
                165                 170                 175

Tyr Trp Val Val Phe Gly Ile Ser His Ala Ala Asp Ser Val Gln Trp
            180                 185                 190

Arg Phe Pro Val Ala Leu Gln Ile Phe Phe Ala Leu Val Val Ala Thr
            195                 200                 205

Gly Ala Leu Met Leu Pro Asp Ser Pro Ser Trp Phe Val Ser Arg Gly
             210                 215                 220

Leu Asp Asn Glu Ala Cys Glu Val Leu Gly Lys Ile Lys Gly Thr Ser
225                 230                 235                 240

Pro Asp Ser Asp Gln Val Leu His Asp Phe Asn Leu Ile Lys Thr Asp
                245                 250                 255

Met Glu Ser Thr Lys Ser Glu Gln Ser Asn Trp Lys Thr Val Phe Thr
            260                 265                 270

Phe Gly Lys Thr Gln Glu Phe Gln Arg Leu Leu Ile Gly Cys Ser Gly
        275                 280                 285

Gln Phe Phe Gln Gln Phe Thr Gly Cys Asn Ala Ala Ile Tyr Tyr Ser
    290                 295                 300

Thr Leu Leu Phe Gln Glu Asn Leu His Met Glu Lys Tyr Leu Ser Leu
305                 310                 315                 320

Ile Met Gly Gly Val Phe Ala Ser Val Tyr Ala Leu Ala Thr Ile Pro
                325                 330                 335

Ser Phe Phe Met Ile Glu Arg Val Gly Arg Arg Lys Leu Tyr Leu Ile
                340                 345                 350

Gly Phe Leu Gly Gln Gly Leu Ser Phe Val Ile Thr Phe Ala Cys Leu
            355                 360                 365

Ile Lys Glu Thr Glu Glu Asn Ser Lys Gly Ala Ala Val Gly Ile Phe
370                 375                 380

Leu Phe Ile Thr Phe Phe Ala Phe Thr Leu Leu Pro Leu Pro Trp Ile
385                 390                 395                 400

Tyr Pro Pro Glu Ile Asn Pro Leu Arg Thr Arg Thr Val Gly Ala Ser
                405                 410                 415

Ala Ser Thr Cys Thr Asn Trp Met Cys Asn Phe Ala Val Val Met Phe
                420                 425                 430

Thr Pro Leu Phe Ala Gly Gln Ser Pro Trp Gly Val Tyr Leu Phe Phe
            435                 440                 445

Ala Leu Phe Asn Phe Val Gly Leu Ile Phe Gly Tyr Phe Phe Tyr Val
            450                 455                 460

Glu Thr Ala Gly Arg Glu Leu Glu Glu Val Asp Ile Ile Tyr Ala Lys
465                 470                 475                 480

Ala His Val Glu Gly Lys Met Pro Phe Arg Val Ala His Asp Leu Pro
                485                 490                 495

Lys Leu Ser Phe Glu Glu Ile Val Gln Gln Ser Arg Glu Leu Gly Leu
            500                 505                 510

Asp Thr Asn Asp His Val Met Leu Glu Lys Lys Glu Leu Gly Leu Ser
            515                 520                 525

Ser Asp Ser Ala Gln Glu Thr Glu Glu Val Tyr Glu Lys Gln
530                 535                 540

<210> SEQ ID NO 33
<211> LENGTH: 539
<212> TYPE: PRT
<213> ORGANISM: Aspergillus terreus

<400> SEQUENCE: 33

Met Trp Thr Thr Thr Ser Gly Thr Ser Gly Arg Leu Leu Arg Ala Ser
1               5                   10                  15

Ile Thr Phe Thr Ala Val Met Gly Phe Ser Leu Phe Gly Tyr Asn Gln
            20                  25                  30

Gly Met Met Ser Gly Leu Ile Ala Gly Asp Glu Phe Thr Lys Thr Phe

```
            35                  40                  45
Gly Thr Leu Ala Met Pro Asp Asn Pro Asp Ala Thr Tyr Arg His
 50                  55                  60

Ile Asn Val Ile Arg Gly Ala Val Thr Ala Cys Tyr Glu Ile Gly Cys
 65                  70                  75                  80

Phe Phe Gly Ala Leu Phe Ser Met Phe Phe Gly Glu Lys Ile Gly Arg
                 85                  90                  95

Thr Arg Ile Ile Phe Ser Gly Ala Leu Val Leu Ile Ile Gly Ala Val
                100                 105                 110

Ile Ser Thr Ala Ala Phe Gly Pro Gln Trp Gly Leu Gly Gln Phe Val
            115                 120                 125

Val Gly Arg Val Ile Ser Gly Leu Gly Asn Gly Met Asn Thr Ala Thr
            130                 135                 140

Ile Pro Val Trp Gln Ser Glu Cys Ser Ser Ala His Asn Arg Gly Leu
145                 150                 155                 160

Leu Val Cys Phe Glu Gly Ala Met Ile Ala Val Gly Thr Phe Ile Ala
                165                 170                 175

Tyr Trp Val Val Phe Gly Leu Ser Tyr Val Pro Glu Thr Val Gln Trp
                180                 185                 190

Arg Phe Pro Val Ala Leu Gln Val Phe Phe Ala Leu Ile Val Ala Ala
            195                 200                 205

Gly Ala Met Met Phe Pro Glu Ser Pro Arg Trp Phe Val Met Arg Gly
210                 215                 220

Tyr His Lys Glu Ala Cys Glu Val Ile Ala Lys Leu Lys Asn Ser Thr
225                 230                 235                 240

Pro Asp Ser Asp Glu Val Leu Thr Glu Phe Asn Phe Met Lys Ala Asp
                245                 250                 255

Val Glu Met Thr Ser Ala Ser Gln Ala Ser Trp Lys Thr Val Phe Thr
                260                 265                 270

Phe Gly Lys Thr Gln Glu Phe Gln Arg Leu Leu Val Gly Cys Ser Gly
            275                 280                 285

Gln Phe Phe Gln Gln Phe Thr Gly Cys Asn Ala Ala Ile Tyr Tyr Ser
            290                 295                 300

Thr Leu Leu Phe Glu Glu Asn Leu Asn Leu Glu His Arg Leu Ala Leu
305                 310                 315                 320

Ile Met Gly Gly Val Phe Ala Thr Val Tyr Ala Leu Ala Thr Ile Pro
                325                 330                 335

Ser Phe Phe Met Val Glu Arg Val Gly Arg Arg Lys Leu Tyr Leu Ile
                340                 345                 350

Gly Phe Leu Gly Gln Gly Leu Ser Phe Val Ile Thr Phe Ala Cys Leu
            355                 360                 365

Ile Lys Pro Thr Thr Glu Asn Ser Lys Gly Ala Ile Val Gly Ile Phe
            370                 375                 380

Leu Phe Ile Thr Phe Phe Ala Phe Thr Leu Pro Leu Pro Trp Ile
385                 390                 395                 400

Tyr Pro Pro Glu Ile Asn Pro Leu Arg Thr Arg Thr Val Gly Ala Ala
                405                 410                 415

Ala Ser Thr Cys Thr Asn Trp Ile Cys Asn Phe Ala Val Val Met Phe
            420                 425                 430

Thr Pro Leu Phe Ala Ala Ser Ser Gly Trp Gly Val Tyr Leu Phe Phe
            435                 440                 445

Ala Leu Ile Asn Leu Ile Gly Val Pro Phe Gly Trp Phe Phe Phe Val
            450                 455                 460
```

Glu Thr Ala Gly Arg Glu Leu Glu Ile Asp Ile Val Tyr Ala Lys
465                 470                 475                 480

Ala His Val Glu Lys Lys Trp Pro Phe Met Val Ala Lys Asp Met Pro
            485                 490                 495

Lys Leu Ser Leu Glu Glu Ile Thr Gln Gln Ser Arg Glu Leu Gly Leu
            500                 505                 510

Asp Leu Asn Asp Ser Ser Pro Pro Asp Gln Asn Glu Ser Gly Leu Ser
            515                 520                 525

Ser Asp Asn Asp Gln Ser Val Ala Glu Lys Gln
            530                 535

<210> SEQ ID NO 34
<211> LENGTH: 572
<212> TYPE: PRT
<213> ORGANISM: Cordyceps militaris

<400> SEQUENCE: 34

Met Val Asp Phe Lys Ala Leu Thr Glu Lys His Asn Val Ala His Lys
1               5                   10                  15

Leu Tyr Lys Ser Ser Leu Leu Asn Thr Val Cys Leu Val Ala Gly Leu
            20                  25                  30

Ser Ile Phe Phe Phe Gly Tyr Asp Gln Gly Leu Met Gly Gly Val Asn
            35                  40                  45

Thr Thr Arg Asn Tyr Ala Glu Thr Met Gly Phe Gly His Trp Asp Glu
50                  55                  60

Glu Gln Gly Ile Val Val Asp Lys Pro Leu Leu Gln Gly Gly Ile
65                  70                  75                  80

Val Ala Val Tyr Tyr Leu Pro Gly Thr Leu Ala Gly Cys Leu Leu Gly
                85                  90                  95

Gly Trp Met Gly Asp Arg Tyr Gly Arg Ile Thr Thr Ile Gly Leu Ala
                100                 105                 110

Cys Ile Trp Cys Ile Phe Ala Ala Ala Leu Gln Ser Ala Ala Gln Asn
            115                 120                 125

Ala Ser Trp Met Phe Cys Ala Arg Val Leu Asn Gly Ile Gly Thr Gly
130                 135                 140

Ile Leu Asn Ala Ile Thr Pro Val Trp Ala Thr Glu Thr Ala Ser His
145                 150                 155                 160

Thr Ser Arg Gly Gln Phe Val Ala Phe Glu Phe Thr Leu Asn Ile Phe
                165                 170                 175

Gly Val Val Ala Tyr Trp Leu Glu Phe Gly Thr Ser Lys Tyr His
            180                 185                 190

Asp Pro Glu Ser Ser Phe Ile Trp Arg Phe Pro Val Ala Phe Gln Ile
            195                 200                 205

Leu Pro Leu Ile Val Leu Leu Ala Val Ile Trp Phe Met Pro Glu Ser
210                 215                 220

Pro Arg Trp Leu Val Lys Val Gly Arg Glu Glu Ala Arg Phe Ile
225                 230                 235                 240

Leu Gly Arg Leu Arg Gly Asn Glu Gly Glu Glu Gly Glu Ala Ala Glu
            245                 250                 255

Ala Glu Leu Gln Asp Ile Ile Ser Ile Lys Asn Leu Glu Asn Asp Thr
            260                 265                 270

Ser Glu Gln Gln Ser Tyr Phe His Met Phe Phe Gly Ile Gly Ser Gly
            275                 280                 285

Lys Leu His Thr Gly Arg Arg Val Gln Leu Val Ile Trp Leu Gln Ile

```
                290                 295                 300
Leu Gln Glu Trp Ile Gly Ile Ala Gly Ile Thr Ile Tyr Gly Pro Gln
305                 310                 315                 320

Ile Phe Thr Ile Ala Gly Ile Gly Ala Ser Asp Arg Leu Trp Val Ser
                325                 330                 335

Gly Val Asn Asn Ile Thr Tyr Met Phe Ala Thr Leu Ile Cys Val Phe
                340                 345                 350

Thr Leu Asp Arg Ile Gly Arg Arg Trp Thr Leu Tyr Trp Gly Ala Val
                355                 360                 365

Gly Gln Gly Ile Cys Met Phe Ala Gly Gly Leu Ala Arg Ala Thr
370                 375                 380

Ile Asn Ala Ser Asp Ser Asn Arg Gly Gln Ile Gly Gly Ala Ala Thr
385                 390                 395                 400

Phe Phe Val Phe Leu Tyr Thr Ala Ile Phe Gly Ala Thr Trp Leu Thr
                405                 410                 415

Val Pro Trp Leu Tyr Pro Ala Glu Ile Phe Pro Leu Gln Val Arg Ala
                420                 425                 430

Lys Gly Asn Ala Trp Gly Val Val Gly Trp Ser Ile Gly Asn Gly Trp
                435                 440                 445

Cys Val Leu Leu Pro Thr Ile Phe Asp Lys Leu Lys Glu Lys Thr
450                 455                 460

Leu Tyr Ile Phe Gly Ala Val Asn Val Val Ser Ile Val Ala Val Trp
465                 470                 475                 480

Ala Leu Tyr Pro Glu Ser Asn Gln Arg Thr Leu Glu Glu Met Asp Leu
                485                 490                 495

Val Phe Ala Ser Asp Ser Ile Trp Thr Trp Asp Ala Glu Arg Asn Phe
                500                 505                 510

Ala Lys Leu Lys Ala Glu Asn Pro Asp Leu Ile Lys Ser His Lys Asp
                515                 520                 525

Thr Arg Gly Ala Asn Asp Leu Glu Arg Gly Ile Phe Ala Ser Arg Arg
                530                 535                 540

Ala Ser Lys Ala Ser Ala Thr Pro Pro Ser Val Asp Lys Glu Thr Thr
545                 550                 555                 560

Val Glu Asn Val Glu Asn Ser Ser Arg Pro His Pro
                565                 570

<210> SEQ ID NO 35
<211> LENGTH: 524
<212> TYPE: PRT
<213> ORGANISM: Diplodia corticola

<400> SEQUENCE: 35

Met Gly Ala Lys Gly Leu Phe Gly Cys Thr Gly His Ala Ile Glu Arg
1               5                   10                  15

Leu Gln Leu Ala Leu Ile Val Ala Pro Ser Phe Ile Leu Phe Gly Tyr
                20                  25                  30

Asn Gln Ala Gly Leu Gly Gly Leu Leu Thr Glu Ala Asp Trp Val Lys
                35                  40                  45

Thr Phe Pro Glu Ile Asp Thr Val Asn Thr Glu Gly Ala Glu Lys Ser
                50                  55                  60

His Asn Ser Thr Ile Gln Gly Leu Val Val Ala Thr Phe Val Ile Gly
65                  70                  75                  80

Ala Leu Ile Gly Ser Leu Ser Cys Ser Tyr Thr Gly Asp Lys Tyr Gly
                85                  90                  95
```

-continued

```
Arg Arg Ala Val Val Met Ala Gly Ala Ile Cys Thr Leu Ile Gly Glu
            100                 105                 110

Val Leu Glu Cys Ser Ser Phe Gly Leu Pro Gln Phe Ile Val Gly Arg
        115                 120                 125

Ile Ile Val Gly Leu Gly Ile Gly Gln Leu Ser Ala Thr Val Pro Val
    130                 135                 140

Trp Gln Ser Glu Thr Ser Gly Ala Lys Asn Arg Gly Gln His Val Val
145                 150                 155                 160

Leu Asp Gly Leu Phe Ile Cys Val Gly Tyr Val Leu Glu Ser Trp Ile
                165                 170                 175

Asp Leu Gly Phe Phe Glu Leu Pro Glu Gly Gln Val Thr Trp Arg Pro
            180                 185                 190

Pro Ile Ala Ile Ala Ile Val Phe Ser Leu Ile Leu Ile Gly Ser Val
        195                 200                 205

Tyr Leu Phe Pro Glu Ser Pro Arg Trp Leu Val Arg Lys Ala Arg Asn
    210                 215                 220

Asp Glu Ala Arg Ser Ala Ile Ala Leu Phe Arg Gly His Glu Glu Asp
225                 230                 235                 240

Ala Ile Glu Val Gln Ala Glu Leu Ala Gly Ile Glu Leu Ser Leu Glu
                245                 250                 255

Glu Thr Ser Lys Ser Gly Ala Lys Leu Lys Asp Met Leu Lys Met Gly
            260                 265                 270

Glu Asp Lys Leu Leu Tyr Arg Phe Gly Leu Cys Ile Leu Leu Gln Phe
        275                 280                 285

Tyr Gln Gln Met Ser Gly Ser Asn Leu Ile Ser Val Tyr Thr Ser Ile
    290                 295                 300

Leu Phe Gln Gln Asn Leu Gly Leu Ser Pro Glu Leu Ser Arg Val Leu
305                 310                 315                 320

Ser Gly Gly Ala Leu Thr Trp Lys Phe Leu Ser Ser Phe Val Ala Phe
                325                 330                 335

Phe Thr Ile Asp Arg Phe Gly Arg Arg Ala Val Phe Met Phe Ser Gly
            340                 345                 350

Ala Gly Met Ser Leu Cys Met Ile Ala Leu Ala Ile Thr Thr Ser Met
        355                 360                 365

Thr Asp Ser His Gly Ala Gln Val Ala Gly Cys Phe Ile Tyr Met
    370                 375                 380

Phe Asn Phe Phe Val Pro Ile Gly Phe Leu Gly Ala Asn Phe Leu Tyr
385                 390                 395                 400

Cys Thr Glu Val Ala Pro Leu Arg Leu Arg Val Ala Met Ser Ser Ile
                405                 410                 415

Ser Thr Ala Asn His Trp Leu Trp Asn Phe Val Ile Met Val Thr
            420                 425                 430

Pro Val Ala Leu Ala Asn Ile Ala Trp Arg Tyr Tyr Ile Val Tyr Ala
        435                 440                 445

Ala Val Ala Phe Cys Ile Pro Leu Ser Val Tyr Phe Tyr Pro Glu
    450                 455                 460

Thr Met Gly Arg Asn Leu Glu Glu Leu Asp Met Met Phe Arg Glu Ser
465                 470                 475                 480

Pro Ser Val Met Gly Thr Val Asn Phe Ala Lys Thr Arg Pro Ile Ala
                485                 490                 495

Met Pro Gln Glu Phe Ala Val Asp His Thr Lys Gly Gly Ala Glu His
            500                 505                 510

Glu Ser Asp Leu Glu Ala Lys Glu Lys Asp Leu Val
```

515    520

<210> SEQ ID NO 36
<211> LENGTH: 558
<212> TYPE: PRT
<213> ORGANISM: Eremothecium gossypii

<400> SEQUENCE: 36

Met Ile Lys Glu Ser Phe Ser Arg Thr Ala Thr Gly Gly Phe Ser Gly
1               5                   10                  15

Arg Ala Leu Arg Leu Ala Val Thr Ile Thr Ala Val Thr Gly Phe Ser
            20                  25                  30

Leu Phe Gly Tyr Asp Gln Gly Leu Leu Ser Gly Leu Ile Asn Gly Glu
        35                  40                  45

Gln Phe Asn His Glu Phe Pro Ala Thr Leu Glu Gln Gly Asp Asn Asp
    50                  55                  60

Arg His Ala Thr Val Val Gln Gly Ala Val Thr Ser Cys Tyr Glu Leu
65                  70                  75                  80

Gly Cys Phe Phe Gly Ser Leu Tyr Val Met Val Asp Gly Glu Arg Arg
                85                  90                  95

Gly Arg Lys Pro Leu Ile Ile Met Gly Ser Leu Leu Thr Ile Leu Gly
            100                 105                 110

Thr Val Val Ser Val Ala Ala Phe Arg Glu His Trp Gly Leu Gly Gln
        115                 120                 125

Phe Val Ile Gly Arg Val Val Thr Gly Leu Gly Thr Gly Leu Asn Thr
    130                 135                 140

Ser Thr Ile Pro Val Trp Gln Ser Glu Met Ser Lys Pro Lys Asn Arg
145                 150                 155                 160

Gly Leu Leu Val Asn Leu Glu Gly Ser Val Ile Ala Val Gly Thr Met
                165                 170                 175

Ile Ala Tyr Trp Ile Asp Phe Gly Leu Ser Tyr Val Asp Ser Ser Val
            180                 185                 190

Gln Trp Arg Phe Pro Val Ala Met Gln Ile Val Phe Ala Val Leu Leu
        195                 200                 205

Leu Val Gly Ile Val Gln Leu Pro Glu Ser Pro Arg Trp Leu Met Ala
    210                 215                 220

His Gly Arg Thr Ala Glu Ser Lys Tyr Val Leu Gly Lys Leu Asp Asn
225                 230                 235                 240

Leu Asp Pro Ser Asp Ser Val Leu Ala Glu Ala Ala Ile Glu
                245                 250                 255

Asp Ala Val Asn Arg Phe Lys His Glu Lys Arg Ser Leu Lys Asp Ala
            260                 265                 270

Leu Thr Gly Gly Arg Gly Gln Asn Leu Gln Arg Thr Leu Val Ala Cys
        275                 280                 285

Ser Thr Gln Phe Phe Gln Gln Phe Thr Gly Cys Asn Ala Ala Ile Tyr
    290                 295                 300

Tyr Ser Thr Val Leu Phe His Lys Thr Ile Asn Leu Glu Tyr Arg Leu
305                 310                 315                 320

Ser Leu Ile Leu Gly Gly Val Phe Ser Thr Val Tyr Thr Leu Ala Thr
                325                 330                 335

Ile Pro Ser Phe Phe Leu Ile Glu Thr Val Gly Arg Arg Lys Leu Phe
            340                 345                 350

Leu Ile Gly Ala Leu Gly Gln Gly Phe Ser Phe Thr Ile Thr Phe Ala
        355                 360                 365

Cys Leu Ile Asn Asp Thr Lys Asn Asn Ala Lys Gly Ala Ala Val Gly
    370                 375                 380

Leu Phe Leu Phe Ile Ile Phe Phe Gly Met Thr Ile Leu Ser Leu Pro
385                 390                 395                 400

Trp Ile Tyr Pro Pro Glu Ile Ser Ser Met Lys Val Arg Ser Ile Thr
                405                 410                 415

Asn Ala Met Ser Thr Cys Thr Asn Trp Leu Cys Asn Phe Ala Val Val
            420                 425                 430

Met Phe Thr Pro Ile Phe Ile His Glu Ala Gly Trp Gly Cys Tyr Leu
        435                 440                 445

Phe Phe Ala Val Met Asn Phe Leu Tyr Val Pro Ile Ile Phe Phe Phe
450                 455                 460

Tyr Pro Glu Thr Ala Gly Arg Ser Leu Glu Glu Ile Asp Ile Tyr
465                 470                 475                 480

Ala Lys Ser Phe Val Asp Gly Thr Gln Ala Trp Arg Val Ala Ala Asn
                485                 490                 495

Leu Pro Lys Leu Ser Leu Lys Glu Val Glu Tyr Gly Ile Gln Leu
            500                 505                 510

Gly Leu Tyr Asn Asn Glu His Asp Phe Lys Asp Glu Met Lys Val Ile
        515                 520                 525

Thr Glu Ala Glu Gly Gln Val Pro Arg Ser Ser Ile Ser Asp Ser Asn
530                 535                 540

Met Glu Ser Ser Ser Thr Gly Asn Gly Ile Met Lys Lys Pro
545                 550                 555

<210> SEQ ID NO 37
<211> LENGTH: 557
<212> TYPE: PRT
<213> ORGANISM: Eremothecium sinecaudum

<400> SEQUENCE: 37

Met Glu Ser Thr Val Arg Lys Trp Phe Ser Arg Thr Ala Thr Ala Ser
1               5                   10                  15

Leu Ser Gly Arg Ala Leu Arg Leu Ala Ile Thr Ile Thr Ala Val Thr
            20                  25                  30

Gly Phe Ser Leu Phe Gly Tyr Asp Gln Gly Leu Leu Ser Gly Leu Ile
        35                  40                  45

Asn Gly Asp Lys Phe Asn His Glu Phe Pro Ala Thr Leu Glu Lys His
50                  55                  60

Asp Asn Asp Thr His Ala Thr Val Val Gln Gly Ala Val Thr Ser Cys
65                  70                  75                  80

Tyr Glu Leu Gly Cys Phe Phe Gly Ser Leu Phe Val Val Met Lys Gly
                85                  90                  95

Glu Lys Met Gly Arg Lys Pro Leu Ile Ile Cys Gly Ala Leu Leu Thr
            100                 105                 110

Ile Val Gly Thr Ile Ile Ser Thr Leu Ala Phe Arg Glu His Trp Gly
        115                 120                 125

Leu Gly Gln Phe Val Val Gly Arg Val Ile Thr Gly Leu Gly Thr Gly
130                 135                 140

Phe Asn Thr Ser Thr Ile Pro Val Trp Gln Ser Glu Met Ser Lys Pro
145                 150                 155                 160

Glu Asn Arg Gly Leu Leu Val Asn Leu Glu Gly Ser Val Ile Ala Val
                165                 170                 175

Gly Thr Met Ile Ala Tyr Trp Ile Asp Phe Gly Leu Ser Tyr Val Asp
            180                 185                 190

Ser Ser Ala Gln Trp Arg Phe Pro Val Ala Met Gln Ile Val Phe Ala
        195                 200                 205

Val Phe Leu Leu Ile Gly Cys Thr Gln Leu Pro Glu Ser Pro Arg Trp
210                 215                 220

Leu Met Ala His Gly Arg Gly Glu Ala Arg Tyr Ile Leu Ser Gln
225                 230                 235                 240

Leu Asp Gly Val Pro Ile Asp Pro Thr Val Leu Ala Glu Ala Ala
                245                 250                 255

Ala Ile Glu Glu Val Asp Lys Phe Lys Asn Gln Arg Trp Ser Leu
                260                 265                 270

Lys Asp Ala Phe Thr Gly Gly Arg Gly Gln Asn Leu Gln Arg Thr Leu
                275                 280                 285

Val Ala Cys Ser Thr Gln Phe Phe Gln Gln Phe Thr Gly Cys Asn Ala
                290                 295                 300

Ala Ile Tyr Tyr Ser Thr Val Leu Phe His Lys Thr Ile Lys Leu Glu
305                 310                 315                 320

Tyr Arg Met Ser Leu Ile Leu Gly Gly Val Phe Ala Thr Val Tyr Thr
                325                 330                 335

Leu Ser Thr Ile Pro Ser His Phe Leu Ile Glu Thr Val Gly Arg Arg
                340                 345                 350

Lys Leu Phe Leu Val Gly Ala Leu Gly Gln Gly Val Ala Phe Thr Ile
                355                 360                 365

Thr Phe Ala Cys Leu Ile His Asp Thr Lys Gln Asn Ala Lys Gly Ala
370                 375                 380

Ala Phe Gly Leu Phe Leu Phe Ile Val Phe Phe Gly Met Thr Ile Leu
385                 390                 395                 400

Ser Leu Pro Trp Ile Tyr Pro Pro Glu Ile Ser Ser Leu Arg Val Arg
                405                 410                 415

Ser Leu Thr Asn Ser Leu Ser Thr Cys Thr Asn Trp Leu Ser Asn Phe
                420                 425                 430

Ala Val Val Met Phe Thr Pro Ile Phe Ile Gln Lys Ser Ser Trp Gly
                435                 440                 445

Cys Tyr Met Phe Phe Ala Ile Val Asn Phe Ser Tyr Leu Pro Ile Ile
                450                 455                 460

Phe Phe Phe Tyr Pro Glu Thr Ser Gly Arg Ser Leu Glu Glu Ile Asp
465                 470                 475                 480

Ile Ile Tyr Ala Lys Ser Asn Lys Asp Gly Ile Ala Ser Trp Arg Val
                485                 490                 495

Ala Ala His Leu Pro Lys Leu Ser Leu Lys Glu Ile Glu Gln Tyr Ala
                500                 505                 510

Ile Glu Tyr Asp Leu Tyr Asp Gly Pro Val Ser Glu Ala Ser Thr Glu
                515                 520                 525

Ser Asp Asn Glu Arg Asn Gln Ser Glu Leu Asp Leu Lys Gln Asp Ser
530                 535                 540

Pro Gln Asn Leu Ala Asp Lys Ser Lys Asp Gly Ser Leu
545                 550                 555

<210> SEQ ID NO 38
<211> LENGTH: 525
<212> TYPE: PRT
<213> ORGANISM: Gaeumannomyces tritici

<400> SEQUENCE: 38

Met Thr Val Ala Thr Thr Gly Val Ser Lys Ser Tyr Phe Gly Gly Leu

```
          1               5                  10                 15
        Thr Gly His Arg Leu Ala Val Leu Gln Thr Ala Leu Ile Thr Ala Pro
                        20                  25                 30
        Ser Phe Ile Leu Phe Gly Tyr Asn Gln Ala Gly Leu Gly Gly Leu Ile
                        35                  40                 45
        Gly Leu Lys Asp Trp Glu Arg Thr Phe Pro Glu Ile Asp Thr Thr His
                50                          55                         60
        His Lys Glu Ser Ser Val Ser Thr Leu Lys Gly Phe Val Val Ala Thr
         65                     70                     75                 80
        Phe Val Ile Gly Ala Leu Phe Gly Ser Leu Leu Cys Ser Tyr Thr Gly
                                85                  90                 95
        Asp Lys Phe Gly Arg Arg His Val Ile Phe Ala Gly Leu Cys Thr
                            100                 105                110
        Leu Val Gly Glu Val Leu Glu Cys Ala Ala Phe Gly Leu Ala Gln Leu
                            115                 120                125
        Ile Val Gly Arg Val Ile Val Gly Phe Gly Ile Gly Gln Leu Ser Ser
                        130                 135                 140
        Ile Val Pro Val Trp Gln Ser Glu Thr Ser Gly Ala Lys Asn Arg Gly
        145                     150                     155                160
        Arg His Val Val Leu Asp Gly Val Phe Ile Cys Leu Gly Phe Val Leu
                            165                 170                175
        Glu Ser Trp Ile Asn Leu Gly Phe Phe Gln Phe Gly Asp Ser Pro Ile
                        180                 185                 190
        Thr Trp Arg Pro Pro Ile Ala Ile Ala Ile Leu Phe Ser Leu Ile Leu
                        195                 200                 205
        Ser Gly Ser Val Tyr Leu Phe Pro Glu Ser Pro Arg Trp Leu Met Ala
                    210                 215                 220
        Lys Asn Arg Lys Ser Asp Ala Val Ala Val Leu Ser Val Leu Arg Gly
        225                     230                     235                240
        Leu Pro Gln Asp Ser Ile Glu Val Gln Ala Glu Ile Ser Gly Ile Glu
                            245                 250                 255
        Leu Ser Leu Glu Asp Val Thr Gly Lys Asp Ala Lys Leu Ser Glu Met
                        260                 265                 270
        Leu Ser Pro Lys Asn Glu Asp Lys Leu Leu Tyr Arg Phe Gly Leu Cys
                    275                 280                 285
        Ile Leu Leu Gln Phe Gln Gln Met Ser Gly Thr Asn Leu Val Ser
                290                     295                 300
        Val Tyr Ala Thr Ile Leu Phe Gln Asp Asn Leu Gly Met Ser Pro Gln
        305                     310                     315                320
        Leu Ala Arg Val Leu Thr Gly Gly Ala Leu Thr Trp Lys Phe Leu Ser
                            325                 330                 335
        Ser Phe Leu Ala Phe Phe Cys Ile Asp Arg Phe Gly Arg Val Cys
                        340                 345                 350
        Phe Met Ile Ser Gly Gly Met Ala Ala Cys Met Val Ala Leu Ala
                        355                 360                 365
        Val Ala Thr Ser Phe Pro Glu Asp Asn Arg Gly Ala Gln Ile Ser Ala
                370                     375                 380
        Ala Cys Phe Leu Tyr Leu Phe Asn Thr Phe Val Pro Ile Gly Phe Leu
        385                     390                     395                400
        Gly Ala Asn Phe Leu Tyr Cys Thr Glu Val Ala Pro Val Arg Leu Arg
                            405                 410                 415
        Met Val Met Thr Ser Ile Ser Thr Ala Asn His Trp Leu Trp Asn Phe
                            420                 425                 430
```

```
Val Ile Val Met Ile Thr Pro Val Ala Ile Ser Thr Ile Gly Ser Arg
            435                 440                 445

Tyr Tyr Ile Met Tyr Ala Val Ile Ala Ala Cys Ile Pro Leu Ser Val
450                 455                 460

Tyr Phe Leu Phe Pro Glu Thr Met Gly Arg Asn Leu Glu Glu Ile Asn
465                 470                 475                 480

Leu Met Phe Arg Asp Ser Pro Ser Val Trp Ala Thr Val Lys Tyr Ala
            485                 490                 495

Arg Asn Arg Pro Ile Gly Met Pro Gln Glu Phe Asp Arg Lys Gln Lys
            500                 505                 510

Thr Asp His Ile Glu Gly Asn Gly Asp Glu Ser Ser Lys
            515                 520                 525

<210> SEQ ID NO 39
<211> LENGTH: 550
<212> TYPE: PRT
<213> ORGANISM: Isaria fumosorosea

<400> SEQUENCE: 39

Met Thr Arg Lys Thr Tyr Met Gly Met Ser Gly Ser Asn Leu Asn Trp
1               5                   10                  15

Ala Ile Ser Thr Ile Ala Gly Cys Asp Phe Leu Leu Phe Gly Tyr Asp
            20                  25                  30

Gln Gly Val Met Gly Gly Ile Leu Thr Leu Pro Ile Phe Leu Asp Gln
            35                  40                  45

Phe Pro Gln Ile Asn Asp Leu Ala Asp Ala Arg Asn Met Ala Gln Leu
50                  55                  60

Pro Gly Thr Arg Ser Gln Arg Ser Leu Asn Gln Gly Ile Ala Ile Ala
65                  70                  75                  80

Ser Tyr Asn Leu Gly Cys Phe Leu Gly Ala Val Ile Thr Ile Phe Ile
                85                  90                  95

Gly Asn Pro Leu Gly Arg Arg Arg Met Ile Phe Leu Gly Thr Ala Ile
            100                 105                 110

Met Thr Val Gly Ala Ala Leu Gln Ala Ser Ala Phe Thr Ile Glu His
            115                 120                 125

Phe Ile Ile Gly Arg Ile Ile Thr Gly Ile Gly Asn Gly Gly Asn Thr
130                 135                 140

Ser Thr Val Pro Met Trp Gln Ser Glu Thr Cys Ser Ser His Lys Arg
145                 150                 155                 160

Gly Lys Leu Val Met Ile Glu Gly Ala Leu Ile Thr Phe Gly Ile Met
                165                 170                 175

Val Ser Tyr Trp Ile Asp Leu Gly Leu Ser Phe Thr Asp Ser Ser Val
            180                 185                 190

Ser Trp Arg Phe Pro Leu Ala Phe Gln Leu Val Phe Cys Ile Phe Ile
            195                 200                 205

Leu Ala Phe Val Leu Gly Leu Pro Glu Ser Pro Arg Trp Leu Ile Leu
            210                 215                 220

Lys Gly Gln Glu Asp Glu Ala Arg Ala Val Ile Ala Ala Ile Ala Asp
225                 230                 235                 240

Lys Glu Ile Glu Asp Pro Phe Val Ala Asn Glu Phe Arg Ala Ile Lys
                245                 250                 255

Asp Thr Ala Val Lys Ser Ala Gly Gly Tyr Gly Glu Val Phe His Met
            260                 265                 270

Asp Glu Asn Arg Thr Leu His Arg Thr Ile Leu Gly Tyr Val Asn Gln
```

```
                    275                 280                 285
Met Phe Gln Gln Ile Ser Gly Ile Asn Leu Ile Thr Tyr Tyr Ala Ala
    290                 295                 300

Lys Ile Tyr Ala Asp Leu Gly Met Ser Pro Phe Leu Ala Arg Leu Leu
305                 310                 315                 320

Ala Ala Leu Asn Gly Thr Glu Tyr Phe Leu Ala Ser Trp Pro Ala Val
                325                 330                 335

Phe Leu Val Glu Arg Val Gly Arg Arg Lys Leu Met Leu Phe Gly Ala
            340                 345                 350

Val Gly Gln Ala Cys Thr Met Ala Ile Leu Ala Gly Val Asn Ser His
        355                 360                 365

Lys Thr Asp Ala Ser Arg Ile Ala Gly Val Val Phe Leu Phe Val Phe
    370                 375                 380

Asn Ser Phe Phe Ala Val Gly Trp Leu Gly Met Thr Trp Leu Tyr Pro
385                 390                 395                 400

Ala Glu Ile Thr Pro Leu Arg Thr Arg Ala Pro Ala Asn Ala Leu Ser
                405                 410                 415

Thr Ser Ala Asn Trp Ile Phe Asn Phe Met Val Val Met Ile Thr Pro
            420                 425                 430

Val Ser Phe Thr Asn Ile Asp Tyr His Thr Tyr Thr Ile Phe Ala Val
        435                 440                 445

Ile Asn Ala Ile Met Val Pro Ser Val Tyr Phe Phe Pro Glu Thr
    450                 455                 460

Ala Tyr Arg Ser Leu Glu Glu Met Asp Ser Ile Phe Arg Lys Val Thr
465                 470                 475                 480

Gly Leu Arg Gly Ala Leu Asp Val Val Lys Val Ala Arg Glu Met Pro
                485                 490                 495

His Arg Tyr Gly Lys Asn Gly Glu Leu Leu Ile Ala Phe Asp Glu Ser
            500                 505                 510

Thr Glu Lys Val Gln Ala Glu His Ala Ser Gly Ser Val Ser Asp Gly
        515                 520                 525

Ser Gly Asn Asn Asn Asn Thr Met Phe Thr Lys Thr Asp Glu Glu Thr
    530                 535                 540

Ser Arg Pro Arg Glu Lys
545                 550

<210> SEQ ID NO 40
<211> LENGTH: 498
<212> TYPE: PRT
<213> ORGANISM: Metarhizium majus

<400> SEQUENCE: 40

Met Ala Val Pro Glu Leu Glu Gly Arg Ala Leu Leu Leu Thr Val Thr
1               5                   10                  15

Thr Leu Thr Ser Leu Gly Phe Met Leu Ile Gly Tyr Asp Asn Gly Leu
            20                  25                  30

Met Gly Gly Leu Val Asn Ser Pro Ala Phe Gly Ser Ser Phe Asn Tyr
        35                  40                  45

Pro Gly Ser Lys Met Ile Gly Val Ile Val Ala Ile Phe Glu Val Gly
    50                  55                  60

Cys Phe Leu Gly Ser Ile Leu Ser Ala Ile Phe Gly Glu Arg Leu Gly
65              70                  75                  80

Arg Arg Ser Thr Ile Gly His Gly Cys Trp Ile Met Ile Val Gly Ala
                85                  90                  95
```

```
Val Leu Gln Ala Ser Ser Tyr Gly Arg Ala Gln Leu Ile Val Gly Arg
                100                 105                 110

Ile Val Ser Gly Leu Gly Leu Gly Ile Ile Asn Ser Thr Val Pro Val
                115                 120                 125

Leu Gln Ala Glu Phe Ser Pro Lys Ala Thr Arg Gly Val Tyr Val Cys
            130                 135                 140

Ala Gln Leu Ser Thr Leu Asn Phe Gly Ile Phe Leu Val Tyr Trp Ile
145                 150                 155                 160

Asp Tyr Ala Phe Ser Ser His Thr Ser Ser Tyr Ala Trp Arg Val Pro
                165                 170                 175

Val Ile Leu Gln Cys Val Cys Ile Leu Pro Met Met Gly Ile Leu Met
                180                 185                 190

Leu Ile Pro Glu Thr Pro Arg Trp Leu Ala Ser His Asp Arg Pro Asp
            195                 200                 205

Asp Cys Leu Arg Val Leu Ala Arg Met Lys Ser Ser Ile Asn Asp
            210                 215                 220

Pro Glu Val Gln Arg Gln His His Asn Ile Leu Gln Val Ala Phe
225                 230                 235                 240

Glu Ala Ser Ile Gly Thr Gly Ser Trp Lys Asp Leu Leu Ser Asn Asp
                245                 250                 255

Arg Val Lys Ser Gln Thr Arg Leu Leu Ile Ala Cys Ser Ile Gln Ala
            260                 265                 270

Phe Gln Gln Leu Gly Gly Ile Asn Ala Val Ile Tyr Tyr Thr Asn Thr
                275                 280                 285

Leu Phe Ser Lys Ser Ile Gly Phe Asp Glu Arg Met Ser Ala Leu Met
290                 295                 300

Ser Gly Phe Leu Gln Thr Trp Phe Phe Val Ala Ser Phe Ile Pro Trp
305                 310                 315                 320

Phe Leu Ile Asp Arg Ile Gly Arg Lys Pro Leu Phe Val Ser Met Ile
                325                 330                 335

Ser Leu Met Ala Ala Ala Met Ala Val Gln Ala Gly Leu Ile Tyr Gln
                340                 345                 350

Val Gln Asn Glu Thr Asn Ile Ser His Ser Ala Gly Ile Gly Ala Ala
                355                 360                 365

Val Met Leu Phe Val Phe Gln Gly Ala Phe Thr Ile Gly Phe Gln Ala
                370                 375                 380

Thr Val Trp Val Tyr Pro Ser Glu Ile Leu Pro Leu Arg Leu Arg Gln
385                 390                 395                 400

Lys Gly Ser Ser Ile Ser Thr Ala Ala Asn Trp Ile Phe Asn Tyr Met
                405                 410                 415

Val Val Gln Ile Thr Pro Ile Ala Ile Asp Asn Ile Gly Trp Lys Thr
                420                 425                 430

Tyr Ile Ile Phe Ala Ile Leu Asn Ala Thr Trp Val Pro Ile Ile Phe
                435                 440                 445

Phe Phe Phe Pro Glu Thr Lys Gly Leu Glu Leu Glu Asp Val Asp Arg
450                 455                 460

Leu Phe Ala Gly Asp Asp Val Ile Glu Ser Val Gly Glu Lys Ser Met
465                 470                 475                 480

Ala Leu Ala Thr Val Glu His Val Gly Arg Thr Asp Gly Thr Asn Glu
                485                 490                 495

Arg Val
```

<210> SEQ ID NO 41

```
<211> LENGTH: 498
<212> TYPE: PRT
<213> ORGANISM: Metarhizium robertsii

<400> SEQUENCE: 41
```

| | | | | | | | | | | | | | | |
|---|---|---|---|---|---|---|---|---|---|---|---|---|---|---|
| Met | Ala | Val | Pro | Glu | Leu | Glu | Gly | Arg | Ala | Leu | Leu | Leu | Thr | Val | Thr |
| 1 | | | | 5 | | | | | 10 | | | | | 15 | |
| Ala | Leu | Thr | Ser | Leu | Gly | Phe | Met | Leu | Ile | Gly | Tyr | Asp | Asn | Gly | Leu |
| | | | 20 | | | | | 25 | | | | | 30 | | |
| Met | Gly | Gly | Leu | Val | Asn | Ser | Pro | Ala | Phe | Gly | Ser | Ser | Phe | Asp | Tyr |
| | | 35 | | | | | 40 | | | | | 45 | | | |
| Pro | Asp | Ser | Lys | Met | Ile | Gly | Val | Ile | Val | Ala | Ile | Phe | Glu | Val | Gly |
| | 50 | | | | | 55 | | | | | 60 | | | | |
| Cys | Phe | Leu | Gly | Ser | Ile | Leu | Ser | Ala | Ile | Phe | Gly | Glu | Arg | Leu | Gly |
| 65 | | | | | 70 | | | | | 75 | | | | | 80 |
| Arg | Arg | Ser | Thr | Ile | Gly | His | Gly | Cys | Trp | Ile | Met | Ile | Val | Gly | Ala |
| | | | | 85 | | | | | 90 | | | | | 95 | |
| Val | Leu | Gln | Ala | Ser | Ser | Tyr | Gly | Arg | Ala | Gln | Leu | Ile | Val | Gly | Arg |
| | | | 100 | | | | | 105 | | | | | 110 | | |
| Ile | Val | Ser | Gly | Leu | Gly | Leu | Gly | Ile | Ile | Asn | Ser | Thr | Val | Pro | Val |
| | | | | 115 | | | | | 120 | | | | | 125 | |
| Leu | Gln | Ala | Glu | Phe | Ser | Pro | Lys | Ala | Thr | Arg | Gly | Val | Tyr | Val | Cys |
| | 130 | | | | | 135 | | | | | 140 | | | | |
| Ala | Gln | Leu | Ser | Thr | Leu | Asn | Phe | Gly | Ile | Phe | Leu | Val | Tyr | Trp | Ile |
| 145 | | | | | 150 | | | | | 155 | | | | | 160 |
| Asp | Tyr | Ala | Phe | Ser | Ser | His | Thr | Ser | Ser | Tyr | Ala | Trp | Arg | Val | Pro |
| | | | | 165 | | | | | 170 | | | | | 175 | |
| Val | Ile | Leu | Gln | Cys | Val | Cys | Ile | Leu | Pro | Met | Met | Gly | Ile | Leu | Met |
| | | | 180 | | | | | 185 | | | | | 190 | | |
| Leu | Ile | Pro | Glu | Thr | Pro | Arg | Trp | Leu | Ala | Ser | His | Asp | Arg | Pro | Asp |
| | | | | 195 | | | | | 200 | | | | | 205 | |
| Asp | Cys | Leu | Arg | Val | Leu | Ala | Arg | Met | Lys | Ser | Ser | Ile | Asn | Asp |
| | 210 | | | | | 215 | | | | | 220 | | | | |
| Pro | Glu | Val | Gln | Arg | Gln | His | His | Asn | Ile | Leu | Gln | Val | Val | Ala | Phe |
| 225 | | | | | 230 | | | | | 235 | | | | | 240 |
| Glu | Ala | Ser | Ile | Gly | Thr | Gly | Ser | Trp | Lys | Asp | Leu | Leu | Ser | Asn | Asp |
| | | | | 245 | | | | | 250 | | | | | 255 | |
| Arg | Val | Lys | Ser | Gln | Thr | Arg | Leu | Leu | Ile | Ala | Cys | Ser | Ile | Gln | Ala |
| | | | 260 | | | | | 265 | | | | | 270 | | |
| Phe | Gln | Gln | Leu | Gly | Gly | Ile | Asn | Ala | Val | Ile | Tyr | Tyr | Thr | Asn | Thr |
| | | | | 275 | | | | | 280 | | | | | 285 | |
| Leu | Phe | Ser | Lys | Ser | Ile | Gly | Phe | Asp | Glu | Arg | Met | Ser | Ala | Leu | Met |
| | 290 | | | | | 295 | | | | | 300 | | | | |
| Ser | Gly | Phe | Leu | Gln | Thr | Trp | Phe | Phe | Val | Ala | Ser | Phe | Ile | Pro | Trp |
| 305 | | | | | 310 | | | | | 315 | | | | | 320 |
| Phe | Leu | Ile | Asp | Arg | Ile | Gly | Arg | Lys | Pro | Leu | Phe | Val | Ser | Met | Ile |
| | | | | 325 | | | | | 330 | | | | | 335 | |
| Ser | Leu | Met | Ala | Ala | Ala | Met | Ala | Val | Gln | Ala | Gly | Leu | Ile | Tyr | Gln |
| | | | 340 | | | | | 345 | | | | | 350 | | |
| Val | Gln | Asn | Glu | Thr | Asn | Ile | Ser | His | Ser | Ala | Gly | Ile | Gly | Ala | Ala |
| | | | | 355 | | | | | 360 | | | | | 365 | |
| Val | Met | Leu | Phe | Val | Phe | Gln | Gly | Ala | Phe | Thr | Ile | Gly | Phe | Gln | Ala |
| | 370 | | | | | 375 | | | | | 380 | | | | |
| Thr | Val | Trp | Val | Tyr | Pro | Ser | Glu | Ile | Leu | Pro | Leu | Arg | Leu | Arg | Gln |

```
        385                 390                 395                 400
Lys Gly Ser Ser Ile Ser Thr Ala Ala Asn Trp Ile Phe Asn Tyr Met
                    405                 410                 415

Val Val Gln Ile Thr Pro Ile Ala Ile Glu Asn Ile Gly Trp Lys Thr
                420                 425                 430

Tyr Ile Ile Phe Ala Ile Leu Asn Ala Thr Trp Val Pro Ile Ile Phe
            435                 440                 445

Phe Phe Phe Pro Glu Thr Lys Gly Leu Glu Leu Glu Asp Val Asp Arg
        450                 455                 460

Leu Phe Ala Gly Asp Asp Val Ile Glu Ser Val Gly Glu Lys Ser Met
465                 470                 475                 480

Ala Leu Ala Thr Val Glu His Val Gly Arg Thr Asp Gly Thr Asn Glu
                485                 490                 495

Arg Val

<210> SEQ ID NO 42
<211> LENGTH: 551
<212> TYPE: PRT
<213> ORGANISM: Nannizzia gypsea

<400> SEQUENCE: 42

Met Gly Val Gly Arg Gln Tyr Phe Gly Leu Arg Gly Thr Lys Leu Asn
1               5                   10                  15

Ile Ala Ile Gly Ile Ala Gly Leu Asp Phe Leu Gly Val Met Gly
                20                  25                  30

Gly Leu Leu Thr Leu Pro Ser Phe Glu Lys Val Phe Pro Glu Ile Ala
            35                  40                  45

Thr Ser Lys Glu Ala Val Val Gly Leu Thr Gln Ala Glu Lys Asn His
        50                  55                  60

Arg Ser Thr Ile Gln Gly Ile Ser Val Ala Ser Tyr Asn Leu Gly Cys
65                  70                  75                  80

Phe Val Gly Ala Ile Ala Cys Ile Trp Val Gly Asp Arg Leu Gly Arg
                85                  90                  95

Arg Lys Thr Ile Trp Leu Gly Ala Ala Val Met Val Gly Ala Ala
                    100                 105                 110

Leu Gln Ala Ser Ala Phe Gly Leu Pro His Phe Ile Val Gly Arg Leu
            115                 120                 125

Val Thr Gly Phe Gly Asn Gly Leu Asn Thr Ser Thr Val Pro Thr Trp
        130                 135                 140

Gln Ser Glu Cys Ser Lys Ser His Arg Arg Gly Gln Leu Val Met Val
145                 150                 155                 160

Glu Gly Ala Leu Ile Thr Gly Gly Ile Cys Ile Ser Tyr Trp Leu Asp
                165                 170                 175

Phe Gly Phe Ser Phe Leu Glu Pro Ser Ser Val Thr Trp Arg Phe Pro
            180                 185                 190

Ile Ala Phe Gln Ile Val Phe Ala Leu Ile Ile Met Leu Val Val Met
        195                 200                 205

Gly Leu Pro Glu Ser Pro Arg Trp Leu Val Leu Lys Gly Gln Glu Asp
        210                 215                 220

Glu Ala Met Asn Val Leu Ala Ala Leu Ser Asp Leu Asp Arg Glu Asp
225                 230                 235                 240

Arg Phe Val His Ala Glu Phe Ser Ala Ile Lys Asp Thr Val Ile Glu
                245                 250                 255

Met Gln Lys Gly Gly Phe Arg Asp Leu Phe Thr Met Asp Lys Asp Arg
```

260                 265                 270
His Leu His Arg Val Ile Leu Ala Tyr Val Asn Gln Met Phe Gln Gln
            275                 280                 285

Ile Ser Gly Ile Asn Leu Ile Thr Tyr Tyr Ala Ala Thr Ile Tyr Glu
        290                 295                 300

Gly Ser Ile Gly Leu Ser Pro Phe Leu Ser Arg Val Leu Ala Ala Cys
305                 310                 315                 320

Asn Gly Thr Glu Tyr Phe Ile Ala Ser Trp Ile Ala Val Phe Val Val
                325                 330                 335

Glu Lys Ile Gly Arg Arg Ile Leu Met Leu Phe Gly Ala Val Gly Met
            340                 345                 350

Ser Leu Ser Met Ala Val Leu Ala Ile Ala Thr Ser Phe Lys Gly Gln
        355                 360                 365

Thr Glu Ala Gly Ile Val Ala Ala Val Phe Leu Phe Val Phe Asn Thr
    370                 375                 380

Phe Phe Ala Ile Gly Trp Leu Gly Met Thr Trp Leu Tyr Pro Ala Glu
385                 390                 395                 400

Ile Val Pro Leu Arg Ile Arg Ala Pro Ala Asn Ala Leu Ala Thr Ser
                405                 410                 415

Gly Asn Trp Ile Phe Asn Phe Met Val Val Met Ile Thr Pro Val Ser
            420                 425                 430

Phe Ser Ser Ile Glu Tyr Lys Thr Tyr Ile Ile Phe Ala Val Ile Asn
        435                 440                 445

Ala Phe Ile Val Pro Val Tyr Phe Phe Tyr Pro Glu Thr Ala Tyr
    450                 455                 460

Arg Ser Leu Glu Glu Met Asp Ser Ile Phe Arg Lys Thr Lys Ser Ile
465                 470                 475                 480

Phe Thr Val Val Lys Ile Ala His Glu Thr Pro Arg Arg Tyr Gly Lys
                485                 490                 495

Asn Gly Glu Val Leu Ile Asp Tyr Asp Glu Thr Asp Glu His Arg Ala
            500                 505                 510

Arg Ala Gly Ile Thr Gln Glu Glu Thr Thr Thr Ser Phe Pro Glu Lys
        515                 520                 525

Ser His Ala Asn Pro Asp His Asp Ala Glu Thr Gly Asn Ser Asn Ser
    530                 535                 540

Pro Ser Asn Gln Ser Thr Ala
545                 550

<210> SEQ ID NO 43
<211> LENGTH: 634
<212> TYPE: PRT
<213> ORGANISM: Pachysolen tannophilus

<400> SEQUENCE: 43

Met Asp Ser Asn Ile Asp Asp Thr Ala Ile Pro Pro Ser Gly Tyr Leu
1               5                   10                  15

Val Gly Lys Pro Leu Leu Tyr Phe Thr Ser Val Phe Val Ser Leu Gly
            20                  25                  30

Val Phe Leu Phe Gly Tyr Asp Gln Gly Val Met Ser Gly Ile Ile Thr
        35                  40                  45

Gly Pro Tyr Phe Lys Tyr Tyr Phe Asn Asp Pro Ser Ser Thr Thr Ile
    50                  55                  60

Gly Thr Met Val Ala Ile Leu Glu Ile Gly Ala Leu Ile Ser Ser Leu
65                  70                  75                  80

```
Leu Val Gly Arg Met Gly Asp Ile Ile Gly Arg Arg Thr Ile Arg
                85                  90                  95

Tyr Gly Ala Phe Ile Phe Val Val Gly Gly Ser Ile Gln Thr Phe Ala
            100                 105                 110

Thr Asp Met His His Leu Ile Leu Gly Arg Ile Val Ser Gly Val Ala
            115                 120                 125

Val Gly Leu Leu Ser Ala Thr Val Pro Val Tyr Gln Ser Glu Ile Ser
    130                 135                 140

Gln Pro His Asn Arg Gly Gln Leu Ser Cys Val Gln Phe Thr Gly Asn
145                 150                 155                 160

Ile Phe Gly Tyr Ala Thr Ser Val Trp Thr Asp Tyr Gly Cys Ser Phe
                165                 170                 175

Phe Glu Ser Asn Leu Ser Trp Arg Phe Pro Leu Phe Val Gln Cys Val
            180                 185                 190

Ile Gly Leu Leu Leu Phe Leu Gly Thr Phe Val Ile Val Glu Thr Pro
        195                 200                 205

Arg Trp Leu Leu Asn Asn Asp His Asp Ala Glu Gly Ile Val Val Leu
    210                 215                 220

Ala Asp Leu Tyr Ser Asn Gly Asp Val His Asp Ile Arg Ala Arg Asn
225                 230                 235                 240

Glu Phe Arg Asn Ile Lys Glu Asp Val Leu Met Ser Arg Leu Glu Asp
                245                 250                 255

Thr Gly Thr Ser Tyr Ser Tyr Met Trp Lys Arg Tyr Lys Thr Arg Ile
            260                 265                 270

Leu Ile Ala Met Ser Ser Gln Met Phe Ala Gln Phe Asn Gly Ile Asn
        275                 280                 285

Val Ile Ser Tyr Tyr Ala Pro Leu Val Phe Glu Gln Ala Gly Trp Phe
    290                 295                 300

Gly Arg Asp Ala Ile Leu Met Thr Gly Ile Asn Ser Ile Ile Tyr Phe
305                 310                 315                 320

Leu Ser Ser Ile Pro Pro Trp Tyr Leu Val Asp Arg Trp Gly Arg Lys
                325                 330                 335

Pro Ile Leu Ile Ile Gly Gly Ile Ile Met Ala Ile Ser Leu Phe Ser
            340                 345                 350

Ile Ser Phe Val Leu Phe Ile Asn Val Pro Lys Thr Pro Val Tyr Val
        355                 360                 365

Val Ile Leu Val Ile Ile Tyr Asn Ala Leu Phe Gly Phe Ser Trp Gly
    370                 375                 380

Pro Ile Pro Trp Leu Leu Pro Pro Glu Ile Leu Pro Leu Ser Ile Arg
385                 390                 395                 400

Ser Lys Gly Ala Ser Leu Ser Thr Ala Thr Asn Trp Phe Cys Asn Phe
                405                 410                 415

Leu Val Gly Glu Leu Thr Pro Val Leu Gln Glu Thr Ile Lys Trp Arg
            420                 425                 430

Leu Tyr Leu Ile His Gly Thr Ser Cys Val Leu Ser Phe Leu Val Val
        435                 440                 445

His Tyr Ile Tyr Pro Glu Thr Lys Gly Leu Thr Leu Glu Asp Met Asp
    450                 455                 460

Ser Val Phe Asp Asp Arg Ser Ser Thr Phe Ser Phe Gln Ser Ser Asn
465                 470                 475                 480

Ser Val Thr Gly Leu Asn Gln Gln Gln Gln Gln His Pro Gly Ala
                485                 490                 495

Gly Thr Gly Gly Phe Gly Thr Asn Tyr Gly Ser Ile Thr Asn Glu Asp
```

```
                500             505             510
Gly Leu Pro Val Gln Tyr Gln Ser Pro Ala Val Leu Ala Arg His Pro
            515                 520                 525

Ile Val Ala Ala Gln Gln Leu Gln Asn Leu Lys Ser Ser Thr Pro Ser
            530                 535             540

Leu Arg Ser Thr Ser Asn Tyr Met Asn Asn Val Ser Pro Leu Ile Gln
545                 550                 555                 560

Pro His Glu Leu Glu Pro Pro Asn Ile Glu Glu Ile Arg Ala Tyr Lys
                565                 570                 575

Leu Ser Asp Asn Asn Ser Ile Lys Gly Asn Ile Arg Arg Ser Ser Glu
            580                 585                 590

Asn Ile Gly Ser Met Phe His Lys Val Phe Asn Asn Asn Ser Leu Lys
            595                 600                 605

Arg Ser Asp Ser Thr Ser Glu Phe Thr Asn Asp Ser Glu Asp Glu Glu
            610                 615                 620

Ala Asn Leu Thr Ser Asn Ser Gly Arg His
625                 630

<210> SEQ ID NO 44
<211> LENGTH: 484
<212> TYPE: PRT
<213> ORGANISM: Paracoccidioides lutzii

<400> SEQUENCE: 44

Met Ser Gln Lys Ile Arg Pro Ala Leu Ala Leu Trp Gly Thr Arg Met
1               5                   10                  15

Ala Phe Met Ser Tyr Gly Trp Asp Ala Gly Val Leu Gly Gly Val Leu
            20                  25                  30

Glu Thr Ala Pro Phe Gln Asp Ala Met Lys His Pro Ser Thr Thr Thr
            35                  40                  45

Met Ser Met Ile Val Ala Ala Phe Leu Leu Ala Ser Trp Leu Gly Cys
        50                  55                  60

Cys Ile Val Ala Ser Pro Trp Ser Asp Arg Val Gly Arg Arg Met Trp
65              70                  75                  80

Val Ile Ser Gly Ala Ala Ile Gln Ile Ile Gly Thr Ile Ile Ser Thr
                85                  90                  95

Ala Ser Tyr Ser Ser Gly Gln Met Ile Ala Gly Arg Thr Ile Ile Gly
            100                 105                 110

Ile Gly Asn Gly Ile Val Val Ala Ser Ala Pro Val Tyr Ile Ala Glu
            115                 120                 125

Ile Thr Pro Thr Thr Ser Met Arg Gly Pro Leu Ile Gly Ile Leu Met
        130                 135                 140

Gly Phe Ala Cys Thr Gly Thr Thr Leu Ala Tyr Trp Val Asp Phe Ala
145                 150                 155                 160

Phe Thr His Ala Arg Gly Gln Val Val Trp Arg Val Pro Val Gly Leu
                165                 170                 175

Gln Ile Ile Trp Ser Leu Leu Thr Ile Leu Thr Leu Pro Asn Met
            180                 185                 190

Asp Ser Pro Arg Trp Tyr Tyr Leu Arg Asn Arg Asp His Glu Gly Leu
            195                 200                 205

Asn Val Leu Gln Gln Leu His Pro Asp Gln Glu Val Ala Leu Arg Val
        210                 215                 220

Gln Gly Glu Ile Leu Lys Glu Leu Arg Glu Glu Lys Glu Glu Lys Leu
225                 230                 235                 240
```

```
Gln Leu Ser Asn Leu Ile Phe Asp Lys Ser Pro Thr Gln Ala Met Arg
                245                 250                 255

Arg Ile Arg Asp Gly Val Val Leu Val Gly Val Ala Tyr Leu Met Gly
            260                 265                 270

Ile Asn Met Ile Phe Tyr Tyr Met Thr Thr Ile Phe His Val Tyr Ile
        275                 280                 285

Gly Leu Pro Ala Lys Thr Ser Ser Cys Leu Ser Gly Gly Ala Thr Thr
    290                 295                 300

Leu Leu Ala Ile Gly Val Phe Val Gly Ser Tyr Phe Cys Glu Lys Ser
305                 310                 315                 320

Gly Arg Arg Lys Trp Leu Leu Trp Gly Ser Ala Thr Gln Ser Val Phe
                325                 330                 335

Ile Ile Ala Phe Thr Gly Leu Leu Ala Ala Gly Lys Lys Thr Thr Ser
            340                 345                 350

Ser Ala Ala Ala Met Leu Phe Gly Trp Ile Leu Val Phe Ser Pro
        355                 360                 365

Thr Trp Ala Pro Leu Pro Tyr Ile Tyr Val Ser Glu Thr Met Pro Leu
    370                 375                 380

Arg His Arg His Thr Gly Val Gly Leu Ser Met Ser Ser Gln Trp Leu
385                 390                 395                 400

Met Ala Phe Leu Thr Val Tyr Ala Gly Pro Ile Ala Ile Ala Lys Val
                405                 410                 415

Gly Trp Lys Ala Trp Ile Trp Phe Ala Val Phe Asn Val Ala Ala Phe
            420                 425                 430

Pro Phe Val Tyr Phe Pro Ile Arg Glu Thr Arg Gly Arg Ser Leu Glu
        435                 440                 445

Asn Met Asn Asn Leu Phe Gly Asp Glu His Leu Ile Asp Gly Asn Ser
    450                 455                 460

Ser Ser Gly Asp Thr Ser Asp Asp Val Lys Glu Val Lys Ala Thr Pro
465                 470                 475                 480

Val Ser Lys Ala

<210> SEQ ID NO 45
<211> LENGTH: 523
<212> TYPE: PRT
<213> ORGANISM: Paraphaeosphaeria sporulosa

<400> SEQUENCE: 45

Met Ala Arg Lys Tyr Leu Gly Gly Ser Gly Glu Arg Leu Thr Ile Trp
1               5                   10                  15

Ile Ser Ile Ala Ala Ser Thr Val Leu Ile Phe Tyr Gly Tyr Asp Gln
            20                  25                  30

Gly Val Phe Gly Asn Val Ile Ile Asn Glu His Phe Leu Thr Thr Phe
        35                  40                  45

Gly His Pro Ser Ala Asn Met Gln Gly Val Met Thr Ser Ile Tyr Asn
    50                  55                  60

Ile Gly Cys Phe Ile Gly Ala Met Ser Thr Ile Trp Thr Gly Asp Ile
65              70                  75                  80

Leu Gly Arg Pro Arg Gln Ile Ile Leu Gly Ser Thr Val Ile Gly Ile
                85                  90                  95

Gly Ala Ile Ile Gln Thr Ala Ser Tyr Gly Val Pro Gln Met Met Val
            100                 105                 110

Gly Arg Ile Val Ala Gly Leu Gly Thr Gly Met Asn Thr Ala Thr Ala
        115                 120                 125
```

Gly Val Trp Gln Ala Glu Thr Ser Lys Met Ser Ser Arg Gly Lys Leu
130                 135                 140

Val Ile Ile Gln Met Ala Asn Cys Ile Thr Gly Phe Ser Ile Ser Asn
145                 150                 155                 160

Trp Leu Thr Leu Ala Phe Ser Phe Ala Pro Gly Asp Val Ala Trp Arg
                165                 170                 175

Phe Pro Leu Ala Phe Gln Leu Phe Thr Phe Cys Ile Tyr Ala Leu
                180                 185                 190

Cys Pro Phe Leu Pro Asp Ser Pro Arg Leu Leu Ile Arg Lys Gly Lys
                195                 200                 205

Pro Asp Glu Ala Leu Glu Val Leu Ala Ala Leu Glu Gly His Gly Ala
210                 215                 220

Thr Pro Glu Ser Ala Ser Val Arg Thr Gln Tyr Asn Ile Ile Lys Asp
225                 230                 235                 240

Ile Leu Asp Arg Glu His Met Asn Thr Tyr Thr Trp Trp Gln Leu Leu
                245                 250                 255

Ser Gly Lys Gly Pro Ser Gly Val Leu Arg Arg Met Ile Leu Gly Ala
                260                 265                 270

Trp Met Gln Ala Met Asn Gln Ile Ser Gly Ile Asn Val Thr Ser Tyr
        275                 280                 285

Tyr Met Ser Tyr Ile Phe Ile Asn Ala Leu Gly Ile Ser Glu Leu Leu
        290                 295                 300

Ser Arg Ile Leu Ala Ala Gly Ser Val Asp Tyr Leu Val Phe Ala
305                 310                 315                 320

Cys Leu Ala Phe Phe Val Ile Glu Arg Tyr Gly Arg Arg Lys Val Met
                325                 330                 335

Met Val Ser Ala Ala Ala Cys Ser Thr Cys Trp Ile Val Ile Ala Ile
                340                 345                 350

Ala Leu Gly Leu Ser Ala Asn Gly Gly Asp Ser Tyr Lys Leu Gly Ile
                355                 360                 365

Val Ala Val Ser Phe Phe Val Phe Phe Ala Ser Phe Gly Met Gly
        370                 375                 380

Val Leu Gly Val Pro Trp Leu Tyr Pro Thr Glu Ile Asn Ala Leu Glu
385                 390                 395                 400

Met Arg Thr Lys Gly Ala Ser Leu Ala Met Ser Thr Asn Trp Ile Met
                405                 410                 415

Asn Tyr Ala Val Val Gln Val Thr Leu Pro Gly Ile Gln Asn Ile Gly
                420                 425                 430

Trp Lys Phe Trp Ile Ile Trp Ala Val Ile Cys Phe Ser Phe Ile Pro
                435                 440                 445

Ile Thr Tyr Phe Phe Tyr Pro Glu Thr Ala Asn Arg Thr Leu Glu Asp
450                 455                 460

Ile Asp Arg Phe Phe Glu Thr Asn Pro Gly Leu Phe Val His Arg Asn
465                 470                 475                 480

Lys Leu Ala Ile Gln Leu His Arg Pro Val Glu Phe Ile Glu Ala Asp
                485                 490                 495

Glu Arg Ile Ala Thr Ala Gln Ala Glu Glu Lys Asn Leu Gly Glu
                500                 505                 510

Lys Thr Asp Phe Val Glu Ile Lys Glu Ala Val
                515                 520

<210> SEQ ID NO 46
<211> LENGTH: 198
<212> TYPE: PRT

<213> ORGANISM: Penicillium digitatum

<400> SEQUENCE: 46

Met Glu Lys Tyr Leu Ser Leu Ile Met Val Gly Ala Phe Ala Thr Val
1               5                   10                  15

Tyr Thr Phe Ala Thr Ile Pro Ser Ile Phe Leu Ile Glu Arg Glu Asn
            20                  25                  30

Glu Asp Asn Ala Lys Gly Ala Ala Val Val Phe Pro Phe Ile Thr Phe
        35                  40                  45

Phe Ala Phe Thr Leu Leu Pro Leu Leu Trp Ile Tyr Pro Pro Glu Ile
50                  55                  60

Asn Pro Leu Ser Thr Arg Thr Leu Ile Ala Ser Thr Cys Ala Asn Trp
65                  70                  75                  80

Ile Cys Asn Phe Ala Leu Val Leu Phe Thr Pro Leu Val Ala Asp His
                85                  90                  95

Ser Pro Arg Ser Val Asp Leu Phe Phe Ala Leu Phe Lys Phe Ile Gly
            100                 105                 110

Leu Ile Phe Gly Val Phe Phe Tyr Val Glu Thr Ala Gly Arg Gln Leu
        115                 120                 125

Gly Glu Val Asp Arg Ile Tyr Ala Lys Ala His Ile Glu Gly Lys Met
130                 135                 140

Ala Trp Arg Val Ala Gln Asp Met Pro Lys Leu Asn Phe Glu Glu Ile
145                 150                 155                 160

Val Gln Gln Phe Arg Gly Leu Gly Leu Asp Thr Asn Glu Leu Ala Ala
                165                 170                 175

His Glu Lys Ile Glu Leu Gly Leu Asn Ser Asn Ser Gly Gln Glu Leu
            180                 185                 190

Glu Glu Val Arg Glu Lys
        195

<210> SEQ ID NO 47
<211> LENGTH: 533
<212> TYPE: PRT
<213> ORGANISM: Phialophora attinorum

<400> SEQUENCE: 47

Met Gly Arg Arg Tyr Leu Gly Gly Ser Gly Gln Arg Leu Thr Val Trp
1               5                   10                  15

Ile Ser Ile Ala Ser Ser Thr Val Leu Ile Phe Tyr Gly Tyr Asp Gln
            20                  25                  30

Gly Val Phe Gly Asn Val Leu Val Ser Glu Asp Phe Leu Arg Thr Val
        35                  40                  45

Gly Tyr Pro Ser Val Thr Ala Gln Gly Thr Met Thr Ser Val Tyr Asn
50                  55                  60

Leu Gly Cys Phe Ala Gly Ala Leu Ser Thr Leu Tyr Thr Gly Asp Lys
65                  70                  75                  80

Leu Gly Arg Pro Arg Thr Leu Ile Leu Gly Ser Cys Thr Ile Ala Val
                85                  90                  95

Gly Ala Ile Val Gln Ala Ala Cys Met Asn Ala Ala Met Gln Tyr Ala
            100                 105                 110

Gly Arg Val Ile Ala Gly Met Gly Thr Gly Met Asn Thr Ala Thr Ala
        115                 120                 125

Gly Val Trp Gln Ser Glu Thr Ser Lys Met Arg Ser Arg Gly Lys Leu
130                 135                 140

Ile Ile Ile Gln Met Ala Asn Cys Ile Thr Gly Phe Ala Ile Ser Asn

```
            145                 150                 155                 160
Trp Leu Thr Leu Gly Phe Ser Phe Ala Pro Gly Ser Val Ser Trp Arg
                165                 170                 175

Phe Pro Leu Ala Phe Gln Met Phe Phe Thr Ile Leu Ile Cys Leu Met
                180                 185                 190

Cys Pro Phe Leu Pro Asp Ser Pro Arg Leu Leu Ile Arg Lys Gly Lys
                195                 200                 205

Tyr Asp Glu Ala Tyr Glu Val Leu Ala Ala Leu Glu Gly Asn Gly Ala
            210                 215                 220

Thr Val Asn Ser Pro Val Val Arg Thr Gln Phe Ala Ile Ile Lys Gln
225                 230                 235                 240

Val Leu Asp Glu Glu Tyr Ala Val Lys Tyr Thr Trp Trp Gln Ile Leu
                245                 250                 255

Thr Gly Lys Gly Pro Ser Gly Val Leu Arg Arg Met Val Leu Gly Ala
                260                 265                 270

Trp Met Gln Ala Ser Asn Gln Ile Ser Gly Ile Asn Val Thr Ser Tyr
                275                 280                 285

Tyr Met Thr Tyr Val Phe Ile Asn Ala Ile Asn Phe Ser Gln Leu Thr
            290                 295                 300

Ala Arg Ile Leu Ala Ala Ala Gly Ala Met Asp Tyr Leu Phe Phe Ser
305                 310                 315                 320

Phe Met Ala Tyr Phe Val Ile Glu Arg Phe Gly Arg Arg Ser Val Met
                325                 330                 335

Met Thr Ser Ala Ala Ala Cys Ser Ile Cys Trp Thr Val Ile Ala Ile
                340                 345                 350

Ser Leu Gly Leu Ser Glu Thr Gly Arg Ala Asp Ser Tyr Thr Met Gly
                355                 360                 365

Ala Val Ala Val Ser Phe Phe Leu Phe Phe Ala Ser Phe Ala Met
            370                 375                 380

Gly Val Leu Gly Val Pro Trp Leu Tyr Pro Thr Glu Val Asn Ala Leu
385                 390                 395                 400

Ala Phe Arg Ala Lys Gly Ala Ser Leu Ala Met Ser Thr Asn Trp Ile
                405                 410                 415

Met Asn Tyr Met Val Ala Gln Ile Thr Pro Pro Gly Ile Asp Asn Leu
                420                 425                 430

Gly Tyr Lys Phe Trp Ile Ile Trp Ala Val Ile Cys Ala Ala Phe Val
                435                 440                 445

Pro Ile Thr Tyr Leu Phe Tyr Pro Glu Thr Ala Asn Arg Ser Leu Glu
            450                 455                 460

Asp Ile Asp Arg Phe Phe His Ser Asn His Gly Ile Leu Val Phe Asn
465                 470                 475                 480

Asn Lys Val Ala Thr Gln Leu Lys Arg Pro Glu Ile Tyr Glu Glu Ala
                485                 490                 495

Asp Arg Arg Val Ala Ala His Glu Lys Val Gly Ala Gly Ala Asp
                500                 505                 510

Gln Ala Asp Glu Gly Lys Glu Ala Gly Ala Thr Leu Val Glu Glu Asn
            515                 520                 525

Gly Ala Ala Arg Ala
            530

<210> SEQ ID NO 48
<211> LENGTH: 213
<212> TYPE: PRT
<213> ORGANISM: Pochonia chlamydosporia
```

<400> SEQUENCE: 48

```
Met Gly Leu Ile Gly Arg Pro Leu Asn Trp Ala Ile Thr Ala Thr Ala
1               5                   10                  15

Gly Ala Gly Phe Leu Leu Phe Gly Tyr Asp Gln Gly Val Met Ser Gly
            20                  25                  30

Leu Leu Ala Gly Asp Ala Phe Thr Arg Thr Phe Pro Glu Met Asp Thr
        35                  40                  45

Thr Glu Ser Gly His Gly Ser Ala Ser Leu Gln Gly Thr Val Val Ala
    50                  55                  60

Ile Tyr Glu Ile Gly Cys Phe Gly Ala Leu Ile Ala Phe Val Phe
65                  70                  75                  80

Ala Glu Arg Leu Gly Arg Arg Thr Ile Met Leu Gly Cys Val Ile
            85                  90                  95

Leu Ser Ile Gly Gly Ala Leu Gln Ala Cys Ala Ser Thr Ile Pro His
            100                 105                 110

Met Ile Ala Gly Arg Ile Val Ala Gly Leu Gly Asn Gly Leu Asn Thr
        115                 120                 125

Ser Thr Ile Pro Val Cys His Ser Glu Leu Met Val Ala Ser Lys Arg
    130                 135                 140

Gly Lys Gly Leu Cys Ile Glu Leu Ser Ile Thr Val Phe Gly Val Met
145                 150                 155                 160

Ile Ala Tyr Trp Val Asp Cys Gly Met Ser Tyr Val Pro Asn Asp Ala
                165                 170                 175

Gln Phe Arg Phe Pro Leu Ala Leu Gln Cys Leu Phe Ala Ile Ile Thr
            180                 185                 190

Val Ile Gly Ile Leu Phe Leu Pro Glu Ser Pro Arg Trp Leu Val Ala
        195                 200                 205

His Asp Arg His Asp
    210
```

<210> SEQ ID NO 49
<211> LENGTH: 498
<212> TYPE: PRT
<213> ORGANISM: Pyrenophora tritici-repentis

<400> SEQUENCE: 49

```
Met Pro Glu Leu Arg Gly Arg Ala Leu Met Leu Thr Ile Ser Val Leu
1               5                   10                  15

Thr Ser Leu Gly Phe Met Leu Ile Gly Tyr Asp Asn Gly Leu Met Gly
            20                  25                  30

Gly Leu Val Gly Ala Pro Ala Phe Asn Lys Thr Phe Asp His Pro Ser
        35                  40                  45

Ser Asp Met Ile Gly Thr Ile Val Ala Ile Phe Glu Ile Gly Cys Phe
    50                  55                  60

Phe Gly Ala Met Ala Thr Ala Val Ile Gly Glu Lys Leu Gly Arg Arg
65                  70                  75                  80

Lys Ser Val Ala Ile Gly Ala Val Ile Ser Ile Leu Gly Ala Leu Leu
            85                  90                  95

Gln Ala Thr Ala Tyr Gly Arg Ala His Leu Ile Val Gly Arg Ile Val
            100                 105                 110

Ser Gly Val Gly Leu Gly Ile Ile Asn Ser Thr Val Pro Val Met Gln
        115                 120                 125

Ala Glu Phe Ser Pro Lys Ala Ser Arg Gly Ile Tyr Val Cys Ala Gln
    130                 135                 140
```

```
Leu Ser Thr Leu Asn Phe Gly Ile Phe Leu Val Tyr Trp Ile Asp Tyr
145                 150                 155                 160

Ala Phe Val Ser His Thr Ser Asp Tyr Ala Trp Arg Ile Pro Thr Ile
                165                 170                 175

Leu Gln Cys Ile Ile Val Leu Ala Ile Leu Gly Leu Leu Thr Val Ile
            180                 185                 190

Pro Glu Thr Pro Arg Trp Leu Ala Ala His Asp Arg Pro Asp Glu Cys
        195                 200                 205

Leu Arg Val Leu Ala Arg Val Ala Asp Val Pro Glu Thr Asp Pro Glu
    210                 215                 220

Val Gln Arg Leu His Thr Val Ile Thr Glu Thr Val Ala Phe Glu Gln
225                 230                 235                 240

Ser Arg Gln Ala Gly Trp Lys Asp Ile Val Arg Ser Asp Pro Ile Lys
                245                 250                 255

Ser Arg Arg Arg Phe Leu Ile Ala Cys Gly Ile Gln Met Phe Gln Gln
            260                 265                 270

Leu Gly Gly Ile Asn Ala Ile Ile Tyr Tyr Ser Gly Thr Leu Phe Gln
        275                 280                 285

Lys Ser Ile Gly Phe Asp Thr His Met Ser Ala Leu Met Ser Gly Phe
    290                 295                 300

Leu Gln Thr Trp Phe Phe Val Ala Ser Phe Ile Pro Trp Phe Leu Ile
305                 310                 315                 320

Asp Arg Val Gly Arg Arg Pro Leu Leu Leu Ser Met Ile Ser Leu Met
                325                 330                 335

Ala Ala Val Met Ala Val Gln Ser Gly Leu Ile Tyr Gln Val Gln Tyr
            340                 345                 350

Lys Thr Ala Ser Ala Lys Gly Ala Gly Ile Ala Ala Ala Ala Met Leu
        355                 360                 365

Phe Ile Phe Gln Gly Ala Phe Thr Ile Gly Phe Gln Ala Thr Val Trp
    370                 375                 380

Val Tyr Pro Ser Glu Ile Leu Pro Leu Arg Leu Arg Gln Arg Gly Ser
385                 390                 395                 400

Ala Ile Ser Thr Ala Ala Asn Trp Ile Cys Asn Tyr Ile Ile Val Gln
                405                 410                 415

Ile Thr Pro Arg Ala Ile Ser Asn Ile Gly Trp Lys Thr Tyr Ile Ile
            420                 425                 430

Phe Ala Val Leu Asn Gly Leu Trp Val Pro Ile Ile Phe Phe Phe Phe
        435                 440                 445

Pro Glu Thr Lys Gly Leu Glu Leu Glu Asp Val Asp Arg Leu Phe Ser
    450                 455                 460

Gly Glu Ala Ser Arg Thr Asp Leu Leu Asp Lys Asp Leu Asp Asp Glu
465                 470                 475                 480

Arg Val Glu Ser Val Val Val Ala Lys Thr Val Glu Cys Ala Gly His
                485                 490                 495

Val Ser

<210> SEQ ID NO 50
<211> LENGTH: 533
<212> TYPE: PRT
<213> ORGANISM: Pyricularia oryzae

<400> SEQUENCE: 50

Met Trp Leu Thr Asp Lys Phe Tyr Gly Leu Arg Gly Lys Ser Leu Asn
1               5                   10                  15
```

```
Tyr Ala Ile Val Cys Ile Ala Gly Val Asp Phe Leu Leu Phe Gly Tyr
                20              25                  30
Asp Gln Gly Val Met Gly Gly Ile Leu Thr Leu Pro Val Phe Leu Ser
            35              40                  45
Gln Phe Pro Thr Ile Asn Pro Glu Ala Asp Gly Leu Thr Ser Ile Glu
 50              55                  60
Ser Ala Gln Arg Ala Thr Asn Gln Gly Ile Ala Val Ala Ser Tyr Asn
 65                  70                  75                  80
Leu Gly Cys Phe Val Gly Ala Val Ile Ala Ile Trp Ile Ser Asn Pro
                85                  90                  95
Leu Gly Arg Lys Arg Met Ile Ile Leu Gly Thr Ser Ile Met Val Val
            100                 105                 110
Gly Thr Ile Ile Lys Ile Thr Ala Phe Ser Leu Val His Leu Val Ile
            115                 120                 125
Gly Arg Ile Ile Met Gly Leu Gly Asn Gly Met Asn Thr Ser Thr Val
        130                 135                 140
Pro Thr Trp Gln Ser Glu Thr Ser Ser Ser His Lys Arg Gly Lys Met
145                 150                 155                 160
Val Met Ile Glu Gly Ala Leu Ile Thr Cys Gly Ile Met Ile Ser Tyr
                165                 170                 175
Trp Ile Asp Leu Gly Leu Ser Phe Ala Pro Gly Ser Val Ala Trp Arg
            180                 185                 190
Phe Pro Ile Ala Phe Gln Leu Val Phe Cys Phe Phe Ile Leu Ala Phe
        195                 200                 205
Val Trp Asn Leu Pro Glu Ser Pro Arg Trp Leu Ile Leu Lys Gly His
    210                 215                 220
His Glu Glu Ala Lys Leu Val Ile Ala Ala Ile Ala Asp Leu Glu Val
225                 230                 235                 240
Glu Asp Asn Phe Val Gln Asn Glu Phe Leu Ala Ile Lys Glu Thr Val
                245                 250                 255
Glu Glu Met Ser Lys Gly Ser Phe Arg Asp Leu Phe Ala Thr Asn Glu
            260                 265                 270
Asn Arg Asn Leu His Arg Thr Phe Leu Ala Tyr Leu Asn Gln Val Phe
        275                 280                 285
Gln Gln Ile Ser Gly Ile Asn Leu Ile Thr Tyr Tyr Ala Ala Val Ile
    290                 295                 300
Tyr Ser Gly Leu Gly Met Ser Asp Phe Met Ser Arg Leu Leu Ala Ala
305                 310                 315                 320
Leu Asn Gly Thr Glu Tyr Phe Ile Ala Ser Trp Pro Ala Val Trp Leu
                325                 330                 335
Val Glu Arg Val Gly Arg Arg Lys Leu Met Leu Phe Gly Ala Ala Gly
            340                 345                 350
Gln Ala Leu Thr Met Ala Ala Ser Ala Gly Val Thr Ser Arg Ser Glu
        355                 360                 365
Glu Gly Phe Gln Ile Ala Gly Val Val Leu Leu Phe Ile Phe Asn Thr
    370                 375                 380
Phe Phe Ala Ile Gly Trp Leu Gly Met Thr Trp Leu Tyr Pro Ala Glu
385                 390                 395                 400
Ile Val Pro Leu Arg Ile Arg Ala Pro Ala Asn Ala Leu Ser Thr Ser
                405                 410                 415
Ala Asn Trp Ile Phe Asn Phe Met Val Val Met Ile Thr Pro Val Ala
            420                 425                 430
```

```
Phe Asn Thr Ile Lys His His Thr Tyr Thr Ile Phe Ala Ile Ile Asn
            435                 440                 445

Ala Ile Met Val Pro Ser Val Tyr Phe Leu Phe Pro Glu Thr Ala Tyr
    450                 455                 460

Arg Ser Leu Glu Glu Met Asp Thr Ile Phe Gln Lys Val His Gly Trp
465                 470                 475                 480

Lys Gly Leu Phe Thr Val Val Arg Gln Ala Glu Ile Glu Pro Arg Arg
                485                 490                 495

Tyr Gly Lys Asn Gly Glu Leu Leu Asp Val Asp Ala Val Arg Ala
                500                 505                 510

Glu Lys Gly Asp Ser Ser Ala Gly Arg Glu Asn Glu His Arg Glu
            515                 520                 525

Val Arg Thr Glu Pro
            530

<210> SEQ ID NO 51
<211> LENGTH: 540
<212> TYPE: PRT
<213> ORGANISM: Scedosporium apiospermum

<400> SEQUENCE: 51

Met Ser Val Gln Glu Asn Gly Val Cys Ile Pro Thr Phe Trp Gly Thr
1               5                   10                  15

Ser Gly Arg Lys Leu Gln Met Leu Val Thr Ala Val Ala Thr Ala Asp
            20                  25                  30

Phe Leu Leu Phe Gly Tyr Asp Gln Gly Val Met Ser Gly Ile Ile Ser
        35                  40                  45

Ala Asp Ala Phe Thr Glu Asp Phe Pro Glu Val Val Thr Gly Gly Ser
    50                  55                  60

Ala Tyr Glu Gly Phe Val Thr Ser Ile Tyr Ala Val Gly Cys Phe Leu
65                  70                  75                  80

Gly Ala Val Phe Ile Leu Leu Phe Gly Asp His Leu Gly Arg Arg Met
                85                  90                  95

Ser Ile Tyr Leu Gly Ala Thr Thr Met Ile Val Gly Val Ile Ile Gln
            100                 105                 110

Val Ser Cys Val Pro Val Ser Gly Gly Thr Thr Ala Gln Phe Ile Ile
        115                 120                 125

Gly Arg Cys Ile Thr Gly Val Gly Asn Gly Ile Asn Thr Ser Thr Ile
    130                 135                 140

Pro Thr Tyr Gln Ala Glu Cys Ser His Ser His Asn Arg Gly Lys Leu
145                 150                 155                 160

Ile Cys Ile Glu Gly Gly Asn Val Ala Ile Gly Thr Leu Ile Ala Tyr
                165                 170                 175

Trp Ile Asp Tyr Gly Ala Ile Tyr Gly Pro His Asp Phe Thr Trp Arg
            180                 185                 190

Phe Pro Ile Ala Phe Gln Cys Val Phe Ala Ile Thr Val Leu Ile Leu
        195                 200                 205

Asn Thr Arg Leu Pro Glu Ser Pro Arg Trp Leu Leu Thr Lys Asp Lys
    210                 215                 220

His Glu Glu Ala Ala Met Val Leu Ala Ala Leu Ala Gly Lys Pro Thr
225                 230                 235                 240

Asp Asp Tyr Glu Val Arg Ser Gln Met Thr Ala Ile Val Glu Ser Ile
                245                 250                 255

Lys Ala Ser Gly His Ser Gly Gly Val Thr Pro Met Ser Ala Leu Phe
            260                 265                 270
```

```
Thr Asn Gly Lys Thr Gln His Phe Arg Arg Met Ile Leu Gly Phe Ser
            275                 280                 285

Ser Gln Met Met Gln Leu Ser Gly Cys Asn Ala Val Ile Tyr Tyr
    290                 295                 300

Phe Pro Ile Leu Phe Gln Thr Ser Ile Gly Val Ser His Asn Met Ala
305                 310                 315                 320

Leu Leu Leu Gly Gly Val Asn Met Ile Val Tyr Ser Ile Phe Ala Thr
                325                 330                 335

Thr Ser Trp Phe Ala Val Glu Arg Ile Gly Arg Arg Lys Leu Phe Leu
                340                 345                 350

Ile Gly Thr Val Gly Gln Cys Leu Ser Met Val Leu Ala Phe Gly Ala
            355                 360                 365

Leu Ile Pro Gly Thr Glu Ala Ala Arg Gly Ala Ala Val Gly Leu
            370                 375                 380

Phe Thr Tyr Ile Ala Phe Phe Gly Ala Thr Trp Leu Pro Leu Pro Trp
385                 390                 395                 400

Leu Tyr Pro Ala Glu Ile Asn Pro Leu Lys Thr Arg Thr Lys Ala Asn
                405                 410                 415

Ala Val Ser Thr Val Ser Asn Trp Leu Trp Asn Phe Phe Ile Val Met
            420                 425                 430

Ile Thr Pro Val Leu Val Asp Asn Ile Gly Trp Gly Thr Tyr Leu Phe
            435                 440                 445

Phe Ala Val Leu Asn Ala Ile Phe Phe Pro Ile Ile Tyr Phe Phe Tyr
            450                 455                 460

Pro Glu Thr Ser Gln Arg Ser Leu Glu Glu Ile Asp His Ile Phe Ala
465                 470                 475                 480

Lys Gly Tyr Thr Glu Asn Met Ser Tyr Val Arg Ala Ala Lys Glu Leu
                485                 490                 495

Pro Arg Leu Ser Gly Glu Ile Asn Ala Gln Thr Val Gly Arg Asp Asp
            500                 505                 510

Val Asp Val Glu Lys Ser Gly Glu Val Ser Asp Glu Met Asp Ser Arg
            515                 520                 525

Ser Val Glu Asn Thr Glu Lys Leu Ser His Leu Asp
            530                 535                 540

<210> SEQ ID NO 52
<211> LENGTH: 512
<212> TYPE: PRT
<213> ORGANISM: Sphaerulina musiva

<400> SEQUENCE: 52

Met Ala Phe Glu Leu Arg Gly Ser Lys Leu Ile Ala Val Ile Leu Leu
1               5                   10                  15

Ala Ser Gly Leu Asp Phe Leu Leu Phe Gly Tyr Asp Gln Gly Leu Phe
            20                  25                  30

Gly Gly Ile Leu Gly Gly Lys Arg Phe Lys Ala Met Leu Gly Glu Pro
        35                  40                  45

Gly Pro Thr Met Thr Gly Phe Val Thr Gly Val Tyr Asp Ile Gly Cys
    50                  55                  60

Ala Ile Gly Ala Val Ala Phe Phe Gly Glu Ile Gly Arg
65                  70                  75                  80

Lys Lys Ser Ile Ile Tyr Ala Asn Val Ile Val Ile Gly Ala Thr
                85                  90                  95

Ile Gln Thr Ala Cys Tyr Ser Tyr Ala Gln Met Ala Val Ala Arg Val
```

```
                100             105             110
Ile Ala Gly Val Gly Val Gly Leu Ser Thr Val Ala Val Pro Ile Leu
            115             120             125
Gln Ser Glu Thr Leu Pro Ser His Asn Arg Gly Ala Leu Leu Val Val
130             135             140
Gln Ser Ala Leu Ile Ile Gly Val Ala Ile Ala Ser Trp Leu Cys
145             150             155             160
Phe Ala Thr Leu Phe Ala Asn Ser Ser Leu Gln Trp Arg Phe Pro Ile
            165             170             175
Ala Cys Gln Ile Leu Phe Ser Leu Leu Val Leu Cys Cys Pro Phe
            180             185             190
Leu Pro Glu Thr Pro Arg Trp Leu Cys Lys His Asn Arg Ile Asp Glu
            195             200             205
Ala Arg Tyr Thr Ile Ser Arg Leu Leu Asp Lys Pro Glu Asp Asp Ala
            210             215             220
Glu Val Lys Gly Gln Leu His Glu Ile Leu Ala Asn Ile Glu Ala Glu
225             230             235             240
Asn Glu Asp Gly Glu Pro Ser Trp Ser Glu Val Phe Ser Asn Ala Thr
                245             250             255
Lys Ala Arg Asn Leu Gln Arg Val Leu Leu Gly Met Gly Pro Tyr Met
            260             265             270
Met Asn Gln Trp Ser Gly Ile Asn Ala Leu Cys Tyr Tyr Leu Ala Tyr
            275             280             285
Ile Leu Glu Thr Tyr Leu Asp Phe Ser Gln Asn Met Ser Leu Ile Leu
            290             295             300
Ala Ser Val Ala Phe Thr Gln Tyr Ala Ile Phe Ser Trp Pro Pro Tyr
305             310             315             320
Phe Tyr Ile Asp Lys Ile Gly Arg Arg Trp Thr Val Met Leu Ser Ser
                325             330             335
Ile Gly Cys Ala Ile Cys Met Ala Val Ile Ala Gly Cys Leu Ile Lys
            340             345             350
Gln Ser Tyr Ser Ser Ala Ala Ala Val Ala Phe Met Phe Leu Tyr
            355             360             365
Leu Asp Cys Phe Thr Leu Gly Ile Leu Pro Val Ser Trp Ser Tyr Ser
            370             375             380
Ala Glu Ile Gln Pro Leu Arg Val Arg Asn Lys Ala Thr Ala Val Gly
385             390             395             400
Val Phe Ser His Trp Thr Ser Asn Phe Val Val Met Val Thr Pro
                405             410             415
Ile Gly Leu Asn His Ile Gly Gly Asn Tyr Phe Trp Ile Trp Ala Ile
            420             425             430
Val Cys Ala Ser Phe Val Pro Leu Thr Tyr Phe Gly Val Glu Thr
            435             440             445
Ser Gly Arg Thr Leu Glu Gln Ile Asp Glu Ser Phe Phe Glu Asn Pro
            450             455             460
Arg Ile Leu Met Gly Leu Asp Lys Lys Asn Thr Val Val Ile Lys Ala
465             470             475             480
Ser Lys Gln Asp Glu Glu Ser Arg Phe Arg Ala Leu Ala Lys Glu Glu
                485             490             495
Glu Lys His Pro Glu Arg Val Ser Val Glu Gln Val Glu Glu Lys Ser
            500             505             510

<210> SEQ ID NO 53
```

<211> LENGTH: 534
<212> TYPE: PRT
<213> ORGANISM: Talaromyces atroroseus

<400> SEQUENCE: 53

```
Met Trp Thr Thr Thr Ser Gly Leu Arg Gly Lys Lys Leu His Leu Ala
1               5                   10                  15

Ile Thr Phe Thr Ser Val Ile Gly Phe Ser Leu Phe Gly Tyr Asp Gln
            20                  25                  30

Gly Leu Met Ser Gly Leu Ile Ser Gly Asp Gln Phe Lys Glu Phe
        35                  40                  45

Pro Val Leu Asp Gly Asp Ser Leu His Val Ser Val Leu Gln Gly Ala
    50                  55                  60

Val Thr Ser Cys Tyr Glu Ile Gly Cys Phe Phe Gly Ala Ile Phe Thr
65                  70                  75                  80

Leu Leu Phe Gly Gln Arg Ile Gly Arg Thr Pro Leu Leu Val Gly Gly
                85                  90                  95

Gly Ala Leu Met Val Val Gly Thr Val Ile Ser Thr Ala Ser Phe Gly
            100                 105                 110

Pro His Trp Gly Leu Gly Gln Phe Val Ile Gly Arg Val Ile Ser Gly
        115                 120                 125

Val Gly Asn Gly Met Asp Thr Ala Thr Ile Pro Val Trp Gln Ser Glu
130                 135                 140

Cys Ser Arg Ala His Asn Arg Gly Phe Leu Val Cys Phe Glu Gly Ala
145                 150                 155                 160

Ile Ile Ala Val Gly Thr Phe Ile Ala Tyr Trp Ile Asp Phe Gly Leu
                165                 170                 175

Ser Tyr Val Glu Ser Ser Val Gln Trp Arg Phe Pro Val Ala Phe Gln
            180                 185                 190

Ile Leu Phe Ala Leu Leu Val Ile Gly Ala Leu Met Leu Pro Glu
        195                 200                 205

Ser Pro Arg Trp Phe Ile Met Ser Gly Lys Thr Gln Glu Ala Leu His
    210                 215                 220

Val Leu Ala Gln Leu Asn Asp Ser Ser Glu Asp Ala Asp Asp Val Leu
225                 230                 235                 240

Arg Asp Phe Asn Leu Met Gln Ala Asp Leu Lys Ser Leu Glu Asn Ala
                245                 250                 255

Glu Ala Ser Ser Trp Lys Thr Leu Phe Thr Phe Gly Lys Thr Gln Glu
            260                 265                 270

Phe Gln Arg Met Met Ile Gly Cys Ser Gly Gln Phe Gln Gln Phe
        275                 280                 285

Thr Gly Cys Asn Ala Ala Ile Tyr Tyr Ser Thr Leu Leu Phe Lys Asn
    290                 295                 300

Asn Leu His Met Thr Gly Lys Leu Pro Leu Val Leu Gly Gly Val Phe
305                 310                 315                 320

Ala Thr Val Tyr Ala Leu Ala Thr Ile Pro Ser Phe Phe Met Val Glu
                325                 330                 335

Lys Val Gly Arg Arg Asn Leu Phe Leu Ile Gly Phe Leu Gly Gln Gly
            340                 345                 350

Leu Ser Phe Ile Ile Thr Met Gly Cys Leu Val Asp Asp Thr Thr Gln
        355                 360                 365

Asn Ala Lys Gly Ala Ala Val Gly Ile Phe Leu Phe Ile Thr Phe Phe
    370                 375                 380

Ala Phe Thr Thr Leu Pro Leu Pro Trp Ile Tyr Pro Pro Glu Ile Asn
```

```
                    385                 390                 395                 400
Pro Leu Arg Thr Arg Thr Met Ala Ala Ser Ala Ser Thr Cys Val Asn
                        405                 410                 415

Trp Ile Cys Asn Phe Ala Val Val Met Phe Thr Pro Val Phe Ser Asn
                420                 425                 430

Lys Ser Ala Trp Gly Ile Tyr Leu Phe Ala Leu Val Asn Phe Ile
                435                 440                 445

Ala Ile Pro Phe Ala Trp Phe Phe Tyr Val Glu Thr Ala Gly Arg Asp
            450                 455                 460

Leu Glu Glu Val Asp Ile Ile Phe Ala Lys Ala His Val Glu Asn Lys
465                 470                 475                 480

Trp Pro Phe Gln Ile Ala Gln Gln Met Pro Lys Leu Thr His Glu Glu
                    485                 490                 495

Ile Ser Gln Gln Leu Phe Asp Leu Gly Leu Ser Val Ser Asp His Ser
                500                 505                 510

Ala Ser Ser Glu Ser Glu Lys Val Glu Ile Ala Ala Thr Asn Asn Glu
            515                 520                 525

His Arg Thr Ala Ser Asp
            530

<210> SEQ ID NO 54
<211> LENGTH: 488
<212> TYPE: PRT
<213> ORGANISM: Trichophyton benhamiae

<400> SEQUENCE: 54

Met Ala Gly Ile Ile Ser Ala Met Pro Phe Asn Thr Val Phe Pro Glu
1               5                   10                  15

Thr Lys Asp Asn Pro Thr Asn Gln Gly Phe Val Thr Ala Ile Tyr Glu
                20                  25                  30

Ile Gly Cys Leu Leu Gly Ala Val Ser Ile Ile Trp Gly Gly Asp Met
            35                  40                  45

Leu Gly Arg Arg Lys Ser Ile Val Thr Gly Ala Ile Ile Met Ala Ile
50                  55                  60

Gly Ala Ile Ile Gln Val Thr Ser Phe Val Gly His Gln Pro Tyr Ala
65                  70                  75                  80

Gln Phe Ile Ile Gly Arg Ile Ile Thr Gly Val Gly Asn Gly Ile Asn
                85                  90                  95

Thr Ser Thr Ile Pro Thr Tyr Gln Ala Glu Cys Ser His Ala Ser Asn
                100                 105                 110

Arg Gly Leu Leu Ile Cys Ile Glu Gly Ala Thr Ile Ala Phe Gly Thr
            115                 120                 125

Leu Ile Ala Tyr Trp Ile Asp Tyr Gly Ala Ser Tyr Gly Pro Asp Ser
            130                 135                 140

Phe Ser Trp Arg Phe Pro Ile Ala Phe Gln Ile Ala Phe Ser Ile Val
145                 150                 155                 160

Met Val Thr Gly Met Ile Trp Leu Pro Glu Ser Pro Arg Trp Leu Cys
                165                 170                 175

Met Arg Asp Arg Ser Asp Glu Gly Glu Arg Val Ile Ala Ala Leu His
            180                 185                 190

Gly Val Pro Ile Thr Asp Pro Leu Val Gln Ala Glu Lys Asn Ala Val
            195                 200                 205

Met Glu Ser Ile Arg Ala Ser Gly Glu Val Gly Lys Pro Thr Pro Leu
210                 215                 220
```

```
Ser Val Val Phe Thr Gly Gly Lys Thr Gln His Arg Arg Met Phe
225                 230                 235                 240

Leu Gly Val Phe Gly Gln Phe Ala Gln Gln Leu Ser Gly Cys Asn Ala
                245                 250                 255

Ile Ile Tyr Phe Phe Pro Val Leu Phe Glu Lys Ser Ile Gly Val Asp
                260                 265                 270

His Asn Met Ala Thr Leu Leu Gly Gly Val Asn Met Ile Val Tyr Ser
            275                 280                 285

Ile Phe Ala Thr Thr Ser Trp Phe Leu Ile Glu Arg Ala Gly Arg Arg
        290                 295                 300

Lys Leu Phe Leu Tyr Gly Ala Ala Gly Gln Ala Ile Ser Met Thr Ile
305                 310                 315                 320

Thr Phe Ala Cys Leu Ile Pro Asn Thr Pro Ala Thr Ala Lys Gly Ala
                325                 330                 335

Ala Val Gly Leu Phe Thr Tyr Ile Ala Ser Phe Gly Ala Thr Trp Leu
                340                 345                 350

Pro Leu Pro Trp Leu Tyr Ala Ala Glu Ile Ser Pro Ile Lys Thr Arg
            355                 360                 365

Ala Lys Ala Asn Ala Leu Ser Thr Cys Ser Asn Trp Leu Phe Asn Phe
        370                 375                 380

Phe Ile Val Met Ile Thr Pro Val Met Leu Ala Gly Ile Gly Trp Gly
385                 390                 395                 400

Thr Tyr Leu Phe Phe Ala Ile Ile Asn Val Cys Phe Leu Pro Ile Ile
                405                 410                 415

Tyr Phe Tyr Pro Glu Thr Ala Lys Arg Ser Leu Glu Glu Ile Asp
            420                 425                 430

Ile Ile Phe Ala Lys Gly Tyr Cys Glu Asn Lys Ser Tyr Val Gln Ala
        435                 440                 445

Ala Arg Glu Leu Pro Tyr Leu Thr Glu Glu Ile Ser Arg Met Asp
    450                 455                 460

Ala Glu Tyr Gly His Gly Lys Pro Ser Glu Thr Ala Ser Pro Val Asn
465                 470                 475                 480

Glu Lys Glu Ser Asp Ser Glu Gln
                485

<210> SEQ ID NO 55
<211> LENGTH: 472
<212> TYPE: PRT
<213> ORGANISM: Verticillium alfalfae

<400> SEQUENCE: 55

Met Ser Glu Lys Ser Asp Arg Ala Asp Thr Ile Asn Asn His Gln Gly
1               5                   10                  15

Thr Val Asp Ser Thr Pro Lys Ser Gly Phe Ser Arg Phe Cys Ser Lys
                20                  25                  30

Met Gly Asp Leu Pro Gln Trp Lys Val Asn Gly Lys Leu Leu Arg Gly
            35                  40                  45

Ala Ala Leu Asn Trp Gly Ile Gly Val Ile Ala Ser Cys Gly Phe Leu
        50                  55                  60

Met Phe Gly Tyr Asp Gln Gly Val Leu Ser Gly Leu Thr Leu Asp
65                  70                  75                  80

Asp Phe Gln Lys Asn Gln Ala Leu Met Thr Pro Leu Asp Ala Ser Asn
                85                  90                  95

Pro Leu Cys Trp Asn Asp Asp Gly Ser Arg Asp Glu Arg Tyr Cys His
                100                 105                 110
```

Gly Asp Ala Asn Thr Gln Ala Ala Gly Val Ala Met Tyr Gln Ile Gly
            115                 120                 125

Cys Phe Leu Gly Ala Val Leu Ile Leu Phe Tyr Gly Glu Ser Trp Gly
        130                 135                 140

Arg Arg Ser Ser Thr Phe Trp Gly Ser Leu Ile Met Ile Ile Gly Gly
145                 150                 155                 160

Ile Met Gln Ala Ala Ser Leu Glu Tyr Gly Leu Phe Val Ser Gly Arg
                165                 170                 175

Val Ile Gly Gly Arg Phe Lys Arg Leu Leu Thr Asn Arg Pro Ser Gln
            180                 185                 190

Lys Leu Arg Arg Thr Leu Leu Gly Ile Ala Ala Gln Phe Phe Gln Gln
        195                 200                 205

Ile Cys Gly Ile Thr Leu Ile Thr Tyr Tyr Ala Thr Phe Val Phe Glu
    210                 215                 220

Asn Ser Leu Gly Phe Gly Pro Gln Leu Ser Arg Leu Leu Ala Ala Leu
225                 230                 235                 240

Asn Gly Thr Glu Tyr Phe Leu Ala Ser Leu Val Ala Leu Pro Leu Ile
                245                 250                 255

Glu Arg Val Gly Arg Arg Lys Leu Met Leu Phe Gly Ala Phe Gly Met
            260                 265                 270

Met Gly Ser Met Ala Ile Leu Ala Gly Thr Thr Ser Thr Gly Thr Thr
        275                 280                 285

Asn Glu Asp Gly Ala Pro Gln Leu Ser Thr Ala Tyr Gly Val Thr Ala
    290                 295                 300

Val Val Phe Leu Phe Ala Phe Asn Ser Phe Phe Ala Val Gly Trp Leu
305                 310                 315                 320

Gly Met Thr Trp Leu Tyr Pro Ala Glu Val Thr Gly Leu Asn Ile Arg
                325                 330                 335

Ile Gln Ala Asn Ala Leu Ser Thr Cys Ser Asn Trp Ile Ser Asn Phe
            340                 345                 350

Leu Ile Val Met Ile Thr Pro Pro Ala Phe Ala Asn Leu Gln Trp Lys
        355                 360                 365

Thr Tyr Val Met Phe Ala Val Phe Asn Ala Ala Leu Ile Pro Cys Val
    370                 375                 380

Tyr Leu Tyr Phe Pro Glu Thr Ser Lys Arg Ser Leu Glu Glu Ile Asp
385                 390                 395                 400

Leu Tyr Phe Ala Arg Ala Trp Ser Glu Gly Val Ser Pro Val Lys Met
                405                 410                 415

Ala Lys Thr Met Pro Arg Tyr Thr Ala Thr Glu Leu Asp Asn Glu Leu
            420                 425                 430

Ala Lys Tyr Phe Ser Ala Ala Asp Ile Glu Gln Arg Arg Gly Ser Met
        435                 440                 445

Leu Gln Ser Arg Arg Pro Ser Ala Met Thr Gln Ala Pro Asp Glu Pro
    450                 455                 460

Ser Val Asn Lys Asn Ala Thr Gln
465                 470

<210> SEQ ID NO 56
<211> LENGTH: 533
<212> TYPE: PRT
<213> ORGANISM: Verticillium dahliae

<400> SEQUENCE: 56

Met Gly Tyr Thr Thr Trp Trp Lys Arg Leu Ser Pro Arg Gln Leu Asn

-continued

```
1               5                   10                  15
Ile Ala Ile Gln Thr Phe Ser Val Ile Ser Ile Phe Phe Glu Gly Tyr
                20                  25                  30
Asp Gln Gly Val Met Gly Val Asn Ala Ser Pro Arg Tyr Val Glu
            35                  40                  45
Glu Val Gly Ile Gly Leu Pro Asp Gly Thr Val Thr Asp Thr Leu His
            50                  55                  60
Gln Gly Gly Ile Val Ser Val Tyr Tyr Leu Gly Cys Ile Ala Gly Cys
65                  70                  75                  80
Phe Ala Gly Gly Trp Leu Ala Asp Arg Ile Gly Arg Ile Asn Gly Leu
                85                  90                  95
Phe Ile Gly Cys Ile Phe Ala Ile Ile Gly Gly Ala Leu Gln Ala Ala
                100                 105                 110
Ala Gln Ser Ser Asn Phe Ile Ile Val Ala Arg Val Ile Thr Gly Ile
                115                 120                 125
Gly Thr Gly Ala Leu Thr Gly Ile Thr Pro Val Met Val Ser Glu Thr
            130                 135                 140
Ser Thr Ala Glu His Arg Gly Gly Phe Leu Gly Tyr Val Phe Ile Ala
145                 150                 155                 160
Asn Tyr Leu Gly Ile Ser Ile Ala Tyr Trp Leu Ser Phe Gly Leu Ala
                165                 170                 175
Phe Ile Asp Gly Gly Tyr Ser Asp Ile Arg Trp Arg Phe Gln Leu Ala
                180                 185                 190
Phe Gln Cys Leu Pro Ala Leu Leu Leu Phe Leu Gly Ile Lys Ile Leu
                195                 200                 205
Pro Asp Thr Pro Arg Phe Leu Ala Ser Val Gly Arg Tyr Asp Glu Ala
            210                 215                 220
Arg Glu Val Ile Glu His Val Arg Gly Asn Phe Gly Pro Leu Val Glu
225                 230                 235                 240
Arg Glu Phe Leu Glu Ile Arg Thr Val Ala Glu Glu Ser Thr Lys Ser
                245                 250                 255
Ser Pro Ile Glu Phe Ile Lys Ile Leu Phe Gly Arg Gly Pro Lys Pro
            260                 265                 270
Gly Tyr Asn Leu Gly Gln Arg Ala Trp Leu Cys Leu Phe Leu Gln Ile
            275                 280                 285
Met Ala Ser Trp Thr Gly Ile Thr Ala Val Thr Ala Tyr Ser Pro Ile
            290                 295                 300
Leu Leu Ser Gln Ala Gly Tyr Thr Glu Leu Thr Gln Asn Gly Leu Ala
305                 310                 315                 320
Gly Gly Leu Asn Thr Val Gly Ile Val Gly Thr Ile Ile Ser Ala Gln
                325                 330                 335
Ile Val Asp Arg Leu Gly Arg Arg Thr Cys Leu Met Gly Gly Ala Leu
                340                 345                 350
Ala Leu Ser Ala Val Asn Leu Ile Ala Gly Ala Leu Tyr Glu Gly Ser
                355                 360                 365
Arg Ala His Pro Asp Arg Ala Ser Gln Phe Ala Pro Val Ala Val Ala
            370                 375                 380
Met Leu Phe Leu Phe Asn Leu Ser Tyr Ala Ala Thr Trp Gly Thr Val
385                 390                 395                 400
Ala Phe Leu Ile Pro Thr Glu Ile Trp Ser Ser Asp Leu Arg Ala Gln
                405                 410                 415
Gly Asn Gly Phe Gly Ile Thr Gly Trp Ala Val Gly Val Gly Met Thr
            420                 425                 430
```

```
Thr Leu Val Asn Pro Ile Met Phe Gly Val Leu Lys Asn Trp Thr Tyr
            435                 440                 445

Phe Leu Phe Ala Gly Leu Asn Leu Leu Trp Val Pro Val Val Phe Leu
    450                 455                 460

Phe Tyr Pro Glu Thr Ser Gly Arg Ser Leu Glu Ser Ile Asp Ala Leu
465                 470                 475                 480

Phe Ala Ala Asn Ser Ile Phe Asn Thr Lys Met Glu Arg Ser Tyr Met
                485                 490                 495

Ala His Gly Asp Val Leu Ala Glu Arg Gly Asn His Asp Asn Gln Val
            500                 505                 510

Leu Ser Ala Ser Asp Ser Gly Ser Lys Pro Gly Pro Pro Gly Ser Val
            515                 520                 525

Glu Lys Leu Gln Val
            530

<210> SEQ ID NO 57
<211> LENGTH: 573
<212> TYPE: PRT
<213> ORGANISM: Torulaspora delbrueckii

<400> SEQUENCE: 57

Met Ile Glu Lys Lys Ser Leu Lys Ser Arg Phe Phe Ser Arg Thr Ser
1               5                   10                  15

His Phe Gly Leu Thr Gly Lys Thr Leu Arg Tyr Val Ile Thr Leu Cys
            20                  25                  30

Ala Met Thr Gly Phe Ser Leu Phe Gly Tyr Asp Gln Gly Leu Met Ala
        35                  40                  45

Ser Leu Ile Thr Gly Thr Gln Phe Asn Tyr Glu Phe Pro Ala Thr Lys
    50                  55                  60

Ser Lys Ser Asp Asn Asp Thr His Ala Ser Thr Val Gln Gly Ala Val
65                  70                  75                  80

Thr Ser Cys Tyr Glu Ile Gly Cys Phe Phe Gly Ser Leu Phe Val Met
                85                  90                  95

Phe Tyr Gly Glu Lys Ile Gly Arg Lys Pro Leu Ile Val Ile Gly Ser
            100                 105                 110

Val Ile Thr Ile Val Gly Ala Val Ile Ser Thr Thr Ala Phe Arg Asp
        115                 120                 125

Tyr Trp Ala Leu Gly Gln Phe Val Gly Arg Val Ile Thr Gly Val
    130                 135                 140

Gly Thr Gly Leu Asn Thr Ser Thr Ile Pro Val Trp Gln Ser Glu Met
145                 150                 155                 160

Ser Asp Pro Ser Ile Arg Gly Ile Leu Val Asn Leu Glu Gly Ser Thr
                165                 170                 175

Ile Ala Ile Gly Thr Met Leu Ala Tyr Trp Ile Asp Phe Gly Phe Ser
            180                 185                 190

Phe Ile Asp Ser Ser Val Gln Trp Arg Phe Pro Val Ser Met Gln Ile
        195                 200                 205

Leu Phe Ala Leu Ile Leu Cys Phe Met Ile Val Asn Leu Pro Glu Ser
    210                 215                 220

Pro Arg Trp Leu Ile Ser Gln Ser Arg Thr Glu Glu Ala Arg Tyr Leu
225                 230                 235                 240

Leu Gly Gln Leu Asp Asp Val Asp Pro Asn Asp Arg Ile Val Ala
                245                 250                 255

Glu Val Ala Met Ile His Asp Ala Val Asn Arg Ser Lys Gln Glu Lys
```

```
            260                 265                 270
Asn Ser Met Ser Val Leu Phe Ser Gly Gly Lys Ser Gln Asn Met Gln
            275                 280                 285

Arg Ala Leu Val Ala Ala Ser Thr Gln Phe Phe Gln Gln Phe Thr Gly
    290                 295                 300

Cys Asn Ala Ala Ile Tyr Tyr Ser Thr Val Leu Phe His Glu Thr Ile
305                 310                 315                 320

Gln Leu Ser Pro Arg Leu Ser Met Ile Leu Gly Ala Val Phe Ser Thr
                325                 330                 335

Val Tyr Ala Leu Ser Thr Ile Pro Ser Phe Phe Leu Ile Glu Arg Leu
            340                 345                 350

Gly Arg Arg Lys Leu Phe Leu Leu Gly Ala Thr Gly Gln Ala Ile Ser
        355                 360                 365

Phe Thr Ile Thr Phe Ala Cys Leu Val Arg Gln Thr Glu Glu Asn Ala
    370                 375                 380

Lys Gly Ala Ala Val Gly Leu Phe Leu Phe Ile Val Phe Phe Gly Cys
385                 390                 395                 400

Ser Met Leu Ser Leu Pro Trp Ile Tyr Pro Pro Glu Ile Ala Ser Met
                405                 410                 415

Lys Val Arg Ala Ser Thr Asn Ala Phe Ser Thr Cys Thr Asn Trp Leu
            420                 425                 430

Cys Asn Phe Ala Val Val Met Phe Thr Pro Ile Phe Ile Asn Lys Ser
        435                 440                 445

Gly Trp Gly Cys Tyr Leu Phe Phe Ala Cys Ile Asn Tyr Leu Tyr Ile
    450                 455                 460

Pro Val Ile Phe Phe Phe Tyr Pro Glu Thr Ala Gly Arg Ser Leu Glu
465                 470                 475                 480

Glu Ile Asp Ile Ile Tyr Ala Lys Ser His Glu Glu Gly Thr Gln Ala
                485                 490                 495

Trp Arg Val Ala Ala His Leu Pro Lys Leu Ser Leu Gln Glu Val Asp
            500                 505                 510

Asp His Ala Asn Ala Leu Gly Leu Tyr Glu Asp Asp Leu Glu Lys Glu
        515                 520                 525

Asp Phe Ala Ala Glu Glu Gly Lys Glu Ala Gly Ala His Gly Tyr
    530                 535                 540

Ala Leu Phe Ala Arg Asn Thr Ser Thr Ser Asn Asn Glu Asp Gly Ser
545                 550                 555                 560

Ser Glu Ser Glu Lys Asp Gln Asn Ala Thr Pro Arg Ala
                565                 570

<210> SEQ ID NO 58
<211> LENGTH: 532
<212> TYPE: PRT
<213> ORGANISM: Penicillium rubens

<400> SEQUENCE: 58

Met Gly Tyr Thr Thr Leu Trp Lys Arg Leu Ser Pro Arg Gln Leu Asn
1               5                   10                  15

Val Ala Ile Gln Ile Phe Ser Leu Ile Ser Ile Phe Phe Glu Gly Tyr
            20                  25                  30

Asp Gln Gly Val Met Gly Gly Val Asn Asn Ser Pro Arg Tyr Val Glu
        35                  40                  45

Glu Val Gly Ile Gly Lys Pro Asp Gly Thr Val Thr Asp Thr Thr His
    50                  55                  60
```

-continued

Gln Gly Gly Ile Val Ser Ile Tyr Tyr Leu Gly Ala Ile Phe Gly Cys
65                  70                  75                  80

Phe Ala Gly Gly Trp Leu Ala Asp Arg Val Gly Arg Ile Asn Gly Leu
            85                  90                  95

Leu Ala Gly Ser Leu Phe Ala Leu Val Gly Gly Ala Leu Gln Ala Gly
            100                 105                 110

Ala Gln Asn Ser Asp Phe Met Leu Cys Ala Arg Val Ile Thr Gly Ile
            115                 120                 125

Gly Thr Gly Ala Leu Thr Gly Ile Thr Pro Val Leu Val Ser Glu Thr
            130                 135                 140

Ser Ser Ala Asn His Arg Gly Gly Phe Leu Gly Tyr Val Phe Ile Ala
145                 150                 155                 160

Asn Tyr Leu Gly Ile Ser Val Ala Tyr Trp Ile Ser Phe Gly Leu Ala
            165                 170                 175

Phe Val Asp Asn Gly Tyr Ser Asp Val Arg Trp Arg Phe Leu Leu Ala
            180                 185                 190

Phe Gln Cys Phe Pro Ala Leu Leu Leu Ala Ala Phe Ile Lys Met Leu
            195                 200                 205

Pro Asp Ser Pro Arg Phe Leu Ala Ser Val Gly Arg Asn Asp Glu Ala
210                 215                 220

Arg Asp Leu Leu Asn Arg Ile Arg Lys Asp Arg Ala Ser Gln Asp Asp
225                 230                 235                 240

Ile Asp Arg Glu Tyr Leu Glu Ile Ile Val Thr Ala Lys Gly Ser Lys
            245                 250                 255

Phe Ser Ser Pro Ile Glu Phe Val Lys Ile Leu Phe Gly Lys Gly Gly
            260                 265                 270

Arg Pro Gly Met Asn Leu Gly Arg Arg Ala Trp Leu Cys Val Trp Leu
            275                 280                 285

Gln Ile Met Ala Ser Trp Thr Gly Ile Thr Ala Val Thr Ala Tyr Ser
            290                 295                 300

Pro Val Leu Leu Ala Gln Ala Gly Tyr Ser Asp Ile Lys Gln Asn Gly
305                 310                 315                 320

Leu Ala Gly Gly Ile Asn Thr Ile Gly Ile Ile Gly Thr Ile Ile Ser
            325                 330                 335

Ala Ile Ile Ile Asp Arg Leu Gly Arg Arg Val Cys Leu Met Gly Gly
            340                 345                 350

Ala Ala Val Leu Phe Ala Val Asn Leu Ile Ala Gly Ala Val Tyr Glu
            355                 360                 365

Gly Ser Leu His Asn Pro Glu Lys Ala Ser Gln Tyr Ala Pro Gly Ala
            370                 375                 380

Val Thr Met Leu Phe Leu Phe Asn Leu Gly Tyr Ala Ala Thr Trp Gly
385                 390                 395                 400

Thr Val Ala Phe Leu Val Pro Thr Glu Ile Phe Pro Ser Asp Leu Arg
            405                 410                 415

Ala Gln Gly Asn Gly Phe Gly Ile Thr Gly Trp Ala Ile Gly Val Gly
            420                 425                 430

Met Thr Thr Leu Val Asn Pro Ile Met Phe Asp Val Met Thr Ser Arg
            435                 440                 445

Thr Tyr Phe Leu Phe Ala Gly Leu Asn Leu Ile Trp Ile Pro Ile Val
            450                 455                 460

Tyr Leu Phe Tyr Pro Glu Thr Arg Asn Arg Ser Leu Glu Ser Ile Asp
465                 470                 475                 480

Ala Leu Phe Ser Thr Pro Ser Pro Phe His Trp Lys Met Glu Gln Ala

```
                485                 490                 495
Tyr Lys Leu His Gly Asp Val Leu Ala Glu His Gly Val Asn Arg Asn
            500                 505                 510
Glu Ala Leu Gly Asp Gly Lys Ser Glu Leu Thr Thr Ser Pro Thr Glu
            515                 520                 525
Leu Gly Thr Val
        530

<210> SEQ ID NO 59
<211> LENGTH: 237
<212> TYPE: PRT
<213> ORGANISM: Trichophyton rubrum

<400> SEQUENCE: 59

Met Ala Lys Lys Tyr Leu Gly Gly Ser Gly Asp Lys Leu Thr Ile Trp
1               5                   10                  15
Ile Ser Ile Ala Ala Ser Thr Val Leu Ile Phe Tyr Gly Tyr Asp Gln
            20                  25                  30
Gly Val Phe Gly Asn Val Leu Ile Gly Glu Asp Phe Leu Gln Thr Met
        35                  40                  45
Gly Tyr Pro Ser Thr Asn Leu Gln Gly Thr Met Thr Ser Val Tyr Asn
    50                  55                  60
Ile Gly Cys Phe Val Gly Ala Met Ser Thr Val Trp Thr Gly Asp Tyr
65                  70                  75                  80
Phe Gly Arg Pro Arg Gln Ile Ile Val Gly Ser Thr Ile Ala Ile
                85                  90                  95
Gly Gly Ile Ile Gln Ala Ser Ala Tyr Gly Val Pro Gln Met Met Val
            100                 105                 110
Gly Arg Val Val Ala Gly Leu Gly Thr Gly Met Asn Thr Ser Thr Ala
        115                 120                 125
Gly Val Trp Gln Ser Glu Thr Ser Lys Met Ser Ser Arg Gly Lys Leu
    130                 135                 140
Val Ile Ile Gln Met Val Phe Phe Thr Leu Cys Ile Tyr Ala Met Cys
145                 150                 155                 160
Pro Phe Leu Pro Asp Ser Pro Arg Leu Leu Ile Arg Lys Gly Glu Tyr
                165                 170                 175
Ser Glu Ala Leu Glu Val Leu Ala Ala Leu Glu Gly Asn Gly Ala Thr
            180                 185                 190
Ser Asn Ser His Ser Val Lys Thr Gln Phe Asn Val Ile Lys Asp Val
        195                 200                 205
Leu Asp Arg Glu Asn Leu Asn Ser Tyr Thr Trp Phe Lys Leu Leu Met
    210                 215                 220
Gly Lys Gly Glu Ser Ser Arg Phe Pro Ser Val Tyr Thr
225                 230                 235

<210> SEQ ID NO 60
<211> LENGTH: 568
<212> TYPE: PRT
<213> ORGANISM: Lachancea thermotolerans

<400> SEQUENCE: 60

Met Pro Ser Arg Leu Ser Val Asn Arg Thr Ser Thr Leu Gly Leu Asn
1               5                   10                  15
Gly Arg Ser Leu Arg Leu Ala Ile Thr Ile Thr Ser Val Ile Gly Phe
            20                  25                  30
Ser Leu Phe Gly Tyr Asp Gln Gly Leu Met Ser Gly Leu Ile Thr Gly
```

```
            35                  40                  45
Lys Glu Phe Asn Ser Glu Phe Pro Ala Thr Gly Gly Asp Arg Arg
 50                  55                  60

Thr Lys Leu Val Gln Gly Ala Val Thr Ala Cys Tyr Glu Ile Gly Cys
 65                  70                  75                  80

Phe Phe Gly Ser Leu Phe Val Met Phe Arg Gly Glu Gln Ile Gly Arg
                 85                  90                  95

Lys Pro Leu Val Ile Leu Gly Ala Cys Leu Thr Ile Val Gly Thr Val
                100                 105                 110

Ile Ser Thr Ala Ala Phe Gly Pro His Trp Gly Leu Gly Gln Phe Val
                115                 120                 125

Val Gly Arg Val Cys Thr Gly Val Gly Thr Gly Leu Asn Thr Ser Thr
                130                 135                 140

Ile Pro Val Trp Gln Ser Glu Met Ser Lys Pro Glu Asn Arg Gly Ile
145                 150                 155                 160

Leu Val Asn Leu Glu Gly Ser Met Ile Ala Val Gly Thr Met Ile Ala
                165                 170                 175

Tyr Trp Ile Asp Phe Gly Leu Ser Tyr Val Asp Ser Ser Val Gln Trp
                180                 185                 190

Arg Phe Pro Val Ala Met Gln Ile Phe Phe Ala Leu Leu Leu Leu Ala
                195                 200                 205

Gly Ile Trp Glu Leu Pro Asp Ser Pro Arg Trp Leu Met Ser Arg Gly
210                 215                 220

Arg Arg Asp Asp Ala Leu His Val Leu Ala Lys Leu Asp Asn Leu Pro
225                 230                 235                 240

Glu Asp Asp Asp Ala Ile Ile Ala Glu Ala Thr Val Ile Gln Asp Ala
                245                 250                 255

Val Asn Arg Phe Arg His Glu Lys Arg Ser Val Lys Asp Leu Phe Thr
                260                 265                 270

Gly Gly Lys Thr Gln Asn Leu Gln Arg Ala Leu Val Ala Ser Ser Thr
                275                 280                 285

Gln Phe Phe Gln Gln Phe Thr Gly Cys Asn Ala Ala Ile Tyr Tyr Ser
                290                 295                 300

Thr Val Leu Phe Gln Glu Ser Ile Gly Leu Thr Gly Lys Leu Pro Leu
305                 310                 315                 320

Ile Leu Gly Gly Val Phe Ala Thr Ile Tyr Ala Cys Phe Thr Ile Pro
                325                 330                 335

Ser Phe Phe Leu Val Glu Thr Leu Gly Arg Arg Lys Leu Phe Met Leu
                340                 345                 350

Gly Ala Ala Gly Gln Ala Ile Ser Phe Thr Ile Thr Phe Gly Cys Leu
                355                 360                 365

Thr Lys Asp Asp Thr Glu Val Ala Lys Gly Ala Ala Val Gly Leu Phe
                370                 375                 380

Leu Phe Ile Cys Phe Phe Gly Met Ser Met Leu Ser Leu Pro Trp Ile
385                 390                 395                 400

Tyr Pro Pro Glu Ile Ala Ser Met Arg Val Arg Ser Ala Thr Asn Ala
                405                 410                 415

Leu Ser Thr Cys Thr Asn Trp Leu Cys Asn Phe Ala Val Met Phe
                420                 425                 430

Thr Pro Ile Phe Ile Met Asp Thr Gly Tyr Gly Cys Tyr Leu Phe Phe
                435                 440                 445

Ala Val Met Asn Tyr Leu Tyr Leu Pro Val Ile Phe Phe Phe Tyr Pro
                450                 455                 460
```

```
Glu Thr Ala Gly Arg Ser Leu Glu Glu Ile Asp Ile Ile Phe Ala Lys
465                 470                 475                 480

Ala His Val Asp Gly Thr Met Pro Trp Arg Val Ala Ala Asn Leu Pro
            485                 490                 495

Lys Leu Ser Phe Ser Glu Ile Glu Asp Gln Ala Asn Ala Leu Gly Leu
        500                 505                 510

Tyr Glu Asp Asn Glu Lys Gln Asp Leu Asp Leu Asp Glu Ala Ala
        515                 520                 525

Asp Arg Glu Asp Ala Ile Arg Gln Asn Ser Gly Val Gln Gly Tyr Thr
            530                 535                 540

Leu Phe Glu Lys Arg Glu Asn Gly Ala Glu Ser Gly Gln Pro Asp Gly
545                 550                 555                 560

Ser Ser Thr Ser Gln Lys Ser Asp
                565
```

<210> SEQ ID NO 61
<211> LENGTH: 542
<212> TYPE: PRT
<213> ORGANISM: Aspergillus oryzae

<400> SEQUENCE: 61

```
Met Trp Thr Thr Thr Ser Gly Leu Ser Gly Arg Ser Leu Arg Leu Ser
1               5                   10                  15

Ile Thr Phe Ala Ala Val Val Gly Phe Ser Leu Phe Gly Tyr Asn Gln
            20                  25                  30

Gly Met Met Ala Gly Leu Leu Asn Gly Asp Glu Phe Val Asp Ser Phe
        35                  40                  45

Pro Ile Leu Lys Met Pro Asp Asn Pro Thr Ala Gly Glu Lys His Tyr
    50                  55                  60

Ile Asp Val Ile Arg Gly Ala Val Thr Ser Cys Tyr Glu Leu Gly Cys
65                  70                  75                  80

Phe Phe Gly Ala Leu Phe Ser Met Phe Leu Gly Asp Lys Leu Gly Arg
                85                  90                  95

Thr Arg Leu Ile Phe Met Gly Ala Ser Ile Leu Ile Ile Gly Ala Leu
            100                 105                 110

Leu Thr Thr Val Cys Phe Thr Gly His Trp Glu Val Gly Gln Phe Val
        115                 120                 125

Ile Gly Arg Val Val Ser Gly Ile Gly Asn Gly Met Asn Thr Ala Thr
    130                 135                 140

Ile Pro Val Trp Gln Ser Glu Cys Ser Gly Ala His Asn Arg Gly Phe
145                 150                 155                 160

Leu Val Cys Phe Glu Gly Ala Met Ile Ala Gly Gly Thr Phe Ile Ala
                165                 170                 175

Tyr Trp Val Val Phe Gly Met Ser His Ala Ala Asp Ser Val Gln Trp
            180                 185                 190

Arg Phe Pro Val Ala Leu Gln Ile Phe Ala Leu Val Val Ala Ala
        195                 200                 205

Gly Ala Met Met Leu Pro Asp Ser Pro Ser Trp Phe Val Met Arg Gly
    210                 215                 220

Leu Asp Lys Glu Ala Cys Glu Val Leu Gly Lys Leu Lys Gly Thr Ser
225                 230                 235                 240

Pro Asp Ser Asp Gln Val Leu His Asp Phe Asn Phe Leu Lys Gln Asp
                245                 250                 255

Met Glu Ser Ser Lys Asn Thr Gln Ser Asn Trp Lys Thr Val Phe Thr
```

```
                 260              265              270
Phe Gly Lys Thr Gln Glu Phe Gln Arg Leu Leu Ile Gly Cys Ser Gly
            275              280              285

Gln Phe Phe Gln Gln Phe Thr Gly Cys Asn Ala Ala Ile Tyr Tyr Ser
290              295              300

Thr Leu Leu Phe Gln Glu Asn Leu Gly Met Glu Lys Tyr Leu Ser Leu
305              310              315              320

Ile Met Gly Gly Val Phe Ala Thr Val Tyr Val Leu Ala Thr Ile Pro
            325              330              335

Ser Phe Phe Met Ile Glu Lys Val Gly Arg Arg Asn Leu Tyr Leu Val
            340              345              350

Gly Phe Leu Gly Gln Gly Leu Ser Phe Val Ile Thr Phe Ala Cys Leu
            355              360              365

Ile Lys Glu Thr Glu Glu Asn Ser Lys Gly Ala Ala Val Gly Ile Phe
            370              375              380

Leu Phe Ile Thr Phe Phe Ala Phe Thr Leu Leu Pro Leu Pro Trp Ile
385              390              395              400

Tyr Pro Pro Glu Ile Asn Pro Leu Arg Thr Arg Thr Val Gly Ala Ser
            405              410              415

Ala Ser Thr Cys Thr Asn Trp Ile Cys Asn Phe Ala Val Val Met Phe
            420              425              430

Thr Pro Leu Phe Ala Gly Gln Ser Pro Trp Gly Val Tyr Leu Phe Phe
            435              440              445

Ala Leu Phe Asn Phe Leu Gly Leu Ile Phe Gly Phe Phe Phe Tyr Val
450              455              460

Glu Thr Ala Gly Arg Glu Leu Glu Glu Val Asp Ile Ile Tyr Ala Lys
465              470              475              480

Ala His Val Glu Gly Lys Met Ala Trp Arg Val Ala Asn Thr Met Pro
            485              490              495

Lys Leu Ser Phe Glu Glu Ile Thr Gln Gln Ser Arg Glu Leu Gly Leu
            500              505              510

Asp Thr Asn Asp His Gly Val His Glu Lys Thr Glu Leu Gly Leu Ser
            515              520              525

Ser Asp Ser Gly Gln Glu Thr Glu Glu Val His Glu Lys His
            530              535              540

<210> SEQ ID NO 62
<211> LENGTH: 488
<212> TYPE: PRT
<213> ORGANISM: Trichophyton verrucosum

<400> SEQUENCE: 62

Met Ala Gly Ile Ile Ser Ala Met Pro Phe Asn Thr Val Phe Pro Glu
1               5               10              15

Thr Lys Asp Asn Pro Thr Asn Gln Gly Phe Val Thr Ala Ile Tyr Glu
            20              25              30

Ile Gly Cys Leu Leu Gly Ala Val Ser Ile Ile Trp Ser Gly Asp Met
            35              40              45

Leu Gly Arg Arg Lys Ser Ile Val Thr Gly Ala Ile Ile Met Ala Ile
            50              55              60

Gly Ala Ile Ile Gln Val Thr Ser Phe Val Gly His Gln Pro Tyr Ala
65              70              75              80

Gln Phe Ile Ile Gly Arg Ile Ile Thr Gly Val Gly Asn Gly Ile Asn
            85              90              95
```

```
Thr Ser Thr Ile Pro Thr Tyr Gln Ala Glu Cys Ser His Ala Ser Asn
                100                 105                 110
Arg Gly Leu Leu Ile Cys Ile Glu Gly Ala Thr Ile Ala Phe Gly Thr
            115                 120                 125
Leu Ile Ala Tyr Trp Ile Asp Tyr Gly Ala Ser Tyr Gly Ala Asp Ser
        130                 135                 140
Phe Ser Trp Arg Phe Pro Ile Ala Phe Gln Ile Ala Phe Ser Ile Val
145                 150                 155                 160
Met Val Thr Gly Met Ile Trp Leu Pro Glu Ser Pro Arg Trp Leu Cys
                165                 170                 175
Met Arg Asp Arg Ser Asp Glu Gly Glu Arg Val Ile Ala Ala Leu His
            180                 185                 190
Gly Val Pro Val Thr Asp Pro Leu Val Gln Ala Glu Lys Asn Ala Val
        195                 200                 205
Met Glu Ser Ile Arg Ala Ser Gly Glu Val Gly Lys Pro Thr Pro Leu
210                 215                 220
Ser Val Val Phe Thr Gly Gly Lys Thr Gln His Arg Arg Met Phe
225                 230                 235                 240
Leu Gly Val Phe Gly Gln Phe Ala Gln Gln Leu Ser Gly Cys Asn Ala
            245                 250                 255
Ile Ile Tyr Phe Phe Pro Val Leu Phe Glu Lys Ser Ile Gly Val Asp
        260                 265                 270
His Asn Met Ala Thr Leu Leu Gly Gly Val Asn Met Ile Val Tyr Ser
275                 280                 285
Ile Phe Ala Thr Thr Ser Trp Phe Leu Ile Glu Arg Ala Gly Arg Arg
        290                 295                 300
Lys Leu Phe Leu Tyr Gly Ala Ala Gly Gln Ala Ile Ser Met Thr Ile
305                 310                 315                 320
Thr Phe Ala Cys Leu Ile Pro Asn Thr Pro Ala Thr Ala Lys Gly Ala
                325                 330                 335
Ala Val Gly Leu Phe Thr Tyr Ile Ala Ser Phe Gly Ala Thr Trp Leu
            340                 345                 350
Pro Leu Pro Trp Leu Tyr Ala Ala Glu Ile Ser Pro Ile Lys Thr Arg
        355                 360                 365
Ala Lys Ala Asn Ala Leu Ser Thr Cys Ser Asn Trp Leu Phe Asn Phe
370                 375                 380
Phe Ile Val Met Ile Thr Pro Val Met Leu Ala Gly Ile Gly Trp Gly
385                 390                 395                 400
Thr Tyr Leu Phe Phe Ala Ile Ile Asn Val Cys Phe Leu Pro Ile Ile
                405                 410                 415
Tyr Phe Phe Tyr Pro Glu Thr Ala Lys Arg Ser Leu Glu Glu Ile Asp
            420                 425                 430
Ile Ile Phe Ala Lys Gly Tyr Cys Glu Asn Lys Ser Tyr Val Gln Ala
        435                 440                 445
Ala Arg Glu Leu Pro Tyr Leu Thr Glu Glu Ile Ser Arg Met Asp
450                 455                 460
Ala Glu Tyr Gly His Gly Lys Pro Ser Glu Thr Ala Ser Pro Val Asn
465                 470                 475                 480
Glu Lys Glu Ser Asp Ser Asp Gln
                485

<210> SEQ ID NO 63
<211> LENGTH: 488
<212> TYPE: PRT
```

<213> ORGANISM: Neofusicoccum parvum

<400> SEQUENCE: 63

```
Met Ser Gly Leu Leu Thr Gly Ser Ala Phe Thr Lys Val Phe Pro Glu
1               5                   10                  15

Ile Asp Thr Gln Asn Gly Gly Ser Ser Ser Leu Gln Gly Thr Val Val
            20                  25                  30

Ala Ile Tyr Glu Ile Gly Cys Phe Ala Gly Leu Ile Thr Phe Ala
        35                  40                  45

Phe Gly Glu Gln Leu Gly Arg Arg Lys Cys Ile Met Ala Gly Cys Thr
50                  55                  60

Ile Leu Thr Ile Gly Ala Thr Ile Gln Cys Ala Ser Tyr Gly Ile Pro
65                  70                  75                  80

Gln Leu Ile Val Gly Arg Ile Val Ala Gly Ile Gly Asn Gly Leu Asn
                85                  90                  95

Thr Ser Thr Ile Pro Val Trp His Ala Glu Leu Met Gln Ala His Asp
            100                 105                 110

Arg Gly Lys Gly Leu Ala Ile Glu Phe Ile Leu Asn Ile Phe Gly Val
        115                 120                 125

Ala Leu Ala Tyr Trp Val Asp Tyr Ala Phe Ser Phe Val Asp Asn Glu
    130                 135                 140

Ser Gln Phe Arg Phe Pro Ile Ala Phe Gln Ile Ala Phe Ala Leu Val
145                 150                 155                 160

Thr Leu Ala Ser Ile Ile Phe Leu Pro Glu Ser Pro Arg Trp Leu Leu
                165                 170                 175

Asn His Asp Arg Glu Ala Glu Ala Arg Asn Ile Leu Trp Arg Leu Gln
            180                 185                 190

Pro Asn Ala Lys Glu Ile Ala Glu Asp Ser Asp Val Val Asn Asn Glu
        195                 200                 205

Met Ala Ile Ile Gln His Ala Leu Tyr Glu Glu Lys Glu Val Ala Gly
    210                 215                 220

Gly Thr Thr Phe Lys Ala Ile Phe Lys Asp Gly Pro Gln Arg Phe Arg
225                 230                 235                 240

Tyr Arg Thr Leu Leu Gly Ile Gly Gly Gln Phe Met Gln Gln Leu Ser
                245                 250                 255

Gly Ile Asn Leu Ile Thr Tyr Tyr Ala Ala Val Ile Phe Glu Thr Ser
            260                 265                 270

Ile Gly Met Ser His Asn Thr Ala Leu Leu Val Ala Gly Ala Asn Gly
        275                 280                 285

Ile Ala Tyr Phe Leu Ser Thr Phe Pro Val Val Trp Val Leu Asp Arg
    290                 295                 300

Leu Gly Arg Arg Lys Leu Met Leu Phe Ala Val Ile Gly Gln Ser Cys
305                 310                 315                 320

Cys Met Ala Ile Leu Ala Gly Thr Val Ser Asn Gly Gly Lys Ser Ala
                325                 330                 335

Gly Ile Val Ala Ala Val Met Leu Phe Leu Asn Phe Phe Phe Ala
            340                 345                 350

Ile Gly Leu Leu Ala Ile Pro Trp Leu Leu Pro Ala Glu Tyr Ala Pro
        355                 360                 365

Leu Ala Ile Arg Thr Lys Ala Ala Ser Leu Ala Thr Ala Ser Asn Trp
    370                 375                 380

Ile Phe Thr Phe Leu Val Val Glu Ile Val Pro Val Ser Ile Asn Asn
385                 390                 395                 400
```

```
Ile Ala Trp Arg Thr Tyr Ile Tyr Phe Ala Val Phe Asn Ala Phe Phe
                405                 410                 415

Val Pro Ile Ile Tyr Phe Phe Tyr Pro Glu Thr Lys Asn Leu Ser Leu
            420                 425                 430

Glu Glu Ile Asp Met Leu Phe Thr Gly Asp Lys Val Leu Met His Leu
            435                 440                 445

Pro Asp Ser Met Arg Ile Pro Ala Asn Asp Asn Ala Ala Val Ala Ser
450                 455                 460

Ala Ile Arg Gly Glu Lys Asp Asn Val Ala Val Glu Asp Val Asn
465                 470                 475                 480

Asn Gly Asn Asn Ser Glu Lys Ser
                485
```

<210> SEQ ID NO 64
<211> LENGTH: 516
<212> TYPE: PRT
<213> ORGANISM: Eutypa lata

<400> SEQUENCE: 64

```
Met Ser Ser Pro Thr Thr Phe Leu Gly Phe Gln Gly Ser Ser Leu Thr
1               5                   10                  15

Leu Ala Gln Leu Phe Leu Val Val Cys Pro Ala Phe Val Leu Phe Gly
            20                  25                  30

Tyr Asn Gln Ser Gly Leu Gly Gly Leu Val Gly Leu Gln Asp Trp Ser
        35                  40                  45

Gln Thr Phe Pro Arg Ile Asp Thr Leu Asn Thr Glu Gly Ala Gln Lys
    50                  55                  60

Asp Asn Asn Ala Thr Ile Gln Gly Leu Val Val Ala Thr Phe Thr Leu
65                  70                  75                  80

Gly Ala Leu Pro Gly Cys Leu Ser Cys Ala Tyr Thr Ala Asp Arg Phe
                85                  90                  95

Gly Arg Arg Thr Val Ile Phe Val Gly Ala Leu Leu Thr Leu Ile Gly
            100                 105                 110

Glu Val Leu Glu Ala Ser Ala Phe His Leu Ala Gln Met Ile Val Gly
        115                 120                 125

Arg Val Ile Leu Gly Ala Gly Val Gly Met Leu Ser Gly Val Val Pro
    130                 135                 140

Thr Trp Gln Ser Glu Cys Ser Asn Ser Lys Asn Arg Gly Lys His Val
145                 150                 155                 160

Val Leu Glu Gly Leu Phe Ile Ser Met Gly Tyr Val Leu Gln Ala Trp
                165                 170                 175

Ile Asn Leu Gly Phe Tyr Gln Phe Glu Thr Gly Pro Val Thr Trp Arg
            180                 185                 190

Pro Pro Ile Ala Ile Pro Ile Phe Phe Ser Leu Val Leu Met Ser Phe
        195                 200                 205

Ile Tyr Leu Met Pro Glu Ser Pro Arg Trp Leu Ile Arg Gln Gly Arg
    210                 215                 220

Val Ser Glu Ala Arg Ala Ala Met Ser Ala Leu Lys Gly Leu Ala Asp
225                 230                 235                 240

Asp Ala Gln Glu Ile His Ala Glu Val Ala Val Glu Leu Ser Leu
                245                 250                 255

Glu Glu Thr Gly Gln Lys Lys Ala Ala Leu Ala Asp Leu Leu Arg Met
            260                 265                 270

Asp Glu Asp Lys Leu Leu Tyr Arg Phe Gly Ile Cys Ile Leu Leu Gln
        275                 280                 285
```

```
Phe Phe Gln Gln Met Ser Gly Gly Asn Leu Ile Ser Val Tyr Ser Thr
    290                 295                 300

Ile Ile Phe Gln Arg Gly Leu Asn Leu Glu Ala Glu Thr Ser Arg Ile
305                 310                 315                 320

Leu Ser Gly Gly Thr Leu Thr Trp Lys Phe Leu Ser Cys Phe Val Ser
                325                 330                 335

Phe Phe Thr Ile Asp Arg Phe Gly Arg Arg Val Ala Leu Met Val Ser
            340                 345                 350

Gly Thr Gly Met Ala Val Cys Met Met Ser Leu Ala Ile Ala Thr Ser
        355                 360                 365

Phe Pro Thr Ser Asn Leu Ala Ala Gln Ile Val Ser Val Leu Phe Val
370                 375                 380

Phe Leu Phe Asn Phe Phe Ile Pro Ile Gly Phe Leu Gly Ala Asn Phe
385                 390                 395                 400

Leu Tyr Cys Thr Glu Val Ala Pro Leu Arg Leu Arg Val Ala Met Ser
                405                 410                 415

Ser Ile Ser Thr Ala Asn His Trp Leu Trp Asn Phe Val Val Thr Met
            420                 425                 430

Ile Thr Pro Val Ala Ile Glu Ser Ile Gly Tyr Lys Tyr Tyr Ile Val
        435                 440                 445

Tyr Thr Val Val Gly Phe Cys Ile Pro Leu Thr Val Tyr Phe Leu Tyr
450                 455                 460

Pro Glu Thr Met Gly Met Arg Leu Glu Asp Ile Asp Leu Val Phe Arg
465                 470                 475                 480

Glu Ser Pro Ser Val Leu Ala Thr Val Lys Tyr Ala Arg Ser Arg Ser
                485                 490                 495

Gln Arg Ser Asn Glu Glu Val Leu Ala Asp Lys Lys Val Glu Tyr
            500                 505                 510

Ala Glu Lys Ile
        515

<210> SEQ ID NO 65
<211> LENGTH: 517
<212> TYPE: PRT
<213> ORGANISM: Phaeoacremonium minimum

<400> SEQUENCE: 65

Met Gly Phe Lys Thr Ala Phe Gly Leu Thr Gly His Ala Leu Ser Ile
1               5                   10                  15

Leu Gln Ile Ala Leu Ile Val Ala Pro Ser Phe Val Leu Phe Gly Tyr
            20                  25                  30

Asn Gln Ala Gly Ile Gly Gly Leu Leu Ser Glu Glu Asp Trp Val Lys
        35                  40                  45

Thr Phe Pro Glu Ile Asp Thr Val His Ala Thr Gly Thr Thr Lys Ser
50                  55                  60

Ser Lys Ser Thr Leu Gln Gly Phe Val Val Ala Thr Phe Val Ile Gly
65                  70                  75                  80

Ala Leu Ile Gly Ala Leu Ser Cys Ser Tyr Thr Gly Asp Ile Phe Gly
                85                  90                  95

Arg Arg Asn Val Ile Phe Ala Gly Ala Val Phe Thr Leu Val Gly Glu
            100                 105                 110

Val Leu Glu Ala Ser Ser Phe Ser Leu Ala Gln Phe Ile Val Gly Arg
        115                 120                 125

Val Leu Ile Gly Ala Gly Val Gly Gln Leu Ser Ser Ile Val Pro Val
```

```
              130                 135                 140
Trp Gln Ser Glu Thr Ser Gly Ala Lys Asn Arg Gly Arg Ser Val Val
145                 150                 155                 160

Val Thr Gly Leu Phe Ile Cys Leu Gly Tyr Val Leu Glu Ser Trp Ile
                165                 170                 175

Asp Leu Gly Phe Phe Glu Phe Lys Thr Gly Pro Leu Thr Trp Arg Pro
                180                 185                 190

Pro Ile Ala Ile Ala Val Ala Phe Ser Leu Val Leu Met Ala Ser Val
                195                 200                 205

Tyr Val Phe Pro Glu Ser Pro Arg Trp Leu Leu Met Lys Asn Arg Val
                210                 215                 220

Gln Glu Ala Arg Glu Ser Leu Ser Val Leu Arg Gly His Ala Glu Asp
225                 230                 235                 240

Ser Leu Glu Val Gln Ala Glu Leu Ala Gly Ile Glu Leu Ser Leu Glu
                245                 250                 255

Glu Thr Ser Gly Asn Ala Ala Lys Leu Gly Asp Met Leu Lys Met Gly
                260                 265                 270

Glu Glu Lys Leu Leu Tyr Arg Phe Phe Leu Cys Met Leu Leu Gln Phe
                275                 280                 285

Tyr Gln Gln Met Ser Gly Ser Asn Leu Val Ser Val Tyr Ala Thr Thr
                290                 295                 300

Leu Phe Gln Thr Asn Leu Gly Leu Ser Ser Glu Leu Ser Arg Val Leu
305                 310                 315                 320

Thr Gly Gly Ala Leu Thr Trp Lys Phe Leu Ser Ser Phe Ile Ala Phe
                325                 330                 335

Val Thr Ile Asp Arg Phe Gly Arg Arg Ala Val Phe Ile Leu Ser Gly
                340                 345                 350

Ile Gly Met Ser Cys Cys Met Ile Ala Leu Ala Val Ser Thr Ser Phe
                355                 360                 365

Gly Lys Glu Asn Arg Ala Ala Gln Ile Ala Ala Gly Cys Phe Ile Tyr
                370                 375                 380

Leu Tyr Asn Thr Phe Val Pro Ile Gly Phe Leu Gly Ala Asn Phe Leu
385                 390                 395                 400

Tyr Cys Thr Glu Val Ala Pro Ile Arg Leu Arg Met Ala Met Ser Ser
                405                 410                 415

Ile Ser Thr Ala Asn His Trp Leu Trp Asn Phe Val Val Met Val
                420                 425                 430

Thr Pro Val Ala Ile Glu Thr Ile Gly Trp Gln Phe Tyr Ile Val Phe
                435                 440                 445

Ala Val Ile Ala Ala Cys Val Pro Val Ser Val Tyr Phe Leu Phe Pro
450                 455                 460

Glu Thr Met Gly Arg Asn Leu Glu Glu Ile Asp Met Val Phe Arg Glu
465                 470                 475                 480

Ser Pro Ser Val Trp Ala Thr Val Arg Phe Ala Arg Ser Arg Pro Ala
                485                 490                 495

Leu Thr Ala Val Glu Tyr Ala Glu Lys His Asp Asn Val Asp His Leu
                500                 505                 510

Glu Lys Thr Ala Glu
                515

<210> SEQ ID NO 66
<211> LENGTH: 517
<212> TYPE: PRT
<213> ORGANISM: Aureobasidium namibiae
```

-continued

<400> SEQUENCE: 66

```
Met Val Gly Tyr Leu Asp Gly Ile Gln Gly Lys Thr Leu Tyr Lys Ile
1               5                   10                  15

Met Ser Ala Ala Cys Gly Ser Ala Phe Met Leu Tyr Gly Trp Asp Ala
            20                  25                  30

Gly Val Leu Gly Gly Ile Gln Glu Thr Lys Glu Phe Arg Ala Ala Ile
        35                  40                  45

Gly Asp Pro Gln Gly Ala Phe Ile Ile Pro Ile Ala Ala Ile Tyr
    50                  55                  60

Asn Leu Ala Ala Gly Val Met Ser Leu Cys Val Ser Phe Tyr Gly Met
65                  70                  75                  80

Gln Ile Gly Arg Lys Gly Thr Ile Leu Gly Cys Leu Leu Ile Cys
                85                  90                  95

Ile Gly Ala Leu Leu Gln Ala Ser Thr Tyr Ser Val Gly Gln Ile Ile
                100                 105                 110

Val Gly Arg Ile Val Thr Gly Ala Gly Ile Gly Asn Ile Ala Ala Ala
            115                 120                 125

Val Pro Thr Tyr Met Ala Glu Met Ser Leu Glu Ala Lys Glu Arg Gly
        130                 135                 140

Pro Glu Val Ser Tyr Gln Leu Ala Leu Leu Ile Thr Gly Val Ala Leu
145                 150                 155                 160

Ala Tyr Trp Ile Asp Leu Gly Phe Val Gln Gly Leu Asp Arg His Pro
                165                 170                 175

Trp Leu Trp Arg Ile Pro Leu Ala Leu Gln Ser Cys Phe Ala Ile Phe
            180                 185                 190

Ser Ala Val Leu Leu Phe Met Leu Pro Asp Thr Pro Arg Trp Tyr Tyr
        195                 200                 205

Ala Arg Gly Lys Glu Ala Lys Gly Asp Arg Val Leu Ala Arg Leu His
    210                 215                 220

Gly Leu Pro Val Glu His Gln Asn Val Gln Ala Val Lys Ala Asp Ile
225                 230                 235                 240

Met Ala Ser Met Glu Glu Glu Asp Glu Thr Gly Lys Ile Ser Ile Val
                245                 250                 255

Ser Leu Phe Trp Asp Asn Thr Glu Leu Gln Phe Gly Arg Arg Leu Arg
            260                 265                 270

Thr Ser Phe Leu Ile Asn Trp Ala Gln Gln Phe Leu Gly Ile Asn Met
        275                 280                 285

Leu Val Tyr Phe Ser Thr Gln Ile Phe Ser Asn Leu Asn Tyr Ser Pro
    290                 295                 300

Leu Leu Ser Gly Ile Leu Ala Gly Val Leu Asn Thr Ala Phe Ala Ile
305                 310                 315                 320

Ala Ser Tyr Pro Pro Ile Trp Tyr Ile Glu Lys Val Gly Arg Arg Ala
                325                 330                 335

Met Met Ile Trp Ser Ala Leu Gly Cys Gly Val Cys Met Leu Ile Tyr
            340                 345                 350

Val Val Leu Thr Thr Leu Pro Ala His Met Gln Ser Ala Gly Thr Asn
        355                 360                 365

Trp Gly Ala Val Ala Ile Ile Ile Leu Tyr Glu Ile Val Phe Ala Phe
    370                 375                 380

Gly Trp Leu Gly Thr Cys Trp Ile Tyr Gly Pro Glu Ile Ala Pro Leu
385                 390                 395                 400

Lys Tyr Arg His Val Ala Gly Ser Leu Gly Ala Ala Gly Glu Trp Phe
```

```
            405                 410                 415
Ser Thr Phe Val Met Val Phe Gly Gly Gly Thr Gly Ile Asn Ala Val
                420                 425                 430

Gly Pro Lys Ile Phe Ile Trp Pro Leu Leu Cys Cys Phe Leu Ala Ala
                435                 440                 445

Ala Tyr Val Tyr Phe Leu Cys Pro Glu Thr Thr Gly Lys Thr Leu Glu
                450                 455                 460

Glu Ile Asp Ala Leu Phe Ala Arg Ser Pro Glu Val Arg Glu Arg Leu
465                 470                 475                 480

Glu Arg Asp Ile Ala Ala Arg Arg Ala Gly Val Leu Pro Gly Asn Glu
                485                 490                 495

Lys Ser Met Ser Arg Asp Ser Ser Asp Met Ser Lys Met Glu Val Ser
                500                 505                 510

Asn Ile Glu Lys Ile
                515

<210> SEQ ID NO 67
<211> LENGTH: 677
<212> TYPE: PRT
<213> ORGANISM: Kluyveromyces lactis

<400> SEQUENCE: 67

Met Ser Asp Ser Thr Asp Lys Asp Arg His Asn Lys Asn Ser Ser Arg
1               5                   10                  15

Gly Ile Val Asn Thr Asp Ile Glu Asp Asn Ser Pro Ser Pro Leu
                20                  25                  30

Asp Thr Asp Lys Lys Gly Ala Pro Glu Leu Gln Lys Pro Gly Asn
                35                  40                  45

Pro Ser Leu Phe Lys Glu Ser Ala Leu Lys Asn Ser Asp Gln Leu Gln
50                  55                  60

Phe Arg Asn Ser Phe Asn Ile Pro Asn Ala Val Gly Gly Thr Asn Gly
65                  70                  75                  80

Ile Val Ile Pro Pro Asn Val Gln Pro Leu Asp Gln Gln Arg Ile Pro
                85                  90                  95

Pro Ser Tyr Thr Asp His Leu Gln Val Lys Asp Thr Tyr Leu Thr Gly
                100                 105                 110

Arg Thr Leu Leu Tyr Phe Thr Ser Ile Phe Val Ser Leu Gly Val Phe
                115                 120                 125

Leu Phe Gly Tyr Asp Gln Gly Val Met Ser Gly Ile Ile Thr Gly Pro
130                 135                 140

Tyr Phe Lys Thr Tyr Phe Asn Asn Pro Thr Ala Ala Thr Ile Gly Thr
145                 150                 155                 160

Met Val Ser Ile Leu Glu Ile Gly Ala Leu Val Ser Ser Leu Leu Val
                165                 170                 175

Ser Asn Ile Gly Glu Lys Phe Gly Arg Arg Phe Thr Ile Lys Tyr Gly
                180                 185                 190

Ser Leu Ile Phe Ile Leu Gly Gly Leu Val Gln Thr Phe Ser Trp Glu
                195                 200                 205

Met Gly His Met Ile Phe Gly Arg Ile Ile Ser Gly Ile Gly Val Gly
                210                 215                 220

Leu Leu Ser Thr Ile Val Pro Ile Tyr Gln Ser Glu Ile Ser Pro Pro
225                 230                 235                 240

His Asn Arg Gly Lys Leu Ala Cys Ile Glu Phe Thr Gly Asn Ile Val
                245                 250                 255
```

```
Gly Tyr Ala Ser Ser Val Trp Val Asp Tyr Ala Cys Ser Tyr Ile Glu
            260                 265                 270

Ser Asp Thr Ser Trp Arg Leu Pro Leu Phe Ile Gln Cys Val Met Gly
            275                 280                 285

Leu Leu Leu Phe Leu Gly Ser Phe Val Ile Val Glu Thr Pro Arg Trp
            290                 295                 300

Leu Leu Asn His Asp His Asp Ile Glu Gly Leu Val Val Ile Ala Asp
305                 310                 315                 320

Leu His Ser Asp Gly Asp Val Leu His Ser Lys Ala His Glu Glu Tyr
                325                 330                 335

Lys Leu Ile Lys Glu Thr Val Leu Ile Ser Arg Leu Glu Gly Glu Lys
            340                 345                 350

Lys Ser Leu Arg Phe Ala Phe Lys Arg Tyr Arg Thr Arg Met Leu Ile
            355                 360                 365

Ala Met Ser Ser Gln Met Phe Ala Gln Leu Asn Gly Ile Asn Val Ile
            370                 375                 380

Ser Tyr Tyr Ala Pro Leu Val Phe Glu Gln Ala Gly Trp Val Gly Arg
385                 390                 395                 400

Glu Ala Leu Leu Met Thr Gly Ile Asn Ser Ile Ile Tyr Ile Leu Ser
                405                 410                 415

Thr Ile Leu Pro Trp Lys Leu Val Asp Lys Trp Gly Arg Lys Pro Ile
            420                 425                 430

Leu Leu Ser Gly Ala Leu Val Met Gly Thr Ser Leu Leu Ala Ile Ala
            435                 440                 445

Met Ser Leu Trp Ala Asn Val Ala Ala Thr Pro Arg Leu Val Val Val
450                 455                 460

Phe Val Ile Ile Phe Asn Ala Phe Phe Gly Tyr Ser Trp Gly Pro Ile
465                 470                 475                 480

Pro Trp Leu Tyr Pro Val Glu Ile Ala Pro Ala Met Ala Arg Ser Ala
                485                 490                 495

Met Ala Ser Ala Ser Thr Ala Thr Asn Trp Leu Phe Asn Trp Leu Val
            500                 505                 510

Gly Ile Met Thr Pro Ile Leu Gln Glu Lys Ile His Trp Arg Met Tyr
            515                 520                 525

Leu Ile His Thr Val Ser Cys Tyr Leu Ser Phe Trp Cys Val Leu Lys
530                 535                 540

Val Tyr Pro Glu Thr Ala Gly Leu Arg Leu Glu Asp Met Asp Ser Val
545                 550                 555                 560

Phe Asp Asp Arg Ser Ser Thr Phe Ser Phe Gln Ser Gly Thr Ser Ala
                565                 570                 575

Glu Ile Glu Gln Gln Ser His Leu Val Ser Gly Gly Glu Val Ala
            580                 585                 590

Pro Ser Thr Arg Ser Arg Lys Ser Val Tyr Ser Asn Ala Gln Ser Met
            595                 600                 605

Phe Asn Lys Asp Glu Ile Gln Pro Pro Thr Leu Thr Gln Val Leu Gln
610                 615                 620

Trp Lys Glu Glu Arg Thr Gln Thr Lys Pro Leu Lys Lys Phe Ile Arg
625                 630                 635                 640

Arg Gly Ser Glu Thr Val Cys Leu Ile Tyr Asn Lys Val Arg Asn Leu
                645                 650                 655

Arg Ser Thr Asn Asp Thr Asn Gln Ile Glu Tyr Gly Ala Val Ser Asn
            660                 665                 670

Asn Gln Pro Pro Asn
```

<210> SEQ ID NO 68
<211> LENGTH: 163
<212> TYPE: PRT
<213> ORGANISM: Rasamsonia emersonii

<400> SEQUENCE: 68

```
Met Thr Ser Ile Gly Gly Pro Lys Cys Gly Ile Val Ala Ala Thr Phe
1               5                   10                  15

Leu Phe Val Phe Asn Thr Phe Ala Leu Gly Trp Leu Ser Ile Pro
            20                  25                  30

Trp Leu Tyr Pro Ala Glu Leu Val Pro Leu Glu Ile Arg Ala Gln Ala
            35                  40                  45

Asn Ala Leu Ser Thr Ser Ala Asn Trp Ile Phe Asn Phe Met Val Val
            50                  55                  60

Met Ile Thr Pro Val Ala Phe Ser Ser Ile Gly Trp Arg Thr Tyr Ile
65                  70                  75                  80

Ile Phe Ala Val Phe Asn Ala Ala Ser Ile Pro Ile Leu Tyr Trp Cys
                    85                  90                  95

Tyr Pro Glu Thr Ala Tyr Arg Ser Leu Glu Glu Met Asp Ile Ile Phe
            100                 105                 110

Ala Lys Ala Thr Gly Val Val Asp Ala Val Arg Val Ala Arg Thr Glu
        115                 120                 125

Pro Arg His Phe Gly Lys His Gly Glu Val Leu Arg Glu Met Val Pro
    130                 135                 140

Asp Val Lys Asp Thr Thr Gly Ile Gly Ser Glu Lys Gly Gly Val Glu
145                 150                 155                 160

His Val Gln
```

<210> SEQ ID NO 69
<211> LENGTH: 575
<212> TYPE: PRT
<213> ORGANISM: Pachysolen tannophilus

<400> SEQUENCE: 69

```
Met Phe Lys Lys Ile Asp Lys Ile Asp Lys Ser Asp Tyr Val Ala Ser
1               5                   10                  15

Ser Ser Lys Lys Tyr Leu Gly Met Arg Gly Ala Pro Leu His Lys Ala
            20                  25                  30

Ile Ala Thr Ile Ala Gly Leu Gly Phe Leu Leu Phe Gly Tyr Asp Gln
            35                  40                  45

Gly Val Met Gly Ser Leu Leu Thr Leu Asp Ser Phe Leu Glu Thr Phe
    50                  55                  60

Pro Gln Ile Asn Asp Ser Val Asp Thr Ser Lys Ser Thr Leu Lys Gly
65                  70                  75                  80

Phe Val Ile Ala Val Tyr Glu Leu Gly Cys Met Thr Gly Ala Phe Phe
                    85                  90                  95

Thr Met Trp Lys Gly Asp Ile Phe Gly Arg Arg Lys Met Ile Phe Tyr
            100                 105                 110

Gly Ser Ile Ile Met Thr Ile Gly Gly Ile Leu Gln Cys Thr Ser Tyr
        115                 120                 125

Ser Val Ala Gln Leu Ala Val Ala Arg Val Val Ser Gly Val Gly Asn
    130                 135                 140

Gly Phe Ile Thr Ser Thr Ile Pro Thr Leu Gln Ser Glu Cys Ala Lys
145                 150                 155                 160
```

```
Pro His Arg Arg Gly Ala Leu Ile Met Met Ser Gly Ala Leu Ile Ser
            165                 170                 175

Phe Gly Ile Cys Phe Ser Tyr Trp Val Asp Phe Gly Leu Tyr Phe Ala
            180                 185                 190

Thr Gly Asp Val Gln Trp Arg Phe Pro Ile Ala Phe Gln Ile Val Phe
            195                 200                 205

Ser Leu Leu Leu Thr Ser Leu Ile Phe Glu Leu Pro Glu Ser Pro Arg
            210                 215                 220

Trp Leu Val Lys Ile His Glu Ile Glu Arg Ala Arg Glu Thr Phe Ala
225                 230                 235                 240

Ala Leu Asp Asp Val Ser Val Asp Asp Pro Leu Ile Asp Glu Ile
            245                 250                 255

Lys Asp Ile Gln Ala Val Leu Lys Arg Asp Leu Asp Leu Gly Ala Asp
            260                 265                 270

Lys Phe Ser Phe Ser Val Val Phe Lys Phe Asp Glu Lys Lys Thr Phe
            275                 280                 285

His Arg Thr Met Leu Ala Tyr Phe Val Gln Val Met Gln Gln Ile Ser
            290                 295                 300

Gly Ile Asn Leu Ile Thr Tyr Tyr Ala Gly Thr Ile Tyr Glu Thr Tyr
305                 310                 315                 320

Ile Gly Met Asn Ala Leu Asp Ser Arg Ile Leu Ala Ala Cys Asn Gly
            325                 330                 335

Thr Glu Tyr Phe Leu Ala Ser Leu Ile Pro Phe Tyr Thr Val Glu Arg
            340                 345                 350

Phe Gly Arg Arg Ser Leu Phe Leu Phe Gly Thr Ala Gly Gln Ala Ile
            355                 360                 365

Thr Met Ala Ile Leu Thr Gly Val Gln Trp Ala Ser Glu Tyr Lys Gly
            370                 375                 380

Asp Gln Gly Ala Ala Ile Ala Cys Ala Val Phe Leu Phe Val Phe Asn
385                 390                 395                 400

Thr Phe Phe Ala Ile Gly Met Leu Gly Met Thr Trp Leu Leu Pro Pro
            405                 410                 415

Glu Leu Val Thr Leu Glu Ser Arg Ala Ser Val Thr Gly Leu Ser Thr
            420                 425                 430

Ser Ala Asn Trp Leu Phe Asn Phe Val Val Met Ile Thr Pro Val
            435                 440                 445

Cys Phe Thr His Ile Gly Pro Tyr Thr Tyr Thr Ile Phe Ala Val Val
            450                 455                 460

Asn Ala Ile Met Val Pro Cys Ile Phe Phe Tyr Pro Glu Thr Lys
465                 470                 475                 480

Gly Arg Ser Leu Glu Glu Met Asp Arg Ile Phe Glu Gln Ser Asn Pro
            485                 490                 495

Lys Thr Pro Trp Asp Val Val Arg Ile Ala Arg Glu Met Pro Phe Glu
            500                 505                 510

Asn Arg Asp Ile Asp Asn Glu Asp Glu Asp Lys Ile Asn Leu Asp
            515                 520                 525

Arg Ser Ser Glu Thr Ser Ser Val Ser Asn Glu Lys Gly Ser Ala Ser
            530                 535                 540

Phe Thr Leu Asp Ser Val Asn Asp Thr Gly Phe Phe Val Lys Asn Glu
545                 550                 555                 560

Glu Asn Lys Asn Glu Gln Glu Thr Ser Gln Pro Glu Lys Lys Glu
            565                 570                 575
```